US009012217B2

(12) United States Patent
Mercola et al.

(10) Patent No.: US 9,012,217 B2
(45) Date of Patent: Apr. 21, 2015

(54) BENZIMIDAZOLE COMPOUNDS DIFFERENTIATE A MAMMALIAN STEM CELL INTO MESODERMAL OR CARDIOMYOCYTE CELLS

(75) Inventors: Mark Mercola, La Jolla, CA (US); Marcia Dawson, La Jolla, CA (US); John Cashman, San Diego, CA (US); Paul J. Bushway, San Diego, CA (US)

(73) Assignees: Burnham Institute for Medical Research, La Jolla, CA (US); Human Biomolecular Research Institute, San Diego, CA (US)

( * ) Notice: Subject to any disclaimer, the term of this patent is extended or adjusted under 35 U.S.C. 154(b) by 390 days.

(21) Appl. No.: 12/561,235

(22) Filed: Sep. 16, 2009

(65) Prior Publication Data

US 2010/0159596 A1   Jun. 24, 2010

Related U.S. Application Data

(60) Provisional application No. 61/097,823, filed on Sep. 17, 2008.

(51) Int. Cl.
C12N 5/0735 (2010.01)
C12N 5/074 (2010.01)
(Continued)

(52) U.S. Cl.
CPC ............ *C07D 215/54* (2013.01); *C12N 5/0623* (2013.01); *C12N 5/0606* (2013.01);
(Continued)

(58) Field of Classification Search
CPC ........ C12N 15/63; C12N 15/65; C12N 15/66; C12N 15/88; C12N 5/0735; C12N 5/18; C12N 5/22; C12N 5/0623; C12N 2501/16; C12N 2501/999; C12N 2502/098; C12N 2502/02; C12N 2502/03; C12N 2506/00; C12N 2506/02; C12N 5/0696; C12N 5/0606; C12N 5/0603

See application file for complete search history.

(56) References Cited

U.S. PATENT DOCUMENTS 5,455,253 A   10/1995 Ohnmacht, Jr. et al.
(Continued)

FOREIGN PATENT DOCUMENTS

WO  WO 2008/056166 A2  5/2008
WO  WO 2008/070875 A2  6/2008
WO  WO 2009/006580 A1  1/2009

OTHER PUBLICATIONS

Takahashi et al. Ascorbic Acid Enhances Differentiation of Embryonic Stem Cells Into Cardiac Myocytes. Circulation, 2003, vol. 107, pp. 1912-1916.*
(Continued)

*Primary Examiner* — Deborah Crouch
(74) *Attorney, Agent, or Firm* — DLA Piper LLP (US)

(57) ABSTRACT

Methods and small molecule compounds for stem cell differentiation are provided. One example of a class of compounds that may be used is represented by the compound having the structure IA or IB in the form of free base or a pharmaceutically acceptable salt, hydrate, solvate or N-oxide thereof:

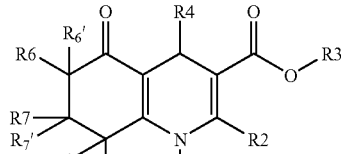

IA

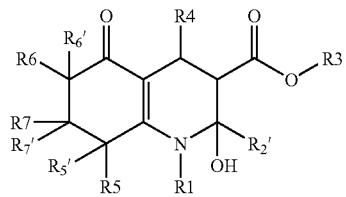

IB $R_1$ is independently hydrogen or $(C_1$-$C_6)$alkyl; $R_2$ is independently hydrogen, $(C_1$-$C_6)$alkyl, aryl, or heteroaryl; $R_{2'}$ is independently hydrogen, $(C_1$-$C_6)$alkyl, $CF_3$ or $C_2F_5$; $R_3$ is independently $(C_1$-$C_6)$alkyl, aryl, 2-tetrahydrofurylmethyl, an aliphatic tertiary amine, or 4-methoxybenzyl; or $R_2$ and $R_3$ may be joined together to form a 5 or 6 member ring lactone; $R_4$ is independently hydrogen, $(C_1$-$C_6)$alkyl, a 2- or 4-$R_5$-substituted aromatic ring selected from a 4-$R_5$-phenyl or a 2-$R_5$-5-pyridyl, aryl, heteroaryl, aliphatic tertiary amine or halogen; and $R_5$, $R_{5'}$, $R_6$, $R_{6'}$, $R_7$, $R_{7'}$, are each independently hydrogen, $(C_1$-$C_6)$alkyl, aryl, optionally substituted phenyl, heteroaryl, a heterocyclic ring, an aliphatic tertiary amine, or halogen.

11 Claims, 7 Drawing Sheets

(51) Int. Cl.
| | |
|---|---|
| C07D 215/54 | (2006.01) |
| C12N 5/0797 | (2010.01) |
| C12N 5/073 | (2010.01) |
| C07D 235/06 | (2006.01) |
| C07D 279/20 | (2006.01) |
| C07D 279/22 | (2006.01) |
| C07D 279/28 | (2006.01) |
| C07D 401/04 | (2006.01) |
| C07D 401/10 | (2006.01) |
| C07D 401/12 | (2006.01) |
| C07D 401/14 | (2006.01) |
| C07D 403/12 | (2006.01) |
| C07D 405/04 | (2006.01) |
| C07D 405/12 | (2006.01) |
| C07D 409/04 | (2006.01) |
| C07D 491/04 | (2006.01) |

(52) U.S. Cl.
CPC ........... *C12N5/0603* (2013.01); *C07D 235/06* (2013.01); *C07D 279/20* (2013.01); *C07D 279/22* (2013.01); *C07D 279/28* (2013.01); *C07D 401/04* (2013.01); *C07D 401/10* (2013.01); *C07D 401/12* (2013.01); *C07D 401/14* (2013.01); *C07D 403/12* (2013.01); *C07D 405/04* (2013.01); *C07D 405/12* (2013.01); *C07D 409/04* (2013.01); *C07D 491/04* (2013.01)

(56) References Cited

U.S. PATENT DOCUMENTS

| | | | |
|---|---|---|---|
| 6,121,284 A | 9/2000 | Urbahns et al. | |
| 6,194,428 B1 | 2/2001 | Urbahns et al. | |
| 2005/0214939 A1 | 9/2005 | Gold et al. | |
| 2007/0254359 A1 | 11/2007 | Rezania et al. | |
| 2010/0159596 A1 | 6/2010 | Mercola et al. | |

OTHER PUBLICATIONS

Lemming et al., "The Role of Potassium Channels in Neuronal Differentiation of Stm Cells from Umbilical Cord Matrix", *The FASEB Journal*, Apr. 2008, vol. 22, Meeting Abstracts, 1197.11 (abstract only).

Berge et al., "Pharmaceutical Salts", Journal of Pharmaceutical Sciences, 66(1):1-19 (1977).

Vitalina et al., "Synthesis and study of the pharmacological activity of derivatives of condensed 1, 4-dihydropyridines", Khimiko-Farmatsevticheskii Zhurnal, 15(1):39-42 (1981), Inst. Org. Sint., Riga USSR., CAPLUS Accession No. 1981:497547, Document No. 95:97547.

Wang et al., "Facile Yb(OTf)3 promoted one-pot synthesis of polyhydroquinoline derivatives through Hantzsch reaction", Tetrahedron, 61(6):1539-1543 (2005).

Reddy and Raghu, "Facile $ZrCl_4$ promoted four-component coupling one-pot synthesis of polyhydroquinoline derivatives through unsymmetric Hantzsch reaction", *Indian Journal of Chemistry*, 47B(10): 1578-1582 (2008).

Su et al., "5-Pyrrolidin-2-yltetrazole-Promoted One-Pot Hantzsch Polyhydroquinoline Synthesis Using $NH_4HCO_3$ as Nitrogen Source", *Australian Journal of Chemistry*, 61(11):860-863 (2008).

Zhou et al., "Synthesis of Chiral Ethyl 5-(Acetoxyimino)-2,7,7-trimethyl-4-(1-naphthyl)-5,6,7,8-tetrahydroquinoline-3-carboxylate via Lipase-Catalyzed Hydrolysis", Synlett 2008(13):1999-2004 (2008).

\* cited by examiner

BENZIMIDAZOLE COMPOUNDS DIFFERENTIATE A MAMMALIAN STEM CELL INTO MESODERMAL OR CARDIOMYOCYTE CELLS

CROSS REFERENCE TO RELATED APPLICATION(S)

This application claims the benefit under 35 USC §119(e) of U.S. Application Ser. No. 61/097,823, filed Sep. 17, 2008, the entire content of which is incorporated herein by reference.

GRANT INFORMATION

This invention is made with government support under Comprehensive NIH Grant No. HL071913 awarded by the National Institutes of Health. The Government has certain rights in the invention.

FIELD OF THE DISCLOSURE

The disclosure relates generally to small molecule compounds and more specifically to derivatives of dihydropyridines, benzimidazoles, phenothiazines, and tamoxifen, and their use in stem cell differentiation.

BACKGROUND OF THE DISCLOSURE

Stem cells are a type cells that could be a source for the replacement of damaged or diseased tissues, and embryonic stem cells (ESCs) are a type of stem cells attracting particular interest. It has been previously shown that embryonic stem cells have the capacity to differentiate into many different cell types including heart, bone, neurons, liver tissue, and the like, both in vitro and in vivo. The differentiation potential of these cells has created substantial interest, since embryonic stem cells can thus provide a resource for replacing diseased cells for regenerating purposes.

ESCs are pluripotent cells which are derived from the inner cell mass of a blastocyst. The unique characteristics of ESCs are their capacities to regenerate themselves and to be capable of developing into various cell types of all three embryonic germ layers, ectoderm, mesoderm and endoderm, under appropriate environments. Such differentiated cell types include, but are not limited to, muscle, nerve, heart, liver, bone and blood. The potential of ESCs, induced pluripotent stem cells (iPSCs), adult or tissue specific stem cells and the like to grow into specialized cells attracts interest for research and disease treatment using these cells. The clinical application of stem cells involves harvest of the cells and transplantation of cells into failing organs to restore the function of the organs with or without prior in vitro differentiation.

Adult cardiomyocytes retain little, if any, ability to replicate, thus, heart failure is principally a disease of cardiomyocyte loss. No stem cell therapies to date have yielded significant replacement. Rather, transplanted cells, if they persist, produce endothelial cells or fibroblasts, and their reported ameliorating effects on heart function are probably the consequence of improvements in contractility, perfusion or other impaired processes. Replacement strategies by transplantation or stimulation of endogenous regeneration have been hypothesized. Whether endogenous cardiomyocyte stem cells exist and can be mobilized remains controversial, although a few populations have been proposed. Cardiomyocytes have potential in restoring heart function after myocardial infarction or in heart failure. Human embryonic stem cells (hESCs) are a potential source of transplantable cardiomyocytes but detailed comparison of hESC-derived cardiomyocytes with primary human cardiomyocytes is necessary before transplantation into patients becomes feasible.

While a clear alternative is to use hESCs, their cardiomyocyte yields are currently low. Generating sufficient new myocytes is a major obstacle when 25% of the ~4 billion cardiomyocytes in the average left ventricle are lost in infarction-induced heart failure. Transplanted cell survival is currently about 5%, thus improving replication of committed precursors either pre- or post-implantation is essential. Interestingly, transplanted hESC-derived cardiomyocytes tend to retain some proliferative capacity, perhaps due to their relative immaturity; however, the number of engrafted cells remains small in all studies to date, thereby reinforcing the need for molecules that promote cell division.

The American Diabetes Association estimates that there are currently 5 million people in the United States with confirmed diabetes, and over 10 million at risk. The cost of this disease and its sequelae to the American economy is staggering. Care of diabetics consumes a total of $98 billion per year, accounting for one of every seven healthcare dollars spent in the U.S. There are 24,000 new cases of diabetes-caused blindness caused by diabetes each year. Diabetes is the leading cause of kidney failure, contributing about 40% of new dialysis patients. Diabetes is also the most frequent cause of lower limb amputation, with 56,000 limbs lost to diabetes each year. The per capita health care costs incurred per diabetic person is $10,071 annually, compared with $2,669 for non-diabetics.

Type I diabetes mellitus (also known as insulin-dependent diabetes) is a severe condition accounting for 5-10% all diabetics. The pathology arises because the patient's insulin-secreting beta cells in the pancreas have been eliminated by an autoimmune reaction. Under current practice, the condition is managed by regular injection of insulin, constant attention to diet, and continuous monitoring of blood glucose levels to adjust the insulin dosing. It is estimated that the market for recombinant insulin will reach $4 billion by 2005. Of course, the availability of insulin is life-saving for Type I diabetics. But there is no question that the daily regimen of administration and monitoring that diabetics must adhere to is troublesome to the end user, and not universally effective.

Developmental work has been done in several institutions to capitalize on the promise of pluripotent stem cells from the embryo to differentiate into other cell types. Cells bearing features of the islet cell lineage have reportedly been derived from embryonic cells of the mouse.

It is necessary to develop new paradigms to differentiate human pluripotent cells into fully functional differentiated cell types.

SUMMARY OF THE DISCLOSURE

In one aspect the disclosure provides dihydropyridine-based compounds of structure IA or IB in the form of a free base or a pharmaceutically acceptable salt, hydrate, solvate or N-oxide thereof:

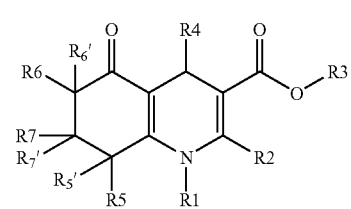

IA

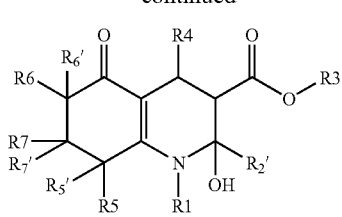

wherein $R_1$ is independently hydrogen, $(C_1-C_6)$alkyl, or is a moiety forming a salt; $R_2$ is independently hydrogen, $(C_1-C_6)$alkyl, aryl, or heteroaryl; $R_{2'}$ is independently hydrogen, $(C_1-C_6)$alkyl, $CF_3$ or $C_2F_5$; $R_3$ is independently hydrogen, $(C_1-C_6)$alkyl optionally substituted by an amine, aryl, 2-tetrahydrofurylmethyl, an aliphatic tertiary amine, or 4-methoxybenzyl; or $R_2$ and $R_3$ may be joined together to form a 5 or 6 member ring lactone; $R_4$ is independently hydrogen, $(C_1-C_6)$alkyl, a 2- or 4-$R_5$-substituted aromatic ring selected from a phenyl, pyridyl, aryl, and heteroaryl; and $R_5$, $R_{5'}$ $R_6$, $R_{6'}$, $R_7$, $R_{7'}$ are each independently hydrogen, $(C_1-C_6)$alkyl, aryl, optionally substituted phenyl, heteroaryl, a heterocyclic ring, an aliphatic tertiary amine, or halogen.

In another aspect, the disclosure provides methods for stem cell differentiation, comprising contacting the embryonic stem cells with a dihydropyridine-based compound of structure IA or IB in the form of a free base or a pharmaceutically acceptable salt, hydrate, solvate or N-oxide thereof, wherein $R_1$, $R_2$, $R_{2'}$, $R_3$, $R_4$, $R_5$, $R_{5'}$, $R_6$, $R_{6'}$, $R_7$, and $R_{7'}$ are as described above.

In another aspect, the disclosure provides benzimidazole-based compounds of structure II in the form of a free base or a pharmaceutically acceptable salt, hydrate, solvate or N-oxide thereof:

II wherein A is independently a bond, NH, O, $CH_2$, C(O)NH, C(O)O, or $CH_2NH$; B is independently an aromatic ring or a saturated 4, 5, or 7 membered ring optionally containing a heteroatom such as N or O, directly attached to A, or with a saturated spacer such as a methylene of a 4-methylpiperidine; D is independently N or CH, E is independently N, CH, C=O, C—R, C—$NH_2$, or C—$N(R)_2$; F is independently N or CH; G is independently phenyl, pyridine or cyclohexyl optionally substituted by 1 to 5 $R_1$; I is independently N or CH; $R_1$ is independently hydrogen or $(C_1-C_6)$alkyl; $R_2$ is independently hydrogen, $(C_1-C_6)$alkyl, $(C_1-C_6)$alkoxy, $(C_1-C_6)$thioalkoxy, hydroxy, halogen, haloalkyl, $CF_3$, or $C_2F_5$; R is independently hydrogen or $(C_1-C_6)$alkyl.

In another aspect, the disclosure provides methods for stem cell differentiation, comprising contacting the embryonic stem cells with a benzimidazole-based compound of structure I in the form of a free base or a pharmaceutically acceptable salt, hydrate, solvate or N-oxide thereof, wherein A, B, D, E, F, G, and I are as described above.

In another aspect, the disclosure provides benzimidazole-based compounds of structure II, IIA, IIB, IIC, IID, IIE, IIF, IIG, IIH, IIJ, IIK, IIL, and IIM in the form of a free base or a pharmaceutically acceptable salt, hydrate, solvate or N-oxide thereof:

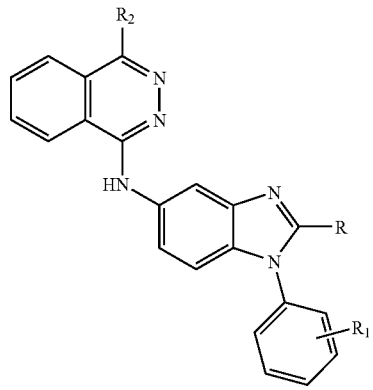

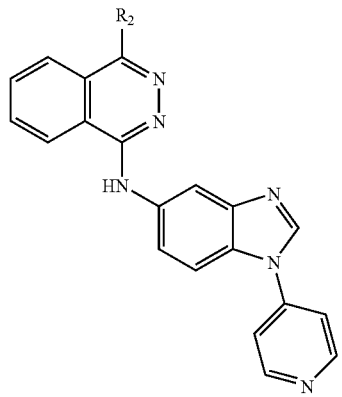

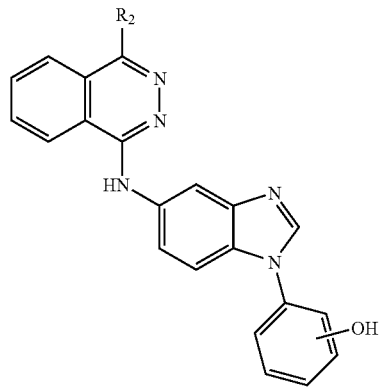

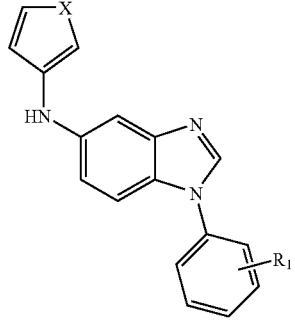

-continued
IID
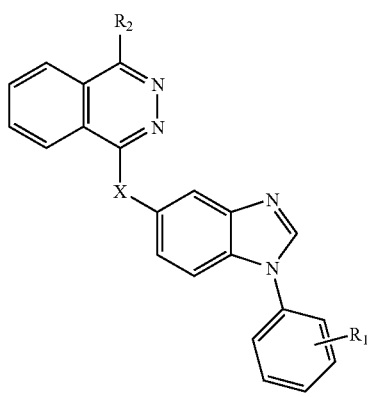
IIE
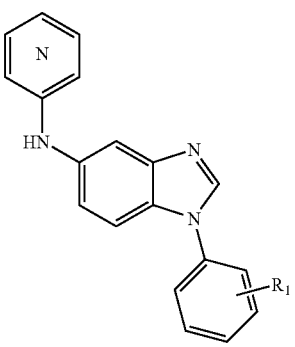
IIF
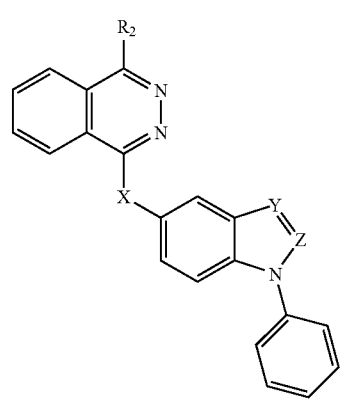
IIG
-continued
IIH
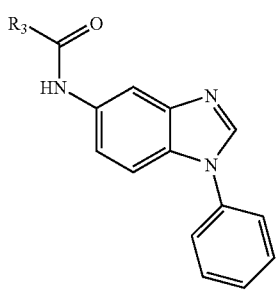
IIJ
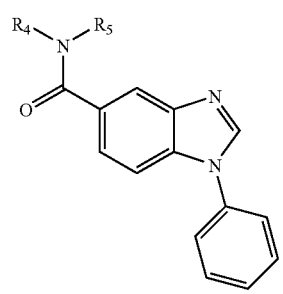
IIK
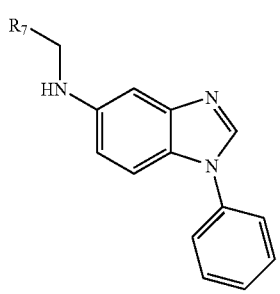
IIL
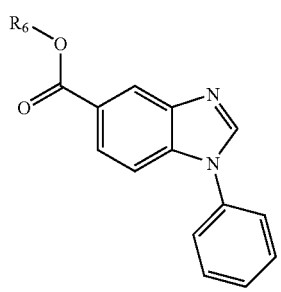
IIM
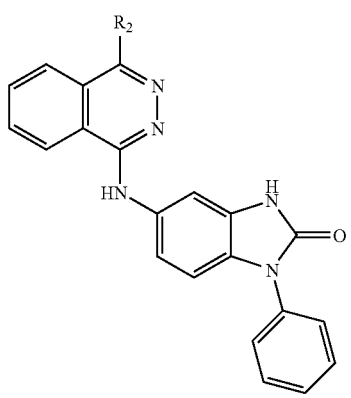
wherein R is independently hydrogen, methyl, or amino; $R_1$ is independently hydrogen, hydroxyl, pyridyl, methyl, trifluoromethyl, methoxy or methylthio, with the further proviso that when $R_1$ is a methoxy group in position 2 to the benzimidazole ring, a further methyl group in position 6 to the benzimidazole is optionally present; $R_2$ is independently hydrogen, phenyl, benzyl, methoxy, methyl or halogen; each of Y and Z is independently CH or N; and X is independently $CH_2$, NH, O, S, S=O, $SO_2$, CH(OH), or C=O.

In another aspect, the disclosure provides methods for stem cell differentiation, comprising contacting the embryonic stem cells with a benzimidazole-based compound of structure II, IIA, IIB, IIC, IID, IIE, IIF, IIG, IIH, IIJ, IIK, IIL, or IIM as described above, in the form of a free base or a pharmaceutically acceptable salt, hydrate, solvate or N-oxide thereof.

In another aspect, the disclosure provides phenothiazine-based compounds of structures I and II in the form of a free base or a pharmaceutically acceptable salt, hydrate, solvate or N-oxide thereof:

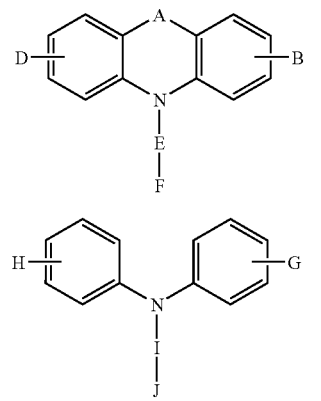

wherein A is independently S, O or $(CH_2)_n$, and n is independently an integer from 0 to 2; B and D are each independently alkyl, aryl, halo, $SCH_3$, or $CF_3$; E is independently $(CH_2)_m$, and m is independently an integer from 0 to 5; F is independently a primary or secondary alkyl amine, cyclic amine, an aryl amine or aliphatic cyclic amine, G and H are each independently alkyl, aryl, halo, $SCH_3$, or $CF_3$; I is independently $(CH_2)_m$, and m is independently an integer from 0 to 5; J is independently a primary or secondary alkyl amine, cyclic amine, an aryl amine or aliphatic cyclic amine.

In another aspect, the disclosure provides phenothiazine-based compounds of structure III (10-(aminoalkyl)-2-(substituted)-10H-phenothiazine):

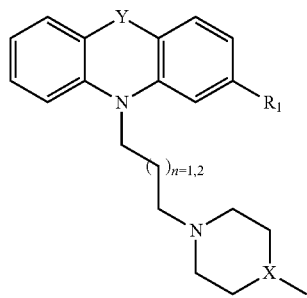

wherein $R_1$ is independently hydrogen, $CH_3$, $SCH_3$, or $CF_3$; X is independently CH, N, or O; Y is independently S, O, $(CH_2)_n$, where n is an integer from 0 to 2.

In another aspect, the disclosure provides methods for stem cell differentiation, comprising contacting embryonic stem cells with a phenothiazine-based compound of structure I, II, or III in the form of a free base or a pharmaceutically acceptable salt, hydrate, solvate or N-oxide thereof:

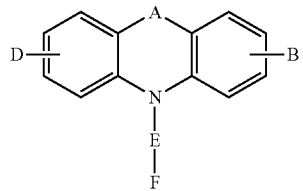

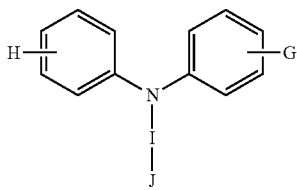

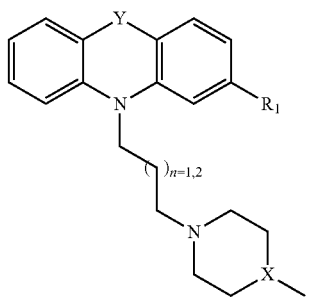

wherein A, B, D, E, F, G, H, I, J, X, Y, and $R_1$ are as described above.

In another aspect, the disclosure provides tamoxifen-based compounds of structure V, VI or VII in the form of free base or a pharmaceutically acceptable salt, hydrate, solvate or N-oxide thereof:

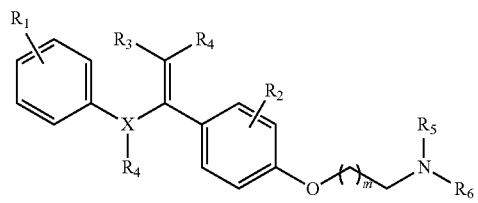

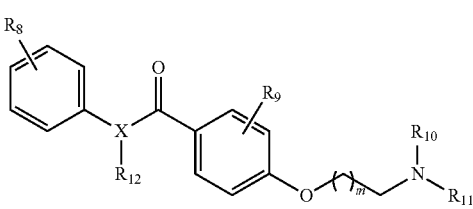

-continued

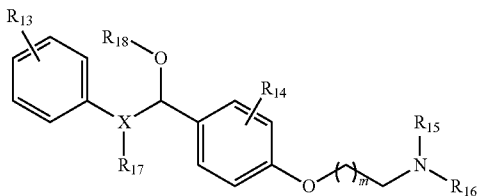

VII wherein for compound V, X is independently a bond, $CH_2$, or $CHR_7$; $R_1$ is independently methyl, ethyl, $(C_1-C_6)$alkyl, halogen, phenyl, methoxy, phenoxy, nitro, trifluoromethyl, or alkylamino; $R_2$ is independently methyl, ethyl, phenyl, $(C_1-C_6)$alkyl, trifluoromethyl, or halogen; $R_3$ is independently methyl, ethyl, $(C_1-C_6)$alkyl, phenyl, or aryl; $R_4$ is independently methyl, ethyl, $(C_1-C_6)$alkyl, phenyl, or aryl; $R_5$ is independently methyl, ethyl, $(C_1-C_6)$alkyl, phenyl, or aryl; $R_6$ is independently methyl, ethyl, $(C_1-C_6)$alkyl, phenyl, or aryl, wherein $R_5$ and $R_6$ may be joined via a ring, $R_7$ is independently methyl, ethyl, propyl, $(C_1-C_6)$alkyl, phenyl, or benzyl; and m is independently 0-4 methylene units; and wherein for compound VI, X is independently a bond, $CH_2$, or $CHR_{12}$; $R_8$ is independently methyl, ethyl, $(C_1-C_6)$alkyl, halogen, phenyl, methoxy, phenoxy, nitro, trifluoromethyl, or alkylamino, $R_9$ is independently methyl, ethyl, phenyl, $(C_1-C_6)$alkyl, trifluoromethyl, or halogen; $R_{10}$ is independently methyl, ethyl, $(C_1-C_6)$alkyl, phenyl, or aryl, $R_{11}$ is independently methyl, ethyl, $(C_1-C_6)$alkyl, phenyl, or aryl, wherein $R_{10}$ and $R_{11}$ can be joined via a ring; $R_{12}$ is independently methyl, ethyl, propyl, $(C_1-C_6)$alkyl, phenyl, or benzyl; and m is independently 0-4 methylene units; and wherein for compound VII, X is independently a bond, $CH_2$, or $CHR_{17}$; $R_{13}$ is independently methyl, ethyl, $(C_1-C_6)$ alkyl, halogen, phenyl, methoxy, phenoxy, nitro, trifluoromethyl, or alkylamino; $R_{14}$ is independently methyl, ethyl, phenyl, $(C_1-C_6)$alkyl, trifluoromethyl, or halogen; $R_{15}$ is independently methyl, ethyl, $(C_1-C_6)$alkyl, phenyl, or aryl; $R_{16}$ is independently methyl, ethyl, $(C_1-C_6)$alkyl, phenyl, or aryl, wherein $R_{15}$ and $R_{16}$ may be joined via a ring; $R_{17}$ is independently methyl, ethyl, propyl, $(C_1-C_6)$alkyl, phenyl, or benzyl; $R_{18}$ is independently methyl, ethyl, propyl, $(C_1-C_6)$ alkyl, phenyl, or benzyl; and m is independently 0-4 methylene units.

In another aspect, the disclosure provides methods for stem cell differentiation, comprising contacting the embryonic stem cells with a compound of structure V, VI or VII, in the form of free base or a pharmaceutically acceptable salt, hydrate, solvate or N-oxide thereof.

DETAILED DESCRIPTION OF THE DISCLOSURE

Figure 1:
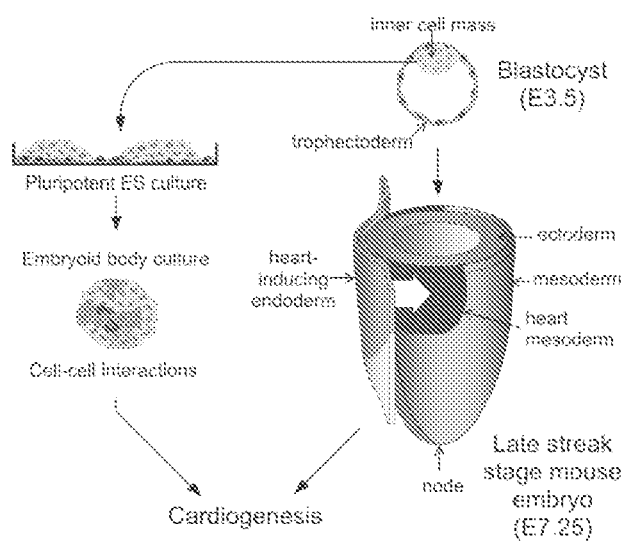
FIG. 1 demonstrates schematically comparison of heart induction in mouse embryos and mESCs.

The following terms, definitions and abbreviations apply. Abbreviations used herein have their conventional meaning within the chemical and biological arts.

The term "lipophilic" refers to moieties having an affinity for lipids and other fat-like substances, tending to combine with, and capable of dissolving, them.

The term "cardiomyocytes" refers to cells of muscular tissue in the heart.

The term "embryonic stem cell" refers to cell from the inner group of cells of an early embryo (blastocyst), with the potential to become most or all of the body tissues.

The term "stem cell differentiation" refers to series of events involved in the development of specialized cells from stem cells, where the specialized cells have specific structural, functional, and biochemical properties.

The term "patient" refers to organisms to be treated by the methods of the disclosure. Such organisms include, but are not limited to, humans. In the context of the disclosure, the term "subject" generally refers to an individual who will receive or who has received treatment described below (e.g., administration of the compounds of the disclosure, and optionally one or more additional therapeutic agents).

Where substituent groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight (i.e. unbranched) or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Alkyl groups which are limited to hydrocarbon groups are termed "homoalkyl".

The term "alkylene" by itself or as part of another substituent means a divalent radical derived from an alkyl, as exemplified, but not limited, by —$CH_2CH_2CH_2CH_2$—, —$CH_2CH=CHCH_2$—, —$CH_2CCCH_2$—, —$CH_2CH_2CH$ ($CH_2CH_2$ $CH_3$)$CH_2$—. Typically, an alkyl (or alkylene) group will have from 1 to 24 carbon atoms. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or cyclic hydrocarbon radical, or combinations thereof, consisting of at least one carbon atoms and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH═CH—O—CH$_3$, —Si(CH$_3$)$_3$, —CH$_2$—CH═N—O—CH$_3$, —CH═CH—N(CH$_3$)—CH$_3$, O—CH$_3$, —O—CH$_2$—CH$_3$, and —CN. Up to two or three heteroatoms may be consecutive, such as, for example, —CH$_2$—NH—O—CH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—. As described above, heteroalkyl groups, as used herein, include those groups that are attached to the remainder of the molecule through a heteroatom, such as —C(O)R', —C(O)NR', —NR'R", —OR', —SR, and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo(C$_1$-C$_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent which can be a single ring or multiple rings, which are fused together or linked covalently. The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent radicals of aryl and heteroaryl, respectively.

For brevity, the term "aryl" when used in combination with other terms (e.g., aryloxo, arylthioxo, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). However, the term "haloaryl," as used herein is meant to cover only aryls substituted with one or more halogens.

Where a heteroalkyl, heterocycloalkyl, or heteroaryl includes a specific number of members (e.g. "3 to 7 membered"), the term "member" referrers to a carbon or heteroatom.

The term "oxo" as used herein means an oxygen that is double bonded to a carbon atom.

The terms "heterocycle" and "heterocyclic" refer to a monovalent unsaturated group having a single ring or multiple condensed rings, from 1 to 8 carbon atoms and from 1 to 4 heteroatoms nitrogen, sulfur or oxygen within the ring.

The term "methylthio" refers to a moiety —S—CH$_3$.

The term "dihydropyridine" refers to compound A shown below, as well as to the moieties derived from compound A:

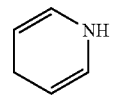

A

The term "benzimidazole" refers to compound B shown below, as well as to the moieties derived from compound B:

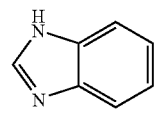

B

The term "phenothiazine" refers to compound C shown below, as well as to the moieties derived from compound C:

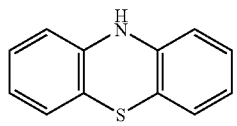

C

The terms "furyl," "tetrahydrofuryl," and "pyridyl" refer to radicals formed by removing one hydrogen from the molecules of furan, tetrahydrofuran, and pyridine, respectively.

The terms "alkyl amine" and "cyclic amine" refer to alkanes or cycloalkanes, respectively, having one hydrogen substituted by a primary, secondary or tertiary amino group, as well as to the moieties and radicals derived from such amines.

The term "alkyl amide" refers to alkanes, having one hydrogen substituted by a primary, secondary or tertiary amino group.

Each of above terms (e.g., "alkyl," "heteroalkyl," "cycloalkyl, and "heterocycloalkyl", "aryl," "heteroaryl" as well as their divalent radical derivatives) are meant to include both substituted and unsubstituted forms of the indicated radical.

Substituents for alkyl, heteroalkyl, cycloalkyl, heterocycloalkyl monovalent and divalent derivative radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R''', —OC(O)R', —C(O)R', —CO2R', —C(O)NR'R", —OC(O)NR'R", —NR"C(O)R', —NR'—C(O)NR"R''', —NR"C(O)OR', —NR—C(NR'R")=NR''', —S(O)R', —S(O)$_2$R', —S(O)2NR'R", —NRSO$_2$R', —CN and —NO$_2$ in a number ranging from zero to (2m'+1), where m' is the total number of carbon atoms in such radical. R', R", R''' and R'''' each independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. When a compound of the disclosure includes more than one R group, for example, each of the R groups is independently selected as are each R', R", R''' and R'''' groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$O CH$_3$, and the like).

The term "alkoxy" refers to the moiety —O-alkyl, wherein alkyl is as defined above. Examples of alkoxy structures that are within the purview of the definition include, but are not limited to, (C$_1$-C$_6$)alkoxy radicals, such as methoxy, ethoxy, propoxy, isopropoxy, butoxy, iso-butoxy, sec-butoxy, tent-butoxy, pentoxy, 3-pentoxy, or hexyloxy.

Similar to the substituents described for alkyl radicals above, exemplary substituents for aryl and heteroaryl groups (as well as their divalent derivatives) are varied and are selected from, for example: halogen, —OR', —NR'R", —SR', -halogen, —SiR'R"R''', —OC(O)R', —C(O)R', —CO2R', —C(O)NR'R", —OC(O)NR'R", —NR"C(O)R', —NR'—C(O)NR"R''', —NR"C(O)OR', —NR—C(NR'R"R''')=NR", —NR—C(NR'R")=NR''', —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxo, and fluoro(C$_1$-C$_4$)alkyl, in a number ranging from zero to the total number of open valences on aromatic ring system; and where R', R", R''' and R'''' are independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the disclosure includes more than one R group, for example, each of the R groups is independently selected as are each R', R", R''' and R'''' groups when more than one of these groups is present.

Two of the substituents on adjacent atoms of aryl or heteroaryl ring may optionally form a ring of the formula -T-C(O)—(CRR')q-U—, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula -A-(CH$_2$)r-B—, wherein A and B are independently —CRR'—, —O—, —NR—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'—(C"R''')$_d$—, where s and d are independently integers of from 0 to 3, and X' is —O—, —NR'—, —S—, —S(O)—, —S(O)$_2$—, or —S(O)$_2$NR'—. The substituents R, R', R" and R''' are independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "heteroatom" or "ring heteroatom" is meant to include oxygen (O), nitrogen (N), sulfur (S), phosphorus (P), and silicon (Si).

An "aminoalkyl" as used herein refers to an amino group covalently bound to an alkylene linker. The amino group is —NR'R", wherein R' and R" are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

A "substituent group," as used herein, means a group selected from the following moieties: (A) —OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from: (i) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from: (a) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, and each substituted or unsubstituted heterocycloalkyl is a substituted or unsubstituted 4 to 8 membered heterocycloalkyl.

A "lower substituent" or "lower substituent group," as used herein means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, and each substituted or unsubstituted heterocycloalkyl is a substituted or unsubstituted 5 to 7 membered heterocycloalkyl.

The compounds of the present disclosure may exist as salts. The present disclosure includes such salts. Examples of applicable salt forms include hydrochlorides, hydrobromides, sulfates, methanesulfonates, nitrates, maleates, acetates, citrates, fumarates, tartrates (e.g., (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present disclosure contain both basic and acidic functionalities that allow the compounds to be converted into either base or acid addition salts.

The term "pharmaceutically acceptable salt" refers to salts that may be used where the compounds used in the methods of the disclosure are sufficiently basic or acidic to form stable nontoxic acid or base salts. Examples of pharmaceutically acceptable salts include organic acid addition salts formed with acids which form a physiological acceptable anion, for example, oxalate, tosylate, methanesulfonate, acetate, citrate, malonate, tartarate, succinate, benzoate, ascorbate, ketoglutarate, and glycerophosphate. Suitable inorganic salts may also be formed, including hydrochloride, sulfate, nitrate, bicarbonate, and carbonate salts. Pharmaceutically acceptable salts may be obtained using standard procedures well known in the art, for example by treating a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The neutral forms of the compounds may be regenerated by contacting the salt with a base or acid and isolating the parent compound in the conventional manner. The parent form of the compound differs from the various salt forms in certain physical properties, such as solubility in polar solvents.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those which are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

The term "tautomer," as used herein, refers to one of two or more structural isomers which exist in equilibrium and which are readily converted from one isomeric form to another.

It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this disclosure.

The compounds of the present disclosure may also contain unnatural proportions of atomic isotopes at one or more of atoms that constitute such compounds. For example, the compounds may be radiolabeled with radioactive isotopes, such as for example tritium (.$^3$H), iodine-125 ($^{125}$I) or carbon-14 (.$^{14}$C). All isotopic variations of the compounds of the present disclosure, whether radioactive or not, are encompassed within the scope of the present disclosure.

The term "pharmaceutically acceptable salts" is meant to include salts of active compounds which are prepared with relatively nontoxic acids or bases, depending on the particular substituent moieties found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science, 1977, 66, 1-19). Certain specific compounds of the present disclosure contain both basic and acidic functionalities that allow the compounds to be converted into either base or acid addition salts.

In addition to salt forms, the present disclosure provides compounds, which are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

The terms "a," "an," or "a(n)", when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

Description of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The terms "treating" or "treatment" in reference to a particular disease includes prevention of the disease.

In one aspect, the disclosure provides dihydropyridine-based compounds of structure IA or IB in the form of a free base or a pharmaceutically acceptable salt, hydrate, solvate or N-oxide thereof:

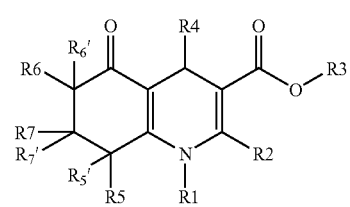

IA

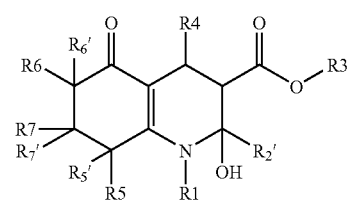

IB wherein $R_1$ is independently hydrogen or is a moiety forming a salt; $R_2$ is independently hydrogen, $(C_1-C_6)$alkyl, aryl, or heteroaryl; $R_2'$ is independently hydrogen, $(C_1-C_6)$alkyl, $CF_3$ or $C_2F_5$; $R_3$ is independently $(C_1-C_6)$alkyl optionally substituted by an amine, aryl, 2-tetrahydrofurylmethyl, or 4-methoxybenzyl; or $R_2$ and $R_3$ may be joined together to form a 5 or 6 member ring lactone; $R_4$ is independently, $(C_1-C_6)$alkyl, a 2- or 4-$R_8$-substituted aromatic ring selected from a phenyl, pyridyl, aryl, heteroaryl; and $R_5$, $R_{5'}$, $R_6$, $R_{6'}$, $R_7$, $R_{7'}$, are each independently hydrogen, $(C_1-C_6)$alkyl, aryl, optionally substituted phenyl, heteroaryl, a heterocyclic ring, an aliphatic tertiary amine, or halogen; R8 is independently hydrogen, $(C_1-C_6)$alkyl, alkoxy, CF3, aliphatic tertiary amine, cyano or halogen;

In another aspect, the disclosure provides methods for stem cell differentiation, comprising contacting the embryonic stem cells with a compound of structure IA or IB in the form of a free base or a pharmaceutically acceptable salt, hydrate, solvate or N-oxide thereof, wherein $R_1$, $R_2$, $R_{2'}$, $R_3$, $R_4$, $R_5$, $R_{5'}$, $R_6$, $R_{6'}$, $R_7$, and $R_{7'}$ are as described above.

Some specific dihydropyridine-based compounds within structure I include, but are not limited to, compounds 1-14

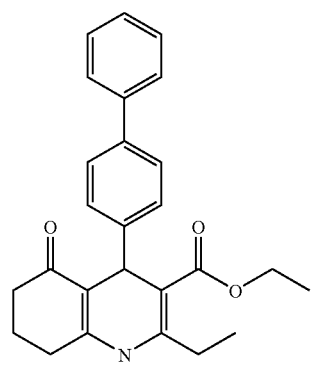

1

19
-continued
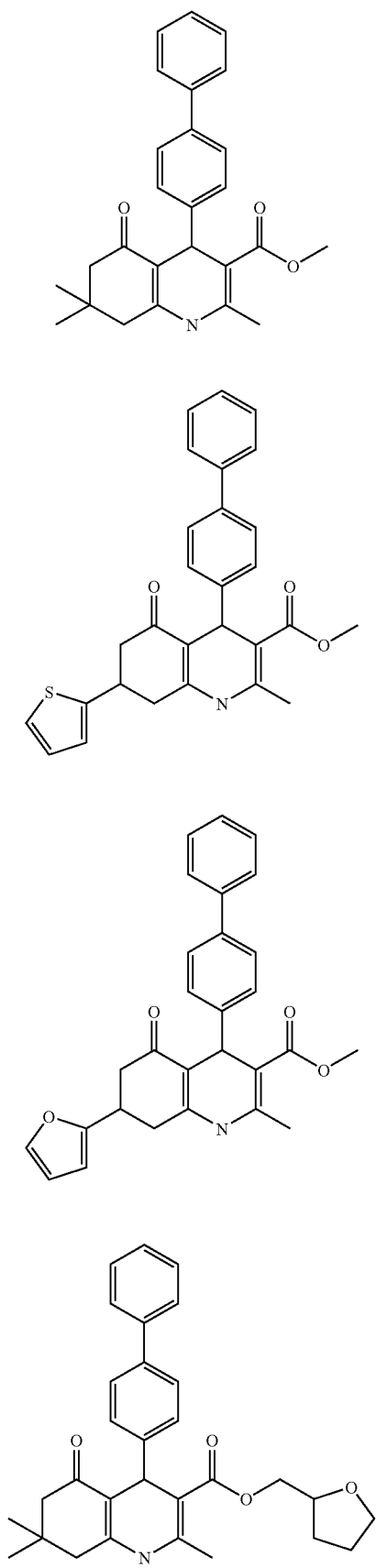
2
3
4
5
20
-continued
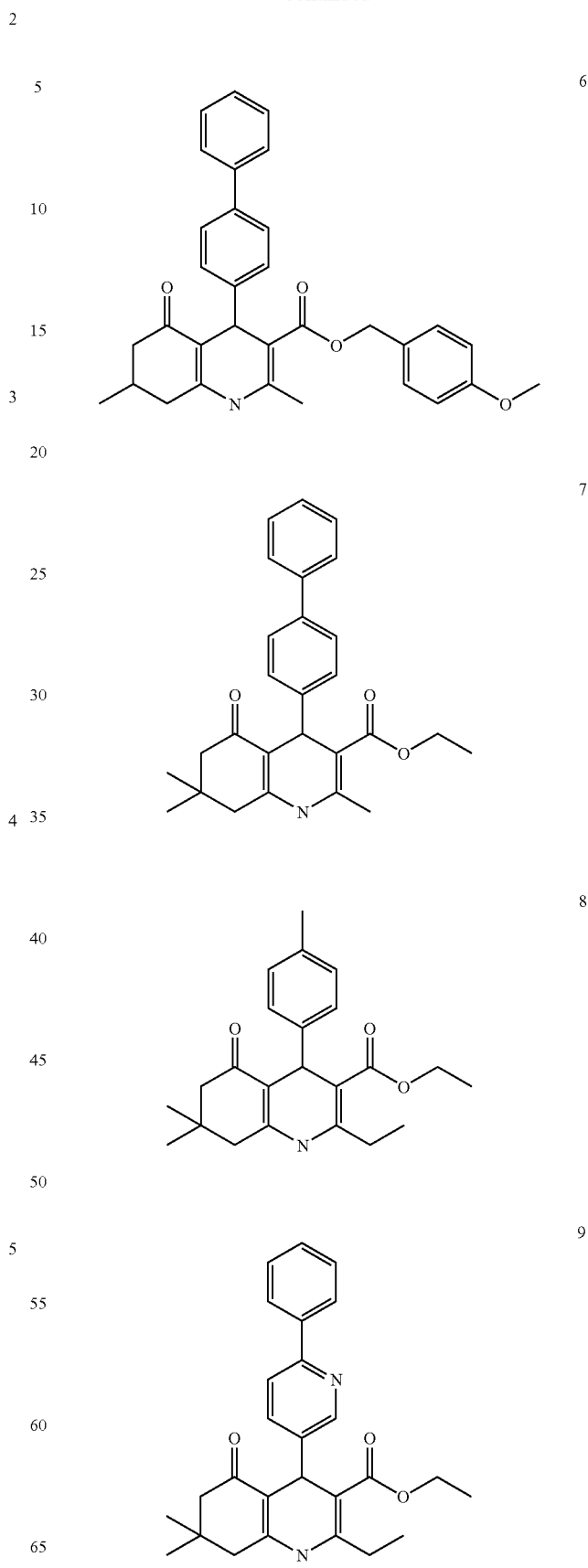
5
6
7
8
9

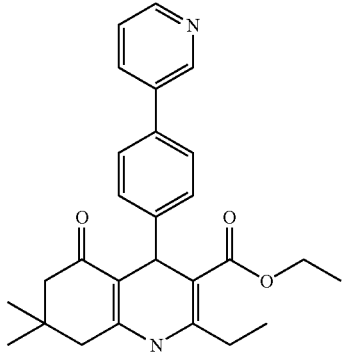

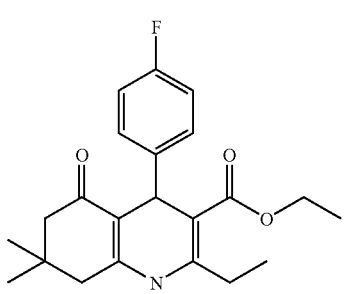

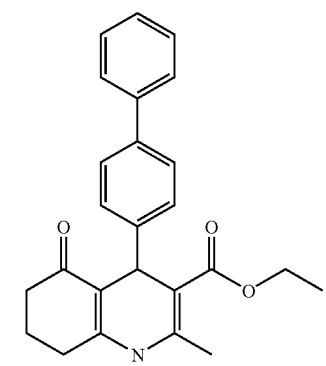

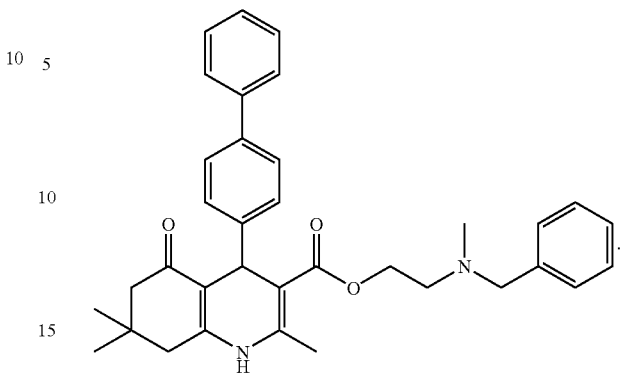

In another aspect, the disclosure provides benzimidazole-based compounds of structure II in the form of a free base or a pharmaceutically acceptable salt, hydrate, solvate or N-oxide thereof:

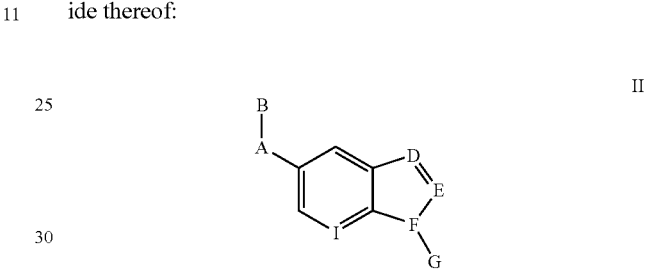

wherein A is independently NH or O; B is independently an aryl or heteroaryl moiety or a saturated 4, 5, 6 or 7 member ring optionally containing a heteroatom such as N or O, that is directly attached to A; A is a bond, a methylene, an ester, an amide, $NHCH_2$; D is independently N or CH, E is independently N, CH, C—$R_1$, C=O, C—$NH_2$, or C—$N(R_1)_2$; F is independently N or C, G is independently phenyl, aryl or cyclohexyl optionally substituted by 1 to 5 $R_2$; I is independently N or CH; $R_1$ is independently hydrogen or $(C_1-C_6)$ alkyl; $R_2$ is independently hydrogen, $(C_1-C_6)$alkyl, $(C_1-C_6)$ alkoxy, $(C_1-C_6)$thioalkoxy, hydroxy, halogen, $CF_3$, or $C_2F_5$.

In another aspect, the disclosure provides methods for stem cell differentiation, comprising contacting the embryonic stem cells with a compound of structure I in the form of a free base or a pharmaceutically acceptable salt, hydrate, solvate or N-oxide thereof, wherein A, B, D, E, F, G, and I are as described above.

In another aspect, the disclosure provides benzimidazole-based compounds of structure II, including 1-phenyl-5-(1-phthalazinoamino)-benzimidazole:

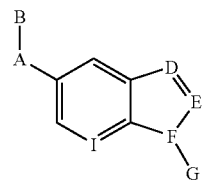

wherein A is a bond, N, O, $NHCH_2$, COO, CONH, or NHCO linker; B is an aromatic ring, heterocycle, or optionally substituted alkyl; D is N or CH; E is CH, $CR_1$, C=O, C=S, or N; $R_1$ is an optionally substituted alkyl or an optionally substituted amine; G is an aromatic ring or a heterocycle; and I is C or N.

The compound of structure II includes the structure: 1-phenyl-5-(1-arylamino)-benzimidazole in the form of a free base or a pharmaceutically acceptable salt, hydrate, solvate or N-oxide thereof:

II

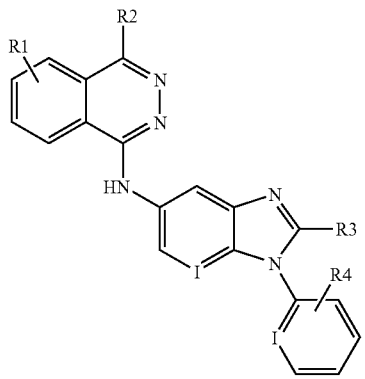

wherein $R_1$ is H, $CH_3$; $R_2$ is $(C_1-C_6)$alkyl, halogen, methoxy, benzyl; $R_3$ is H, $(C_1-C_6)$alkyl, amine optionally substituted by $(C_1-C_6)$alkyl, $R_4$ is H, $CH_3$, $OCH_3$, $SCH_3$, $CF_3$, $(C_1-C_6)$alkyl, halogen, alkoxy; and I is CH, N.

In another aspect, the disclosure provides benzimidazole-based compounds of structures II, IIA, IIB, IIC, IID, IIE, IIF, IIG, IIH, IIJ, IIK, IIL, and IIM in the form of free base or a pharmaceutically acceptable salt, hydrate, solvate or N-oxide thereof:

II

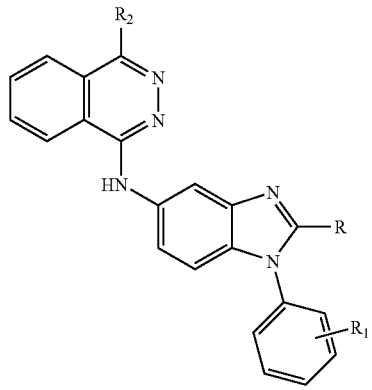

IIA

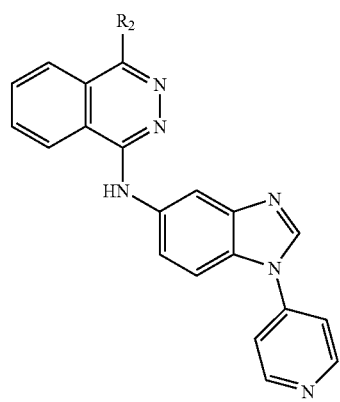

IIB

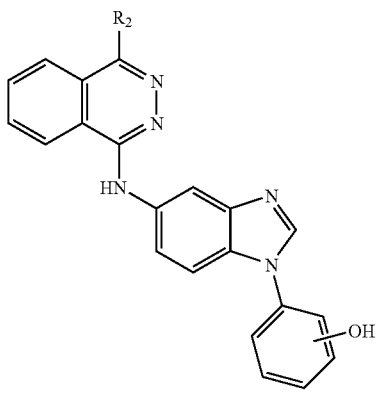

IIC

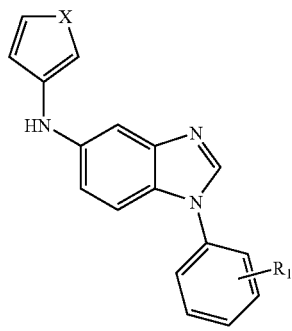

IID

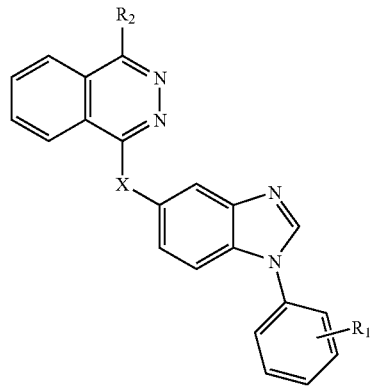

IIE

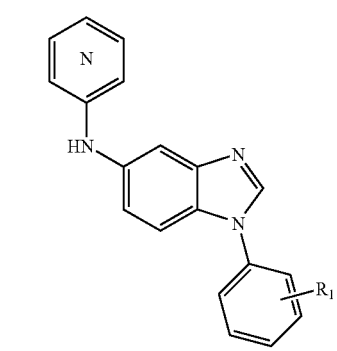

-continued

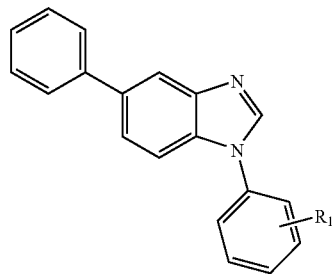

IIF

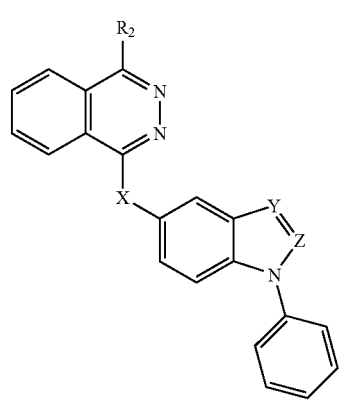

IIG

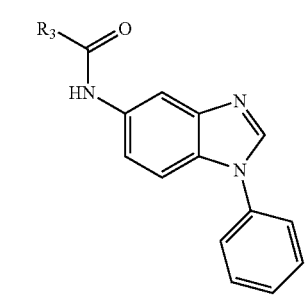

IIH

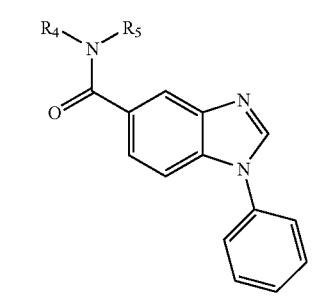

IIJ

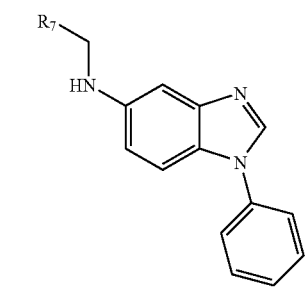

IIK

-continued

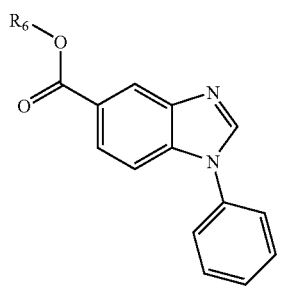

IIL

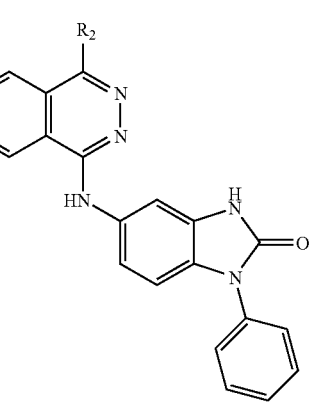

IIM wherein R is independently hydrogen, methyl, or amino; $R_1$ is independently hydrogen, hydroxyl, pyridyl, methyl, trifluoromethyl, methoxy or methylthio, with the further proviso that when $R_1$ is methoxy group in position 2 to the benzimidazole ring, a further methyl group in position 6 to the benzimidazole is optionally present; $R_2$ is independently hydrogen, phenyl, benzyl, methoxy, methyl or halogen; each of Y and Z is independently CH or N; and X is independently $CH_2$, NH, O, S, S=O, $SO_2$, CH(OH), or C=O.

Some specific benzimidazole-based disclosure compounds within structures II, IIA, IIB, IIC, IID, IIE, IIF, IIG, IIH, IIJ, IIK, IIL, and IIM include, but are not limited to compounds 15-37:

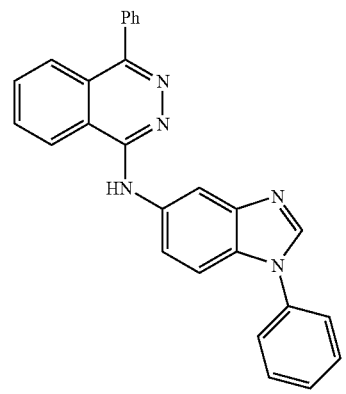

15

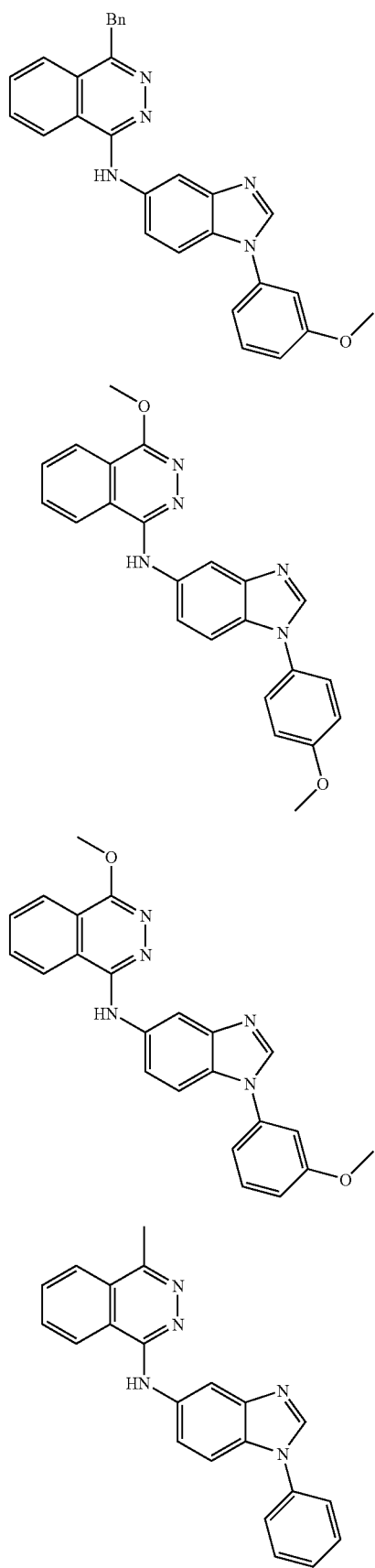
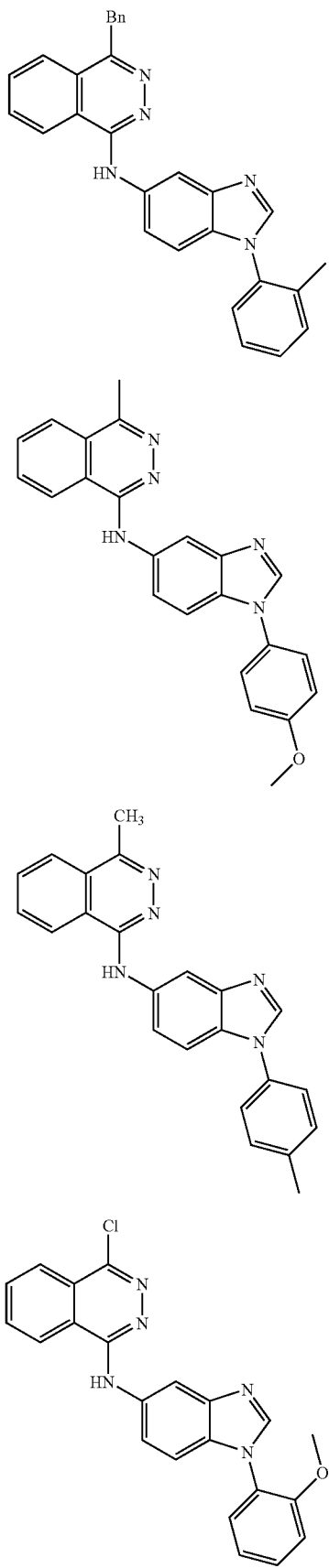

24
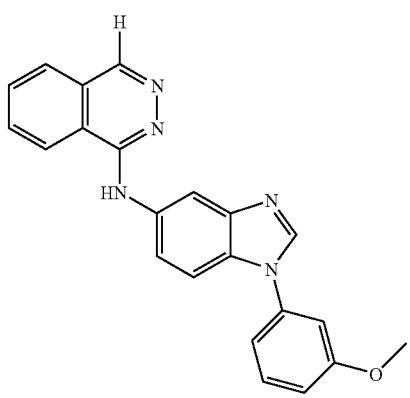
25
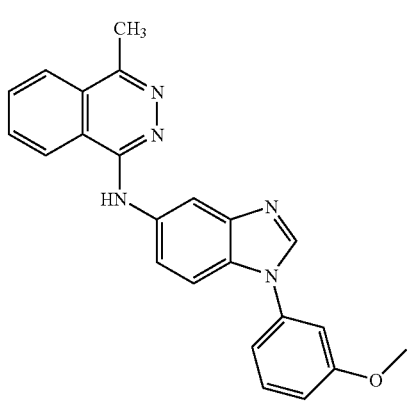
26
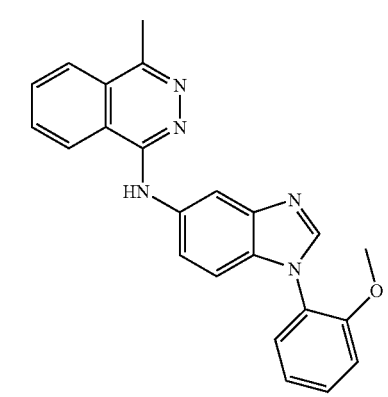
27
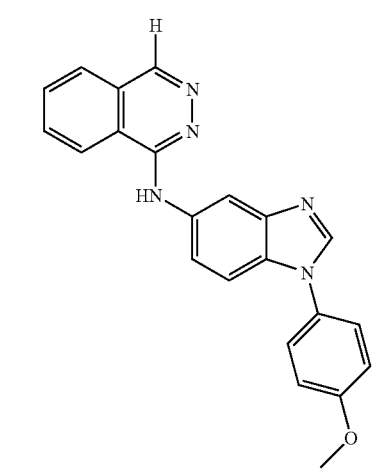
28
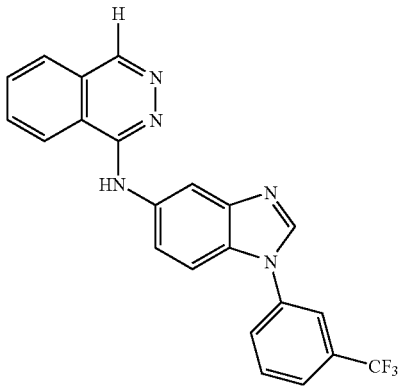
29
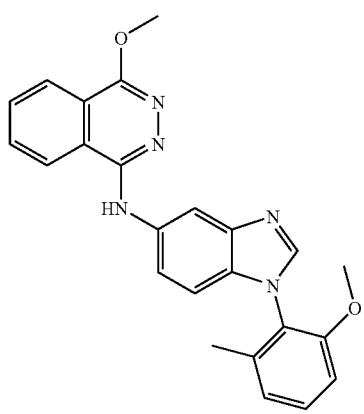
30
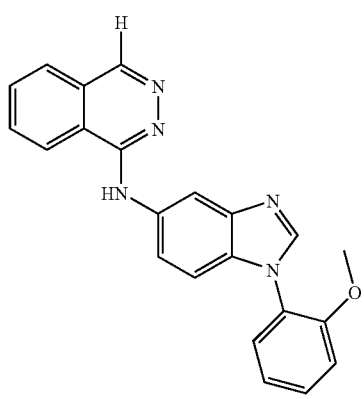
31
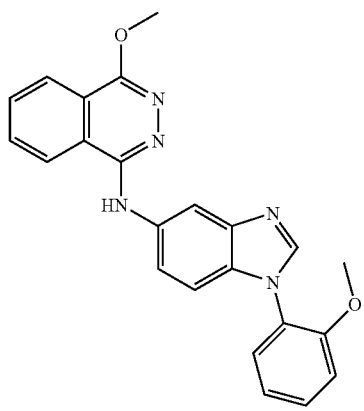

31
-continued

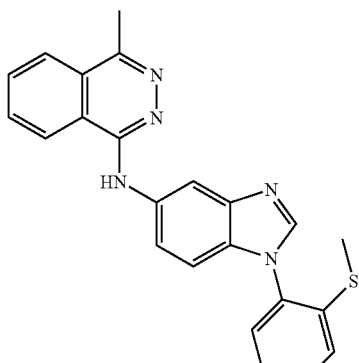
32

32
-continued

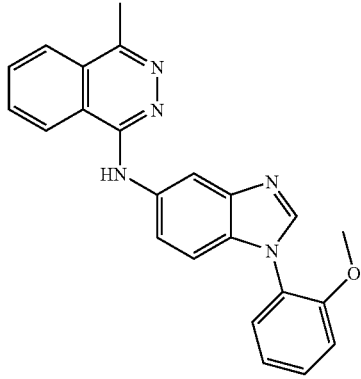
36

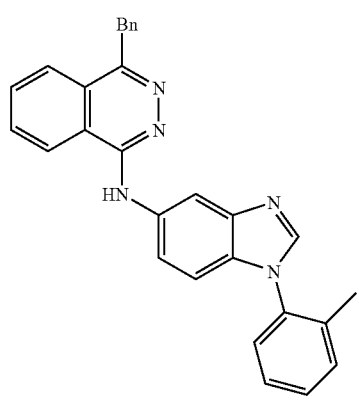
33

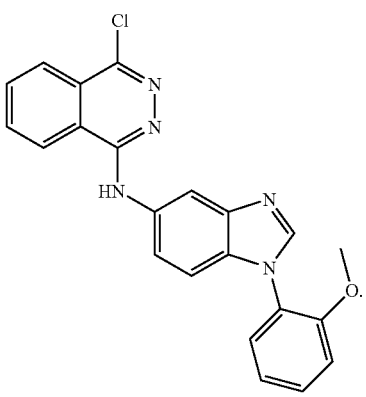
37

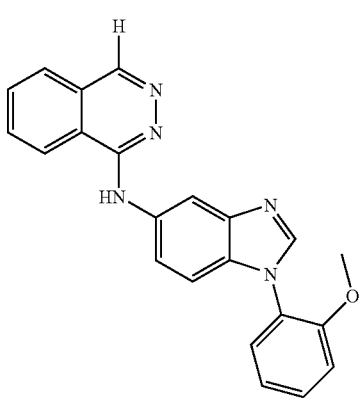
34

In another aspect, the disclosure provides phenothiazine-based compounds of structure IX in the form of free base or a pharmaceutically acceptable salt, hydrate, solvate or N-oxide thereof:

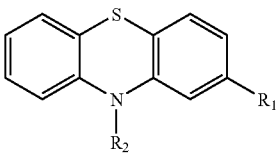
IX wherein $R_1$ is independently $CF_3$ and chloro; and $R_2$ is independently an alkyl amine, a cyclic amine, an aliphatic cyclic amine, or an alkyl amide.

Some specific phenothiazine-based compounds within structure IX include, but are not limited to, compounds 38-43:

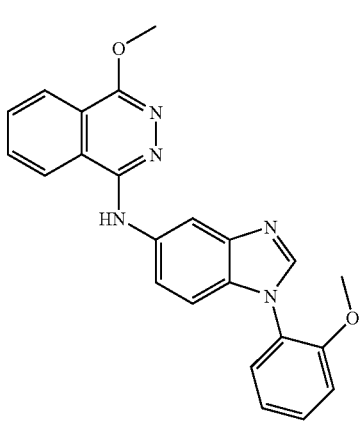
35

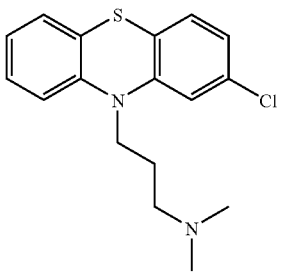
38

-continued

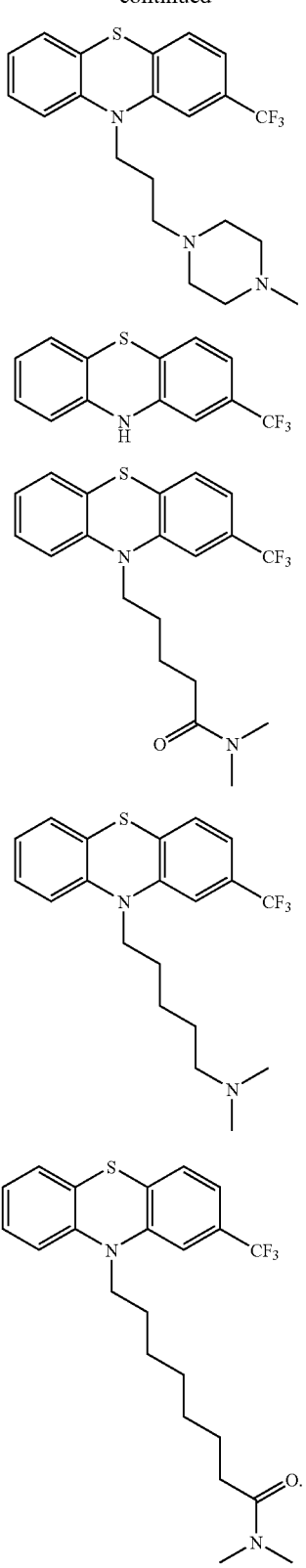

In another aspect, the disclosure provides methods for producing differentiated cells from stem cells. The methods comprise contacting stem cells with the disclosed compounds that stimulate the production of differentiated cells thereby.

The disclosed compounds may be used to carry out such methods include all the compounds within the above-described genera and sub-genera I, II, IIA, IIB, IIC, IID, IIE, IIF, IIG, IIH, IIJ, IIK, IIL, IIM and III, including particular species 1-43, also described above.

In another aspect, the disclosure provides tamoxifen-based compounds of structure VI, VII or VIII in the form of free base or a pharmaceutically acceptable salt, hydrate, solvate or N-oxide thereof:

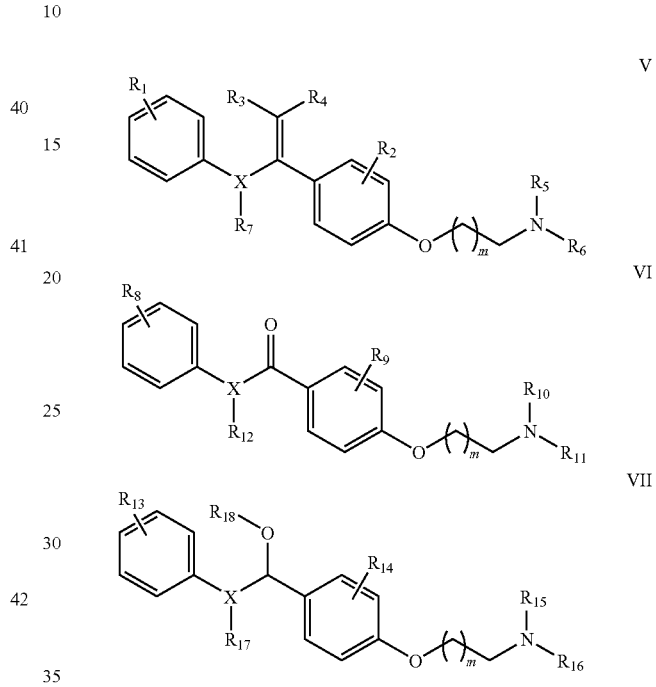

wherein for compound VI, X is independently a bond, $CH_2$, or $CHR_7$; $R_1$ is independently methyl, ethyl, $(C_1-C_6)$alkyl, halogen, phenyl, methoxy, phenoxy, nitro, trifluoromethyl, or alkylamino; $R_2$ is independently methyl, ethyl, phenyl, $(C_1-C_6)$alkyl, trifluoromethyl, or halogen; $R_3$ is independently methyl, ethyl, $(C_1-C_6)$alkyl, phenyl, or aryl; $R_4$ is independently methyl, ethyl, $(C_1-C_6)$alkyl, phenyl, or aryl; $R_5$ is independently methyl, ethyl, $(C_1-C_6)$alkyl, phenyl, or aryl; $R_6$ is independently methyl, ethyl, $(C_1-C_6)$alkyl, phenyl, or aryl, wherein $R_5$ and $R_6$ may be joined via a ring, $R_7$ is independently methyl, ethyl, propyl, $(C_1-C_6)$alkyl, phenyl, or benzyl; and m is independently 0-4 methylene units; and wherein for compound VII, X is independently a bond, $CH_2$, or $CHR_{12}$; $R_8$ is independently methyl, ethyl, $(C_1-C_6)$alkyl, halogen, phenyl, methoxy, phenoxy, nitro, trifluoromethyl, or alkylamino, $R_9$ is independently methyl, ethyl, phenyl, $(C_1-C_6)$alkyl, trifluoromethyl, or halogen; $R_{10}$ is independently methyl, ethyl, $(C_1-C_6)$alkyl, phenyl, or aryl, $R_{11}$ is independently methyl, ethyl, $(C_1-C_6)$alkyl, phenyl, or aryl, wherein $R_{10}$ and $R_{11}$ can be joined via a ring; $R_{12}$ is independently methyl, ethyl, propyl, $(C_1-C_6)$alkyl, phenyl, or benzyl; and m is independently 0-4 methylene units; and wherein for compound VIII, X is independently a bond, $CH_2$, or $CHR_{17}$; $R_{13}$ is independently methyl, ethyl, $(C_1-C_6)$alkyl, halogen, phenyl, methoxy, phenoxy, nitro, trifluoromethyl, or alkylamino; $R_{14}$ is independently methyl, ethyl, phenyl, $(C_1-C_6)$alkyl, trifluoromethyl, or halogen; $R_{15}$ is independently methyl, ethyl, $(C_1-C_6)$alkyl, phenyl, or awl; $R_{16}$ is independently methyl, ethyl, $(C_1-C_6)$alkyl, phenyl, or awl, wherein $R_{15}$ and $R_{16}$ may be joined via a ring; $R_{17}$ is independently methyl, ethyl, propyl, $(C_1-C_6)$alkyl, phenyl, or benzyl; $R_{18}$ is independently methyl, ethyl, propyl, ($C_1$-$C_6$) alkyl, phenyl, or benzyl; and m is independently 0-4 methylene units.

The compounds of structure IV include 1-alkylamino-2'-substituted diphenylamine IVa:

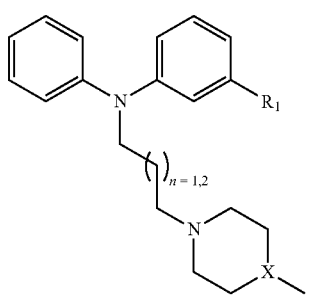

IVa wherein $R_1$ is H, $CH_3$, halogen; X is CH, N, or O.

In another aspect, the disclosure provides methods for stem cell differentiation, comprising contacting the embryonic stem cells with a compound of structure VI, VII or VIII, in the form of free base or a pharmaceutically acceptable salt, hydrate, solvate or N-oxide thereof.

Those skilled in the art may determine the optimal time of contacting the stem cells and with the disclosed compounds described below required achieving the optimal results. As a guideline, the period of contact may be between about 24 hours and about 192 hours, for example, between about 48 hours and about 144 hours. Differentiated cells produced by the disclosed methods may include are cardiomyocytes, liver cells, lung cells, pancreatic cells, and others.

The stem cells suitable for use in the present methods may be derived from a patient's own tissue. This would enhance compatibility of differentiated tissue grafts derived from the stem cells with the patient. In this context it should be noted that embryonic stem cells can include adult stem cells derived from a person's own tissue iPSCs, embryonic stem cells, and the like. Human stem cells may be genetically modified prior to use through introduction of genes that may control their state of differentiation prior to, during or after their exposure to the embryonic cell or extracellular medium from an embryonic cell. They may be genetically modified through introduction of vectors expressing a selectable marker under the control of a stem cell specific promoter, such as Oct-4. The stem cells may be genetically modified at any stage with a marker so that the marker is carried through to any stage of cultivation. The marker may be used to purify the differentiated or undifferentiated stem cell populations at any stage of cultivation.

The disclosure also provides differentiated cells produced according to the disclosed methods that may be used for transplantation, cell therapy or gene therapy. The disclosure further provides a differentiated cell produced according to the disclosed methods that may be used for therapeutic purposes, such as in methods of restoring cardiac function in a subject suffering from a heart disease or condition.

In another aspect, the disclosure provides methods of treating or preventing a cardiac disease or condition, the method including introducing an isolated differentiated cardiomyocyte cell of the disclosure and/or a cell capable of differentiating into a cardiomyocyte cell when treated in accordance with the disclosed methods into cardiac tissue of a subject. The isolated cardiomyocyte cell may be transplanted into damaged cardiac tissue of a subject. The method may result in the restoration of cardiac function in a subject.

In another aspect, the disclosure provides methods of repairing cardiac tissue, the method including introducing an isolated cardiomyocyte cell of the disclosure and/or a cell capable of differentiating into a cardiomyocyte cell when treated in accordance with the method of the disclosure into damaged cardiac tissue of a subject.

The subject may be suffering from a cardiac disease or condition. In the method of the disclosure, the isolated cardiomyocyte cell may be transplanted into damaged cardiac tissue of a subject. The method may result in the restoration of cardiac function in a subject. The disclosure also provides a myocardial model for testing the ability of stem cells that have differentiated into cardiomyocytes to restore cardiac function. The disclosure further provides a cell composition including a differentiated cell of the disclosure, and a carrier. The term "inducing differentiation" as used herein is taken to mean causing a stem cell to develop into a specific differentiated cell type as a result of a direct or intentional influence on the stem cell. Influencing factors in addition to the compounds described herein can include cellular parameters such as ion influx, a pH change and/or extracellular factors, such as secreted proteins, such as but not limited to growth factors and cytokines that regulate and trigger differentiation. It may include culturing the cell to confluence and may be influenced by cell density.

The SC and the cell providing the differentiating factor(s) may be co-cultured in vitro. This typically involves introducing the stem cell to an embryonic cell monolayer produced by proliferation of the embryonic cell in culture.

The cellular and molecular events regulating the induction and tissue-specific differentiation of endoderm are important to understanding the development and function of many organ systems. Stem cell-derived endoderm is important for the development of cellular therapies for the treatment of disease such as diabetes, liver cirrhosis, or pulmonary emphysema (e.g., via development of islet cells, hepatocytes or lung cells, respectively). Accordingly, compounds described in the disclosure find particular use in inducing differentiation of cells in the endoderm lineage, including pancreas, liver, lung and the like.

In one embodiment, the compounds of the disclosure are used to screen for targets of their action. For example, competitive analyses can be performed using compounds with known targets. Such targets include, for example, but not limited to MEF2C; Beta-catenin; TCF/LEF; Smad2, Smad3; Smad4 (binding partners of the above proteins are also potential targets since they would modulate activity); p38, and components of the signaling that activate MEF2C; components of the Wnt pathway, such as Frizzled proteins, CaMK, Axin, Dishevelled, APC, GSK3, FRAP; Calmodulin (in particular for phenothiazine analogues); Potassium channel targets (in particular for dihydropyridine analogues); and Calcium channel targets (in particular for dihydropyridine analogues).

EXAMPLES

The embodiments of the disclosure may be further illustrated by the following non-limiting examples.

Example 1

Biological Assays

The primary screen is conducted with CGR8 mESCs stably transfected with eGFP under control of the alpha myosin heavy chain (aMHC) promoter (Takahashi, et al., Circulation, 107(14):1912, 2003). The bioassay is run essentially as described (Bushway et al., Methods Enzymol, 414:300, 2006). Briefly, cells were seeded onto Greiner 384 well microclear bottom microtiter plates in ½ well volume at a density of ~229 cells/mm2. Compound is administered on day 2 with ½ well volume at 2× concentration and mixed thoroughly with replacement on day 4 by aspiration and replacement of 1× concentrated compound in ½ well volume; otherwise, fresh media is replaced at ½ well volume every second day until the assay is complete. Primary assay is executed on the Beckman FX with robotic arm and integrated cytomats using SAMI scheduler.

The optimal time to stop the differentiation is empirically determined to be at day 9 of differentiation, when cardiomyocytes appear in positive control cultures that have higher density cells or culture the cells in embryoid body (not monolayer) culture. Plates were fixed for 5 minutes in 4% paraformaldehyde in 1×PBS, rinsed 3 times in 1×PBS (includes a DAPI stain). 50% glycerol is then added to each well and plates stored until imaging. A total of 30,000 data points were obtained. That is ~14,000 unique compounds were screened at 1 μg/mL and 5 μg/mL, corresponding to approximately 2 μM and 13 μM (assuming approximate MW 300-500 g/mole). Primary screen imaging is done with Q3DM Eidaq 100 mounted with a 4× objective capturing 4 images/well at 8×8 binning. Plates were loaded manually. Image quantification is done using a simple image subtraction routine that subtracted the red channel images from the green (eGFP) channel images to remove background signal from the eGFP images. This algorithm yielded an integrated value for each well.

Follow-up confirmations and testing of hits for SAR were performed on the Hamilton STAR fluid handler with integrated Kendro Cytomat plate hotel and Kendro Cytomat plate incubators using the Hamilton STAR liquid handler robot. By the time of these later experiments, our imaging infrastructure and algorithms had changed. Imaging is done on the INCell 1000 (GE/Amersham) using a 10× objective capturing 9 images/well at 4×4 binning during image capture. Microtiter plate loading is automated using the CRS/Thermo Catalyst Express robotic arm and Polara scheduler. Image quantification is performed on captured TIFF images using the Developer Toolbox (GE/Amersham) with custom algorithms.

In brief, each image is dynamically thresholded by acquiring a global pixel average and multiplying this value by a scalar to produce an image mask approximating the specific signal. The mask is used to collect integrated intensities in blue (DAPI), green (eGFP), and red (non-specific) channels. Typical data treatment subtracts integrated intensities of the red channel from the specific signal in the green channel. In dose response curves for SAR studies, each compound is tested in a 5-step, 2-fold titration observing a minimum of 4 replicates wells/titer, or 36 separate images.

Example 2

General Synthetic Procedures for Obtaining Compounds of Structure I

The dihydropyridine-based compounds of general structure IA and IB:

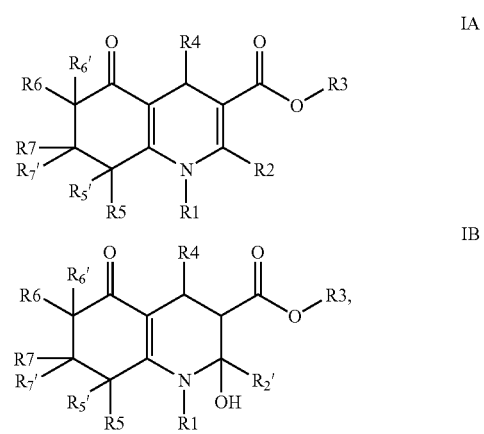

may be synthesized according to the following scheme:

Scheme 1: Synthesis of dihydropyridine-based compounds of general IA and IB.

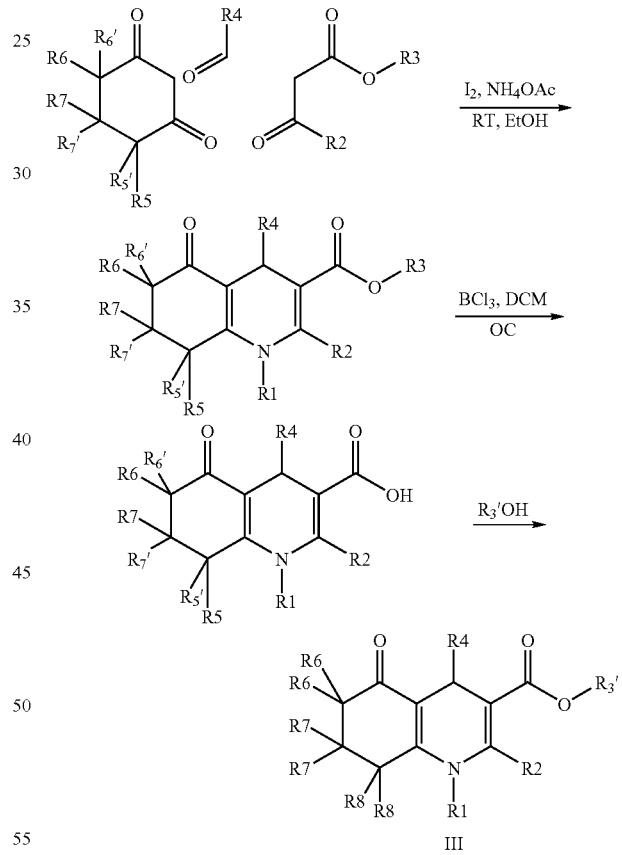

The synthetic procedure shown in Scheme 1 includes a one pot synthesis using catalytic amount of iodine. In individual reaction vessels, an optionally substituted dimedone is reacted with one equivalent methyl or ethyl acethyl acetateetate, 1 equivalent ammonium acetate, 1 equivalent of various aldehydes in the presence of 0.3 equivalent iodine in a minimum amount of ethanol at room temperature overnight to obtain intermediate I shown on the reaction Scheme 1. When $R_3$ is different from methyl or ethyl, the methyl ester, intermediate I is hydrolyzed in the presence of boron trichloride and then esterified in the presence of the desired alcohol using standard techniques to give compound III.

Synthesis of Prop-2-ynyl 4-(Biphenyl-4-yl)-2-ethyl-7,7-dimethyl-5-oxo-1,4,6,6,8,8-hexahydroquinoline-3-carboxylate (BI-3005)

Scheme 2:

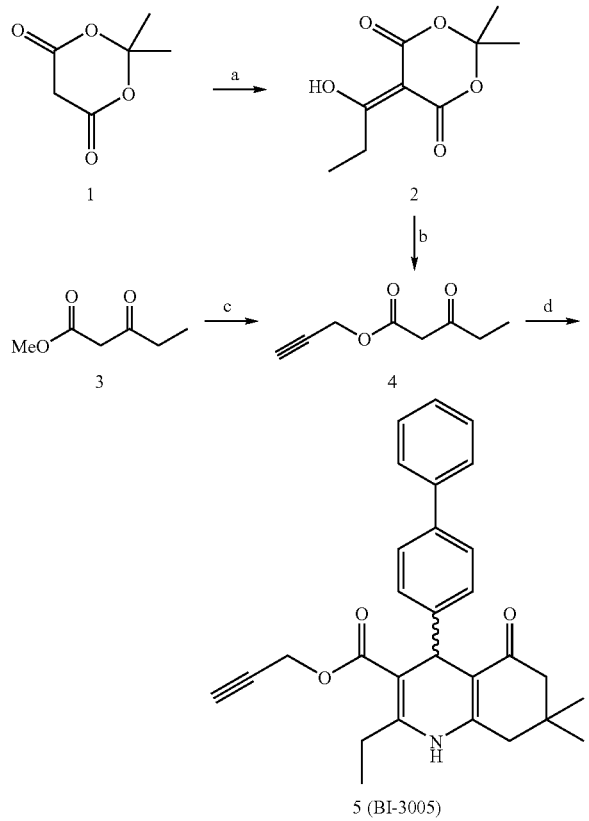

(a) Propionyl chloride, pyridine, dichloromethane, 0° C., 1 h, room temperature, 1 h; dil. HCl (93%). (b) Prop-2-ynol, PhH, 93° C., 3.25 h (95%). (c) Prop-2-ynol, I₂, PhMe, 115° C., 6 h (43%). (d) Dimedone, 4-phenylbenzaldehyde, NH₄OAc, I₂, ethanol, 5 h (64%).

5-(1-Hydroxypropylidene)-2,2-dimethyl-[1,3]dioxane-4,6-dione (2). To a solution of 2,2-dimethyl-1,3-dioxane-4,6-dione (4.41 g, 30.0 mmol) and pyridine (4.85 mL, 60.0 mmol) in dichloromethane (24 mL) at 0° C. under argon is added propionyl chloride (2.95 mL, 33.0 mmol). The mixture is stirred at 0° C. for 1 h and at room temperature for 1 h before being diluted with 2 N HCl (40 mL) and extracted with dichloromethane (80 mL). The extract is washed (brine) and dried. Solvent is removed at reduced pressure to give 5.57 g (93%) of 2 as a yellow solid, mp 43-46° C. IR 3345, 2856, 1715, 1456 cm⁻¹; ¹H NMR (CDCl₃) δ 1.29 (t, J=7.5 Hz, 3H, CH₂CH₃), 1.76 (s, 6H, CH₃, CH₃), 3.14 (q, J=7.5 Hz, 2H, CH₂CH₃), 15.42 (bs, 1H, OH).

Prop-2-ynyl 3-Oxopentanoate (4). Method A. A solution of 5-(1-hydroxypropylidene)-2,2-dimethyl-[1,3]dioxane-4,6-dione (2) (2.00 g, 10.0 mmol) and 2-propynol (1.10 g, 20.0 mmol) in benzene (20 mL) is stirred at 93° C. for 3.25 h and then cooled to room temperature. After solvent removal at reduced pressure, the residue is purified on silica gel (12.5% to 14.3% ethyl acetate/hexane) to give 1.47 g (95%) of 4 as a colorless liquid.

Method B. To a solution of methyl 3-ketopentanoate (3) (822 mg, 6.00 mmol) and 2-propynol (686 mg, 12.0 mmol) in toluene (7 mL) is added I₂ (46 mg, 0.18 mmol). The mixture is stirred at 115° C. for 6 h, then cooled to room temperature, and extracted with ethyl acetate (100 mL). The extract is washed (brine) and dried. After solvent removal at reduced pressure, the residue is distilled (125-130° C., 2 mm) to give 401 mg (43%) of 4 as a colorless liquid. IR 3345, 2856, 1715, 1456 cm⁻¹; ¹H NMR (CDCl₃) δ 1.10 (t, J=7.5 Hz, 3H, CH₂CH₃), 2.52 (t, J=2.4 Hz, 1H, CH≡CCH₂), 2.58 (q, J=7.5 Hz, 2H, CH₂CH₃) 3.51 (s, 2H, CH₂), 4.74 (d, J=2.4 Hz, 2H, CH≡CCH₂).

Prop-2-ynyl 4-(Biphenyl-4-yl)-7,7-dimethyl-2-ethyl-5-oxo-1,4,6,6,8,8-hexahydroquinoline-3-carboxylate (5, BI-3005). A mixture of prop-2-ynyl 3-oxo-pentanoate (4) (196 mg, 1.27 mmol), 4-phenylbenzaldehyde (244 mg, 1.27 mmol), dimedone (180 mg, 1.27 mmol), ammonium acetate (101 mg, 1.27 mmol), I₂ (97 mg, 0.38 mmol), and ethanol (10 drops) is stirred under argon for 5.5 h and then diluted with 5% Na₂S₂O₃ (30 mL). The resultant suspension is extracted with ethyl acetate (50 mL and 30 mL). The extract is washed (5% Na₂S₂O₃, H₂O, and brine) and dried. After solvent removal at reduced pressure, the residue is crystallized (ethanol) to give 139 mg of 5 (BI-3005) as a cream solid. The residue produced on concentration of the mother liquors is purified on silica gel (16.7% to 66.7% ethyl acetate/hexane) to give an additional 212 mg of 5 (BI-3005) as a cream solid for a total of 0.351 mg (64%), mp 220-222° C. IR 3345, 2856, 1715, 1456 cm⁻¹; ¹H NMR (CDCl₃ IR 3332, 2856, 11693, 1225 cm⁻¹; ¹H NMR (CDCl₃) δ 0.99 (s, 3H, CH₃), 1.12 (s, 3H, CH₃), 1.29 (t, J=7.5 Hz, 3H, CH₂CH₃), 2.18-2.44 (m, 5H, COCH₂, CH≡CCH₂, CH₂), 2.77-2.90 (m, 2H, CH₂CH₃), 4.58-4.75 (m, 2H, CH≡CCH₂), 5.16 (s, 1H, CH), 5.87 (bs, 1H, NH), 7.28-7.59 ppm (m, 9H, 4-BiphenylH).

Synthesis of Methyl 7,7-Dimethyl-2-ethyl-5-oxo-4-(4-prop-2-ynyloxy)phenyl)-1,4,6,6,8,8-hexahydroquinoline-3-carboxylate (3, BI-3027)

Scheme 3:

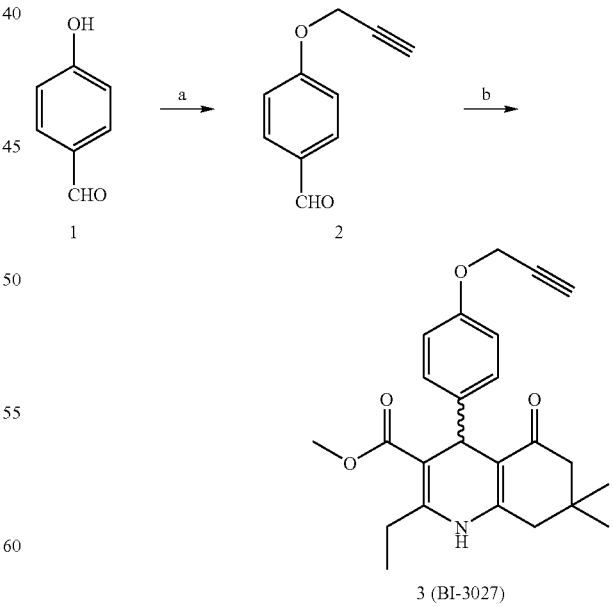

(a) Propionyl bromide, K₂CO₃, DMF, 70° C., 35 min, room temperature, 4.5 h (88%).
(b) Dimedone, methyl 3-oxopentanoate, NH₄OAc, I₂, ethanol, 4.5 h (49%).

4-(Prop-2-ynyloxy)benzaldehyde (2). (Beena et al. 2009) To a suspension of 4-hydroxybenaldehyde (1) (1.22 g, 10.0 mmol) and K$_2$CO$_3$ (4.15 g, 30 mmol) in DMF (20 mL) that is stirred at 70° C. under argon for 35 min and then cooled to room temperature is added 80% prop-2-ynyl bromide (12 mmol) in toluene (1.34 mL). The resulting mixture is stirred for 4.5 h, quenched with cold H$_2$O (80 mL), and filtered. The solid is washed with H$_2$O (2×30 mL) to give 1.41 g (88%) of 2 as a cream solid, mp 80-82° C. IR 2824, 1681, 1250 cm$^{-1}$; $^1$H NMR (CDCl$_3$) δ 2.60 (t, J=2.4 Hz, 1H, CH≡CCH$_2$), 4.81, 2H, CH≡CCH$_2$), 7.12 (d, J=9.3 Hz, 2H, 3,5-ArH), 7.88 (d, J=9.3 Hz, 2H, 2,6-ArH), 9.93 (s, 1H, CHO).

Methyl 7,7-Dimethyl-2-ethyl-5-oxo-4-[(4-prop-2-ynyloxy)phenyl]-1,4,6,6,8,8-hexahydroquinoline-3-carboxylate (3, BI-3027). A mixture of 4-(prop-2-ynyloxy)benzaldehyde (2) (203 mg, 1.27 mmol), methyl 3-oxopentanoate (173 mg, 1.27 mmol), dimedone (180 mg, 1.27 mmol), ammonium acetate (101 mg, 1.27 mmol), I$_2$ (97 mg, 0.38 mmol), and ethanol (10 drops) is stirred under argon for 4.5 h, then quenched with 5% Na$_2$S$_2$O$_3$ (30 mL), and extracted with ethyl acetate (50 mL and 30 mL). The extract is washed (5% Na$_2$S$_2$O$_3$, H$_2$O, and brine) and dried. After solvent removal at reduced pressure, the residue is purified on silica gel (33% to 60% ethyl acetate/hexane) to give 247 mg (49%) of 3 (BI-3027) as a cream solid, mp 162-165° C. IR 3329, 2874, 1684, 1222 cm$^{-1}$; $^1$H NMR (CDCl$_3$) δ 0.95 (s, 3H, CH$_3$), 1.10 (s, 3H, CH$_3$), 1.26 (t, J=7.2 Hz, 3H, CH$_2$CH$_3$), 2.15-2.41 (m, 4H, COCH$_2$, CH$_2$), 2.52 (t, J=2.4 Hz, 1H, CH≡CCH$_2$), 2.76-2.88 (m, 2H, CH$_2$CH$_3$), 3.64 (s, 3H, OCH$_3$), 4.58-4.75 (d, J=2.4 Hz, 2H, CH≡CCH$_2$), 5.05 (s, 1H, CH), 5.84 (bs, 1H, NH), 6.84 (d, J=8.7 Hz, 2H, 3,5-ArH), 7.24 ppm (d, J=8.7 Hz, 2H, 2,6-ArH).

Synthesis of Methyl 7,7-Dimethyl-2-ethyl-4-(4-ethynylphenyl)-5-oxo-1,4,6,6,8,8-hexahydroquinoline-3-carboxylate (2, BI-3029) and Methyl 7,7-Dimethyl-2-ethyl-5-oxo-4-[4-(1-phenyl[1,2,3]triazol-4-yl)phenyl]-1,4,6,6,8,8-hexahydroquinoline-3-carboxylate (3, BI-3041)

Scheme 4:

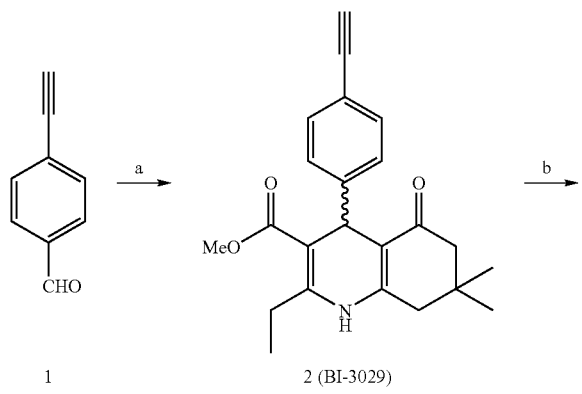

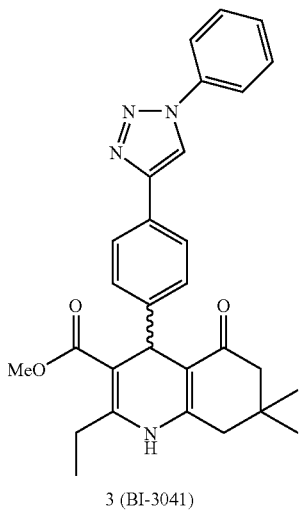

3 (BI-3041)

(a) Dimedone, methyl 3-oxopentanoate, NH$_4$OAc, I$_2$, ethanol, 5.5 h (60%). (b) Phenyl azide, CuI, DIEA, methanol, 23 h (79%).

Methyl 7,7-Dimethyl-2-ethyl-4-(4-ethynylphenyl)-5-oxo-1,4,6,6,8,8-hexahydroquinoline-3-carboxylate (2, BI-3029). A mixture of 4-ethynylbenzaldehyde (1) (171 mg, 1.27 mmol), methyl 3-oxopentanoate (175 mg, 1.27 mmol), dimedone (181 mg, 1.27 mmol), ammonium acetate (101 mg, 1.27 mmol), I$_2$ (97 mg, 0.38 mmol), and ethanol (10 drops) is stirred under argon for 5.5 h, quenched with 5% Na$_2$S$_2$O$_3$ (30 mL), and extracted with ethyl acetate (50 mL and 30 mL). The extract is washed (5% Na$_2$S$_2$O$_3$, H$_2$O, and brine) and dried. After solvent removal at reduced pressure, the residue is purified on silica gel (33% to 60% ethyl acetate/hexane) to give 277 mg (60%) of 2 (BI-3029) as a cream solid, mp 234-236° C. IR 3332, 2933, 1704, 1610, 1482, 1214 cm$^{-1}$; $^1$H NMR (CDCl$_3$) δ 0.93 (s, 3H, CH$_3$), 1.10 (s, 3H, CH$_3$), 1.26 (t, J=7.2 Hz, 3H, CH$_2$CH$_3$), 2.07-2.42 (m, 4H, COCH$_2$, CH$_2$), 2.76-2.89 (m, 2H, CH$_2$CH$_3$), 3.02 (s, 1H, CH≡C), 3.63 (s, 3H, OCH$_3$), 5.09 (s, 1H, CH), 5.90 (bs, 1H, NH), 7.27 (d, J=8.1 Hz, 2H, 3,5-ArH), 7.37 ppm (d, J=8.1 Hz, 2H, 2,6-ArH).

Methyl 7,7-Dimethyl-2-ethyl-5-oxo-4-[4-(1-phenyl[1,2,3]triazol-4-yl)phenyl]-1,4,6,6,8,8-hexahydroquinoline-3-carboxylate (3, BI-3041). A suspension of methyl 7,7-dimethyl-2-ethyl-4-(4-ethynylphenyl)-5-oxo-1,4,6,6,8,8-hexahydroquinoline-3-carboxylate (2, BI-3029) (22 mg, 0.06 mmol), phenyl azide (7 mg, 0.06 mmol), CuI (4.6 mg, 0.024 mmol), and DIEA (105 μL, 0.6 mmol) in methanol (2.4 mL) and tetrahydrofuran (0.5 mL) is stirred for 23 h and then concentrated at reduced pressure. The residue is purified on silica gel (50% to 60% ethyl acetate/hexane) to give 23 mg (79%) of 3 (BI-3041) as a cream solid, mp 238-240° C. IR 3300, 2966, 1689, 1608, 1489, 1215 cm$^{-1}$; NMR (CDCl$_3$) δ 0.81 (s, 3H, CH$_3$), 1.02 (s, 3H, CH$_3$), 1.21 (t, J=7.5 Hz, 3H, CH$_2$CH$_3$), 2.07-2.46 (m, 4H, COCH$_2$, CH$_2$), 2.71-2.91 (m, 2H, CH$_2$CH$_3$), 3.65 (s, 3H, OCH$_3$), 5.14 (s, 1H, CH), 7.47-7.62 (m, 5H, PhH), 7.80 (d, J=7.2 Hz, 2H, 3,5-ArH), 7.83 (d, J=7.2 Hz, 2H, 2,6-ArH), 8.22 (s, 1H, triazH), 8.25 ppm (bs, 1H, NH).

Synthesis of Prop-2-ynyl 4-(Biphenyl-4-yl)-7,7-dimethyl-2-ethyl-5-oxo-1,4,6,6,8,8-hexahydroquinoline-3-carboxylate (3, BI-3036)

Scheme 5:

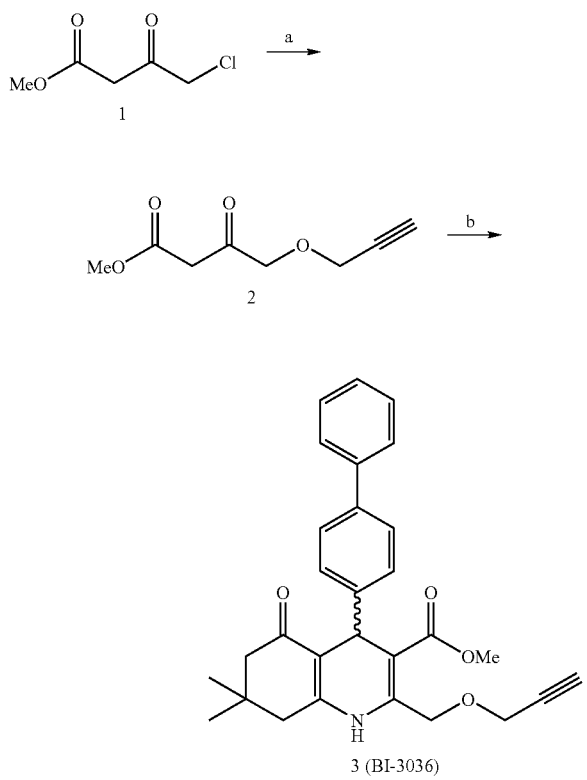

(a) 2- Propynol, NaH, tetrahydrofuran, 0° C., 1.4 h, room temperature, 24 h (82%). (b) Dimedone, 4-phenylbenzaldehyde, NH$_4$OAc, I$_2$, ethanol, 17 h (32%).

Methyl 3-Oxo-4-(prop-2-ynyloxy)butyrate (2). To a solution of methyl 4-chloroacethyl acetateetate (1.2 g, 8.0 mmol) in tetrahydrofuran (12 mL) at 0° C. under argon is added 60% NaH (16 mmol) in mineral oil (640 mg) followed by 2-propynol (448 mg, 8 mmol). This suspension is stirred at 0° C. for 1.4 h and at room temperature for 24 h before dilution with cold 2 N HCl (25 mL) and extraction with Et$_2$O (50 mL and 2×40 mL). The extract is washed (sat. NaHCO$_3$ and brine) and dried. After solvent removal at reduced pressure, the residue is purified on silica gel (20% to 25% ethyl acetate/hexane) to give 987 mg (82%) of 2 as a light-yellow liquid. IR 2960, 1747, 1722, 1328, 1098 cm$^{-1}$; $^1$H NMR (CDCl$_3$) 2.53 (t, J=2.4 Hz, 1H, CH≡CCH$_2$), 3.60 (s, 2H, COCH$_2$CO), 3.78 (s, 3H, OCH$_3$), 4.28 (s, 2H, COCH$_2$O), 4.30 ppm (d, J=2.4 Hz, 2H, CH≡CCH$_2$).

Prop-2-ynyl 4-(Biphenyl-4-yl)-7,7-dimethyl-2-ethyl-5-oxo-1,4,6,6,8,8-hexahydroquinoline-3-carboxylate (3, BI-3036). A mixture of methyl 3-oxo-4-(prop-2-ynyloxy)butyrate (2) (220 mg, 1.29 mmol), 4-phenylbenzaldehyde (247 mg, 1.29 mmol), dimedone (183 mg, 1.29 mmol), ammonium acetate (103 mg, 1.29 mmol), I$_2$ (98 mg, 0.39 mmol), and ethanol (15 drops) is stirred under argon for 17 h, quenched with 5% Na$_2$S$_2$O$_3$ (30 mL), and extracted with ethyl acetate (50 mL and 30 mL). The extract is washed (5% Na$_2$S$_2$O$_3$, H$_2$O, and brine), and dried. After solvent removal at reduced pressure, the residue is crystallized (ethanol) to give 190 mg (32%) of 3 (BI-3036) as a cream solid, mp 204-205° C. IR 3370, 2949, 1691, 1638, 1469, 1216 cm$^{-1}$; NMR (CDCl$_3$) δ 0.99 (s, 3H, CH$_3$), 1.12 (s, 3H, CH$_3$), 2.19-2.48 (m, 4H, COCH$_2$, CH$_2$), 2.56 (t, J=2.4 Hz, 1H, CH≡CCH$_2$), 3.67 (s, 3H, OCH$_3$), 4.34 (d, J=2.4 Hz, 2H, CH≡CCH$_2$), 4.86-4.98 (m, 2H, CH$_2$O), 5.14 (s, 1H, CH), 7.15 (bs, 1H, NH), 7.30-7.60 ppm (m, 9H, 4-BiphenylH).

Example 3

Activity of Compounds of General Structure I

The potency of several compounds of the above shown general structure I using the above-described testing methods is measured. Approximately 150 dihydropyridine diones analogs were synthesized. The results for some of these compounds are shown in Table 1-1.

TABLE 1-1

Activity of compounds of structure IA and IB in the cardiomyocyte screening assay.

| number | STRUCTURE[a] | salt form | Activity[b] |
|---|---|---|---|
| 1 | | none | ++ |

TABLE 1-1-continued
Activity of compounds of structure IA and IB in the cardiomyocyte screening assay.
| 2 | 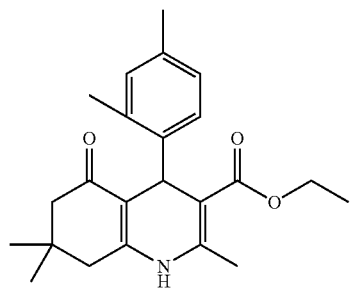 [SMILES: CCOC(=O)C1=C(C)NC2=C(C(=O)CC(C)(C)C2)C1c1ccc(C)cc1C] | none | + |
| 3 | 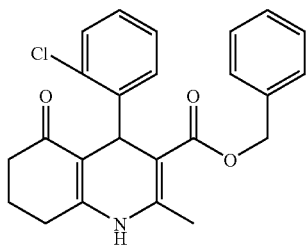 [SMILES: CC1=C(C(=O)OCc2ccccc2)C(c2ccccc2Cl)C2=C(CCCC2=O)N1] | none | + |
| 4 | 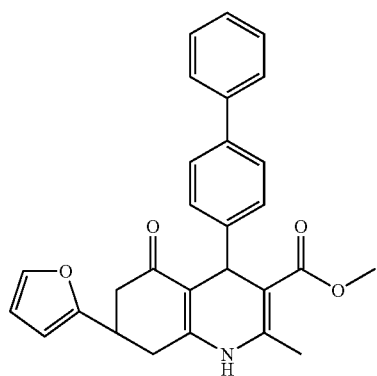 [SMILES: COC(=O)C1=C(C)NC2=C(C(=O)CC(c3ccco3)C2)C1c1ccc(-c2ccccc2)cc1] | none | ++ |
| 5 | 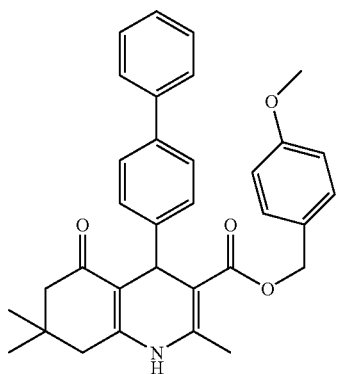 [SMILES: COc1ccc(COC(=O)C2=C(C)NC3=C(C(=O)CC(C)(C)C3)C2c2ccc(-c3ccccc3)cc2)cc1] | None | +++ |

TABLE 1-1-continued
Activity of compounds of structure IA and IB in the cardiomyocyte screening assay.
| 6 | 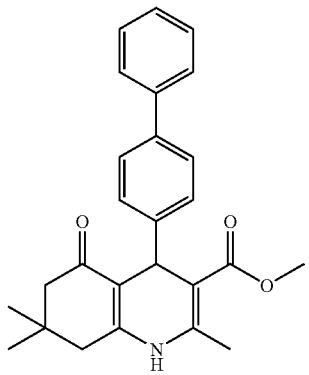 | Oxalate | + |
| 7 | 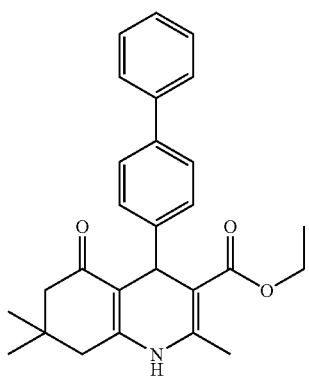 | HCl | +++ |
| 8 | 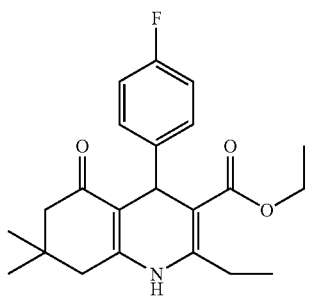 | None | + |
| 9 | 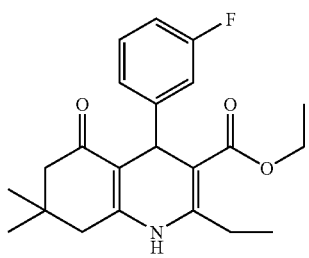 [SMILES: CCOC(=O)C1=C(CC)NC2=C(C(=O)CC(C)(C)C2)C1c1cccc(F)c1] | HCl | + |

TABLE 1-1-continued
Activity of compounds of structure IA and IB in the cardiomyocyte screening assay.
| 10 | 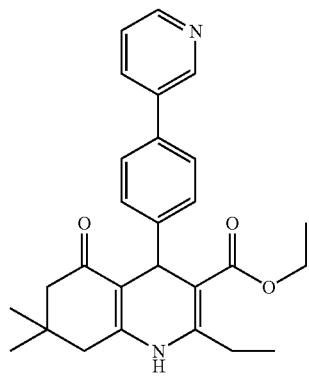 | HCl | ++ |
| 11 | 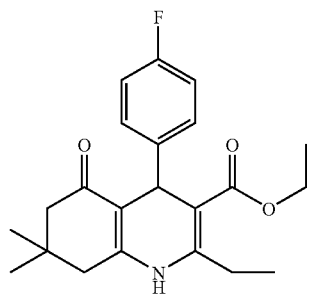 | HCl | ++++ |
| 12 | 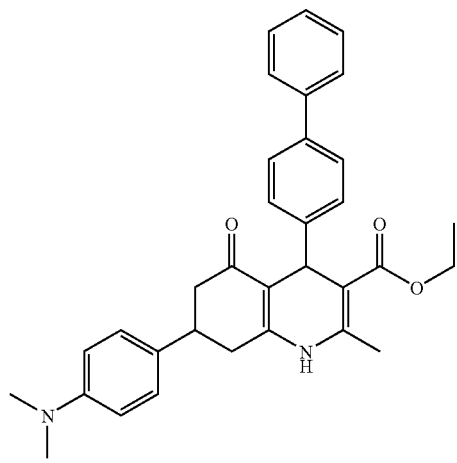 [SMILES: CCOC(=O)C1=C(C)NC2=C(C(=O)CC(c3ccc(N(C)C)cc3)C2)C1c1ccc(-c2ccccc2)cc1] | HCl | NA |
| 13 | 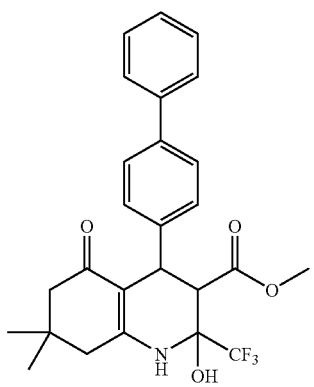 | HCl | NA |

TABLE 1-1-continued
Activity of compounds of structure IA and IB in the cardiomyocyte screening assay.
| number | STRUCTURE | salt form | activity |
|---|---|---|---|
| 14 | 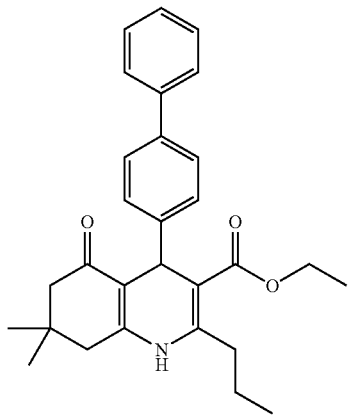 [SMILES: CCCC1=C(C(=O)OCC)C(c2ccc(-c3ccccc3)cc2)C2=C(CC(C)(C)CC2=O)N1] | HCl | NA |
| 15 | 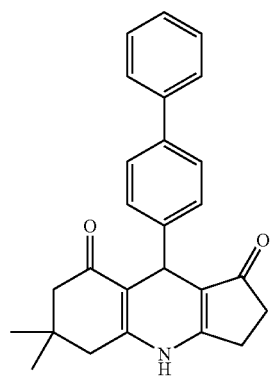 [SMILES: CC1(C)CC(=O)C2=C(C1)NC1=C(C(=O)CC1)C2c1ccc(-c2ccccc2)cc1] | HCl | NA |
| 16 | 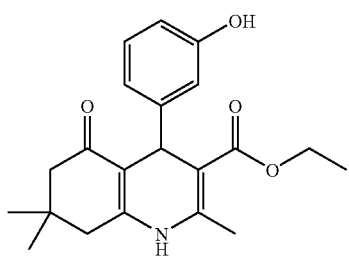 [SMILES: CCOC(=O)C1=C(C)NC2=C(C(=O)CC(C)(C)C2)C1c1cccc(O)c1] | none | + |
| 17 | 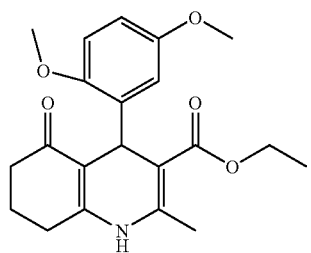 [SMILES: CCOC(=O)C1=C(C)NC2=C(C(=O)CCC2)C1c1cc(OC)ccc1OC] | none | + |

TABLE 1-1-continued
Activity of compounds of structure IA and IB in the cardiomyocyte screening assay.
| | | | |
|---|---|---|---|
| 18 | 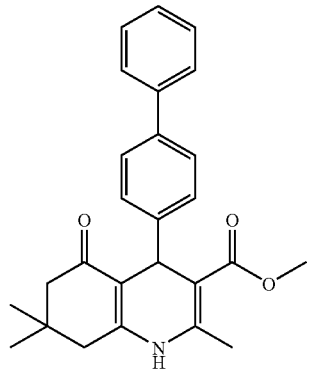 | none | +++ |
| 19 | 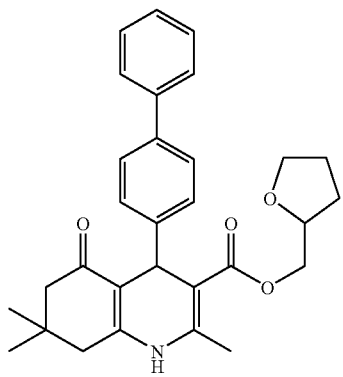 [SMILES: CC1=C(C(=O)OCC2CCCO2)C(c2ccc(-c3ccccc3)cc2)C2=C(CC(C)(C)CC2=O)N1] | None | ++ |
| 20 | 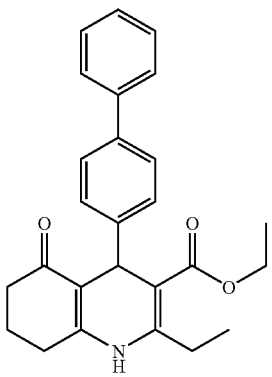 [SMILES: CCOC(=O)C1=C(CC)NC2=C(C(=O)CCC2)C1c1ccc(-c2ccccc2)cc1] | None | + |
| 21 | 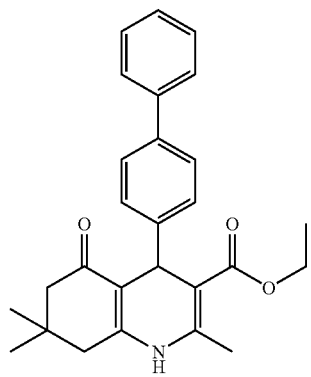 | None | + |

TABLE 1-1-continued
Activity of compounds of structure IA and IB in the cardiomyocyte screening assay.
| 22 | 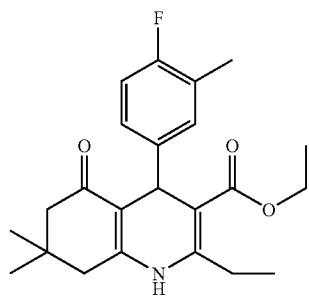 [SMILES: CCOC(=O)C1=C(CC)NC2=C(C(=O)CC(C)(C)C2)C1c1ccc(F)c(C)c1] | HCl | + |
| 23 | 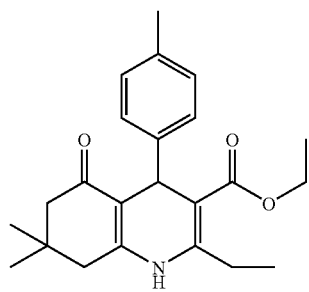 [SMILES: CCOC(=O)C1=C(CC)NC2=C(C(=O)CC(C)(C)C2)C1c1ccc(C)cc1] | HCl | + |
| 24 | 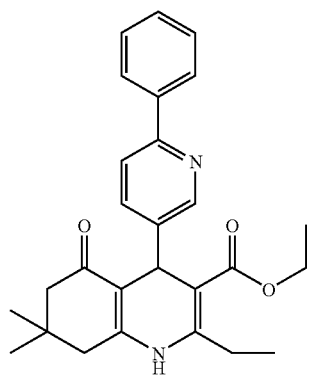 [SMILES: CCOC(=O)C1=C(CC)NC2=C(C(=O)CC(C)(C)C2)C1c1ccc(-c2ccccc2)nc1] | HCl | ++ |
| 25 | 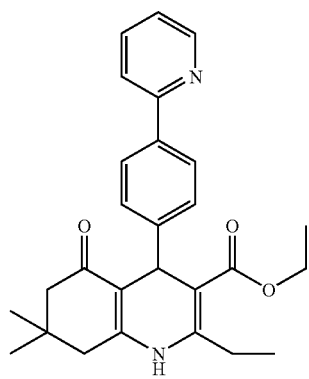 | n | ++ |

TABLE 1-1-continued
Activity of compounds of structure IA and IB in the cardiomyocyte screening assay.
| 26 | 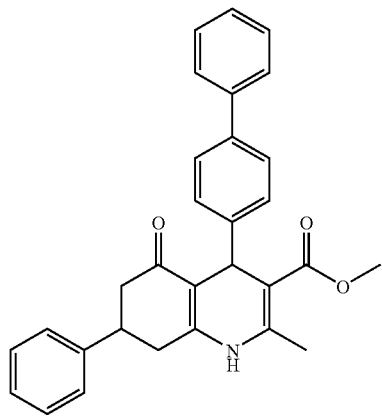 [SMILES: COC(=O)C1=C(C)NC2=C(C(=O)CC(c3ccccc3)C2)C1c1ccc(-c2ccccc2)cc1] | HCl | NA |
| 27 | 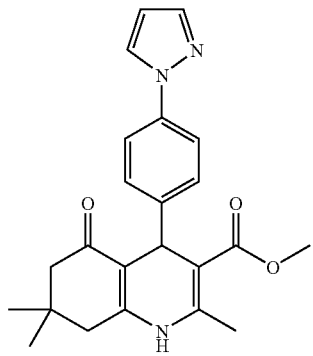 | HCl | NA |
| 28 | 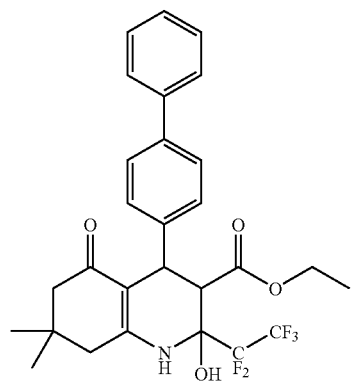 | none | NA |
| 29 | 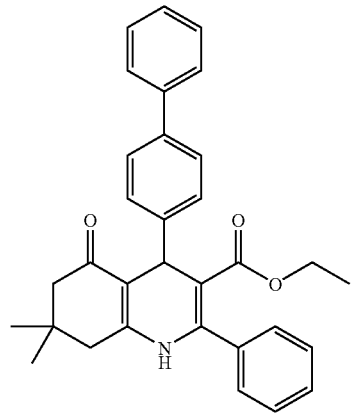 [SMILES: CCOC(=O)C1=C(c2ccccc2)NC2=C(C(=O)CC(C)(C)C2)C1c1ccc(-c2ccccc2)cc1] | none | NA |

TABLE 1-1-continued

Activity of compounds of structure IA and IB in the cardiomyocyte screening assay.

| 30 | 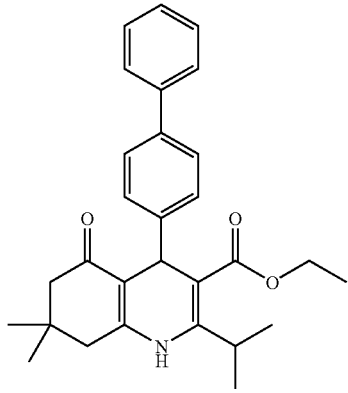 [SMILES: CCOC(=O)C1=C(C(C)C)NC2=C(C(=O)CC(C)(C)C2)C1c1ccc(-c2ccccc2)cc1] | none | NA |

[a] All the compounds have been characterized by LRMS and/or ¹H NMR.
[b] Activity is based on compound 28 being 100% activity; ++++: >80% activity compared to 28; +++ between 60 to 80% activity compared to 28; ++ between 40 to 60% activity compared to 28; +: <40% activity compared to compound 28. NA, not available.

TABLE 1-2

Characterization of compounds of structure IA and IB. Nuclear magnetic resonance data were recorded on a Varian Mercury 300 MHz Spectrometer using TMS as the internal standard and CDCl₃ as the solvent except where indicated. Electrospray mass spectral (MS) data was obtained using a Hitachi M-7000.

| structure | MW (g·mol⁻¹) | M(1 + H) |
|---|---|---|
| 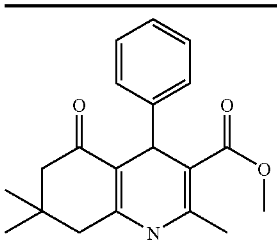 | 325.3 | MS (ESI⁺) m/z 326 (M + H)⁺ |
| 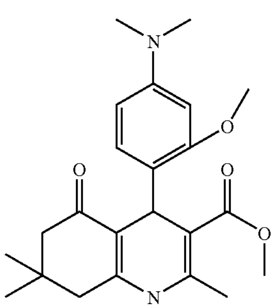 | 398.4 | MS (ESI⁺) m/z 399 (M + H)⁺ |
| 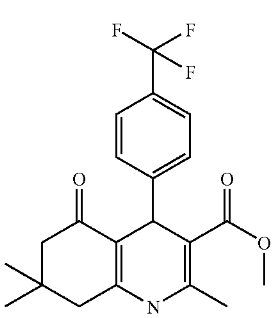 | 393.4 | MS (ESI⁺) m/z 394 (M + H)⁺ |

TABLE 1-2-continued

Characterization of compounds of structure IA and IB. Nuclear magnetic resonance data were recorded on a Varian Mercury 300 MHz Spectrometer using TMS as the internal standard and CDCl$_3$ as the solvent except where indicated. Electrospray mass spectral (MS) data was obtained using a Hitachi M-7000.

| structure | MW (g · mol$^{-1}$) | M(1 + H) |
|---|---|---|
| 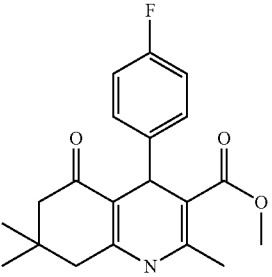 | 343.4 | MS (ESI$^+$) m/z 344 (M + H)$^+$ |
| 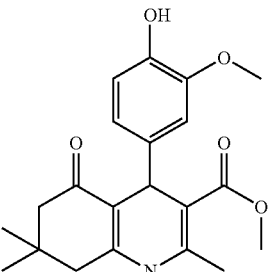 | 371.4 | MS (ESI$^+$) m/z 372 (M + H)$^+$ |
| 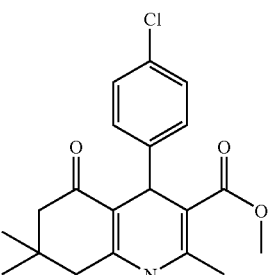 | 359.8 | MS (ESI$^+$) m/z 361 (M + H)$^+$ |
| 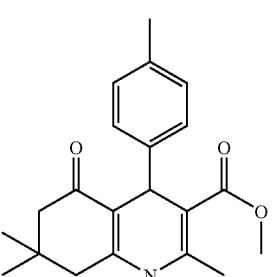 | 339.4 | MS (ESI$^+$) m/z 340 (M + H)$^+$ |
| 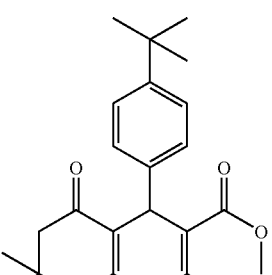 | 381.5 | MS (ESI$^+$) m/z 382 (M + H)$^+$ |

TABLE 1-2-continued

Characterization of compounds of structure IA and IB. Nuclear magnetic resonance data were recorded on a Varian Mercury 300 MHz Spectrometer using TMS as the internal standard and CDCl₃ as the solvent except where indicated. Electrospray mass spectral (MS) data was obtained using a Hitachi M-7000.

| structure | MW (g · mol$^{-1}$) | M(1 + H) |
|---|---|---|
| 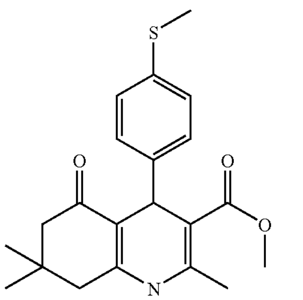 | 371.5 | MS (ESI$^+$) m/z 372 (M + H)$^+$ |
| 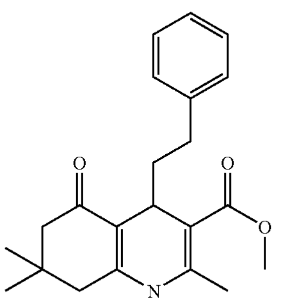 | 353.5 | MS (ESI$^+$) m/z 355 (M + H)$^+$ |
| 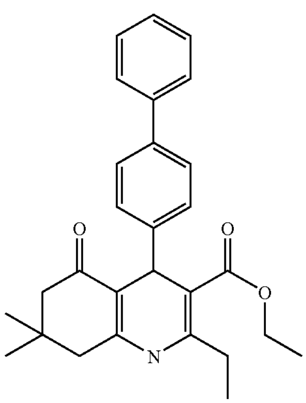 | 429.5 | MS (ESI$^+$) m/z 452 (M + Na)$^+$ |
| 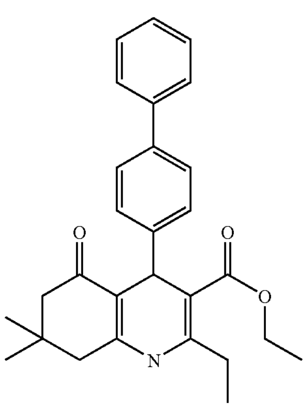 [SMILES: CCOC(=O)C1=C(CC)NC2=C(C(=O)CC(C)(C)C2)C1c1ccc(-c2ccccc2)cc1] | 466 | MS (ESI$^+$) m/z 452 (M + Na)$^+$ |

TABLE 1-2-continued

Characterization of compounds of structure IA and IB. Nuclear magnetic resonance data were recorded on a Varian Mercury 300 MHz Spectrometer using TMS as the internal standard and CDCl$_3$ as the solvent except where indicated. Electrospray mass spectral (MS) data was obtained using a Hitachi M-7000.

| structure | MW (g·mol$^{-1}$) | M(1 + H) |
|---|---|---|
| (structure with 4-trifluoromethylphenyl substituent) | 422.4 | MS (ESI$^+$) m/z 423 (M + H)$^+$ |
| (structure with 3,4-dimethoxyphenyl substituent) | 413.5 | MS (ESI$^+$) m/z 436 (M + Na)$^+$ |
| (structure with 2-naphthyl substituent) | 403.5 | MS (ESI$^+$) m/z 404 (M + H)$^+$ |
| (structure with biphenyl substituent) | 415 | MS (ESI$^+$) m/z 438 (M + Na)$^+$ |

TABLE 1-2-continued

Characterization of compounds of structure IA and IB. Nuclear magnetic resonance data were recorded on a Varian Mercury 300 MHz Spectrometer using TMS as the internal standard and CDCl$_3$ as the solvent except where indicated. Electrospray mass spectral (MS) data was obtained using a Hitachi M-7000.

| structure | MW (g · mol⁻¹) | M(1 + H) |
|---|---|---|
| 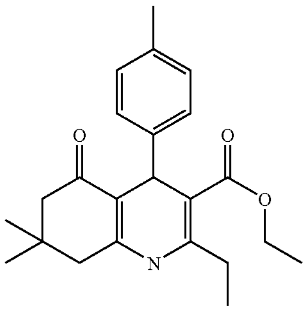 [SMILES: CCOC(=O)C1=C(CC)NC2=C(C(=O)CC(C)(C)C2)C1c1ccc(C)cc1] | 367.5 | MS (ESI⁺) m/z 390 (M + H)⁺ |
| 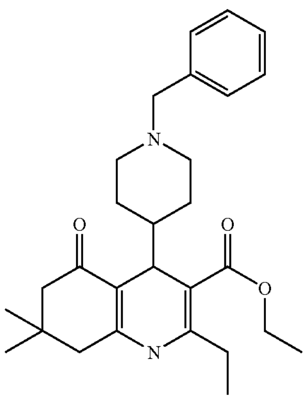 [SMILES: CCOC(=O)C1=C(CC)NC2=C(C(=O)CC(C)(C)C2)C1C1CCN(Cc2ccccc2)CC1] | 450.3 | MS (ESI⁺) m/z 451 (M + H)⁺ |
| 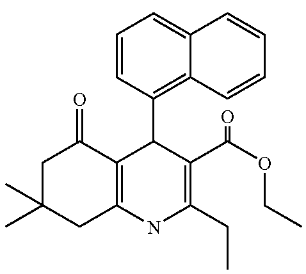 [SMILES: CCOC(=O)C1=C(CC)NC2=C(C(=O)CC(C)(C)C2)C1c1cccc2ccccc12] | 403.5 | MS (ESI⁺) m/z 426 (M + Na)⁺ |
| 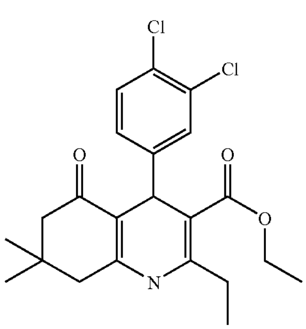 | 422 | MS (ESI⁺) m/z 445 (M + Na)⁺ |

TABLE 1-2-continued

Characterization of compounds of structure IA and IB. Nuclear magnetic resonance data were recorded on a Varian Mercury 300 MHz Spectrometer using TMS as the internal standard and CDCl$_3$ as the solvent except where indicated. Electrospray mass spectral (MS) data was obtained using a Hitachi M-7000.

| structure | MW (g·mol$^{-1}$) | M(1 + H) |
|---|---|---|
| (3-fluorophenyl-substituted dihydroquinolinone ethyl ester) | 371.2 | MS (ESI$^+$) m/z 394 (M + Na)$^+$ |
| (6-phenylpyridin-3-yl-substituted dihydroquinolinone ethyl ester) | 430 | MS (ESI$^+$) m/z 431 (M + H)$^+$ |
| (4-(pyridin-3-yl)phenyl-substituted dihydroquinolinone ethyl ester) | 430 | MS (ESI$^+$) m/z 432 (M + H)$^+$ |
| (4-fluoro-3-methylphenyl-substituted dihydroquinolinone ethyl ester) | 385.5 | MS (ESI$^+$) m/z 387 (M + H)$^+$ |

TABLE 1-2-continued

Characterization of compounds of structure IA and IB. Nuclear magnetic resonance data were recorded on a Varian Mercury 300 MHz Spectrometer using TMS as the internal standard and CDCl₃ as the solvent except where indicated. Electrospray mass spectral (MS) data was obtained using a Hitachi M-7000.

| structure | MW (g · mol⁻¹) | M(1 + H) |
|---|---|---|
| (6-chloropyridin-3-yl structure) | 389 | MS (ESI⁺) m/z 389.9 (M + H)⁺ |
| (4-(pyridin-2-yl)phenyl structure) | 430 | MS (ESI⁺) m/z 453.5 (M + H)⁺ |
| (4-methoxyphenyl structure) | 383 | MS (ESI⁺) m/z 406.6 (M + H)⁺ |
| (4-fluorophenyl structure) | 371 | MS (ESI⁺) m/z 372 (M + H)⁺ |

TABLE 1-2-continued

Characterization of compounds of structure IA and IB. Nuclear magnetic resonance data were recorded on a Varian Mercury 300 MHz Spectrometer using TMS as the internal standard and CDCl$_3$ as the solvent except where indicated. Electrospray mass spectral (MS) data was obtained using a Hitachi M-7000.

| structure | MW (g·mol$^{-1}$) | M(1 + H) |
|---|---|---|
| 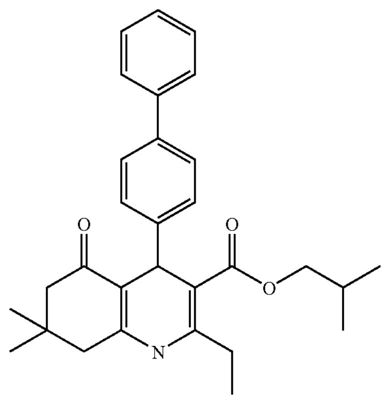 [SMILES: CCC1=C(C(=O)OCC(C)C)C(c2ccc(-c3ccccc3)cc2)C2=C(CC(C)(C)CC2=O)N1] | 457.6 | MS (ESI$^+$) m/z 458 (M + H)$^+$ |
| 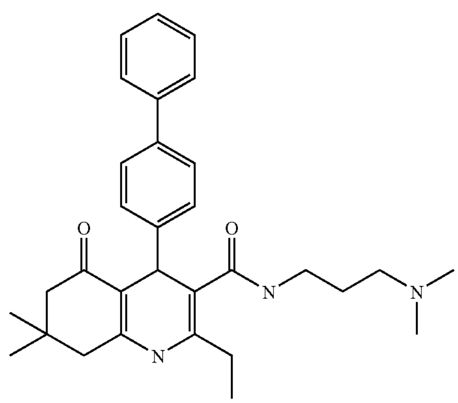 | 485.7 | MS (ESI$^+$) m/z 486 (M + H)$^+$ |
| 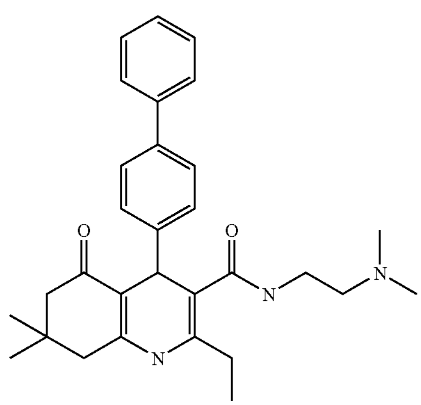 | 471.6 | MS (ESI$^+$) m/z 472 (M + H)$^+$ |

TABLE 1-2-continued

Characterization of compounds of structure IA and IB. Nuclear magnetic resonance data were recorded on a Varian Mercury 300 MHz Spectrometer using TMS as the internal standard and CDCl$_3$ as the solvent except where indicated. Electrospray mass spectral (MS) data was obtained using a Hitachi M-7000.

| structure | MW (g · mol$^{-1}$) | M(1 + H) |
|---|---|---|
| 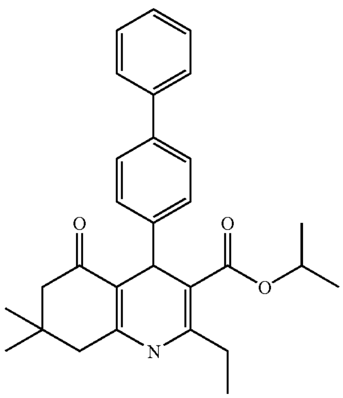 [SMILES: CCC1=C(C(=O)OC(C)C)C(c2ccc(-c3ccccc3)cc2)C2=C(CC(C)(C)CC2=O)N1] | 443.6 | MS (ESI$^+$) m/z 446 (M + H)$^+$ |
| 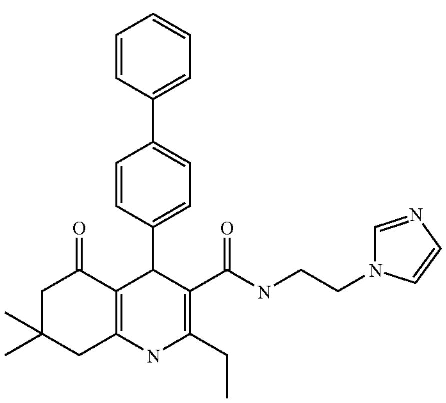 [SMILES: CCC1=C(C(=O)NCCn2ccnc2)C(c2ccc(-c3ccccc3)cc2)C2=C(CC(C)(C)CC2=O)N1] | 494.6 | MS (ESI$^+$) m/z 495.7 (M + H)$^+$ |
| 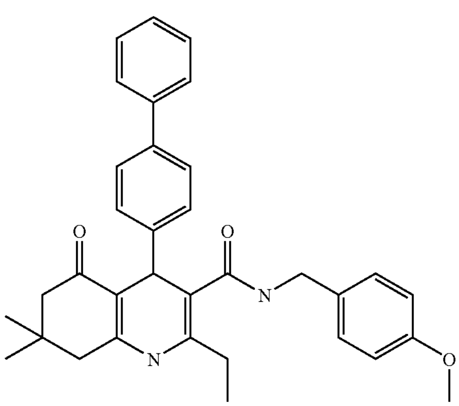 | 520.7 | MS (ESI$^-$) m/z 519.3 (M − H)$^+$ |

As may be observed from the data presented in Table 1-1, both free bases and salts gave significant potency. Solubility may be a significant factor in the bioactivity of the compounds. On the basis of the lipophilic character of many of the "hits", it is likely interaction site on the molecular target has lipophilic character.

Example 4
General Synthetic Procedure for Obtaining Compounds of Structure II The benzimidazole-based compounds of general structure II:

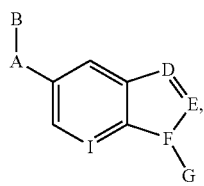

II may be synthesized according to the following schemes (when D is nitrogen or when D is carbon).

Scheme 6: Synthesis of benzimidazole-based compounds of general structure II (when D is nitrogen).

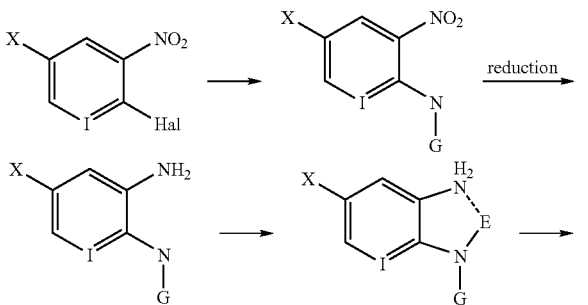

Scheme 7: Synthesis of benzimidazole-based compounds of general structure II (when D is carbon).

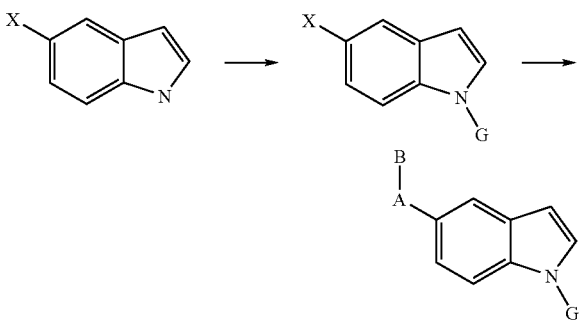

Approximately 600 benzimidazole analogues were synthesized and screened for their ability to facilitate cardiomyocyte differentiation. Analogue solubility is an issue during early phases of screening. Therefore, in addition to the free bases, the salts (i.e., hydrochloride or mono-oxalate) of the target compounds were generated and tested.

Generally, the salts were more soluble under aqueous conditions than the corresponding free bases. In some cases, an $EC_{50}$ value for a free base could not be determined because of compound precipitation from the medium; however, evaluation of the corresponding salt provided the $EC_{50}$ value. Compound library generation is then modified so that hydrochloride salts of the substituted benzimidazoles were isolated from the synthesis. In addition to ease of synthesis, the increased solubility of the benzimidazole salts appeared necessary for potency.

The benzimidazole-based compounds of general structure II may also be prepared as shown in the following schemes.

Scheme 8: Synthesis of benzimidazoles.

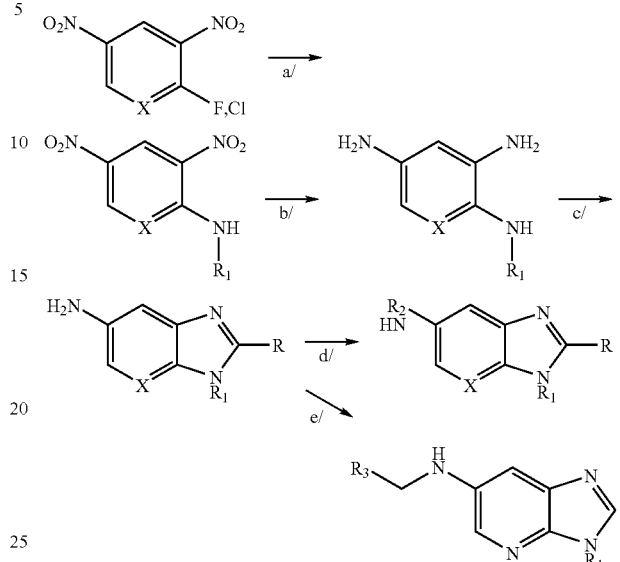

a/ $R_1NH_2$, tetrahydrofuran, room temperature, ovn; b/ $H_2$, Pd/C or $Na_2S_2O_3$; c/ when R = alkyl RCOOH or $(RCO)_2O$, HCl aq., heat. When R = H HCOOH or $CH(OMe)_3$, PTSA, 100 C.; d/ $R_2Cl$, iPrOH, heat; 3/ $R_3CHO$, $BH_3$-Py.

Scheme 9: Synthesis via Buchwald coupling.

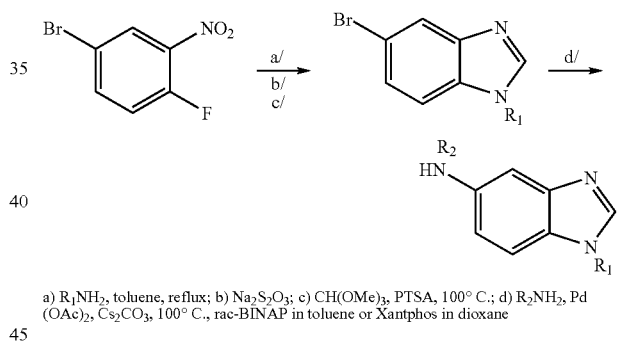

a) $R_1NH_2$, toluene, reflux; b) $Na_2S_2O_3$; c) $CH(OMe)_3$, PTSA, 100° C.; d) $R_2NH_2$, Pd(OAc)$_2$, Cs$_2$CO$_3$, 100° C., rac-BINAP in toluene or Xantphos in dioxane Scheme 10: Synthesis of indole

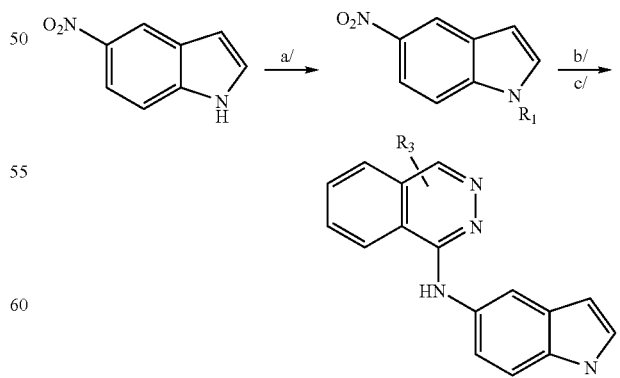

a) $R_1B(OH)_2$, Cu(OAc)$_2$, DIEA, DCM, room temperature; b) $Na_2S_2O_3$, ethanol/H$_2$O, 60° C.; c) 1-chlorophtalazine, IPA, microwave Scheme 11: Synthesis of 2-aminobenzimidazoles and benzotriazole.

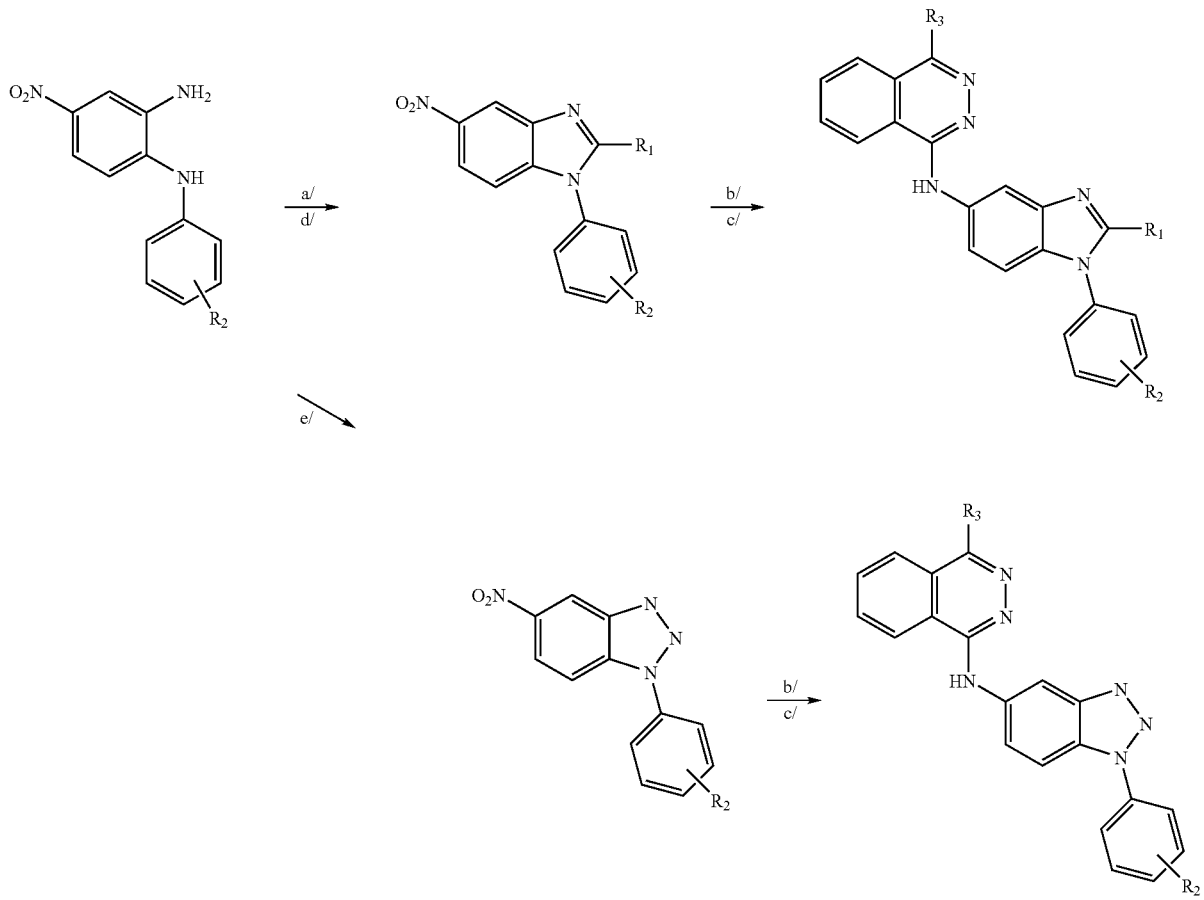

When R₁ is dimethylamino a) (dichloromethylene)dimethyl ammonium chloride, TEA, DCM, room temperature; b) H₂, Pd/C, c) 1-chlorophtalazine, IPA, microwave. When R₁ is amino d) BrCN, DCM, room temperature e) isoamyl nitrite, CHCl₃, room temperature.

Synthesis of 1-Phenyl-5-[(4-phenyl-1-phthalazinyl)(prop-2-ynyl)amino]benzimidazole (6, BI-3001)

Scheme 12:

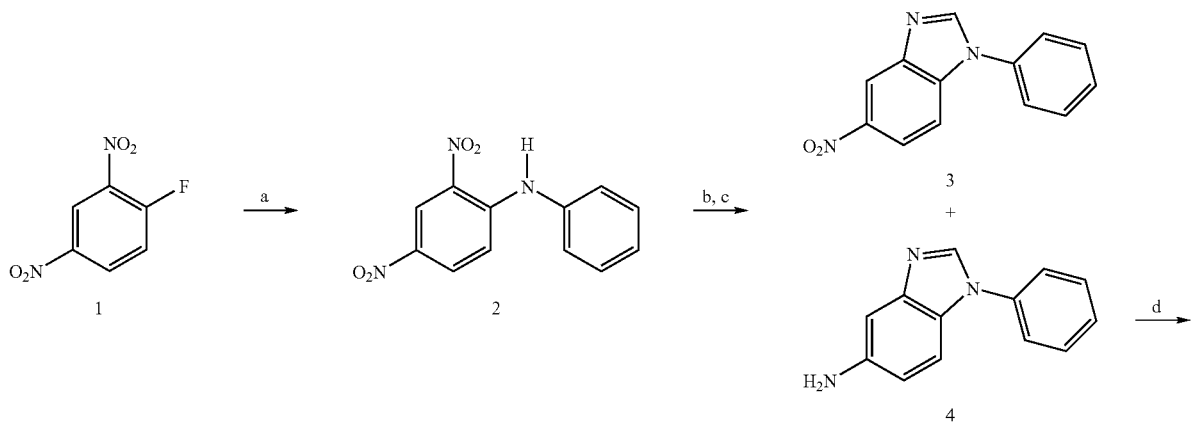

-continued

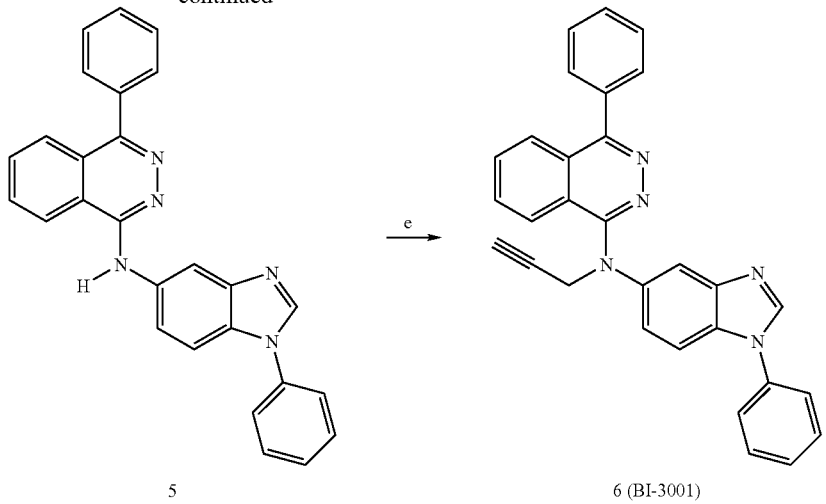

(a) Aniline, K₂CO₃, tetrahydrofuran, 25 h (97%). (b) H₂, Pd/C, Ethyl acetate, 27 h. (c) 4 N HCl, HCO₂H, 70-80° C., (62% for 3 and 25% 4 from 2). (d) 1-Chloro-4-phenylphtalazine, i-PrOH, 95° C., 2 h (99%). (e) 5, NaH, DMF, 1 h; propargyl bromide, 3.5 h (55%).

2,4-Dinitro-N-phenylbenzamine (2). To a solution of 2,4-dinitrofluorobenzene (1) (3.72 g, 20 mmol) and aniline (2.0 mL, 22 mmol) in anhydrous tetrahydrofuran is added K₂CO₃ (5.8 g, 42 mmol). The reaction mixture is stirred under argon for 25 h and then filtered (CHCl₃ rinse, 4×). After solvent removal from the filtrate at reduced pressure, the residue is crystallized (ethanol) to give 5.08 g (97%) of 2 as an orange solid, mp 155°-158° C. IR 3347. 2918, 1509, 1211 cm⁻¹; ¹H NMR (CDCl₃) δ 7.20 (d, J=9.6 Hz, 1H, 6-ArH), 7.30-7.59 (m, 5H, PhH), 8.22 (dd, J=9.6 Hz, 2.4 Hz, 1H, 5-ArH), 9.22 (d, J=2.4 Hz, 1H, 3-ArH), 10.01 (bs, 1H, NH). HRMS calcd C₉H₉ClN₂O₂ [M+H]⁺ 213.0425. found 213.0428.

5-Nitro-1-phenylbenzimidazole (3) and 5-Amino-1-phenylbenzimidazole (4). To a solution of 2,4-dinitro-N-phenylbenzamine (2) (3.0 g, 11.6 mmol) in ethyl acetate (90 mL) is added 10% Pd/C (300 mg). The reaction mixture is stirred under H₂ for 52 h and then filtered through Celite® (Ethyl acetate rinse). After solvent removal from the filtrate at reduced pressure, the residue is used in the next step without further purification.

A mixture of the residue and formic acid (1.6 mL, 40.6 mmol) in 4 N HCl (38 mL) is heated at 78-80° C. under argon for 22 h, then cooled to room temperature, brought to pH 12 with 8.5 N NaOH and NaOH pellets, and extracted with ethyl acetate (200 mL and 2×100 mL). The extract is washed (brine) and dried. After solvent removal at reduced pressure, the residue is purified on silica gel (1% to 6% methanol/ethyl acetate) to give 1.7 g (61%) of 3, mp 155-158° C. IR 3347. 2918, 1509, 1211 cm⁻¹; ¹H NMR (CDCl₃) δ 7.20 (d, J=9.6 Hz, 1H, 6-ArH), 7.30-7.59 (m, 5H, PhH), 8.22 (dd, J=9.6 Hz, 2.4 Hz, 1H, 5-ArH), 9.22 (d, J=2.4 Hz, 1H, 3-ArH), 10.01 (bs, 1H, NH). as a light purple solid, mp 159-161 and 0.6 g (25%) of 4 as a brown solid, mp 129-131° C. 3: IR 2912, 1508, 1225 cm⁻¹; ¹H NMR (CDCl₃) δ 7.53-7.72 (m, 6H, 7-BenzimidH, PhH), 8.30 (dd, J=8.7 Hz, 2.1 Hz, 1H, 6-BenzimidH), 8.32 (s, 1H, 2-BenzimidH), 8.84 (d, J=2.1 Hz, 1H, 4-BenzimidH). 4: IR 3341, 2932, 1498, 1220 cm⁻¹; ¹H NMR (CDCl₃) δ 3.26 (bs, 2H, NH₂), 6.78 (dd, J=8.4 Hz, 2.1 Hz, 1H, 6-BenzimidH), 7.18 (d, J=2.1 Hz, 1H, 4-BenzimidH). 7.36 (d, J=8.4 Hz, 1H, 7-BenzimidH), 7.42-7.61 (m, 5H, PhH), 8.04 (s, 1H, 2-BenzimidH).

1-Phenyl-5-(4-phenyl-1-phthalazinyl)aminobenzimidazole (5). A solution of 1-chloro-4-phenylphthalazine (156 mg, 0.65 mmol) and 5-amino-1-phenylbenzimidazole (4) (105 mg, 0.5 mmol) in i-PrOH (10 mL) is stirred at 95° C. under argon for 2 h. The reaction mixture is concentrated, diluted with sat. NaHCO₃ (15 mL), and extracted with CHCl₃ (100 mL). The extract is washed (brine) and dried. After solvent removal at reduced pressure, the residue is purified on silica gel (1% to 9% methanol/ethyl acetate) to give 206 mg (99%) of 5 as an orange solid, mp 265° C. IR 3285, 2842, 1615, 1476 cm⁻¹; ¹H NMR (CDCl₃) δ 7.45-7.61 (m, 5H, 1-PhH), 7.62-7.77 (m, 6H, 4'-C₆H₅, 7-BenzimidH), 7.82 (dd, J=8.7, 2.1 Hz, 1H, 6-BenzimidH), 7.86-7.90 (m, 1H, 5'-PhthH), 7.91-7.98 (m, 1H, 6'-PhthH), 8.00-8.08 (m, 1H, 7'-PhthH), 8.50 (d, J=2.1 Hz, 1H, 4-BenzimidH), 8.56 (s, 1H, 2-BenzimidH), 8.72 (d, J=8.7 Hz, 1H, 8'-PhthH), 9.37 ppm (s, 1H, NH).

1-Phenyl-5-[(4-phenyl-1-phthalazinyl)(prop-2-ynyl)amino]benzimidazole (6, BI-3001). To a suspension of 1-phenyl-5-(4-phenyl-1-phthalazinyl)aminobenzimidazole (5) (147 mg, 0.35 mmol) and 60% NaH (1.78 mmol) in mineral oil (71 mg) in anhydrous DMF (3 mL) that had been stirred under argon for 1 h added propargyl bromide (218 μL, 1.95 mmol) over a 1-h period. The reaction mixture is stirred for 3.5 h, diluted with H₂O (30 mL), and extracted with ethyl acetate (100 mL and 50 mL). The extract is washed (brine) and dried. After solvent removal at reduced pressure, the residue is purified on silica gel (0:1:1 to 0.1:1:1 methanol/ethyl acetate/hexane) to give 89 mg (55%) of 6 (BI-3001) as a cream solid, mp 178°-180° C. IR 3030, 1502, 1398 cm⁻¹; ¹H NMR (CDCl₃) δ 2.26 (t, J=2.1 Hz, 1H, CH≡—CH₂), 5.08 (d, J=2.1 Hz, 1H, CH≡CCH₂), 7.27 (dd, J=8.7, 2.1 Hz, 1H, 6-BenzimidH), 7.41-7.64 (m, 12H, 1-PhH, 4'-PhH, 4-BenzimidH, 7-BenzimidH), 7.65-7.69 (m, 1H, 5'-PhthH), 7.76-7.85 (m, 2H, 6',7'-PhthH), 7.96-8.02 (m, 1H, 8'-PhthH), 8.16 ppm (s, 1H, 2-BenzimidH).

Synthesis of 1-Phenyl-5-[4-(2-chloroprop-1E-enyl)-1-phthalazinyl]aminobenz-imidazole (6, BI-3004)

Scheme 13:

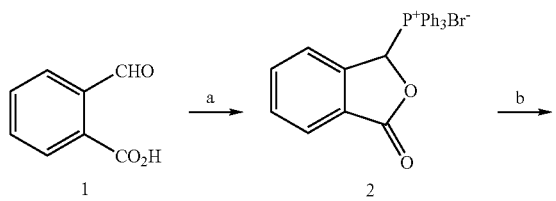

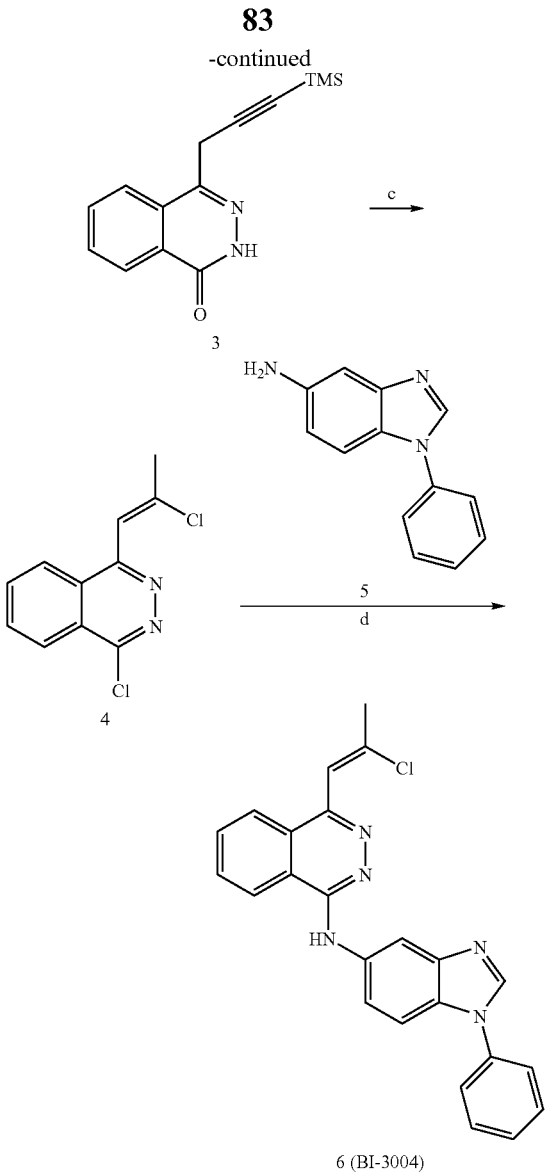

(a) PPh3, HBr, AcOH, 90° C., 1.83 h (50%). (b) (i) 3-Trimethylsilylpropynal, Et₃N, tetrahydrofuran, 77-80° C., 2 h, room temperature, 17 h; (ii) H₂NNH₂•H₂O, ethanol, 90° C., 5 h (63%). (c) POCl₃, 112-120° C., 4 h(40%). (d) 5, i-PrOH, 95° C., 2 h (43%).

4-[1-(Trimethylsilyl)prop-2-ynyl]-1(2H)-phthalazin-1-one (3). A reported procedure (Ishida 2006) is adapted. A suspension of (3-phthalidyl)triphenylphosphonium bromide (Howe 1973) (2) (503 mg, 1.06 mmol), which had been prepared from 1,3-trimethylsilylpropynal (100 mg, 1.06 mmol), and Et₃N (148 μL, 1.06 mmol) in tetrahydrofuran (8 mL) is stirred for 1 h, then at reflux (80° C.) for 2 h, and a room temperature for 16 h, and then filtered. A mixture of the residue obtained from concentration of the filtrate, hydrazine monohydrate (55 μL, 1.14 mmol), and ethanol (8 mL) is heated at reflux (90° C.) for 5 h. Solvent is removed at reduced pressure, and the residue is diluted with water (20 mL) and extracted (ethyl acetate). The residue obtained on work-up is chromatographed (20% to 50% ethyl acetate/hexane) to give 172 mg (63%) of 3 as a cream solid, mp 198-200° C. IR 2903, 1694, 1122 cm⁻¹; ¹H NMR δ 0.15 (s, 9H, TMS), 3.91 (s, 2H, CH₂), 7.79-7.93 (m, 2H, 6,7-PhthH), 8.08 (dd, J=8.1 Hz, 1.2 Hz, 1H, 5-PhthH), 8.50 (dd, J=7.8 Hz, 1.8 Hz, 1H, 8-PhthH), 10.25 ppm (bs, 1H, NH). HRMS calcd $C_{14}H_{16}N_2OSi$ [M+H]⁺ 257.1105. found 257.1109.

1-Chloro-4-(2-chloroprop-1E-enyl)phthalazine (4). A solution of 4-[1-(trimethylsilyl)prop-2-ynyl]-1(2H)-phthalazin-1-one (3) (168 mg, 0.65 mmol) in POCl₃ (5 mL) is heated at reflux for 4 h and then concentrated by azeotroping twice (toluene) to remove unreacted POCl₃. The residue is diluted with sat. Na₂CO₃ and extracted with dichloromethane and Ethyl acetate. The residue obtained on concentration is purified by chromatography (16% to 50% ethyl acetate/hexane) to give 53 mg (40%) of 4 as a cream solid, mp 118-120° C. IR 2916, 1639, 1287 cm⁻¹; ¹H NMR (CDCl₃) δ 2.56 (d, J=1.2 Hz, 3H, CH₃), 7.23 (q, J=1.2 Hz, 1H, CH), 7.98-8.05 (m, 2H, 6,7-PhthH), 8.08-8.16 (m, 1H, 5-PhthH), 8.30-8.40 ppm (m, 1H, 8-PhthH). HRMS calcd $C_{11}H_8Cl_2N_2$ [M+H]⁺ 239.0137 found 239.0147.

1-Phenyl-5-[4-(2-chloroprop-1E-enyl)-1-phthalazinyl]aminobenzimidazole (6, BI-3004). A solution of 1-chloro-4-(2-chloroprop-1E-enyl)phthalazine (4) (50 mg, 0.25 mmol) and 5-amino-1-phenylbenzimidazole (5) (28 mg, 0.14 mmol) in i-PrOH (3.5 mL) is stirred at 95° C. under argon for 2 h, then concentrated, diluted with sat. Na₂CO₃, and extracted with CHCl₃. The residue obtained on workup is purified by chromatography (0% to 9% methanol/ethyl acetate) to give 40 mg (43%) of 6 (BI-3004) as a yellow solid, mp 273-275° C. IR 3341, 1637, 1285 cm⁻¹; ¹H NMR δ 2.46 (bs, 3H, CH₃), 7.05 (bs, 1H, CH), 7.43-8.30 ppm (m, 13H, 5,6,7,8-PhthH, 2,4,6,7-BzmdH, C₆H₅). HRMS calcd $C_{24}H_{18}ClN_5$ [M+H]⁺ 412.1323. found 412.1329

Synthesis of 3-(Prop-2-ynyl)-5-(4-phenyl-1-phthalazinyl)aminobenzimidazole (4, BI-3006), 1-Propynyl-5-(4-phenyl-1-phthalazinyl)aminobenzimidazole (5, BI-3007), and 1-(1-Phenyl[1,2,3]triazol-4-ylmethyl)-5-(4-phenyl-1-phthalazinyl)aminobenzimidazole Hydrochloride (6, BI-3042)

Scheme 14:

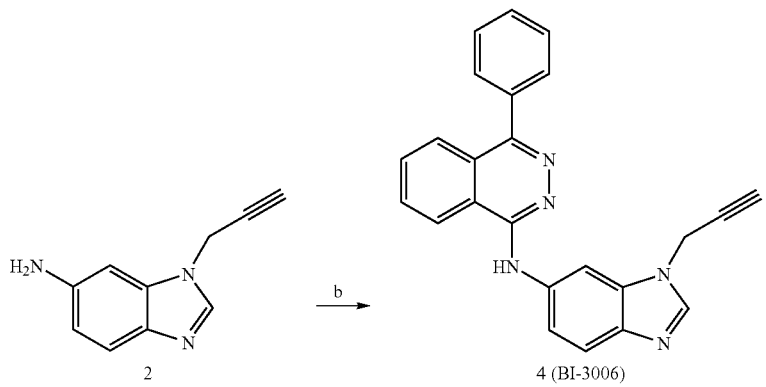

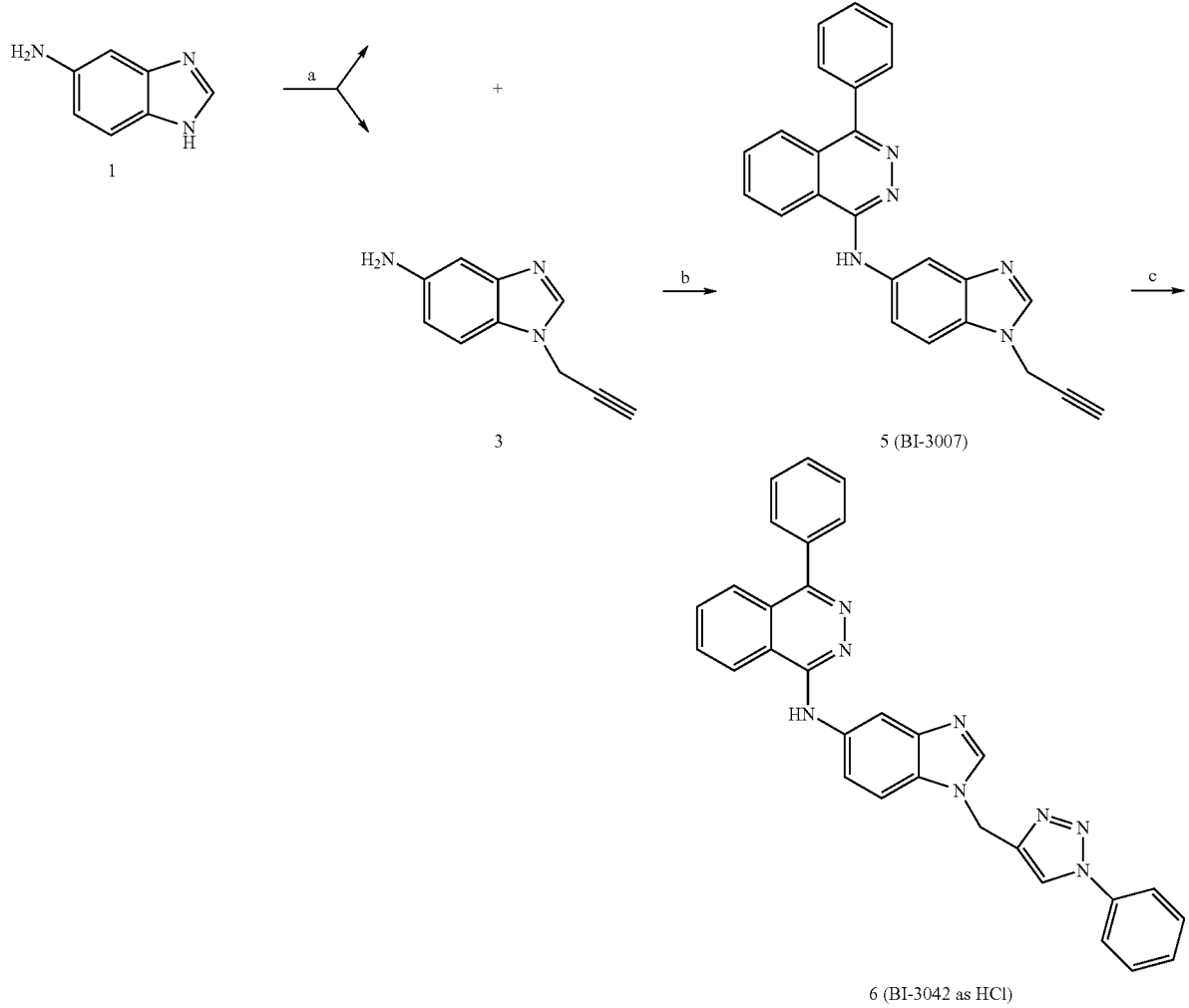

(a) Propargyl bromide, KOH, acetone, 20 h (38% for 2; 34% for 3). (b) 1-Chloro-4-phenylphthalazine, i-PrOH, 95° C., 2 h (84% for 6 (BI-3006); 99% for 5 (BI-3007)). (c) Phenyl azide, CuI, DIEA, methanol, 22 h (83%); HCl, Et$_2$O.

3-(Prop-2-ynyl)-5-aminobenzimidazole (2) and 1-(Prop-2-ynyl)-5-aminobenzimidazole (3). A suspension of 5-aminobenzimidazole (1) (266 mg, 2 mmol) and 80% propargyl bromide (2.1 mmol) in toluene (234 μL), and KOH (112 mg, 2 mmol) in acetone (14 mL) is stirred under argon for 21.5 h, concentrated, then diluted with H$_2$O (30 mL), and extracted with ethyl acetate (60 mL, 40 mL). The extract is washed (brine) and dried. After solvent removal at reduced pressure, the residue is purified on silica gel (0% to 6% methanol/ethyl acetate) to give 130 mg (38%) of 2 as a cream solid, mp 129-131° C., and 117 mg (34%) of 3 as a yellow oil. 2: IR 3272, 3051, 1630, 1504, 1226 cm$^{-1}$; $^1$H NMR (DMSO-d$_6$) δ 3.46 (t, J=2.7 Hz, 1H, CH≡C—CH$_2$), 5.01 (d, J=2.7 Hz, 2H, CH≡C—CH$_2$), 5.07 (bs, 2H, NH$_2$), 6.65 (dd, J=8.7, 2.4 Hz, 1H, 6-BenzimidH), 6.67 (d, J=2.4 Hz, 4-BenzimidH), 7.31 (d, J=8.7 Hz, 7-BenzimidH), 7.88 ppm (s, 1H, 2-BenzimidH). 3: IR 3275, 3106, 1630, 1495, 1232 cm$^{-1}$; $^1$H NMR (DMSO-d$_6$) δ 3.47 (t, J=2.4 Hz, 1H, CH≡C—CH$_2$), 4.83 (bs, 2H, NH$_2$), 5.07 (d, J=2.4 Hz, 2H, CH≡C—CH$_2$), 6.65 (dd, J=8.7, 2.1 Hz, 1H, 6-BenzimidH), 6.81 (d, J=2.1 Hz, 4-BenzimidH), 7.28 (d, J=8.7 Hz, 7-BenzimidH), 7.99 ppm (s, 1H, 2-BenzimidH).

3-(Prop-2-ynyl)-5-(4-phenyl-1-phthalazinyl)aminobenzimidazole (4, BI-3006). A solution of 1-chloro-4-phenylphthalazine (74 mg, 0.31 mmol) and 3-(prop-2-ynyl)-5-aminobenzimidazole (2) (33 mg, 0.19 mmol) in i-PrOH (5 mL) is stirred at 95° C. under argon for 2 h and then concentrated. The residue is diluted with sat. NaHCO$_3$ (15 mL) and extracted with CHCl$_3$ (60 mL). The extract is washed (brine) and dried. After solvent removal at reduced pressure, the residue is purified on silica gel (1% to 10% methanol/ethyl acetate) to give 61 mg (84%) of 4 (BI-3006) as a light-yellow solid, mp 225-227° C. IR 3295, 2822, 1618, 1488, 1408 cm$^{-1}$; $^1$H NMR (CDCl$_3$) δ 2.51 (t, J=2.4 Hz, 1H, CH≡CCH$_2$), 4.96 (d, J=2.4 Hz, 2H, CH≡CCH$_2$), 7.22 (d, J=7.5, 1H, 6-BenzimidH), 7.50-7.75 (m, 5H, C$_6$H$_5$), 7.76-7.99 (m, 5H, 4-BenzimidH, 7-BenzimidH, 5,6,7-PhthH), 8.04 (s, 1H, 2-BenzimidH), 8.12-8.31 ppm (m, 1H, 8-PhthH).

1-(Prop-2-ynyl)-5-(4-phenyl-1-phthalazinyl)aminobenzimidazole (5, BI-3007). A solution of 1-chloro-4-phenylphthalazine (81 mg, 0.34 mmol) and 1-(prop-2-ynyl)-5-aminobenzimidazole (3) (36 mg, 0.21 mmol) in i-PrOH (6 mL) is stirred at 95° C. under argon for 2 h and then concentrated. The residue is diluted with sat. NaHCO$_3$ (15 mL) and extracted with CHCl$_3$ (60 mL). The extract is washed (brine) and dried. After solvent removal at reduced pressure, the residue is purified on silica gel (1% to 10% methanol/ethyl acetate) to give 78 mg (99%) of 5 (BI-3007) as a yellow solid, mp 227-229° C. IR 3304, 2965, 1495, 1401 cm$^{-1}$; NMR (DMSO-d$_6$) δ 3.54 (t, J=2.4 Hz, 1H, CH≡CCH$_2$), 4.83 (bs, 2H, NH$_2$), 5.24 (d, J=2.4 Hz, 2H, CH≡CCH$_2$), 7.52-7.62 (m, 3H, PhH), 7.64 (d, J=8.7 Hz, 1H, 7-BenzimidH), 7.65-7.71 (m, 2H, PhH), 7.79 (dd, J=8.7, 1.8 Hz, 1H, 6-BenzimidH), 7.89 (d, J=8.1 Hz, 1H, 5-PhthH), 7.91-7.98 (m, 1H, 6-PhthH), 7.99-8.08 (m, 1H, 7-PhthH), 8.25 (s, 1H, 2-BenzimidH), 8.34 (d, J=1.8 Hz, 1H, 4-BenzimidH), 8.72 (d, J=8.1 Hz, 1H, 8-PhthH), 9.32 ppm (s, 1H, NH).

1-(1-Phenyl[1,2,3]triazol-4-yl)methyl-5-(4-phenyl-1-phthalazinyl)amino-benzimidazole (6, BI-3042). A suspension of 1-(prop-2-ynyl)-5-(4-phenyl-1-phthalazinyl)aminobenzimidazole (5, BI-3007) (18.5 mg, 0.049 mmol), phenyl azide (6.0 mg, 0.049 mmol), CuI (4.0 mg, 0.019 mmol), and DIEA (88 μL, 0.49 mmol) in methanol (2.1 mL) is stirred for 22 h and then concentrated at reduced pressure. The residue is purified on silica gel (3% to 10% methanol/dichloromethane) to give 20 mg (83%) of 6 (BI-3042) as a cream solid, mp 158-160° C. IR 3293, 2998, 1493, 1405 cm$^{-1}$; $^1$H NMR (DMSO-d$_6$) δ 5.69 (s, 2H, CH$_2$), 7.45-7.79 (m, 11H, 1-PhH, 4-PhH, 7-BenzimidH), 7.87-8.06 (m, 5H, TriazH, 6-BenzimidH, 5,6,7-PhthH), 8.34 (bs, 1H, NH), 8.69 (d, J=8.1 Hz, 8-PhthH), 8.93 (s, 1H, 2-BenzimidH), 9.29 ppm (s, 1H, 4-BenzimidH).

Synthesis of 1-(2-Prop-2-ynyloxy)phenyl)-5-(4-methyl-1-phthalazinyl)aminobenzimidazole (6, BI-3017), 1-[2-(1-Phenyl[1,2,3]triazole-4-ylmethoxy]phenyl-5-(4-methyl-1-phthalazinyl)aminobenzimidazole Hydrochloride (7, BI-3043), and 1-(2-Hydroxyphenyl)-5-(4-methyl-1-phthalazinyl) aminobenzimidazole (8, BI-3019)

Scheme 15:

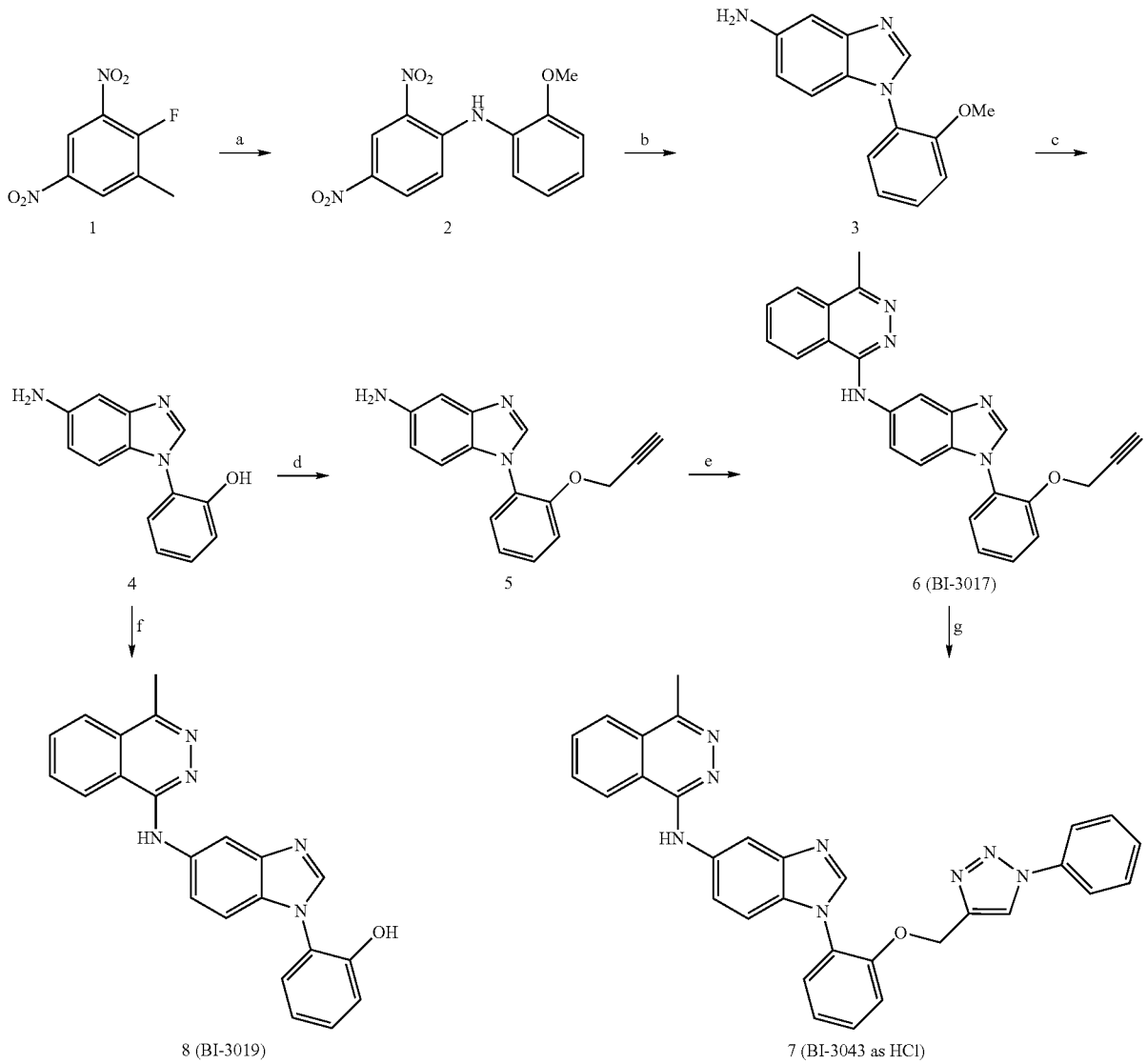

(a) 2-Methoxyaniline, K$_2$CO$_3$, tetrahydrofuran, 18.75 h (97%). (b) (i) 10% Pd/C, Ethyl acetate, 91 h; (ii) 4 N HCl, formic acid, 110° C., 2.75 h (100%). (c) BBr$_3$, dichloromethane, 4 h; aq. NaHCO$_3$ (78%). (d) Propargyl bromide, K$_2$CO$_3$, acetone, 70° C., 18.5 h (39%). (e) 1-Chloro-4-methylphthalazine, i-PrOH, 95° C., 2.75 h (89%). (f) Phenyl azide, CuI, DIEA, methanol, 23.75 h (55%); HCl, Et$_2$O. (g) 1-Chloro-4-methylphthalazine, i-PrOH, 95° C., 3.3 h (82%).

2,4-Dinitro-N-(2-methoxyphenyl)benzamine (2). To a solution of 2,4-dinitrofluorobenzene (1) (1.86 g, 10 mmol) and 2-methoxyaniline (1.24 mL, 11 mmol) in anhydrous tetrahydrofuran (25 mL) is added $K_2CO_3$ (2.9 g, 21 mmol). The reaction mixture is stirred under argon for 18.75 h and filtered ($CHCl_3$ rinse, 4×). The filtrate is concentrated at reduced pressure, and the residue is crystallized (ethanol) to give 2.81 g (97%) of 2 as an orange solid, mp 165°-166° C. [lit.: 165° C.](van Opstall, 1933). IR 3338, 2926, 1522, 1223 $cm^{-1}$; $^1H$ NMR ($CDCl_3$) δ 3.86 (s, 3H, $OCH_3$), 7.02-7.07 (m, 2H, 4′,6′-ArH), 7.09 (d, J=9.1 Hz, 1H, 6-ArH), 7.30-7.35 (m, 2H, 3′,5′-ArH), 8.15 (dd, J=9.1 Hz, 2.4 Hz, 1H, 5-ArH), 9.17 (d, J=2.4 Hz, 1H, 3-ArH), 9.86 ppm (bs, 1H, NH).

5-Amino-1-(2-methoxyphenyl)benzimidazole (3). To a solution of 2,4-dinitro-N-(2-methoxyphenyl)benzamine (2) (2.72 g, 9.4 mmol) in ethyl acetate (95 mL) is added 10% Pd/C (325 mg). The reaction mixture is stirred under $H_2$ for 91 h and then filtered through Celite® (Ethyl acetate rinse). After solvent removal at reduced pressure, the residue is used in the next step without further purification.

The solution of the residue and formic acid (1.5 mL, 38 mmol) in 4 N HCl (32 mL) is heated at 110° C. under argon for 2.75 h. The reaction mixture is cooled to room temperature, brought to pH 12 with NaOH pellets, and extracted with ethyl acetate (150 mL, 100 mL, and 50 mL). The extract is washed (brine) and dried. After solvent removal at reduced pressure, the residue is purified on silica gel (1% to 6% methanol/ethyl acetate) to give 2.3 g (100%) of 3 as a red-brown solid, mp 48-50° C. IR 3323, 2951, 1510, 1260 $cm^{-1}$; $^1H$ NMR ($CDCl_3$) δ 2.98 (bs, 2H, $NH_2$), 3.83 (s, 3H, $CH_3$), 6.74 (dd, J=8.4 Hz, 1.8 Hz, 1H, 6-BenzimidH), 7.10-7.20 (m, 4H, 4,7-BenzimidH, 3,5-PhH), 7.40-7.49 (m, 2H, 4,6-PhH), 8.00 ppm (s, 1H, 2-BenzimidH). HRMS calcd $C_{14}H_{13}N_3O$ $[M+H]^+$ 240.1131. found 240.1133.

5-Amino-1-(2-hydroxyphenyl)benzimidazole (4). A solution of 5-amino-1-(2-methoxyphenyl)benzimidazole (3) (829 mg, 3.46 mmol), 1.0 M boron tribromide (10 mmol) in dichloromethane (10 mL), and dichloromethane (35 mL) is stirred under argon for 4 h, quenched with sat. $NaHCO_3$ (55 mL), and extracted with ethyl acetate (150 mL, 100 mL, and 50 mL). The extract is washed (brine) and dried. After solvent removal at reduced pressure, the crude material is washed (dichloromethane) to give 604 mg (78%) of 4 as a brown solid, mp 202-203° C. IR 3346, 2956, 1512, 1256 $cm^{-1}$; $^1H$ NMR (DMSO-$d_6$) δ 5.18 (bs, 2H, $NH_2$), 6.65 (d, J=8.4 Hz, 1H, 6-BenzimidH), 6.90 (s, 1H, 4-BenzimidH), 6.99 (d, J=8.4 Hz, 1H, 7-BenzimidH), 7.02 (d, J=7.8 Hz, 1H, 3-PhH), 7.13 (d, J=7.8 Hz, 1H, 5-ArH), 7.32 (d, J=7.8 Hz, 1H, 4-PhH), 7.38 (d, J=7.8 Hz, 1H, 6-PhH), 8.13 (s, 1H, 2-BenzimidH), 10.15 ppm (s, 1H, OH). HRMS calcd $C_{13}H_{11}N_3O$ $[M+H]^+$ 226.0975. found 226.0975.

5-Amino-1-[2-(prop-2-ynyloxy)phenyl]benzimidazole (5). A suspension of 5-amino-1-(2-hydroxyphenyl)benzimidazole (4) (499 mg, 2.21 mmol), 80% propargyl bromide (2.43 mmol) in toluene (271 μL), $K_2CO_3$ (398 mg, 2.88 mmol), and acetone (15 mL) is stirred at 70° C. under argon for 18.5 h and then cooled to room temperature. The mixture is concentrated, diluted with $H_2O$ (35 mL), and extracted with ethyl acetate (100 mL and 50 mL). The extract is washed (brine) and dried. After solvent removal at reduced pressure, the residue is purified on silica gel (2% to 7% methanol/ethyl acetate) to give 213 mg (39%) of 5 as a light-brown solid, mp 40-42° C. IR 3379, 2966, 1512, 1239 $cm^{-1}$; $^1H$ NMR ($CDCl_3$) δ 2.51 (t, J=2.4 Hz, 1H, C≡CH), 3.09 (bs, 2H, $NH_2$), 4.68 (d, J=2.4 Hz, 2H, $CH_2$C≡CH), 6.74 (dd, J=8.4 Hz, 2.1 Hz, 1H, 6-BenzimidH), 7.14 (d, J=8.4 Hz, 1H, 7-BenzimidH), 7.16 (d, J=2.1 Hz, 1H, 4-BenzimidH), 7.19 (m, 1H, 3-PhH), 7.29 (m, 1H, 5-PhH), 7.42-7.49 (m, 2H, 4,6-PhH), 8.01 ppm (s, 1H, 2-BenzimidH). HRMS calcd $C_{16}H_{13}N_3O$ $[M+H]^+$ 264.1137. found 264.1129.

1-[2-(Prop-2-ynyloxy)phenyl]-5-(4-methyl-1-phthalazinyl)aminobenzimidazole (6, BI-3017). A solution of 1-chloro-4-methylphthalazine (38 mg, 0.21 mmol) and 5-amino-1-[2-(prop-2-ynyloxy)phenyl]benzimidazole (5) (37 mg, 0.15 mmol) in i-PrOH (3.8 mL) is stirred at 95° C. under argon for 2.75 h, then cooled to room temperature, and concentrated. The residue is diluted with sat. $NaHCO_3$ (15 mL) and extracted with $CHCl_3$ (60 mL). The extract is washed (brine) and dried. After solvent removal at reduced pressure, the residue is purified on silica gel (1% to 10% methanol/ethyl acetate) to give 54 mg (89%) of 6 (BI-3017) as a light-yellow solid, mp 113-115° C. IR 3342, 3065, 1509, 1220 $cm^{-1}$; $^1H$ NMR (DMSO-$d_6$) δ 2.80 (s, 3H, $CH_3$), 3.63 (t, J=2.4 Hz, 1H, C≡CH), 4.93 (d, J=2.4 Hz, 2H, $CH_2$C≡CH), 7.22-7.29 (m, 2H, 3,5-ArH), 7.46 (d, J=7.8 Hz, 1H, 6-BenzimidH), 7.54-7.61 (m, 2H, 4,6-ArH), 7.72 (d, J=7.8 Hz, 1H, 7-BenzimidH), 7.96-8.05 (m, 2H, 6,7-PhthH), 8.10-8.15 (m, 1H, 5-PhthH), 8.31 (s, 1H, 2-BenzimidH), 8.42 (s, 1H, 4-BenzimidH), 8.62-8.66 (m, 1H, 8-PhthH), 9.12 ppm (s, 1H, NH). HRMS calcd $C_{25}H_{19}N_5O$ $[M+H]^+$ 406.1662. found 406.1665.

1-(2-Hydroxyphenyl)-5-(4-methyl-1-phthalazinyl)aminobenzimidazole (8, BI-3019). A solution of 1-chloro-4-methylphthalazine (25 mg, 0.14 mmol) and 5-amino-1-(2′-hydroxyphenyl)benzimidazole (4) (22 mg, 0.10 mmol) in i-PrOH (3.0 mL) is stirred at 95° C. under argon for 3.3 h and cooled to room temperature and concentrated. The residue is diluted with sat. $NaHCO_3$ (15 mL) and extracted with $CHCl_3$ (60 mL). The cream solid suspended in aqueous layer is isolated by filtration ($H_2O$ rinse), dissolved in acetone, which is then triturated with pentane. The resulting precipitate is isolated by filtration and dried at reduced pressure to give 30 mg (82%) of 8 (BI-3019) as a cream solid, mp >260° C. IR 3335, 2961, 1621, 1420 $cm^{-1}$; $^1H$ NMR (DMSO-$d_6$) δ 2.78 (s, 3H, $CH_3$), 6.82 (d, J=8.1 Hz, 1H, 5-ArH), 7.02 (d, J=8.1 Hz, 1H, 3-ArH), 7.23 (d, J=8.1 Hz, 1H, 4-ArH), 7.28 (d, J=8.7 Hz, 1H, 7-BenzimidH), 7.36 (d, J=8.1 Hz, 1H, 6-ArH), 7.67 (d, J=8.7 Hz, 1H, 6-BenzimidH), 7.94-8.01 (m, 2H, 6,7-PhthH), 8.09 (m, 1H, 5-PhthH), 8.29 (s, 1H, 2-BenzimidH), 8.39 (s, 1H, 4-BenzimidH), 8.63 (m, 1H, 8-PhthH), 9.08 ppm (s, 1H, NH).

1-[2-(1-Phenyl[1,2,3]triazol-4-yl)methoxy]phenyl-5-(4-methyl-1-phthalazinyl)aminobenzimidazole (7, BI-3043). A suspension of 1-[2-(prop-2-ynyloxy)phenyl]-5-(4-methyl-1-phthalazinyl)aminobenzimidazole (6, BI-3017) (14 mg, 0.035 mmol), phenyl azide (4.1 mg, 0.035 mmol), CuI (2.7 mg, 0.014 mmol), and DIEA (61 μL, 0.35 mmol) in methanol (1.5 mL) is stirred for 23.75 h and then concentrated at reduced pressure. The residue is purified on silica gel (3% to 9% methanol/dichloromethane) to give 10 mg (55%) of 7 (BI-3043) as a cream solid, mp 155-157° C. IR 3303, 3065, 1679, 1505 $cm^{-1}$; $^1H$ NMR ($CD_3OD$) δ 2.77 (s, 3H, $CH_3$), 5.25 (s, 2H, $OCH_2$), 7.14-7.74 (m, 12H, PhH, TriazH, 3,4,5,6-ArH, 6,7-BenzimidH), 7.78-8.45 (m, 6H, 2,4-BenzimidH, 5,6,7,8-PhthH).

Synthesis of 1-(4-Hydroxyphenyl)-5-(4-methyl-1-phthalazinyl)aminobenzimidazole (5, BI-3020) and 1-[4-(Prop-2-nyloxy)phenyl]-5-(4-methyl-1-phthalazinyl)aminobenzimidazole (6, BI-3025)

Scheme 16:

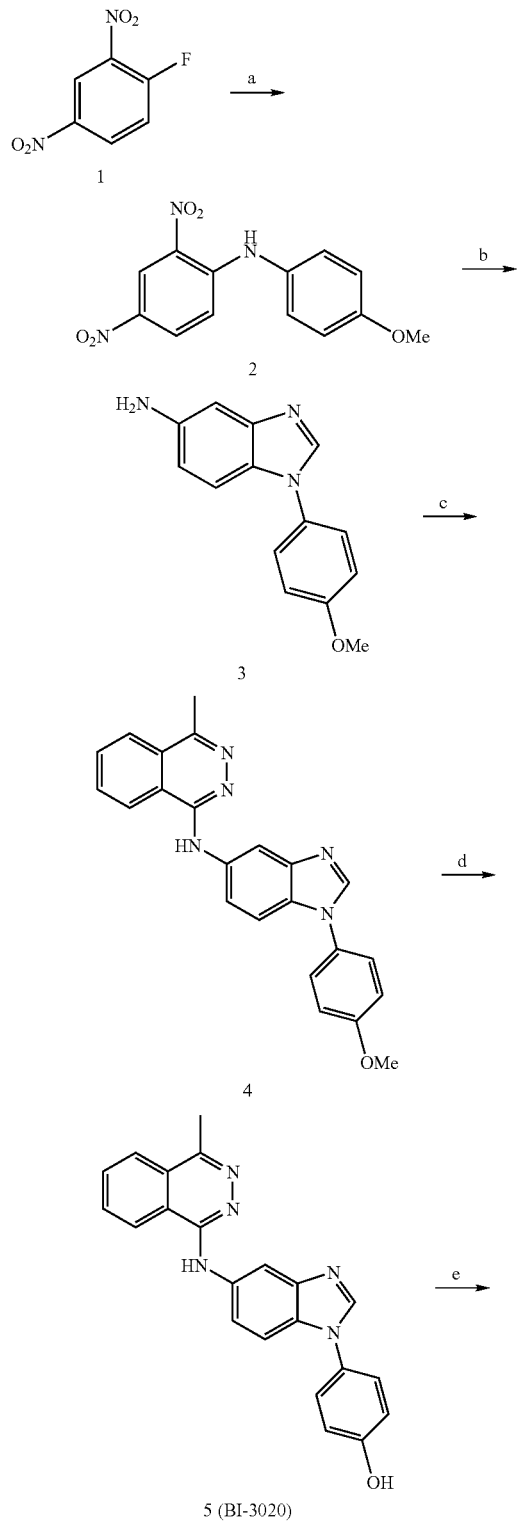

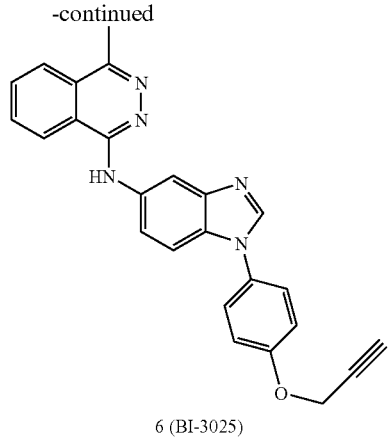

6 (BI-3025)

(a) 4-Methoxyaniline, K₂CO₃, tetrahydrofuran, 23 h (98%). (b) (i) 10% Pd/C, Ethyl acetate, 69 h; (ii) 4 N HCl, formic acid, 110° C., 2.75 h, (91%). (c) 1-Chloro-4-methylphthalazine, i-PrOH, 95° C., 20 h (100%). (d) BBr₃, dichloromethane, 24 h; aq. NaHCO₃ (95%). (e) 5, NaH, DMF, 0° C., 0.5 h, room temperature, 0.5 h; propargyl bromide, 4 h (11%).

2,4-Dinitro-N-(4-methoxyphenyl)benzamine (2). To a solution of 2,4-dinitrofluorobenzene (1) (1.86 g, 10 mmol) and 4-methoxyaniline (1.35 g, 11 mmol) in anhydrous tetrahydrofuran (25 mL) is added K₂CO₃ (2.9 g, 21 mmol). The reaction mixture is stirred under argon for 23 h and filtered (CHCl₃ rinse, 4×80 mL). The filtrate is concentrated at reduced pressure, and the residue is crystallized (ethanol) to give 2.82 g (98%) of 2 as a brown solid, mp 141°-143° C. [lit.: 141° C.](Simonov, A. M. 1959). IR 3342. 2930, 1518, 1235 cm$^{-1}$; $^1$H NMR (CDCl₃) δ 3.53 (s, 3H, OCH₃), 6.97-7.03 (m, 3H, 6-ArH, 3,5-ArH), 8.15 (dd, J=10.3, 3.0 Hz, 1H, 5-ArH), 9.16 (d, J=3.0 Hz, 1H, 3-ArH), 9.86 ppm (bs, 1H, NH).

5-Amino-1-(4-methoxyphenyl)benzimidazole (3). To a solution of 2,4-dinitro-N-(4-methoxyphenyl)benzamine (2) (2.65 g, 9.2 mmol) in ethyl acetate (100 mL) is added 10% Pd/C (320 mg). The reaction mixture is stirred under for 69 h and then filtered through Celite® (Ethyl acetate rinse). After solvent removal at reduced pressure, the residue is used for the next reaction without further purification.

The solution of the residue and formic acid (1.2 mL, 32 mmol) in 4 N HCl (31 mL) is heated at 110° C. under argon for 2.75 h, cooled to room temperature, brought to pH 12 with NaOH (pellets), and extracted with ethyl acetate (150 mL, 100 mL, and 50 mL). The extract is washed (brine) and dried. After solvent removal at reduced pressure, the residue is purified on silica gel (2% to 8% methanol/ethyl acetate) to give 2.0 g (91%) of 3 as a brown solid, mp 44-45° C. [lit.: 122-123° C.](Kada, R. 1966). IR 3308, 3099, 1515, 1248 cm$^{-1}$; $^1$H NMR (CDCl₃) 3.34 (bs, 2H, NH₂), 3.91 (s, 3H, CH₃), 6.76 (dd, J=8.4 Hz, 2.1 Hz, 1H, 6-BenzimidH), 7.08 (d, J=8.7 Hz, 2H, 3,5-PhH), 7.17 (d, J=2.1 Hz, 1H, 4-BenzimidH), 7.28 (d, J=8.4 Hz, 1H, 7-BenzimidH), 7.41 (d, J=8.7 Hz, 2H, 2,6-PhH), 7.96 ppm (s, 1H, 2-BenzimidH).

1-(4-Methoxy)phenyl-5-(4-methyl-1-phthalazinyl)aminobenzimidazole (4). A solution of 1-chloro-4-methylphthalazine (100 mg, 0.56 mmol) and 5-amino-1-(4-methoxy)phenylbenzimidazole (3) (96 mg, 0.40 mmol) in i-PrOH (10 mL) is stirred at 95° C. under argon for 20 h, cooled to room temperature, and concentrated at reduced pressure. The residue is diluted with sat. NaHCO₃ (15 mL) and extracted with CHCl₃ (120 mL). The extract is is washed (brine) and dried. After solvent removal at reduced pressure, the residue is purified on silica gel (1% to 10% methanol/ethyl acetate) to give 162 mg (100%) of 4 as a yellow solid, mp 220-222° C. IR 3340, 3048, 1508, 1245 cm$^{-1}$; $^1$H NMR (DMSO-d₆) δ 2.79 (s, 3H, CH₃), 3.87 (s, 3H, OCH₃), 7.20 (d, J=8.7 Hz, 2H, 3,5-PhH), 7.52 (d, J=9.0 Hz, 1H, 7-BenzimidH), 7.64 (d, J=8.7 Hz, 2H, 2',-PhH), 7.76 (dd, J=9.0 Hz, 1.5 Hz, 1H, 6-BenzimidH), 7.96-8.05 (m, 2H, 6,7-PhthH), 8.10-8.14 (m, 1H, 5-PhthH), 8.44 (s, 1H, 2-BenzimidH), 8.46 (d, J=1.5 Hz, 1H, 4-BenzimidH), 8.62-8.66 (m, 1H, 8-PhthH), 9.12 ppm (s, 1H, NH). HRMS calcd $C_{23}H_{19}N_5O$ [M+H]⁺ 382.1662. found 382.1664.

1-(4-Hydroxy)phenyl-5-(4-methyl-1-phthalazinyl)aminobenzimidazole (5, BI-3020). A solution of 1-(4-methoxy)phenyl-5-(4-methyl-1-phthalazinyl)aminobenzimidazole (4) (145 mg, 0.38 mmol), 1.0 M boron tribromide (1.5 mmol) in dichloromethane (1.5 mL), and dichloromethane (5 mL) is stirred under argon for 24 h, quenched with sat. NaHCO₃ (20 mL), diluted with CHCl₃ (150 mL), and stirred for 10 min. The solid in the aqueous layer is collected by filtration and dried at reduced pressure to give 133 mg (95%) of 5 (BI-3020) as a cream solid, mp 259-262° C. IR 3345, 3057, 1510, 1233 cm⁻¹; ¹H NMR (DMSO-d₆) δ 2.78 (s, 3H, CH₃), 7.01 (d, J=8.4 Hz, 2H, 3,5-PhiI), 7.47 (d, J=8.4 Hz, 1'-1,7-BenzimidH), 7.49 (d, J=8.4 Hz, 2H, 2,6-PhH), 7.74 (d, J=8.4 Hz, 1H, 6-BenzimidH), 7.94-8.01 (m, 2H, 6",7"-PhthH), 8.09-8.13 (m, 1H, 5-PhthH), 8.39 (s, 1H, 2-BenzimidH), 8.44 (s, 1H, 4-BenzimidH), 8.61-8.66 (m, 1H, 8-PhthH), 9.12 (s, 1H, NH), 9.92 ppm (bs, 1H, OH). HRMS calcd $C_{22}H_{17}N_5O$ [M+H]⁺ 368.1506. found 368.1519.

1-[4-(Prop-2-ynyloxy)phenyl]-5-(4-methyl-1-phthalazinyl)aminobenzimidazole (6, BI-3025). To the solution of 1-(4-hydroxy)phenyl-5-(4-methyl-1-phthalazinyl)aminobenz-imidazole (5, BI-3020) (84 mg, 0.23 mmol) in anhydrous DMF (2 mL) at 0° C. under argon is added 60% NaH (0.25 mmol) in mineral oil (10 mg). The suspension is stirred at 0° C. for 0.5 h and room temperature for 0.5 h before 80% propargyl bromide (0.25 mmol) in toluene (28 µL) is added. The reaction mixture is stirred for 4 h, quenched with sat NaHCO₃ (10 mL), and extracted with ethyl acetate (50 mL and 30 mL). The extract is washed (brine) and dried. After solvent removal at reduced pressure, the residue is purified on silica gel (1% to 9% methanol/ethyl acetate) to give 10 mg (11%) of 6 (BI-3025) as a light-purple solid, mp 120-123° C. IR 3337, 3063, 1513, 1218 cm⁻¹; ¹H NMR (CDCl₃) δ 2.62 (t, J=2.4 Hz, 1H, C≡CH), 2.76 (s, 3H, CH₃), 4.81 (d, J=2.4 Hz, 2H, CH₂C≡CH), 7.19 (d, J=9.0 Hz, 2H, 3,5-ArH), 7.45 (d, J=8.7 Hz, 1H, 7-BenzimidH), 7.47 (d, J=9.0 Hz, 2H, 2,6-PhH), 7.52 (m, 1H, 6-PhthH), 7.75-7.87 (m, 3H, 4,6-BenzimidH, 7-PhthH), 7.91 (d, J=7.8 Hz, 1H, 5-PhthH), 8.06 (s, 1H, 2-BenzimidH), 8.24 ppm (d, J=7.8 Hz, 1H, 8-PhthH).

Synthesis of 5-(4-Methyl-1-phthalazinyl)amino-1-phenylbenzimidazole Hydrochloride (2, BI-3031) and 5-[(4-Methyl-1-phthalazinyl)(prop-2-ynyl) amino]-1-phenylbenzimidazole (3, BI-3032)

Scheme 17:

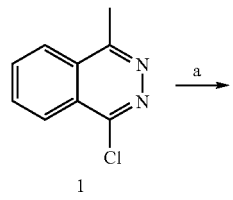

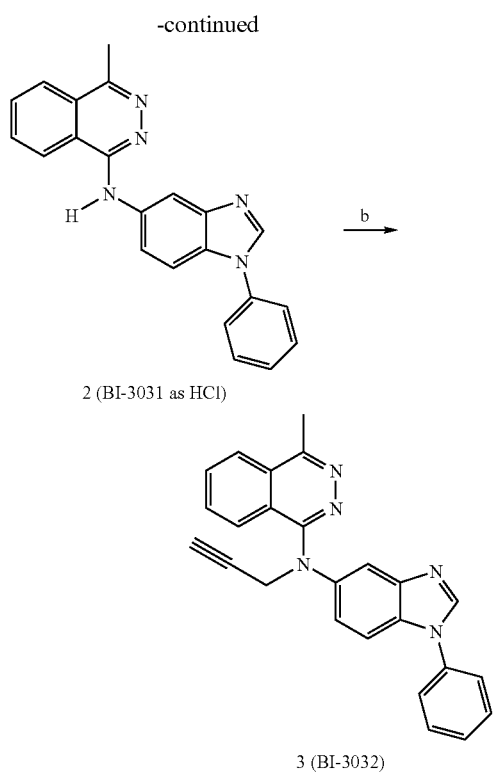

(a) 5-Amino-1-phenylbenzimidazole, i-PrOH, 95° C., 2.5 h (97%); HCl, Et₂O.
(b) 2, KN(TMS)₂, DMF, 1 h; propargyl bromide, 4 h (56%).

5-(4-Methyl-1-phthalazinyl)amino-1-phenylbenzimidazole (2, BI-3031). A solution of 1-chloro-4-methylphthalazine (180 mg, 0.85 mmol) and 5-amino-1-phenylbenzimidazole (4) (132 mg, 0.63 mmol) in i-PrOH (19 mL) is stirred at 95° C. under argon for 2.5 h, cooled to room temperature, and concentrated at reduced pressure. The residue is diluted with sat. NaHCO₃ (15 mL) and extracted with CHCl₃ (120 mL). The extract is washed (brine) and dried. After solvent removal at reduced pressure, the residue is purified on silica gel (1.5% to 10.7% methanol/ethyl acetate) to give 215 mg (97%) of 2 (BI-3031) as a light-yellow solid, mp 239-241° C. IR 3320, 2924, 1502 cm⁻¹; ¹H NMR (CDCl₃ and CD₃OD) δ 7.23-7.42 (m, 7H, 6,7-BenzimidH, 1-C₆H₅), 7.66-7.76 (m, 3H, 6',7',-PhthH, 4-BenzimidH), 7.81 (m, 1H, 5'-PhthH), 7.95 (s, 1H, 2-BenzimidH), 8.14 ppm (m, 1H, 8'-PhthH).

5-[(4-Methyl-1-phthalazinyl(prop-2-ynyl)amino]-1-phenylbenzimidazole (3, BI-3032). A solution of 5-(4-methyl-1-phthalazinyl)amino-1-phenylbenzimidazole (2, BI-3031) (35 mg, 0.1 mmol) and 0.5 M KN(TMS)₂ in toluene (0.6 mL, 0.6 mmol) in anhydrous DMF (0.6 mL) is stirred under argon for 1 h. To this solution is then added 80% propargyl bromide (0.3 mmol) in toluene (33 µL). The reaction mixture is stirred for 4 h, diluted with H₂O (20 mL), and extracted with ethyl acetate (60 mL). The extract is washed (brine) and dried. After solvent removal at reduced pressure, the residue is purified on silica gel (1% to 7.4% methanol/ethyl acetate) to give 22 mg (56%) of 3 (BI-3032) as a cream solid, mp 50-53° C. IR 2911, 1438, 1227 cm⁻¹; ¹H NMR (CDl₃) δ 2.23 (t, J=2.1 Hz, 1H, CH≡C—CH₂), 2.96 (s, 3H, CH₃), 4.95 (d, J=2.1 Hz, CH≡C—CH₂), 7.16 (dd, J=8.7 Hz, 1.8 Hz, 1H, 7-BenzimidH), 7.40-7.69 (m, 8H, 6-BenzimidH, 1-C₆H₅, 6',7'-PhthH), 7.71 (d, J=1.8 Hz, 1H, 4-BenzimidH), 7.96-8.05 (m, 2H, 5',8',-PhthH), 8.13 ppm (s, 1H, 2-BenzimidH).

Synthesis of 5-(4-Hydroxy-1-phthalazinyl)amino-1-phenylbenzimidazole (3, BI-3034)

Scheme 18:

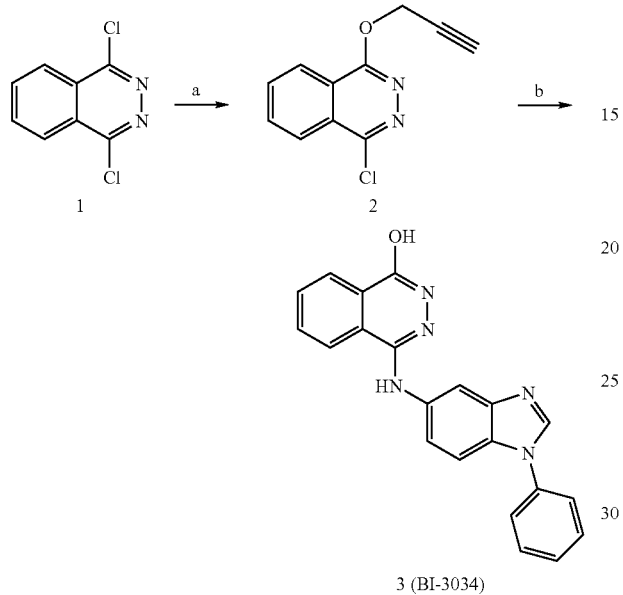

3 (BI-3034)

(a) [2-Propynol, Na]; 1, 121-133° C., 2 h (15%).
(b) 5-Amino-1-phenylbenzimidazole, i-PrOH, 95° C., 43 h (93%).

1-Chloro-4-(prop-2-ynyloxy)phthalazine (2). To 2-propynol (3 mL) is slowly added sodium (70 mg, 3.04 mmol) followed by 1,4-dichlorophthalazine (400 mg, 2.01 mmol). The brown suspension obtained is stirred under argon for 2 min and then heated at 121-133° C. for 2 h. Excess 2-propynol is removed under vacuum, and the residue is diluted with cold water and then extracted with CHCl$_3$ (120 mL). The extract is washed (brine) and dried. After solvent removal at reduced pressure, the residue is purified on silica gel (25% to 50% ethyl acetate/hexane) to give 66 mg (15%) of 2 as a cream solid, mp 134-136° C. IR 2882, 1404, 1292 cm$^{-1}$; $^1$H NMR (CDCl$_3$) δ 2.61 (t, J=2.4 Hz, 1H, C≡CH), 5.33 (d, J=2.4 Hz, 2H, CH$_2$C≡CH), 7.94-8.04 (m, 2H, 6,7-PhthH), 8.24 (m, 5-PhthH), 8.31 ppm (m, 8-PhthH).

5-(4-Hydroxy-1-phthalazinyl)amino-1-phenylbenzimidazole (3, BI-3034). A solution of 1-chloro-4-(prop-2-ynyloxy)phthalazine (2) (44 mg, 0.20 mmol) and 5-amino-1-phenylbenzimidazole (29.90 mg, 0.14 mmol) in i-PrOH (3.5 mL) is stirred at 95° C. under argon for 43 h, concentrated, diluted with sat. NaHCO$_3$ (15 mL), and extracted with CHCl$_3$ (60 mL and 3×15 mL). The extract is washed (brine) and dried. After solvent removal at reduced pressure, the residue is purified on silica gel (1% to 9.1% methanol/ethyl acetate) to give 47 mg (93%) of 3 (BI-3034) as a light-yellow solid, mp 276-278° C. IR 3350, 2942, 1443 cm$^{-1}$; $^1$H NMR (DMSO-d$_6$) δ 7.46-7.76 (m, 7H, PhH, 6,7-BenzimidH), 7.90 (t, J=8.1 Hz, 1H, 7-PhthH), 8.01 (J=7.8 Hz, 1H, 6-PhthH), 8.18 (s, 1H, 4-BenzimidH), 8.31 (d, J=7.8 Hz, 1H, 5-PhthH), 8.43 (t, J=8.1 Hz, 1H, 8-PhthH), 8.52 (s, 1H, 2-BenzimidH), 8.66 ppm (s, 1H, NH).

Synthesis of 1-Phenyl-5-[4-(prop-2-ynyloxy)methyl-1-phthalazinyl]aminobenz-imidazole (4, BI-3035)

Scheme 19:

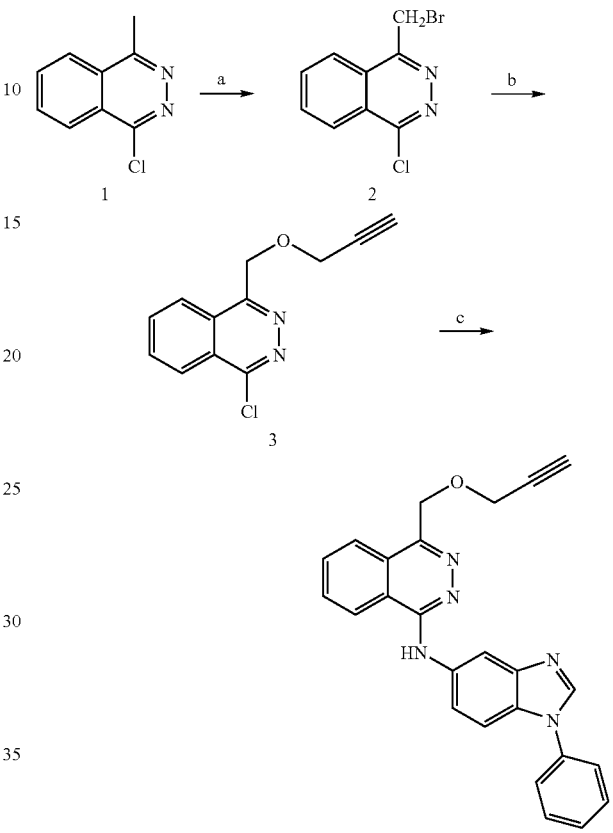

4 (BI-3035)

(a) N-bromosuccinimide, 2,2'-azobisisobutyronitrile, CCl$_4$, 90° C., 2.0 h, (51%).
(b) [2-Propynol, KN(TMS)$_2$, tetrahydrofuran, 0.5 h], 2,3 h (23%).
(c) 5-Amino-1-phenylbenzimidazole, i-PrOH, 95° C., 5 h (27%).

1-Bromomethyl-4-chlorophthalazine (2). To a solution of 1-chloro-4-methyl-phthalazine (179 mg, 1.00 mmol) and N-bromosuccinimide (187 mg, 1.05 mmol) in CCl$_4$ (4 mL) under argon is added 2,2'-azobisisobutyronitrile (25 mg, 0.15 mmol). The mixture is heated at 90° C. for 2 h. After solvent removal at reduced pressure, the residue is purified on silica gel (25% to 50% ethyl acetate/hexane) to recover 49 mg of 1-chloro-4-methylphthalazine and give 132 mg (51%) of 2 as a light-brown solid, mp 96-98° C. (dec). IR 2861, 1530, 1392, 1285 cm$^{-1}$; $^1$H NMR (CDCl$_3$) 5.10 (s, 2H, CH$_2$), 8.01-8.14 (m, 2H, 6,7-PhthH), 8.29 (m, 1H, 5-PhthH), 8.41 (m, 1H, 8-PhthH).

1-Chloro-4-(prop-2-ynyloxy)methylphthalazine (3). A solution of propargyl alcohol (46 mg, 0.81 mmol) and KN(TMS)$_2$ (1.63 mL, 0.81 mmol) in tetrahydrofuran (1.5 mL) is stirred under argon for 30 min before 1-bromomethyl-4-chlorophthalazine (2) (140 mg, 0.54 mmol) is added. The mixture is stirred for 3 h, quenched with 2 N HCl (5 mL) and H$_2$O (15 mL), and extracted with ethyl acetate (80 mL). The extract is washed (brine) and dried. After solvent removal at reduced pressure, the residue is purified on silica gel (20% to 25% ethyl acetate/hexane) to give 29 mg (23%) of 3 as a colorless solid, mp 131-132° C. IR 3079, 1406, 1325 cm$^{-1}$; $^1$H NMR (CDCl$_3$) δ 2.60 (t, J=2.4 Hz, 1H, CH≡CCH$_2$O), 5.17 (s, 2H, CH$_2$), 5.36 (d, J=2.4 Hz, CH≡CCH$_2$O), 7.90-8.02 (m, 2H, 6,7-PhthH), 8.21 (m, 1H, 5-PhthH), 8.36 ppm (m, 1H, 8-PhthH).

1-Phenyl-5-[4-(prop-2-ynyloxy)methyl-1-phthalazinyl]aminobenzimidazole (BI-3035). A solution of 1-chloro-4-(prop-2-ynyloxy)methylphthalazine (3) (20 mg, 0.09 mmol) and 5-amino-1-phenylbenzimidazole (15 mg, 0.07 mmol) in i-PrOH (2 mL) is stirred at 95° C. under argon for 2.5 h. The reaction mixture is concentrated, quenched with sat. NaHCO$_3$ (10 mL), and extracted with CHCl$_3$ (60 mL). The extract is washed (brine) and dried. After solvent removal at reduced pressure, the residue is purified on silica gel (0:1:2 to 1:25:0 methanol/ethyl acetate/hexane) to give 8 mg (27%) of BI-3035 as a light-brown solid, mp 89-91° C. IR 3321, 2927, 1496 cm$^{-1}$; $^1$H NMR (CDCl$_3$) δ 2.60 (t, J=2.4 Hz, 1H, CH≡C—CH$_2$O), 4.98 (s, 2H, CH$_2$), 5.36 (d, J=2.4 Hz, CH≡CCH$_2$O), 6.94 (dd, J=8.7, 2.1 Hz, 1H, 6-BenzimidH), 7.27 (d, J=2.1 Hz, 1H, 4-BenzimidH), 7.41 (d, J=8.7 Hz, 1H, 7-BenzimidH), 7.41-7.63 (m, 5H, PhH), 7.90-8.02 (m, 2H, 6,7-PhthH), 8.06 (s, 1H, 2-BenzimidH), 8.14 (m, 1H, 5-PhthH), 8.35 (m, 1H, 8-PhthH).

Synthesis of 6-(4-Methyl-1-phthalazinyl)amino-1-(prop-2-ynyl)benzimidazole Hydrochloride (2, BI-3038) and 6-(4-Methyl-1-phthalazinyl)amino-1-(1-phenyl[1,2,3]triazole-4-yl)methylbenzimidazole Hydrochloride (3, BI-3040)

The residue is diluted with sat. NaHCO$_3$ (10 mL) and extracted with CHCl$_3$ (60 mL and 3×15 mL). The extract is washed (brine) and dried. After solvent removal at reduced pressure, the residue is purified on silica gel (4.5% to 12.3% methanol/dichloromethane) to give 59 mg (94%) of 2 (BI-3038) as a yellow solid, mp 227-230° C. IR 3316, 2912, 1503 cm$^{-1}$; $^1$H NMR (CDCl$_3$/CD$_3$OD) δ 2.76 (t, J=2.4 Hz, 1H, CH≡CCH$_2$), 2.83 (s, 3H, CH$_3$), 5.05 (d, J=2.4 Hz, 1H, CH≡CCH$_2$), 7.46 (d, J=8.7, 1H, 6-BenzimidH), 7.55 (s, 1H, 4-BenzimidH), 7.66 (d, J=8.7 Hz, 1H, 7-BenzimidH), 7.89-7.96 (m, 2H, 6,7-PhthH), 8.06 (m, 1H, 5-PhthH), 8.08 (s, 1H, 2-BenzimidH), 8.41 ppm (m, 1H, 8-PhthH).

6-(4-Methyl-1-phthalazinyl)amino-1-(1-phenyl[1,2,3]triazole-4-yl)methylbenzimidazole (3, BI-3040). A suspension of 6-(4-methyl-1-phthalazinyl)amino-1-(prop-2-ynyl)benzimidazole (2, BI-3038) (1,418 mg, 0.057 mmol), phenyl azide (6.8 mg, 0.057 mmol), CuI (4.4 mg, 0.023 mmol), and DIEA (99 μL, 0.57 mmol) in methanol (2.3 mL) and tetrahydrofuran (0.5 mL) is stirred for 26 h. After solvent removal at reduced pressure, the residue is purified on silica gel (4% to 9% methanol/dichloromethane) to give 10 mg (41%) of 3 (BI-3040) as a cream solid, mp 273-276° C. IR 3314, 3064, 1625, 1499, 1412 cm$^{-1}$; $^1$H NMR (DMSO-d$_6$) δ 2.80 (s, 3H, CH$_3$), 5.64 (s, 2H, CH$_2$), 7.44-7.62 (m, 6H, 5-BenzimidH, PhH), 7.94-8.02 (m, 3H, 7-BenzimidH, 6,7-PhthH), 8.11 (m, 1H, 5-PhthH), 8.30 (s, 1H, 2-BenzimidH), 8.48 (s, 1H, 4-BenzimidH), 8.60 (m, 1H, 8-PhthH), 8.93 (s, 1H, TriazH), 9.15 ppm (s, 1H, NH).

Synthesis of 1-(Biphen-4-yl)-5-(4-methyl-1-phthalazinyl)aminobenzimidazole Hydrochloride (4, BI-3039)

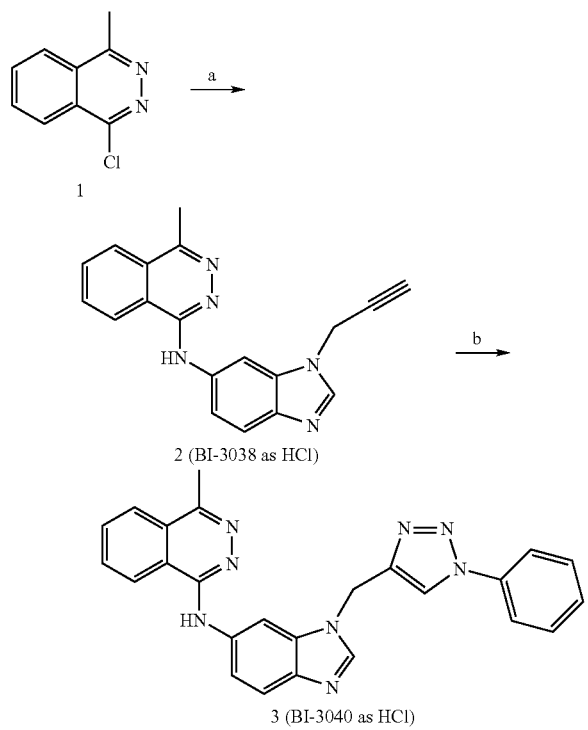

Scheme 20:

2 (BI-3038 as HCl)

3 (BI-3040 as HCl)

(a) 6-Amino-1-(prop-2-ynyl)benzimidazole, i-PrOH, 95° C., 2.5 h (94%); HCl, Et$_2$O.
(b) Phenyl azide, CuI, DIEA, methanol/tetrahydrofuran, 26 h (41%); HCl, Et$_2$O.

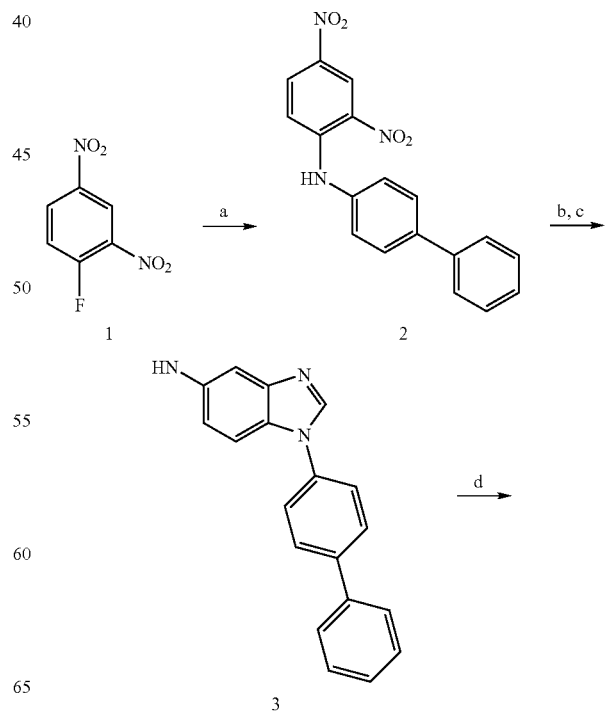

Scheme 21:

6-(4-Methylphthalazinyl)amino-1-(prop-2-ynyl)benzimidazole (2, BI-3038). A solution of 1-chloro-4-methylphthalazine (1) (50 mg, 0.28 mmol) and 6-amino-2-(prop-2-ynyl)benzimidazole (34 mg, 0.20 mmol) in i-PrOH (4 mL) is stirred at 95° C. under argon for 2.5 h and then concentrated.

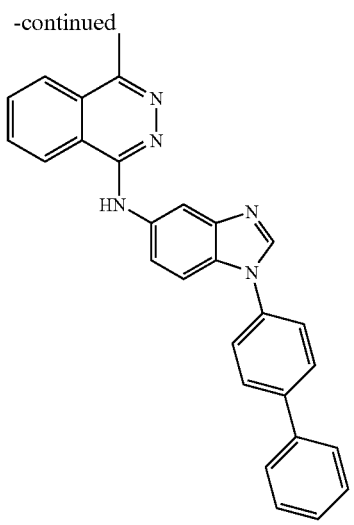

4 (BI-3039 as HCl)

(a) 4-Aminobiphenyl, K$_2$CO$_3$, tetrahydrofuran, 21 h (96%). (b) H$_2$, Pd/C, Ethyl acetate, 93 h. (c) 4 N HCl, formic acid, 115° C., 2.7 h (77% from 2). (d) 1-Chloro-4-phenylphthalazine, i-PrOH, 95° C., 2.5 h (88%); HCl, Et$_2$O.

(Biphen-4-yl)(2,4-dinitrophenyl)amine (2). To a solution of 2,4-dinitrofluorobenzene (1) (1.12 g, 6.0 mmol) and 4-aminobiphenyl (1.12 g, 6.60 mmol) in anhydrous tetrahydrofuran (15 mL) is added K$_2$CO$_3$ (1.74 g, 12.6 mmol). The reaction mixture is stirred under argon for 21 h and then filtered. The solid is rinsed (CHCl$_3$ rinse, 4×). The combined filtrates were concentrated at reduced pressure, and the residue is crystallized (ethanol) to give 1.93 g (96%) of 2 as a red solid, mp 143-145° C. IR 3300, 3080, 1588, 1517, 1333 cm$^{-1}$; $^1$H NMR (CDCl$_3$) δ 7.29 (d, J=9.3 Hz, 1H, 6-PhH), 7.41 (d, J=8.4 Hz, 2H, ArH), 7.52 (m, 3H, PhH), 7.65 (d, J=7.5 Hz, 2H, PhH), 7.75 (d, J=8.4 Hz, 2H, PhH), 8.23 (dd, J=9.3, 2.7 Hz, 1H, 4-PhH), 9.23 (d, J=2.7 Hz, 1H, 3-PhH), 10.05 ppm (s, 1H, NH).

5-Amino-1-(biphen-4-yl)benzimidazole (3). To a solution of (biphen-4-yl)(2,4-dinitrophenyl)amine (2) (1.83 g, 5.46 mmol) in ethyl acetate (60 mL) is added 10% Pd/C (200 mg). The reaction mixture is stirred under H$_2$ for 93 h and then filtered through Celite® (Ethyl acetate rinse). The filtrate is concentrated at reduced pressure. The residue is used in the next step without purification.

A solution of the residue and formic acid (832 μL, 19 mmol) in 4 N HCl (19 mL) is heated at 115° C. under argon for 2.7 h, cooled to room temperature, brought to pH 12 with NaOH pellets, and extracted with ethyl acetate (2×150 mL and 100 mL). The extract is washed (brine) and dried. After solvent removal at reduced pressure, the residue is purified on silica gel (2.3% to 7.4% methanol/ethyl acetate) to give 1.2 g (77%) of 3 as a brown solid, mp 168-170° C. IR 3331, 3070, 2932, 1490, 1253 cm$^{-1}$; $^1$H NMR (CDCl$_3$) δ 3.52 (s, 2H, NH$_2$), 8.23 (dd, J=8.4, 1.8 Hz, 1H, 6-BenzimidH), 7.20 (d, J=1.8 Hz, 1H, 4-BenzimidH), 7.42 (d, J=8.4 Hz, 1H, 7-BenzimidH), 7.43-7.56 (m, 3H, PhH), 7.59 (d, J=8.7 Hz, 2H, PhH), 7.68 (m, 2H, PhH), 7.79 (d, J=8.7 Hz, 2H, PhH), 8.08 ppm (s, 1H, 2-BenzimidH).

1-(Biphen-4-yl)-5-(4-methyl-1-phthalazinyl)aminobenzimidazole (4, BI-3039). A solution of 1-chloro-4-methylphthalazine (25 mg, 0.14 mmol) and 5-amino-1-(biphen-4-yl)benzimidazole (3) (28.5 mg, 0.10 mmol) in i-PrOH (2 mL) is stirred at 95° C. under argon for 2.5 h, cooled to room temperature, and concentrated at reduced pressure. The residue is diluted with sat. NaHCO$_3$ (15 mL) and extracted with CHCl$_3$ (60 mL). The extract is washed (brine) and dried. After solvent removal at reduced pressure, the residue is purified on silica gel (3.2% to 4.8% methanol/ethyl acetate) to give 38 mg (88%) of 4 (BI-3039) as a light-brown solid, mp 272-274° C. IR 3339, 2979, 1522, 1412 cm$^{-1}$; $^1$H NMR (CD$_3$OD/CDCl$_3$) δ 2.82 (s, 3H, CH$_3$), 7.36-7.53 (m, 3H, PhH), 7.62 (d, J=9.00 Hz, 1H, 7-BenzimidH), 7.69 (m, 2H, Aril, 2H PhH), 7.79 (d, J=8.7 Hz, 1H, 6-BenzimidH), 7.86 (d, J=8.1 Hz, 2H, ArH), 7.91-7.98 (m, 2H, 6,7-PhthH), 8.07 (m, 1H, 5-PhthH), 8.10 (s, 1H, 4-BenzimidH), 8.32 (s, 1H, 2-BenzimidH), 8.45 ppm (m, 1H, 8-PhthH).

Synthesis of 1-Phenyl-5-{-4-[4-(prop-2-ynyloxy)benzyl]-1-phthalazinyl}amino-benzimidazole Hydrochloride (6, BI-3047), 5-[4-(4-Benzyloxybenzyl)-1-phthalazinyl]amino-1-phenylbenzimidazole Hydrochloride (7, BI-3052), and 5-[4-(4-Hydroxybenzyl)-1-phthalazinyl]-1-phenyl-aminobenzimidazole Hydrochloride (8, BI-3051)

Scheme 22:

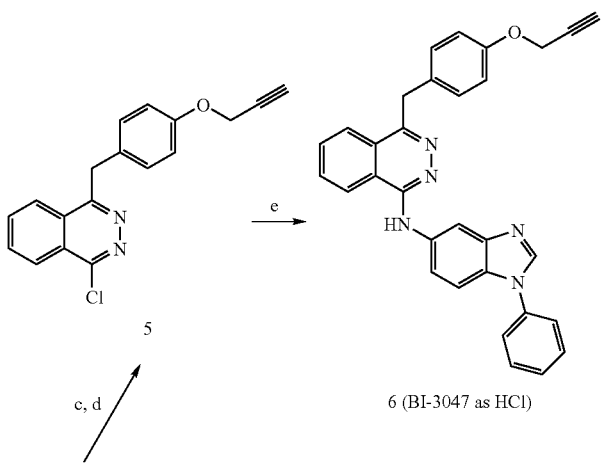

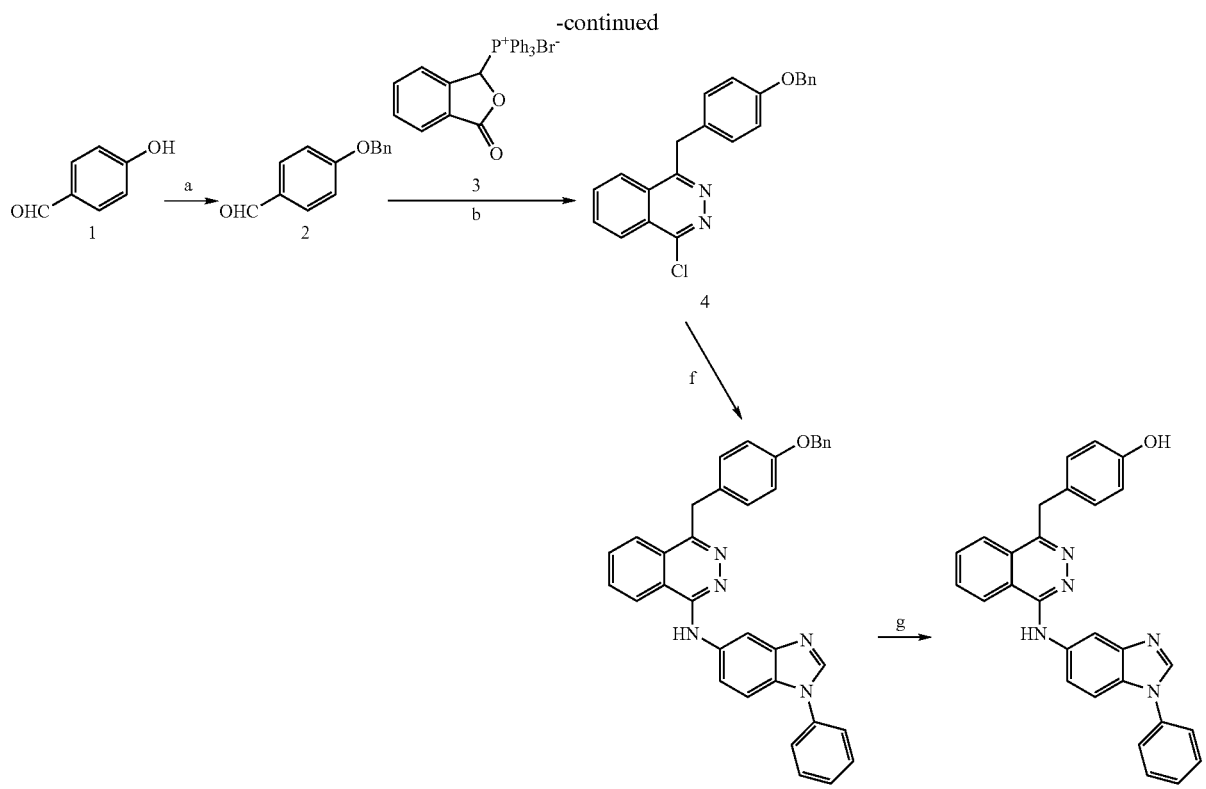

(a) BnBr, K₂CO₃, acetone, 65° C., 19 h (86%). (b) Et₃N, tetrahydrofuran, 4.75 h, 80° C., 1 h, room temperature, 16 h; (ii) H₂NNH₂•H₂O, ethanol, 95-99° C., 5 h; (iii) POCl₃, 120° C., 3.25 h (9% from 2). (c) BBr₃, dichloromethane, -78° C., 2 h; H₂O. (d) Propargyl bromide, K₂CO₃, acetone, 67° C., 21 h (58% from 4). (e) 5-Amino-1-phenylbenzimidazole, i-PrOH, 95° C., 2.3 h (64%); HCl, Et₂O. (g) BBr₃, dichloromethane, -78° C, 2 h; aq. NaHCO₃ (87%); HCl, Et₂O. (f) 5-Amino-1-phenylbenzimidazole, i-PrOH, 95° C., 2.3 h (64%); HCl, Et₂O.

4-Benzyloxybenzaldehyde (2). A mixture of 4-hydroxybenzaldehyde (1) (3.05 g, 25.00 mmol), benzyl bromide (4.4 g, 25.75 mmol), and K₂CO₃ (4.25 g, 30.75 mmol) in acetone (75 mL) is stirred at 65° C. under argon for 19.5 h, then cooled to room temperature, and concentrated at reduced pressure to remove the acetone. The residue is diluted with 2 N HCl (60 mL) and extracted with ethyl acetate (80 mL and 50 mL). The extract is washed (brine) and dried. After solvent removal at reduced pressure, the residue is purified on silica gel (16.7% ethyl acetate/hexane) to give 4.56 g (86%) of 2 as a white solid, mp 70-72° C. IR 2943, 1738, 1484, 1230 cm⁻¹; ¹H NMR (CDCl₃) δ 5.19 (s, 2H, CH₂), 7.11 (d, J=8.7 Hz, 2H, 3,5-ArH), 7.36-7.49 (m, 5H, PhH), 7.87 (d, J=8.7 Hz, 2H, 2,6-ArH), 9.92 ppm (s, 1H, CHO).

1-(4-Benzyloxybenzyl)-4-chlorophthalazine (4). A suspension of (3-phthalidyl)triphenylphosphonium bromide (3) (2.87 g, 6.03 mmol), 4-benzyloxybenzaldehyde (1.28 g, 6.03 mmol), and Et₃N (924 μL, 6.63 mmol) in tetrahydrofuran (60 mL) is stirred for 4.75 h, heated at reflux (80° C.) for 1 h, stirred at room temperature for 16 h, and filtered. To the residue obtained on concentration were added hydrazine monohydrate (307 μL, 6.33 mmol) and ethanol (45 mL). The reaction mixture is heated at reflux (95° C.) for 5 h and then concentrated at reduced pressure. The residue is diluted with 2 N HCl (100 mL) and extracted with ethyl acetate (150 mL) and CHCl₃ (100 mL). The extracts were washed (brine), dried, and concentrated. The residue and POCl₃ (20 mL) were heated at reflux (120° C.) for 3.25 h. POCl₃ is removed at reduced pressure, followed by azeotroping with toluene (2×10 mL). The residue is diluted with sat. NaHCO₃ (70 mL) and extracted with dichloromethane (100 mL and 50 mL). The extract is washed (brine) and dried. After solvent removal at reduced pressure, the residue is purified on silica gel (16% to 50% ethyl acetate/hexane) to give 202 mg (9%) of 4 as a yellow solid, mp 150-152° C. IR 3060, 1510, 1236 cm⁻¹; ¹H NMR (CDCl₃) δ 4.67 (s, 2H, CH₂), 5.02 (s, 2H, OCH₂), 6.91 (d, J=8.7 Hz, 2H, 3,'-ArH), 7.25 (d, J=8.7 Hz, 2H, 2,6-ArH), 7.30-7.46 (m, 5H, PhH), 7.86-7.98 (m, 2H, 6,7-PhthH), 8.11 (d, J=7.5 Hz, 1H, 8-PhthH), 8.33 ppm (d, J=7.5 Hz, 1H, 5-PhthH).

4-Chloro-1-[4-(prop-2-ynyloxy)benzyl]phthalazine (5). A solution of 4-benzyloxybenzaldehyde (3) (86 mg, 0.24 mmol), 1.0 M boron tribromide (1.2 mmol) in dichloromethane (1.2 mL), and dichloromethane (3 mL) is stirred at -78° C. under argon for 2 h, quenched with H₂O (22 mL), and extracted with ethyl acetate (100 mL). The extract is washed (water and brine), dried, and concentrated at reduced pressure. The residue is used for next step without further purification.

A mixture of the crude residue, 80% propargyl bromide (0.29 mmol) in toluene (32 μL), K₂CO₃ (43 mg, 0.31 mmol), and acetone (3 mL) is stirred at 67° C. under argon for 21 h and then cooled to room temperature. After concentration, the residue is diluted with H₂O (20 mL) and extracted with ethyl acetate (70 mL). The extract is washed (brine) and dried. After solvent removal at reduced pressure, the residue is purified on silica gel (20% to 33% ethyl acetate/hexane) to give 43 mg (58% for two steps) of 5 as a light-yellow solid, mp 129-131° C. IR 2911, 1508, 1219 cm⁻¹; ¹H NMR (CDCl₃) δ 2.50 (t, J=2.1 Hz, 1H, C≡CH), 4.64 (d, J=2.1 Hz, 2H, CH₂C≡CH), 4.66 (s, 2H, CH₂), 6.91 (d, J=8.7 Hz, 2H, 3,5-ArH), 7.25 (d, J=8.7 Hz, 2H, 2,6-ArH), 7.85-7.97 (m, 2H, 6,7-PhthH), 8.10 (m, 1H, 8-PhthH), 8.31 ppm (m, 1H, 5-PhthH).

1-Phenyl-5-{-4-[4-(prop-2-ynyloxy)benzyl]-1-phthalazinyl}aminobenzimidazole (6, BI-3047). A solution of 4-chloro-1-[4-(prop-2-ynyloxy)benzyl]phthalazine (5) (40 mg, 0.13 mmol) and 5-amino-1-phenylbenzimidazole (19 mg, 0.09 mmol) in i-PrOH (2 mL) is stirred at 95° C. under argon for 2 h and then concentrated. The residue is diluted with sat. NaHCO$_3$ (15 mL) and extracted with CHCl$_3$ (85 mL). The extract is washed (brine) and dried. After solvent removal at reduced pressure, the residue is purified on silica gel (1.3% to 5.6% methanol/dichloromethane) to give 43 mg (99%) of 6 (BI-3047) as a yellow solid, mp 88-90° C. IR 3310, 3061, 1503, 1220 cm$^{-1}$; $^1$H NMR (CD$_3$OD) δ 2.86 (t, J=2.4 Hz, 1H, C≡CH), 4.41 (s, 2H, CH$_2$), 4.59 (d, J=2.4 Hz, 2H, CH$_2$C≡CH), 6.81 (d, J=8.7 Hz, 2H, 3,5-ArH), 7.17 (d, J=8.7 Hz, 2H, 2,6-ArH), 7.38 (d, J=9.0 Hz, 1H, 7-BenzimidH), 7.41-7.59 (m, 5H, PhH), 7.64-7.78 (m, 3H, 6,7-PhthH, 6-BenzimidH), 7.94 (d, J=8.4 Hz, 1H, 5-PhthH), 8.18 (d, J=1.8 Hz, 1H, 4-BenzimidH), 8.30 (s, 1H, 2-BenzimidH), 8.34 ppm (d, J=8.4 Hz, 1H, 8-PhthH).

5-[4-(4-Benzyloxy)benzyl-1-phthalazinyl]amino-1-phenylbenzimidazole (7, BI-3052). A solution of 1-(4-benzyloxybenzyl)-4-chlorophthalazine (4) (42 mg, 0.12 mmol) and 5-amino-1-phenylbenzimidazole (17 mg, 0.08 mmol) in i-PrOH (2 mL) is stirred at 95° C. under argon for 2.33 h and then concentrated. The residue is diluted with sat. NaHCO$_3$ (15 mL) and extracted with CHCl$_3$ (80 mL). The extract is washed (brine) and dried. After solvent removal at reduced pressure, the residue is purified on silica gel (1.3% to 2.9% methanol/dichloromethane) to give 28 mg (64%) of 7 (BI-3052) as a light-yellow solid, mp 150-152° C. IR 3329, 3039, 1503, 1409, 1240 cm$^{-1}$; $^1$H NMR (CDCl$_3$) δ 4.44 (bs, 2H, CH$_2$), 5.02 (s, 2H, CH$_2$O), 6.91 (d, J=8.4 Hz, 2H, 3,5-ArH), 7.26 (d, J=8.4 Hz, 2H, 2,6-ArH), 7.30-7.64 (m, 12H, 6,7-BenzimidH, 2 PhH), 7.64-7.78 (m, 4H, 5,6,7-PhthH, 4-BenzimidH), 7.87 (m, 1H, 8-PhthH), 8.11 ppm (s, 1H, 2-BenzimidH).

5-[4-(4-Hydroxybenzyl)-1-phthalazinyl]amino-1-phenylbenzimidazole (8, BI-3051). A solution of 5-[4-(4-benzyloxybenzyl)phthalazinyl]amino-1-phenylbenzimidazole (7, BI-3052) (26 mg, 0.05 mmol), 1.0 M boron tribromide (0.24 mmol) in dichloromethane (0.24 mL), and dichloromethane (1.5 mL) is stirred at −78° C. under argon for 2 h, quenched with sat. NaHCO$_3$ (22 mL), and extracted with CHCl$_3$ (80 mL and 2×25 mL). The extract is washed (brine) and dried. After solvent removal at reduced pressure, the residue is purified on silica gel (1.3% to 7.4% methanol/dichloromethane) to give 19 mg (87%) of 8 (BI-3051) as a light-yellow solid, mp 185-187° C. IR 3320, 2944, 1504, 1254 cm$^{-1}$; $^1$H NMR (CD$_3$OD/CDCl$_3$) δ 4.45 (s, 2H, CH$_2$), 6.71 (d, J=8.4 Hz, 2H, 3,5-ArH), 7.11 (d, J=8.4 Hz, 2H, 2,6-PhH), 7.49-7.61 (m, 6H, 7-BenzimidH, PhH), 7.77-7.89 (m, 3H, 6,7-PhthH, 6-BenzimidH), 8.02 (d, J=7.8 Hz, 1H, '-PhthH), 8.14 (s, 1H, 4-BenzimidH), 8.31 (s, 1H, 2-BenzimidH), 8.43 ppm (d, J=7.8 Hz, 1H, 8-PhthH).

Synthesis of 1-Phenyl-5-[(7-(prop-2-ynyloxy)-4-methyl-1-phthalazinyl]aminobenz-imidazole (7, BI-3053) and 5-[(7-Methoxy-4-methyl-1-phthalazinyl]amino-1-phenylbenzimidazole (8, BI-3055)

Scheme 23:

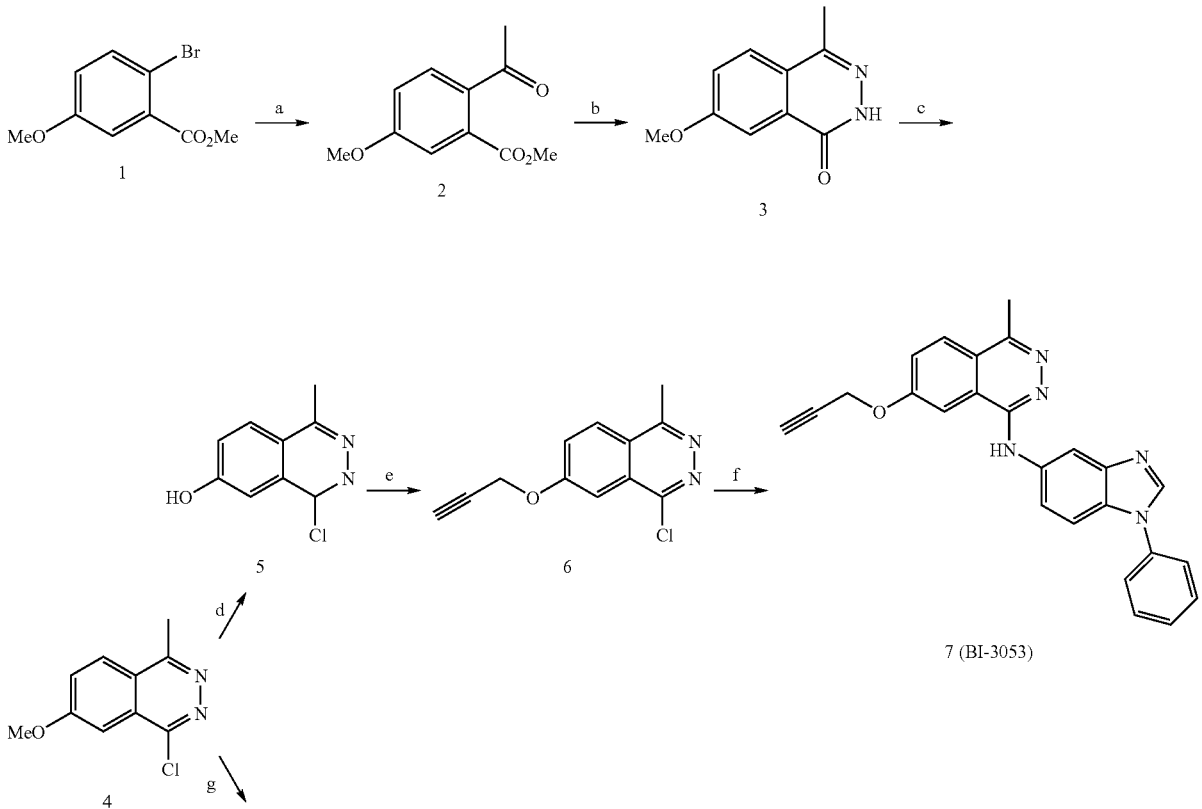

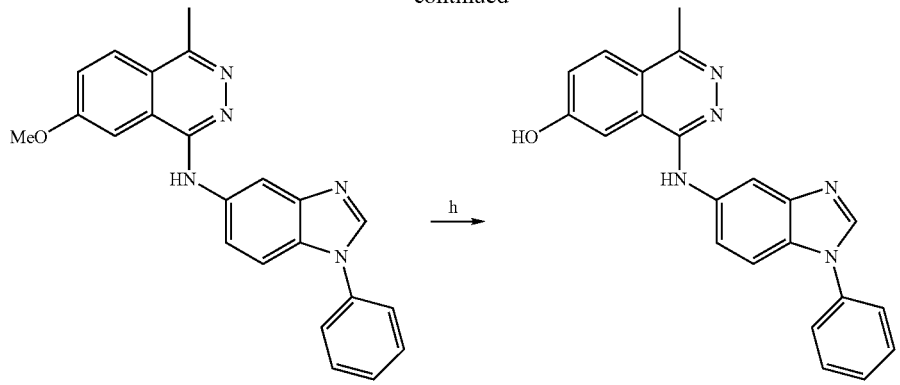

8 (BI-3055)  9

(a) (i) Butyl vinyl ether, Ph$_3$P, Pd(OAc)$_2$, Et$_3$N, MeCN, 99° C., 16.5 h; (ii) 10% aq. HCl, tetrahydrofuran, 2 h (99%). (b) NH$_2$NH$_2$·H$_2$O, methanol, 5 h, 95° C., (95%). (c) POCl$_3$, 120° C., 3.8 h (100%). (d) BBr$_3$, dichloromethane, -78° C., 10 min, room temperature, 38 h, reflux, 3 h; aq. NaHCO$_3$ (70%). (e) Propargyl bromide, K$_2$CO$_3$, acetone, 68° C., 23 h (55%). (f) 5-Amino-1-phenylbenzimidazole, i-PrOH, 95° C., 2.7 h (100%). (g) 5-Amino-1-phenylbenzimidazole, i-PrOH, 95° C., 3 h (100%). (h) BBr$_3$, dichloromethane, room temperature, reflux; aq. NaHCO$_3$.

Methyl 2-Acetyl-5-methoxybenzoate (2). A mixture of methyl 2-bromo-5-methoxybenzoate (1) (5.0 g, 20.4 mmol), butyl vinyl ether (13.1 mL, 102.0 mmol), Ph$_3$P (802.3 mg, 3.1 mmol), Et$_3$N (3.7 mL, 26.5 mmol), and Pd(OAc)$_2$ (343.0 mg, 1.5 mmol) in MeCN (40 mL) is stirred under argon at 99° C. for 16.5 h and then cooled to room temperature. The residue is diluted with H$_2$O (50 mL), and the resultant suspension is filtered through Celite® (H$_2$O rinse). The filtrate is concentrated to dryness at reduced pressure. To the residue is added tetrahydrofuran (125 mL) and 10% HCl (125 mL). The mixture is stirred for 2 h before the tetrahydrofuran is removed at reduced pressure. This residue is extracted with ethyl acetate (100 mL, 70 mL, and 60 mL). The extract is washed (brine) and dried. After solvent removal at reduced pressure, the residue is purified on silica gel (16.7% to 33.3% ethyl acetate/hexane) to give 4.23 g (99%) of 2 as a yellow liquid. IR 2958, 1730, 1683, 1270 cm$^{-1}$; $^1$H NMR (CDCl$_3$) δ 2.55 (s, 3H, CH$_3$CO), 3.90 (s, 3H, CH$_3$O), 3.94 (s, 3H, CO$_2$CH$_3$), 7.04 (dd, J=8.7, 2.7 Hz, 1H, 4-PhH), 7.17 (d, J=2.7 Hz, 1H, 6-PhH), 7.61 ppm (d, J=8.7 Hz, 1H, 3-PhH).

7-Methoxy-4-methyl-2H-phthalazin-1-one (3). To a solution of methyl 2-acetyl-5-methoxybenzoate (2) (2.21 g, 10.60 mmol) in methanol (13 mL) is added hydrazine monohydrate (1.59 g, 31.80 mmol). The mixture is stirred at 95° C. under argon for 5 h, then cooled to room temperature, diluted with H$_2$O (50 mL), and extracted with ethyl acetate (2×100 mL, 2×50 mL, and 2×30 mL). The extract is washed (brine), dried, and concentrated at reduced pressure. The residue is suspended in ethyl acetate (20 mL), heated, then cooled, and filtered to give 1.92 g (95%) of 3 as a white solid, mp 203-205° C. IR 3314, 2918, 1652, 1241 cm$^{-1}$; $^1$H NMR (CDCl$_3$) δ 2.60 (s, 3H, CH$_3$), 4.01 (s, 3H, CH$_3$O), 7.42 (dd, J=9.0, 2.7 Hz, 1H, 6-PhtH), 7.75 (d, J=9.0 Hz, 1H, 5-PhtH), 7.88 (d, J=2.7 Hz, 1H, 8-PhtH), 10.75 ppm (s, 1H, NH).

4-Chloro-6-methoxy-1-methylphthalazine (4). The solution of 7-methoxy-4-methyl-2H-phthalazin-1-one (3) in POCl$_3$ (15 mL) is heated at reflux (120° C.) for 3 h 50 min and then cooled to room temperature. Unreacted POCl$_3$ is removed at reduced pressure followed by azeotroping with toluene (2×10 mL). The residue is diluted with sat. NaHCO$_3$ (60 mL) and extracted with dichloromethane (200 mL, 60 mL, and 50 mL). The extract is washed (brine) and dried. After solvent removal at reduced pressure, the residue is dried under high vacuum to give 2.08 g (100%) of 4 as a yellow solid, mp 151-153° C. IR 2968, 1613, 1218 cm$^{-1}$; $^1$H NMR (CDCl$_3$) δ 2.97 (s, 3H, CH$_3$), 4.07 (s, 3H, CH$_3$O), 7.50-7.59 (m, 2H, 6,8-PhtH), 8.01 ppm (d, J=8.7 Hz, 1H, 5-PhtH).

4-Chloro-6-hydroxy-1-methylphthalazine (5). A solution of 4-chloro-6-methoxy-1-methylphthalazine (4) (2.08 g, 9.99 mmol), 1.0 M boron tribromide (17.00 mmol) in dichloromethane (17 mL), and dichloromethane (50 mL) is stirred under argon at -78° C. for 10 min, room temperature for 38 h, and at reflux for 3 h. The mixture is cooled to room temperature, diluted with sat. NaHCO$_3$ (130 mL), and extracted with ethyl acetate (150 mL and 4×60 mL). The extract is washed (water and brine) and dried. After solvent removal at reduced pressure, the remaining solid is washed with dichloromethane to give 650 mg (70%) of 5 as a yellow solid, mp >260° C. IR 3351, 2938, 1610, 1223 cm$^{-1}$; $^1$H NMR (DMSO-d$_6$) δ 2.84 (s, 3H, CH$_3$), 7.44 (d, J=8.7 Hz, 1H, 8-PhtH), 7.59 (dd, J=9.0, 2.4 Hz, 1H, 6-PhtH), 8.19 (d, J=9.0 Hz, 1H, 5-PhtH), 11.27 ppm (s, 1H, OH).

4-Chloro-1-methyl-6-(prop-2-ynyloxy)phthalazine (6). The mixture of 4-chloro-6-hydroxy-1-methylphthalazine (5) (195 mg, 1.00 mmol), 80% propargyl bromide (1.30 mmol) in toluene (145 μL), K$_2$CO$_3$ (187 mg, 1.35 mmol), and acetone (8 mL) is stirred at 68° C. under argon for 23 h, then cooled to room temperature, and concentrated. The residue is diluted with H$_2$O (50 mL) and extracted with ethyl acetate (70 mL and 60 mL). The extract is washed (brine) and dried. After solvent removal at reduced pressure, the residue is purified on silica gel (33% to 50% ethyl acetate/hexane) to give 129 mg (55%) of 6 as a light-yellow solid, mp 169-171° C. IR 3077, 1401, 1217 cm$^{-1}$; $^1$H NMR (CDCl$_3$) δ 2.66 (t, J=2.4 Hz, 1H, C≡CH), 2.97 (s, 3H, CH$_3$), 4.96 (d, J=2.4 Hz, 2H, CH$_2$C≡CH), 7.62 (dd, J=9.3, 2.7 Hz, 1H, 7-PhtH), 7.69 (d, J=2.7 Hz, 1H, 5-PhtH), 8.05 ppm (d, J=9.3 Hz, 1H, 8-PhtH).

1-Phenyl-5-[7-(prop-2-ynyloxy)-4-methyl-1-phthalazinyl]aminobenzimidazole 7, BI-3053). A solution of 4-chloro-1-methyl-6-(prop-2-ynyloxy)phthalazine (6) (31 mg, 0.14 mmol) and 5-amino-1-phenylbenzimidazole (19 mg, 0.09 mmol) in i-PrOH (2 mL) is stirred at 95° C. under argon for 2.7 h, cooled to room temperature, and concentrated. The residue is diluted with sat. NaHCO$_3$ (15 mL) and extracted with CHCl$_3$ (70 mL and 2×20 mL) The extract is washed (brine) and dried. After solvent removal at reduced pressure, the residue is purified on silica gel (1% to 11% methanol/dichloromethane) to give 37 mg (100%) of 7 (BI-3053) as a yellow solid, mp 229-231° C. IR 3323, 2917, 1501, 1238 cm$^{-1}$; $^1$H NMR (CD$_3$OD/CDCl$_3$) δ 2.79 (s, 3H, CH$_3$), 2.94 (t, J=2.4 Hz, 1H, C≡CH), 5.00 (d, J=2.4 Hz, 2H, CH$_2$C≡CH), 7.50-7.66 (m, 7H, 6,7-BenzimidH, PhH), 7.77 (dd, J=9.0, 2.4

Hz, 1H, 6-PhthH), 7.94 (d, J=2.4 Hz, 1H, 8-PhthH), 8.04 (d, J=9.0 Hz, 1H, 5-PhthH), 8.07 (s, 1H, 4-BenzimidH), 8.32 ppm (s, 1H, 2-BenzimidH).

5-(7-Methoxy-4-methyl-1-phthalazinyl)amino-1-phenyl-benzimidazole (8, BI-3055). A solution of 4-chloro-6-methoxy-1-methylphthalazine (4) (17.5 mg, 0.08 mmol) and 5-amino-1-phenylbenzimidazole (11 mg, 0.05 mmol) in i-PrOH (2 mL) is stirred at 95° C. under argon for 3 h, then cooled to room temperature, and concentrated. The residue is diluted with sat. NaHCO₃ (15 mL) and extracted with CHCl₃ (50 mL and 40 mL) and ethyl acetate (30 mL). The extracts were washed (brine) and dried. After solvent removal at reduced pressure, the residue is purified on silica gel (5.6% to 10.7% methanol/dichloromethane) to give 20 mg (100%) of 8 (BI-3055) as a yellow solid, mp 139-142° C. IR 3307, 2947, 1501, 1422, 1241 cm$^{-1}$; $^1$H NMR (CD$_3$OD/CDCl$_3$) δ 2.61 (s, 3H, CH$_3$), 3.88 (s, 3H, OCH$_3$), 7.31 (d, J=8.4 Hz, 1H, 6-BenzimidH), 7.36-7.51 (m, 6H, 7-BenzimidH, PhH), 7.59 (s, 1H, 4-BenzimidH), 7.69 (m, 2H, 6,8-PhthH), 7.77 (d, J=6.0 Hz, 1H, 5-PhthH), 8.01 ppm (s, 1H, 2-BenzimidH).

Synthesis of 5-(6-Methoxy-4-methyl-1-phthalazinyl)amino-1-phenylbenzimidazole (8, BI-3056) and 1-Phenyl-5-[6-(prop-2-ynyloxy)-4-methyl-1-phthalazinyl]aminobenzimidazole (12, BI-3057)

Scheme 24:

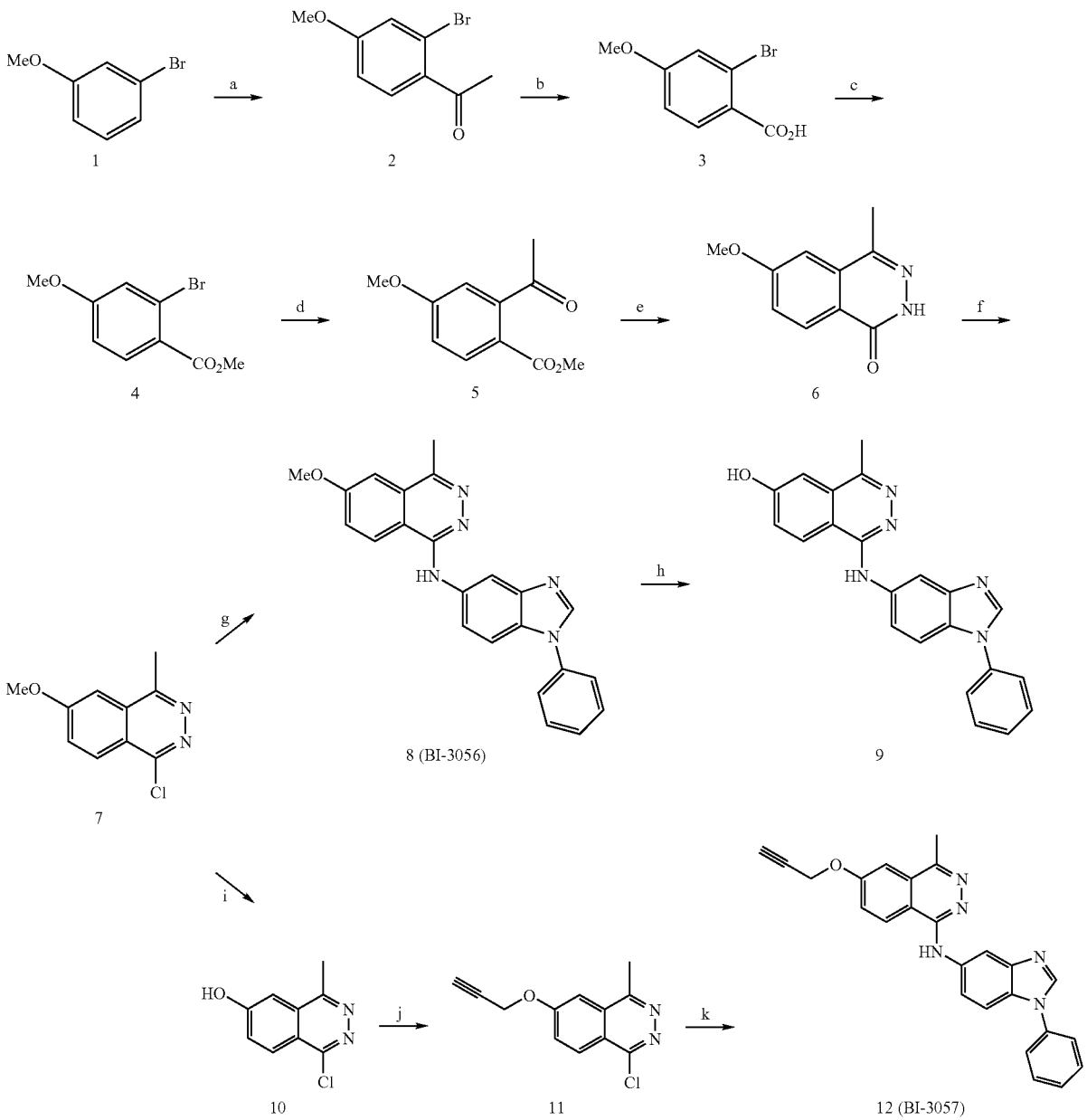

(a) CH₃COCl, AlCl₃, dichloromethane, 0° C., 40 min, room temperature, 1 h (83%). (b) [Br₂, 20% aq. NaOH, 0-10° C.], 2, 36° C., 29 h, room temperature, 17 h; H₃O⁺ (68%). (c) SOCl₂, methanol, 79° C., 18 h (85%). (d) (i) Butyl vinyl ether, Pd(OAc)₂, Ph₃P, Et₃N, MeCN, 97° C., 18 h; (ii) 10% aq. HCl, tetrahydrofuran, 2 h (96%). (e) NH₂NH₂•H₂O, methanol, 95° C., 6 h (94%). (f) POCl₃, 120° C., 4 h (100%). (g) 5-Amino-1-phenylbenzimidazole, i-PrOH, 95° C., 3 h (100%). (h) BBr₃, dichloromethane, -78° C., 30 min, room temperature, 22 h, reflux, 4 h; aq. NaHCO₃. (i) BBr₃, dichloromethane, -78° C., 30 min, room trmperature, 22 h, reflux, 4 hr; aq. NaHCO₃ (68%). (j) Propargyl bromide, K₂CO₃, acetone, 68° C., 23 h (44%). (k) 5-Amino-1-phenylbenzimidazole, 2-propanol, 95° C., 3 h (69%).

1-(2-Bromo-4-methoxyphenyl)ethanone (2). Acetyl chloride (3.56 mL, 0.06 mol) is added dropwise to a stirred suspension of 3-bromoanisole (9.35 g, 0.05 mol) and $AlCl_3$ (8.00 g, 0.06 mol) in dichloromethane (50 mL) at 0° C. under argon. The resulting mixture is stirred at 0° C. for 40 min and then at room temperature for 1 h, and diluted with $H_2O$ (100 mL) and 2 N HCl (35 mL), and extracted with ethyl acetate (2×100 mL and 50 mL). The extract is washed (brine) and dried. After solvent removal at reduced pressure, the residue is purified on silica gel (12.5% to 14.3% ethyl acetate/hexane) to give 9.55 g (83%) of 2 as a colorless liquid. IR 2964, 1688, 1596, 1252 $cm^{-1}$; $^1H$ NMR ($CDCl_3$) δ 2.66 (s, 3H, $CH_3CO$), 3.88 (s, 3H, $CH_3O$), 6.91 (dd, J=8.4 Hz, 2.4 Hz, 1H, 5-PhH), 7.19 (d, J=2.4 Hz, 1H, 3-PhH), 7.63 ppm (d, J=8.4 Hz, 1H, 6-PhH).

2-Bromo-4-methoxybenzoic Acid (3). $Br_2$ (8.5 mL, 165.89 mmol) is added dropwise to 20% NaOH (97 mL) at 0-10° C. in a 15-min period. The resulting solution is warmed to room temperature before 1-(2-bromo-4-methoxyphenyl)ethanone (2) (9.50 g, 41.47 mmol) is added. The mixture is stirred at 36° C. for 29 h and at room temperature for 17 h, diluted with 0.5 M $NaHSO_3$ (25 mL), and extracted with ether (100 mL and 70 mL). The aqueous layer is acidified with conc. HCl (30 mL) to give 6.56 g (68%) of 3 as a white solid, mp 195-197° C. IR 2997, 1686, 1596, 1290 $cm^{-1}$; $^1H$ NMR ($CDCl_3$) δ 3.80 (s, 3H, $CH_3O$), 6.83 (dd, J=7.2, 2.0 Hz, 1H, 5-PhH), 7.15 (d, J=2.0 Hz, 1H, 3PhrH), 7.90 ppm (d, J=7.2 Hz, 1H, 6-PhH).

Methyl 2-Bromo-4-methoxybenzoate (4). $SOCl_2$ (7.5 mL, 103.0 mmol) is added dropwise to a stirred 0° C. suspension of 2-bromo-4-methoxybenzoic acid (3) (6.5 g, 28.1 mmol) in methanol (12 mL). The mixture is next stirred at 79° C. for 18 h and then cooled to room temperature before removal of methanol and excess $SOCl_2$ at reduced pressure. The residue is diluted with $H_2O$ (50 mL) and extracted with ethyl acetate (100 mL and 70 mL). The extract is washed (2 N NaOH and brine) and dried. After solvent removal at reduced pressure, the residue is purified on silica gel (14.3% to 16.7% ethyl acetate/hexane) to give 5.9 g (85%) of 4 as a colorless liquid. IR 2952, 1728, 1597, 1261 $cm^{-1}$; $^1H$ NMR ($CDCl_3$) δ 3.83 (s, 3H, $CH_3O$), 3.89 (s, 3H, $CO_2CH_3$), 6.86 (dd, J=7.2, 2.0 Hz, 1H, 5-PhH), 7.18 (d, J=2.0 Hz, 1H, 3-PhH), 7.85 ppm (d, J=7.2 Hz, 1H, 6-PhH).

Methyl 2-Acetyl-4-methoxybenzoate (5). A mixture of methyl 2-bromo-4-methoxybenzoate (4) (5.9 g, 23.9 mmol), butyl vinyl ether (15.4 mL, 119.4 mmol), $Ph_3P$ (939.0 mg, 3.6 mmol), $Et_3N$ (4.3 mL, 31.0 mmol), and $Pd(OAc)_2$ (343.0 mg, 1.8 mmol) in MeCN (45 mL) is stirred under argon at 97° C. for 18 h, cooled to room temperature, diluted with $H_2O$ (50 mL), and filtered through Celite® ($H_2O$ rinse). The filtrate is concentrated to dryness at reduced pressure. The residue plus tetrahydrofuran (140 mL) and 10% HCl (140 mL) were stirred for 2 h. After tetrahydrofuran removal at reduced pressure, the residue is extracted with dichloromethane (3×70 mL). The extract is washed (brine) and dried. After solvent removal at reduced pressure, the residue is purified on silica gel (16.7% to 33.3% ethyl acetate/hexane) to give 4.8 g (96%) of 5 as a yellow solid, mp 48-50° C. IR 2962, 1733, 1688, 1258 $cm^{-1}$; $^1H$ NMR ($CDCl_3$) δ 2.50 (s, 3H, $CH_3CO$), 3.86 (s, 6H, $CH_3O$, $CO_2CH_3$), 6.76 (d, J=2.0 Hz, 1H, 3-PhH), 6.93 (dd, J=7.2, 2.0 Hz, 1H, 5-PhH), 7.90 ppm (d, J=7.2 Hz, 1H, 6-PhH).

6-Methoxy-4-methyl-2H-phthalazin-1-one (6). To a solution of methyl 2-acetyl-4-methoxybenzoate (5) (2.47 g, 11.86 mmol) in methanol (14.5 mL) is added hydrazine monohydrate (1.78 g, 35.60 mmol). The mixture is stirred at 95° C. under argon for 6 h, the cooled to room temperature, diluted with $H_2O$ (50 mL), and extracted with $CHCl_3$ (2×100 mL) and ethyl acetate (100 mL, 2×50 mL, and 2×40 mL). The extracts were washed (brine) and dried. After solvent removal at reduced pressure, the residue is suspended in ethyl acetate (30 mL), heated, cooled, and filtered to give 2.13 g (94%) of 6 as a white solid, mp 252-254° C. IR 3298, 2941, 1732, 1055 $cm^{-1}$; $^1H$ NMR ($CDCl_3$) δ 2.58 (s, 3H, $CH_3$), 4.00 (s, 3H, $CH_3O$), 7.12 (d, J=1.6 Hz, 1H, 5-PhtH), 7.35 (dd, J=5.6, 1.6 Hz, 1H, 7-PhtH), 8.41 (d, J=5.6 Hz, 1H, 8-PhtH), 10.12 ppm (s, 1H, NH).

1-Chloro-6-methoxy-4-methylphthalazine (7). A solution of 6-methoxy-4-methyl-2H-phthalazin-1-one (6) (2.0 g, 10.5 mmol) in $POCl_3$ (20 mL) is heated at reflux (120° C.) for 4 h and then cooled to room temperature. Unreacted $POCl_3$ is removed at reduced pressure, followed by azeotroping with toluene (2×10 mL). The residue is diluted with sat. $NaHCO_3$ (75 mL) and extracted with dichloromethane (150 mL, 2×60 mL, and 50 mL). The extract is washed (brine) and dried. After solvent removal at reduced pressure, the residue is dried under high vacuum to give 2.2 g (100%) of 7 as a yellow solid, mp 123-126° C. IR 2991, 1611, 1403, 1290, 1234 $cm^{-1}$; $^1H$ NMR ($CDCl_3$) δ 2.95 (s, 3H, $CH_3$), 4.05 (s, 3H, $CH_3O$), 7.25 (d, J=1.2 Hz, 1H, 5-PhtH), 7.55 (dd, J=6.0, 1.2 Hz, 1H, 7-PhtH), 8.21 ppm (d, J=6.0 Hz, 1H, 8-PhtH).

5-(6-Methoxy-4-methyl-1-phthalazinyl)amino-1-phenylbenzimidazole (8, BI-3056). A solution of 1-chloro-6-methoxy-4-methylphthalazine (7) (19.8 mg, 0.09 mmol) and 5-amino-1-phenylbenzimidazole (11 mg, 0.05 mmol) in i-PrOH (2 mL) is stirred at 95° C. under argon for 3 h. After solvent removal at reduced pressure, the residue is purified on silica gel (5.6% to 10.7% methanol/dichloromethane) to give 20 mg (100%) of 8 (BI-3056) as a yellow solid, mp 256-259° C. IR 3313, 2967, 1616, 1502, 1405, 1227 $cm^{-1}$; $^1H$ NMR ($CD_3OD/CDCl_3$) δ 2.62 (s, 3H, $CH_3$), 3.87 (s, 3H, $OCH_3$), 7.09 (d, J=2.7 Hz, 1H, 4-BenzimidH), 7.30 (dd, J=9.1, 2.7 Hz, 1H, 6-BenzimidH), 7.36-7.50 (m, 6H, 7-BenzimidH, PhH), 7.66 (d, J=9.1 Hz, 1H, 7'-PhtH), 7.69 (s, 1H, 5'-PhtH), 8.00 (s, 1H, 2-BenzimidH), 8.11 ppm (d, J=9.1 Hz, 1H, 8'-PhtH).

1-Chloro-6-hydroxy-4-methylphthalazine (10). A solution of 1-chloro-6-methoxy-4-methylphthalazine (7) (1.0 g, 4.8 mmol), 1.0 M boron tribromide (17.00 mmol) in dichloromethane (17 mL), and dichloromethane (50 mL) is stirred under argon at −78° C. for 0.5 h, at room temperature for 22 h, and at reflux for 4 h. After being cooled to room temperature, the mixture is diluted with $H_2O$ (100 mL) and sat. $NaHCO_3$ (80 mL) and extracted with ethyl acetate (150 mL and 4×100 mL). The extract is washed (brine) and dried. Solvent is removed at reduced pressure to give 184 mg of an impure brown solid consisting of by-products. The aqueous layer is filtered, and the isolated solid is washed ($H_2O$) and dried to give 640 mg (68%) of 8 as a yellow solid, mp >260° C. (dec). IR 3328, 2945, 1608, 1221 $cm^{-1}$; $^1H$ NMR (DMSO-$d_6$) δ 2.74(s, 3H, $CH_3$), 7.30 (d, J=1.8 Hz, 1H, 5-PhtH), 7.53 (dd, J=8.5, 1.8 Hz, 1H, 7-PhtH), 8.08 ppm (d, J=8.5 Hz, 1H, 8-PhtH).

1-Chloro-4-methyl-6-(prop-2-ynyloxy)phthalazine (11). The mixture of 1-chloro-6-hydroxy-4-methylphthalazine (8) (195 mg, 1.00 mmol), 80% propargyl bromide (1.30 mmol) in toluene (145 μL), $K_2CO_3$ (187 mg, 1.35 mmol), and acetone (8 mL) is stirred at 68° C. under argon for 23 h, and then cooled to room temperature. The mixture is concentrated, diluted with $H_2O$ (40 mL), and extracted with ethyl acetate (70 mL and 60 mL). The extract is washed (brine) and dried. After solvent removal at reduced pressure, the residue is purified on silica gel (33% to 56% ethyl acetate/hexane) to give 102 mg (44%) of 11 as alight-yellow solid, mp 178-180° C. IR 2946, 1615, 1378, 1234 $cm^{-1}$; $^1H$ NMR (DMSO-$d_6$) δ 2.61 (t, J=2.1 Hz, 1H, CH≡C), 2.93 (s, 3H, $CH_3$), 4.91 (d, J=2.1 Hz, 1H, CH≡CCH$_2$), 7.40 (d, J=2.4 Hz, 1H, 5-PhthH), 7.58 (dd, J=9.1, 2.4 Hz, 1H, 7-PhthH), 8.23 ppm (d, J=9.1 Hz, 1H, 8-PhthH).

1-Phenyl-5-[6-(prop-2-ynyloxy)-4-methyl-1-phthalazinyl]aminobenzimidazole (12, BI-3057). A solution of 1-chloro-4-methyl-6-(propy-2-nyloxy)phthalazine (11) (37 mg, 0.16 mmol) and 5-amino-1-phenylbenzimidazole (24 mg, 0.11 mmol) in i-PrOH (2.5 mL) is stirred at 95° C. under argon for 3 h, cooled to room temperature, and concentrated at reduced pressure. The residue is purified on silica gel (4.7% to 11.5% methanol/dichloromethane) to give 32 mg (69%) of 12 (BI-3057) as a yellow solid, mp 233-236° C. IR 3361, 2965, 1504, 1393, 1220 cm$^{-1}$; $^1$H NMR (CD$_3$OD) δ 2.76 (s, 3H, CH$_3$), 3.07 (t, J=2.4 Hz, 1H, CH≡C), 4.99 (d, J=2.4 Hz, 1H, CH≡CCH$_2$), 7.48-7.66 (m, 8H, 4,6,7-BenzimidH, PhH), 7.67 (dd, 9.1, 2.4 Hz, 1H, 6-PhthH), 8.09 (bs, 1H, 8-PhthH), 8.38 (s, 1H, 2-BenzimidH), 8.39 ppm (d, J=9.1 Hz, 1H, 5-PhthH).

Example 5

Activity of Compounds of General Structure II

The potencies (i.e., the EC$_{50}$ values) of the compounds of the above shown general structure II using the above-described testing methods were measured. In some cases, an EC$_{50}$ value for a free base could not be determined because of compound precipitation from the medium; however, evaluation of the corresponding salt provided this value. Compound library generation is then modified so that only the hydrochloride salts of the substituted benzimidazoles were isolated. In addition to ease of synthesis, the increased solubility of the benzimidazole salts appears necessary for bioactivity. Thus, activity may depend on compound solubility as well as the identity of substituent groups. The results are shown in Table 2-1.

TABLE 2-1

Activity of some compounds of structure II in the cardiomyocyte screening assay.

| # | STRUCTURE | Salt form | Activity | # | STRUCTURE | Salt form | Activity |
|---|---|---|---|---|---|---|---|
| 31 | | HCl | +++ | 66 | | HCl | + |
| 32 | | HCl | ++ | 67 | | oxalate | + |

TABLE 2-1-continued

Activity of some compounds of structure II in the cardiomyocyte screening assay.

| # | STRUCTURE | Salt form | Activity | # | STRUCTURE | Salt form | Activity |
|---|---|---|---|---|---|---|---|
| 33 | | none | +++ | 68 | | none | ++++ |
| 34 | | none | ++ | 69 | | HCl | +++ |

TABLE 2-1-continued

Activity of some compounds of structure II in the cardiomyocyte screening assay.

| # | STRUCTURE[a] | Salt form | Activity[b] | # | STRUCTURE | Salt form | Activity |
|---|---|---|---|---|---|---|---|
| 35 | | HCl | ++ | 70 | 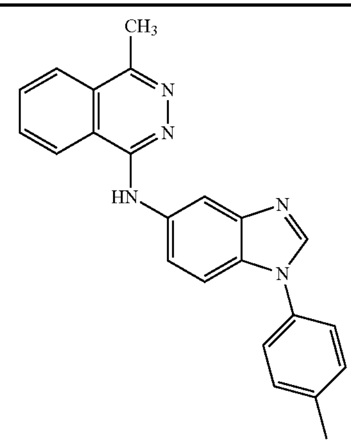 | HCl | ++ |
| 36 | | 2 @ HCl | ++ | 71 | 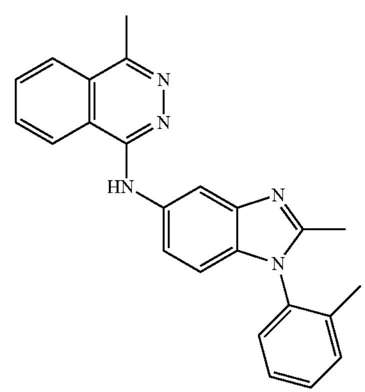 [SMILES: Cc1ccccc1-n1c(C)nc2cc(Nc3nnc(C)c4ccccc34)ccc21] | oxalate | ++ |

TABLE 2-1-continued

Activity of some compounds of structure II in the cardiomyocyte screening assay.

| # | STRUCTURE[a] | Salt form | Activity[b] |
|---|---|---|---|
| 37 | | HCl | ++ |
| 38 | | HCl | ++++ |
| 72 | | oxalate | +++ |
| 73 | | HCl | ++ |

TABLE 2-1-continued

Activity of some compounds of structure II in the cardiomyocyte screening assay.

| # | STRUCTURE[a] | Salt form | Activity[b] | # | STRUCTURE | Salt form | Activity |
|---|---|---|---|---|---|---|---|
| 39 | | HCl | ++++ | 74 | 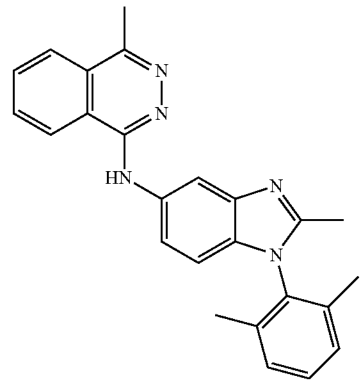 [SMILES: Cc1cccc(C)c1-n1c(C)nc2cc(Nc3nnc(C)c4ccccc34)ccc21] | oxalate | + |
| 40 | | HCl | + | 75 | 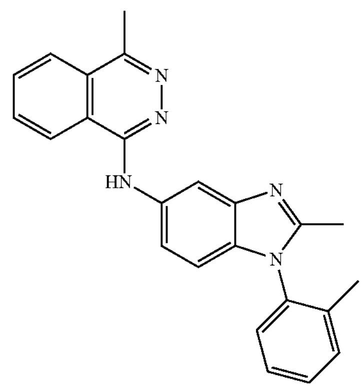 [SMILES: Cc1ccccc1-n1c(C)nc2cc(Nc3nnc(C)c4ccccc34)ccc21] | none | ++ |

TABLE 2-1-continued

Activity of some compounds of structure II in the cardiomyocyte screening assay.

| # | STRUCTURE[a] | Salt form | Activity[b] |
|---|---|---|---|
| 41 | | none | +++ |
| 76 | | none | + |
| 42 | | HCl | +++ |
| 77 | | HCl | +++ |

TABLE 2-1-continued

Activity of some compounds of structure II in the cardiomyocyte screening assay.

| # | STRUCTURE[a] | Salt form | Activity[b] | # | STRUCTURE | Salt form | Activity |
|---|---|---|---|---|---|---|---|
| 43 | | HCl | + | 78 | 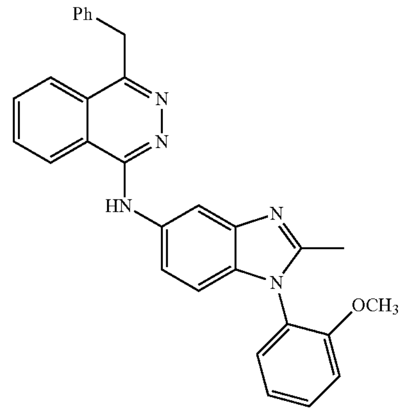 [SMILES: COc1ccccc1-n1c(C)nc2cc(Nc3nnc(Cc4ccccc4)c4ccccc34)ccc21] | none | + |
| 44 | | oxalate | + | 79 | 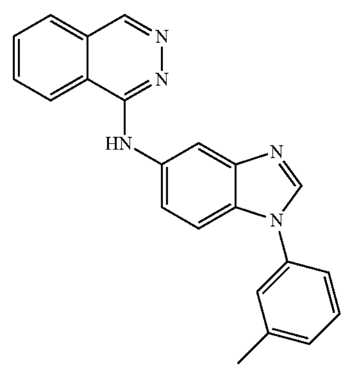 [SMILES: Cc1cccc(-n2cnc3cc(Nc4nncc5ccccc45)ccc32)c1] | none | + |

TABLE 2-1-continued

Activity of some compounds of structure II in the cardiomyocyte screening assay.

| # | STRUCTURE | Salt form | Activity[b] | # | STRUCTURE | Salt form | Activity |
|---|---|---|---|---|---|---|---|
| 45 | | HCl | + | 80 | | none | ++ |
| 46 | | none | + | 81 | | oxalate | ++ |

TABLE 2-1-continued

Activity of some compounds of structure II in the cardiomyocyte screening assay.

| # | STRUCTURE | Salt form | Activity |
|---|-----------|-----------|----------|
| 47 | (structure) | oxalate | +++ |
| 48 | (structure) | none | + |
| 82 | (structure) | oxalate | ++ |
| 83 | (structure) | none | ++ |

TABLE 2-1-continued

Activity of some compounds of structure II in the cardiomyocyte screening assay.

| # | STRUCTURE[a] | Salt form | Activity[b] |
|---|---|---|---|
| 49 | (structure) | HCl | +++ |
| 84 | (structure) | oxalate | ++ |
| 50 | (structure) | oxalate | +++ |
| 85 | (structure) | oxalate | + |

TABLE 2-1-continued

Activity of some compounds of structure II in the cardiomyocyte screening assay.

| # | STRUCTURE[a] | Salt form | Activity[b] |
|---|---|---|---|
| 51 | | HCl | + |
| 86 | | none | + |
| 52 | | HCl | ++ |
| 87 | | HCl | ++ |

TABLE 2-1-continued

Activity of some compounds of structure II in the cardiomyocyte screening assay.

| # | STRUCTURE[a] | Salt form | Activity[b] | # | STRUCTURE | Salt form | Activity |
|---|---|---|---|---|---|---|---|
| 53 | (structure) | oxalate | ++ | 88 | (structure) | HCl | +++ |
| 54 | (structure) | HCl | +++ | 89 | (structure) | none | + |

TABLE 2-1-continued

Activity of some compounds of structure II in the cardiomyocyte screening assay.

| # | STRUCTURE[a] | Salt form | Activity[b] | # | STRUCTURE | Salt form | Activity |
|---|---|---|---|---|---|---|---|
| 55 | | HCl | + | 90 | 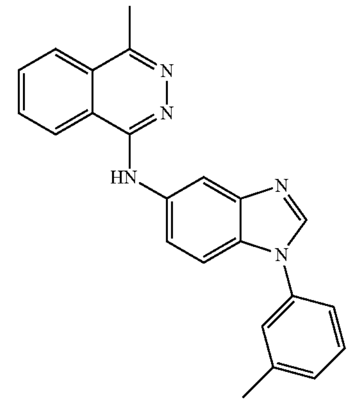 [SMILES: Cc1cccc(-n2cnc3cc(Nc4nnc(C)c5ccccc45)ccc32)c1] | HCl | + |
| 56 | | HCl | + | 91 | 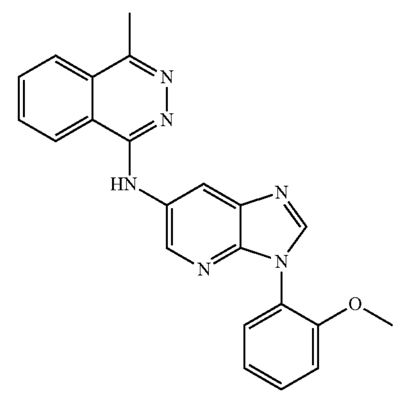 [SMILES: COc1ccccc1-n1cnc2cc(Nc3nnc(C)c4ccccc34)cnc21] | none | + |

TABLE 2-1-continued

Activity of some compounds of structure II in the cardiomyocyte screening assay.

| # | STRUCTURE[a] | Salt form | Activity[b] | # | STRUCTURE | Salt form | Activity |
|---|---|---|---|---|---|---|---|
| 57 | | HCl | + | 92 | 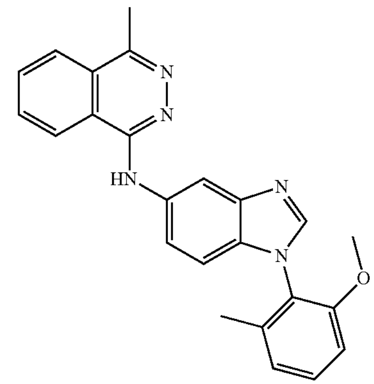 [SMILES: COc1cccc(C)c1-n1cnc2cc(Nc3nnc(C)c4ccccc34)ccc21] | none | + |
| 58 | | none | + | 93 | 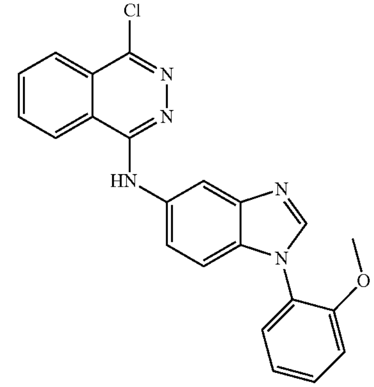 [SMILES: COc1ccccc1-n1cnc2cc(Nc3nnc(Cl)c4ccccc34)ccc21] | none | ++ |

TABLE 2-1-continued

Activity of some compounds of structure II in the cardiomyocyte screening assay.

| # | STRUCTURE | Salt form | Activity |
|---|---|---|---|
| 59 | (structure) | oxalate | + |
| 60 | (structure) | oxalate | + |
| 94 | (structure) | none | + |
| 95 | (structure) | none | + |

TABLE 2-1-continued

Activity of some compounds of structure II in the cardiomyocyte screening assay.

| # | STRUCTURE | Salt form | Activity | # | STRUCTURE | Salt form | Activity |
|---|---|---|---|---|---|---|---|
| 61 | | none | + | 96 | | none | + |
| 62 | | oxalate | + | 97 | | oxalate | + |

TABLE 2-1-continued

Activity of some compounds of structure II in the cardiomyocyte screening assay.

| # | STRUCTURE[a] | Salt form | Activity[b] | # | STRUCTURE | Salt form | Activity |
|---|---|---|---|---|---|---|---|
| 63 | Bn-phthalazine-NH-benzimidazole-2,6-dimethylphenyl | none | ++ | 98 | Cl-phthalazine-NH-benzimidazole-2,6-dimethylphenyl | none | + |
| 64 | Cl-phthalazine-NH-benzimidazole-2,6-dimethylphenyl | oxalate | + | 99 | Bn-phthalazine-NH-benzimidazole-2,6-dimethylphenyl | oxalate | + |

TABLE 2-1-continued

Activity of some compounds of structure II in the cardiomyocyte screening assay.

| # | STRUCTURE[a] | Salt form | Activity[b] | # | STRUCTURE | Salt form | Activity |
|---|---|---|---|---|---|---|---|
| 65 | (structure) | HCl | + | 100 | (structure) | none | + |

[a]All the compounds have been characterized by LRMS and or 1H NMR.
[b]Activity is based on compound 28 being 100% activity;
++++: >80% activity compared to 28;
+++ between 60 to 80% activity compared to 28;
++ between 40 to 60% activity compared to 28;
+: <40% activity compared to compound 28.

Activity of Compounds of General Structure IIA

The compound of structure II includes the structure IIA:

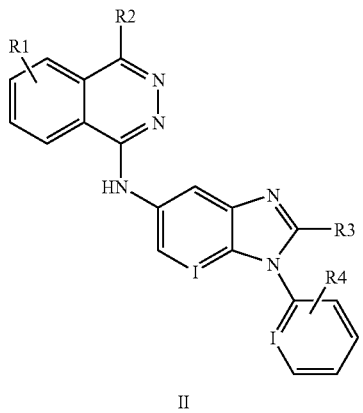

II wherein $R_1$ is H, $CH_3$; $R_2$ is $(C_1$-$C_6)$alkyl, halogen, methoxy, benzyl; $R_3$ is H, $(C_1$-$C_6)$alkyl, amine optionally substituted by a $(C_1$-$C_6)$alkyl, $R_4$ is H, $CH_3$, $OCH_3$, $SCH_3$, $CF_3$, $(C_1$-$C_6)$alkyl, halogen, alkoxy; I is CH, N.

TABLE 2-2

Activity of compounds of structure IIA with potencies in the cardiomyocyte screening assay.

| # | Structure[a] | Salt form | Activity[b] |
|---|---|---|---|
| 101 | | HCl | +++ |
| 102 | | HCl | + |
| 103 | | HCl | + |
| 104 | | HCl | INACTIVE |

[a]All the compounds have been characterized by LRMS and or 1H NMR.
[b]Activity is based on compound 28 being 100% activity;
++++: >80% activity compared to 28;
+++ between 60 to 80% activity compared to 28;
++ between 40 to 60% activity compared to 28;
+: <40% activity compared to compound 28.

Activity of Compounds of General Structure IIB

The compounds of structure IIB include 1-atyl-5-(1-arylamino)-benzimidazole:

IIB wherein A is a aromatic group, an alkyl substituted by an aromatic group; $R_1$ is H, $CH_3$; $R_2$ is $(C_1$-$C_6)$alkyl, halogen, methoxy, benzyl; $R_3$ is H, $(C_1$-$C_6)$alkyl, amine optionally substituted by a $(C_1$-$C_6)$alkyl, $R_4$ is a phenyl, pyridine, alkyl.

The compounds of the above shown general structure IIB may be synthesized according to the following synthetic schemes depending on the nature of A.

TABLE 2-3
Activity of compounds of structure IIB with potencies in the cardiomyocyte screening assay.
| # | Structure[a] | Salt form | Activity[b] |
|---|---|---|---|
| 105 | 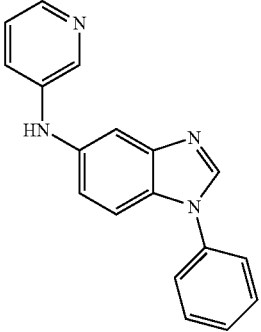 [SMILES: c1ccc(-n2cnc3cc(Nc4cccnc4)ccc32)cc1] | None | ++++ |
| 106 | 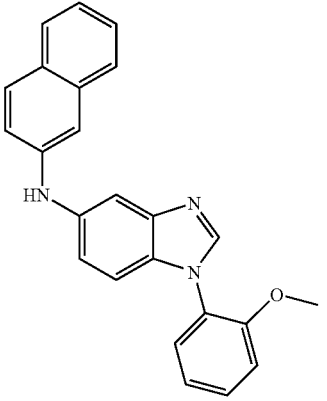 [SMILES: COc1ccccc1-n1cnc2cc(Nc3ccc4ccccc4c3)ccc21] | None | + |
| 107 | 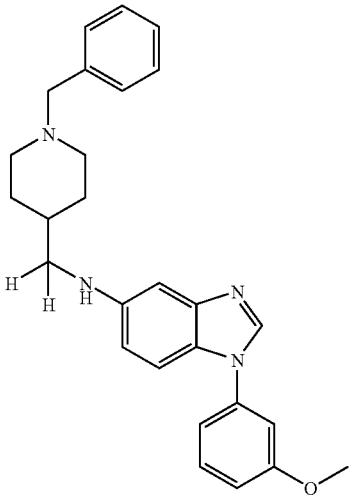 [SMILES: COc1cccc(-n2cnc3cc(NCC4CCN(Cc5ccccc5)CC4)ccc32)c1] | 2HCl | +++ |

TABLE 2-3-continued

Activity of compounds of structure IIB with potencies in the cardiomyocyte screening assay.

| # | Structure[a] | Salt form | Activity[b] |
|---|---|---|---|
| 108 | | HCl | ++ |
| 109 | | HCl | +++ |
| 110 | | HCl | ++ |
| 111 | | 2HCl | ++ |

TABLE 2-3-continued

Activity of compounds of structure IIB with potencies in the cardiomyocyte screening assay.

| # | Structure[a] | Salt form | Activity[b] |
|---|---|---|---|
| 112 | | 2HCl | + |
| 113 | | 2HCl | ++ |
| 114 | | HCl | + |
| 115 | | none | + |

TABLE 2-3-continued

Activity of compounds of structure IIB with potencies in the cardiomyocyte screening assay.

| # | Structure[a] | Salt form | Activity[b] |
|---|---|---|---|
| 116 | *pyrazin-2-yl-NH-benzimidazole, N1-phenyl* | None | + |
| 117 | *4-hydroxy-2-methoxybenzyl-NH-benzimidazole, N1-(3-methoxyphenyl)* | 2HCl | + |
| 118 | *pyridin-3-yl-NH-benzimidazole, N1-phenyl* | HCl | ++++ |
| 119 | *3-methoxyphenyl-NH-benzimidazole, N1-(2-methoxyphenyl)* | HCl | +++ |

TABLE 2-3-continued

Activity of compounds of structure IIB with potencies in the cardiomyocyte screening assay.

| # | Structure[a] | Salt form | Activity[b] |
|---|---|---|---|
| 120 | | None | + |
| 121 | | 2HCl | +++ |
| 122 | | 2HCl | + |
| 123 | | 2HCl | ++ |

TABLE 2-3-continued

Activity of compounds of structure IIB with potencies in the cardiomyocyte screening assay.

| # | Structure[a] | Salt form | Activity[b] |
|---|---|---|---|
| 124 | | | |
| 125 | | 2HCl | ++ |
| 126 | | HCl | + |
| 127 | | None | + |

TABLE 2-3-continued

Activity of compounds of structure IIB with potencies in the cardiomyocyte screening assay.

| # | Structure[a] | Salt form | Activity[b] |
|---|---|---|---|
| 128 | | 2HCl | + |
| 129 | | 2HCl | + |
| 130 | | none | + |

[a]All the compounds have been characterized by LRMS and or 1H NMR.

[b]Activity is based on compound 28 being 100% activity;

++++: >80% activity compared to 28;

+++ between 60 to 80% activity compared to 28;

++ between 40 to 60% activity compared to 28;

+: <40% activity compared to compound 28.

Activity of Compounds of General Structure IIC

The compounds of structure IIC include 1-phenyl-5-(1-arylamino)-benzotriazole:

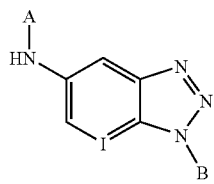

IIC wherein A is aromatic, heteroaromatic, optionally substituted with H, $CH_3$, O $CH_3$, S $CH_3$, $CF_3$, $(C_1\text{-}C_6)$alkyl, halogen, alkoxy, alkyl substituted by an aromatic, heteroaromatic ring; I is CH, N, B is a phenyl, pyridine, alkyl optionally substituted by H, $CH_3$, O $CH_3$, S $CH_3$, $CF_3$, $(C_1\text{-}C_6)$alkyl, halogen, alkoxy.

TABLE 2-4

Activity of compounds of structure IIC with potencies in the cardiomyocyte screening assay.

| # | Structure | salt form | Activity |
|---|-----------|-----------|----------|
| 131 | 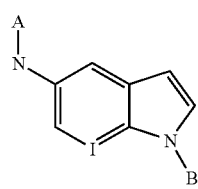 | HCl | ++ |

[a] All the compounds have been characterized by LRMS and or 1H NMR.
[b] Activity is based on compound 28 being 100% activity;
++++: >80% activity compared to 28;
+++ between 60 to 80% activity compared to 28;
++ between 40 to 60% activity compared to 28;
+: <40% activity compared to compound 28.

Activity of Compounds of General Structure IID

The compounds of structure IID include 1-phenyl-5-(1-arylamino)-indole:

IID wherein A is aromatic, heteroaromatic, optionally substituted with H, $CH_3$, O—$CH_3$, S—$CH_3$, $CF_3$, $(C_1\text{-}C_6)$alkyl, halogen, alkoxy, alkyl substituted by an aromatic, heteroaromatic ring; I is CH, N, B is a phenyl, pyridine, alkyl optionally substituted by H, $CH_3$, O—$CH_3$, S—$CH_3$, $CF_3$, $(C_1\text{-}C_6)$alkyl, halogen, alkoxy.

TABLE 2-5

Activity of compounds of structure IID with potencies in the cardiomyocyte screening assay.

| number | structure[a] | salt form | Activity[b] |
|--------|--------------|-----------|-------------|
| 132 |  | HCl | +++ |
| 6-2 |  | HCl | ++ |

[a] All the compounds have been characterized by LRMS and or 1H NMR.
[b] Activity is based on compound 28 being 100% activity;
++++: >80% activity compared to 28;
+++ between 60 to 80% activity compared to 28;
++ between 40 to 60% activity compared to 28;
+: <40% activity compared to compound 28.

TABLE 2-6

Characterization of compounds of structure II. Nuclear magnetic resonance data were recorded on a Varian Mercury 300 MHz Spectrometer using TMS as the internal standard and CDCl$_3$ as the solvent except where indicated. Electrospray mass spectral (MS) data was obtained using a Hitachi M-7000.

| structure | MW (g·mol$^{-1}$) | M(1 + H) |
|---|---|---|
| [structure] | 381.3 | MS (ESI$^+$) m/z 282 (M + H)$^+$ |
| [structure] | 410 | MS (ESI$^+$) m/z 425 (M + Na)$^+$ |
| [structure] | 470 | MS (ESI$^+$) m/z 471.5 (M + H)$^+$ |

TABLE 2-6-continued

Characterization of compounds of structure II. Nuclear magnetic resonance data were recorded on a Varian Mercury 300 MHz Spectrometer using TMS as the internal standard and CDCl₃ as the solvent except where indicated. Electrospray mass spectral (MS) data was obtained using a Hitachi M-7000.

| structure | MW (g·mol$^{-1}$) | M(1 + H) |
|---|---|---|
| 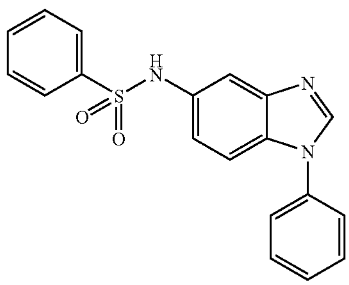 [SMILES: O=S(=O)(Nc1ccc2c(c1)ncn2-c1ccccc1)c1ccccc1] | 349.5 | MS (ESI$^+$) m/z 350 (M + H)$^+$ |
| 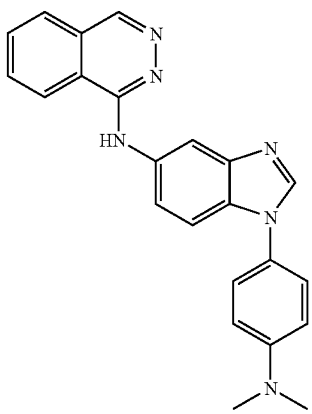 [SMILES: CN(C)c1ccc(-n2cnc3cc(Nc4nncc5ccccc45)ccc32)cc1] | 380 | MS (ESI$^+$) m/z 381.5 (M + H)$^+$ |
| 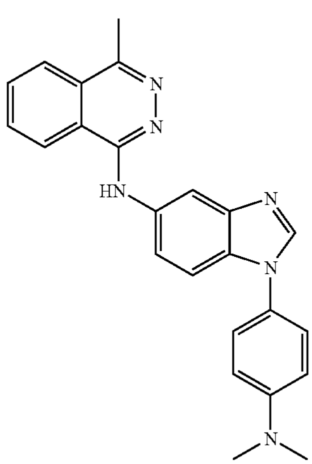 [SMILES: Cc1nnc(Nc2ccc3c(c2)ncn3-c2ccc(N(C)C)cc2)c2ccccc12] | 394 | MS (ESI$^+$) m/z 395.6 (M + H)$^+$ |

TABLE 2-6-continued

Characterization of compounds of structure II. Nuclear magnetic resonance data were recorded on a Varian Mercury 300 MHz Spectrometer using TMS as the internal standard and CDCl₃ as the solvent except where indicated. Electrospray mass spectral (MS) data was obtained using a Hitachi M-7000.

| structure | MW (g·mol$^{-1}$) | M(1 + H) |
|---|---|---|
| 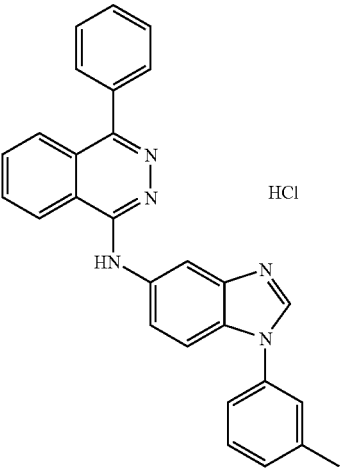 [SMILES: Cc1cccc(-n2cnc3cc(Nc4nnc(-c5ccccc5)c5ccccc45)ccc32)c1 ; Cl] | 427 | MS (ESI⁺) m/z 429.5 (M + H)⁺ |
| 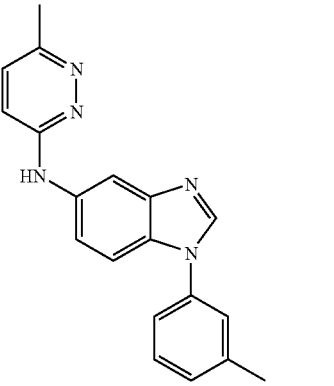 [SMILES: Cc1cccc(-n2cnc3cc(Nc4ccc(C)nn4)ccc32)c1] | 315.4 | MS (ESI⁺) m/z 317.4 (M + H)⁺ |
| 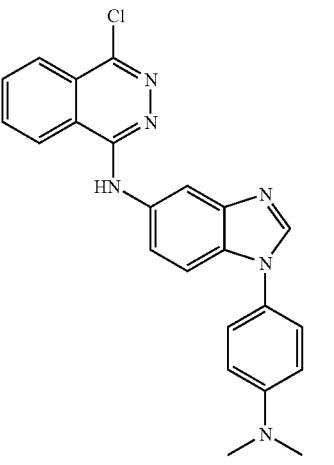 [SMILES: CN(C)c1ccc(-n2cnc3cc(Nc4nnc(Cl)c5ccccc45)ccc32)cc1] | 414 | MS (ESI⁺) m/z 415.1 (M + H)⁺ |

TABLE 2-6-continued

Characterization of compounds of structure II. Nuclear magnetic resonance data were recorded on a Varian Mercury 300 MHz Spectrometer using TMS as the internal standard and CDCl$_3$ as the solvent except where indicated. Electrospray mass spectral (MS) data was obtained using a Hitachi M-7000.

| structure | MW (g · mol$^{-1}$) | M(1 + H) |
|---|---|---|
| [4-phenylphthalazin-1-yl-NH-benzimidazole-N1-(4-dimethylaminophenyl)] | 456 | MS (ESI$^+$) m/z 457.5 (M + H)$^+$ |
| [N-(1-phenylbenzimidazol-5-yl)acetamide] | 251.3 | MS (ESI$^+$) m/z 252.2 (M + H)$^+$ |
| [CF$_3$CH$_2$SO$_2$NH-(1-phenylbenzimidazol-5-yl)] | 355.3 | MS (ESI$^+$) m/z 356 (M + H)$^+$ |

TABLE 2-6-continued

Characterization of compounds of structure II. Nuclear magnetic resonance data were recorded on a Varian Mercury 300 MHz Spectrometer using TMS as the internal standard and CDCl$_3$ as the solvent except where indicated. Electrospray mass spectral (MS) data was obtained using a Hitachi M-7000.

| structure | MW (g·mol$^{-1}$) | M(1 + H) |
|---|---|---|
| [4-benzyl-phthalazin-1-yl]-[1-(3-methylphenyl)-1H-benzimidazol-5-yl]amine · HCl | 441 | MS (ESI$^+$) m/z 442.6 (M + H)$^+$ |
| phthalazin-1-yl-[1-(3-methylphenyl)-1H-benzimidazol-5-yl]amine · HCl | 351 | MS (ESI$^+$) m/z 353.3 (M + H)$^+$ |
| [4-methoxy-phthalazin-1-yl]-[1-(3-methylphenyl)-1H-benzimidazol-5-yl]amine · HCl | 381 | MS (ESI$^+$) m/z 381.1 (M + H)$^+$ |
| cyclobutanecarboxylic acid (1-phenyl-1H-benzimidazol-5-yl)amide | 291.3 | MS (ESI$^+$) m/z 314 (M + Na)$^+$ |

TABLE 2-6-continued

Characterization of compounds of structure II. Nuclear magnetic resonance data were recorded on a Varian Mercury 300 MHz Spectrometer using TMS as the internal standard and CDCl$_3$ as the solvent except where indicated. Electrospray mass spectral (MS) data was obtained using a Hitachi M-7000.

| structure | MW (g·mol$^{-1}$) | M(1 + H) |
|---|---|---|
| 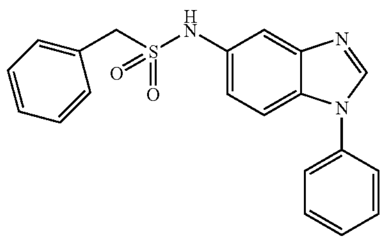 [SMILES: O=S(=O)(Cc1ccccc1)Nc1ccc2c(c1)ncn2-c1ccccc1] | 363 | MS (ESI$^+$) m/z 364 (M + H)$^+$ |
| 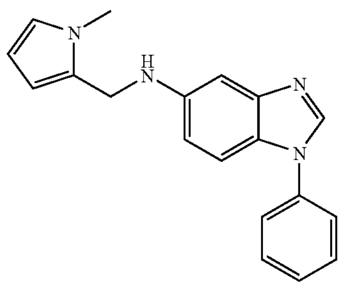 [SMILES: Cn1cccc1CNc1ccc2c(c1)ncn2-c1ccccc1] | 302 | MS (ESI$^+$) m/z 303 (M + H)$^+$ |
| 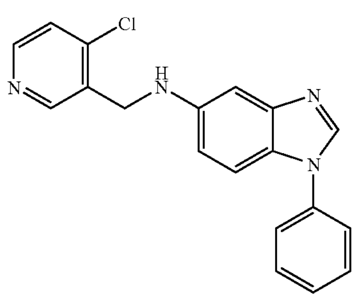 [SMILES: Clc1ccncc1CNc1ccc2c(c1)ncn2-c1ccccc1] | 334.5 | MS (ESI$^+$) m/z 335 (M + H)$^+$ |
| 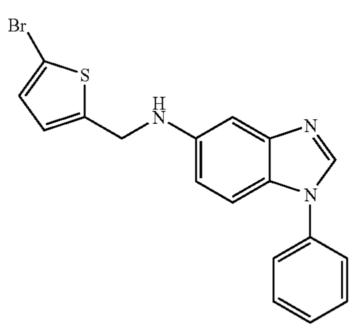 [SMILES: Brc1ccc(CNc2ccc3c(c2)ncn3-c2ccccc2)s1] | 384 | MS (ESI$^+$) m/z 386 (M + H)$^+$ |

TABLE 2-6-continued

Characterization of compounds of structure II. Nuclear magnetic resonance data were recorded on a Varian Mercury 300 MHz Spectrometer using TMS as the internal standard and CDCl$_3$ as the solvent except where indicated. Electrospray mass spectral (MS) data was obtained using a Hitachi M-7000.

| structure | MW (g · mol$^{-1}$) | M(1 + H) |
|---|---|---|
| (structure with methylphthalazine-NH-benzimidazole-tolyl, HCl) | 365 | MS (ESI$^+$) m/z 366.6 (M + H)$^+$ |
| (furfuryl-NH-benzimidazole-phenyl) | 289.1 | MS (ESI$^+$) m/z 290 (M + H)$^+$ |
| (4-methoxybenzyl-NH-benzimidazole-phenyl) | 329.1 | MS (ESI$^+$) m/z 331.7 (M + H)$^+$ |
| (2-methoxybenzyl-NH-benzimidazole-phenyl) | 329.1 | MS (ESI$^+$) m/z 331.9 (M + Na)$^+$ |

TABLE 2-6-continued

Characterization of compounds of structure II. Nuclear magnetic resonance data were recorded on a Varian Mercury 300 MHz Spectrometer using TMS as the internal standard and CDCl₃ as the solvent except where indicated. Electrospray mass spectral (MS) data was obtained using a Hitachi M-7000.

| structure | MW (g·mol$^{-1}$) | M(1 + H) |
|---|---|---|
| 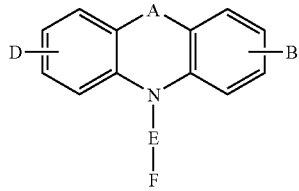 | 305.4 | MS (ESI⁺) m/z 306 (M + H)⁺ |
| 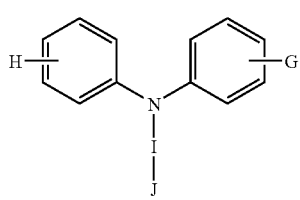 | 376.2 | MS (ESI⁺) m/z 377 (M + H)⁺ |

Example 6

General Synthetic Procedure for Obtaining Compounds of Structure I, II and III The phenothiazine-based compounds of general structure I, II and III:

I

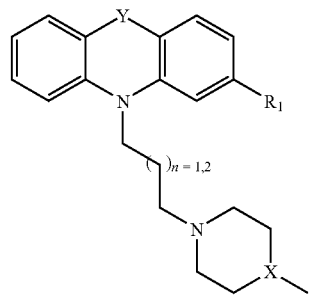

II

III may be synthesized according to the following schemes.

Scheme 25: Synthesis of Phenothiazine Analogs.

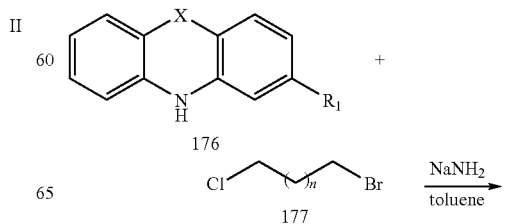

185
-continued

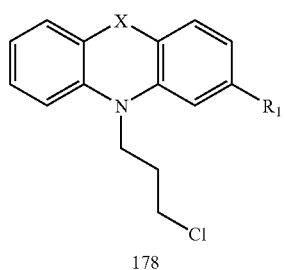

178

+ 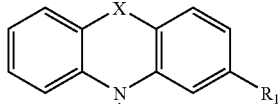

179

→ KI / ACN / 80° C.

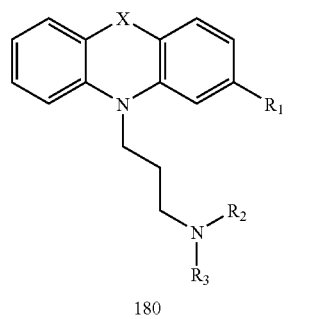

180

→ HCl / Et₂O

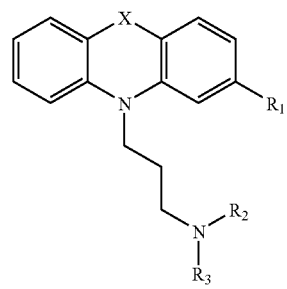

181

•yHCl

X = S, O, (CH₂)$_m$
R₁ = H, Cl, CF₃, SCH₃
R₂ = alkyl, aryl, heteroalkyl
R₃ = alkyl, aryl, heteroalkyl
R₂ and R₃ can be joined via a ring
n = 1 or 2
m = 0 or 2

Scheme 26: Synthesis of Tamoxifen Analogs.

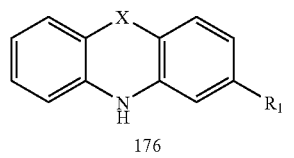

176

+

Cl–(CH₂)$_n$–Br

177

→ NaNH₂ / toluene

186
-continued

178

+ 179

→ KI / ACN / 80° C.

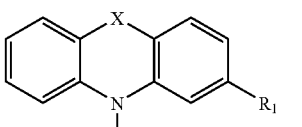

180

→ HCl / Et₂O

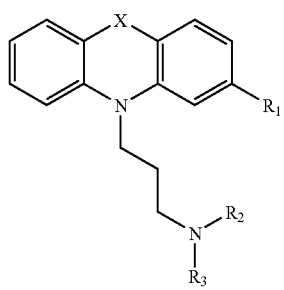

181

•yHCl

X = S, O, (CH₂)$_m$
R₁ = H, Cl, CF₃, SCH₃
R₂ = alkyl, aryl, heteroalkyl
R₃ = alkyl, aryl, heteroalkyl
R₂ and R₃ can be joined via a ring
n = 1 or 2
m = 0 or 2

Activity of Compounds of General Structures I, II and III

The potencies (i.e., the EC$_{50}$ values) of the compounds of the above shown general structure I and III using the above-described testing methods is measured. The results are shown in Table 3-1.

TABLE 3-1

Activity of compounds of structure I and III with potencies in the cardiomyocyte screening assay.

| # | STRUCTURE | Salt form | Activity |
|---|---|---|---|
| 133 | (phenothiazine with CF₃ substituent, N-propyl-4-hydroxypiperidine) | 2 @ HCl | |
| 134 | (phenothiazine with CF₃ substituent, N-propyl-3,5-dimethylpiperidine) | 2 @ HCl | |
| 135 | (phenothiazine with CF₃ substituent, N-propyl-2,6-dimethylmorpholine) | 2 @ HCl | |
| 136 | (phenothiazine with CF₃ substituent, N-propyl-4-methylpiperidine) | 2 @ HCl | |

TABLE 3-1-continued
Activity of compounds of structure I and III with potencies in the cardiomyocyte screening assay.
| # | STRUCTURE | Salt form | Activity |
|---|---|---|---|
| 137 | 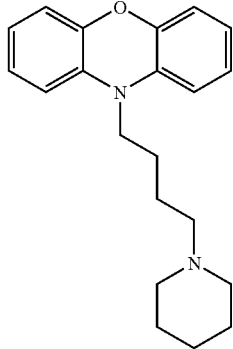 [SMILES: c1ccc2c(c1)Oc1ccccc1N2CCCCN1CCCCC1] | 2 @ HCl | |
| 138 | 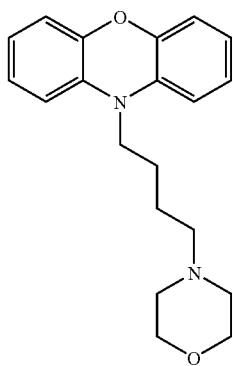 [SMILES: c1ccc2c(c1)Oc1ccccc1N2CCCCN1CCOCC1] | 2 @ HCl | |
| 139 | 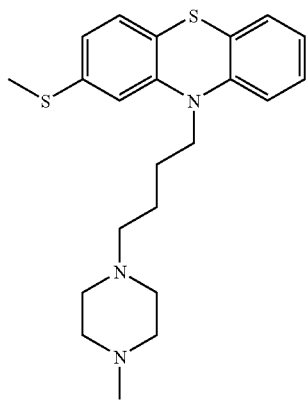 [SMILES: CSc1ccc2c(c1)N(CCCCN1CCN(C)CC1)c1ccccc1S2] | HCl | |

TABLE 3-1-continued

Activity of compounds of structure I and III with potencies in the cardiomyocyte screening assay.

| # | STRUCTURE | Salt form | Activity |
|---|---|---|---|
| 140 | 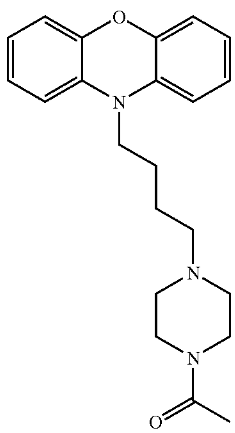 [SMILES: CC(=O)N1CCN(CCCCN2c3ccccc3Oc3ccccc32)CC1] | 2 @ HCl | |
| 141 | 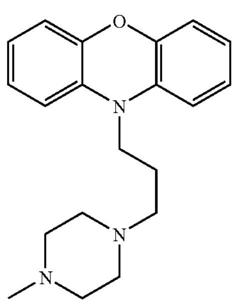 [SMILES: CN1CCN(CCCN2c3ccccc3Oc3ccccc32)CC1] | 2 @ HCl | |
| 142 | 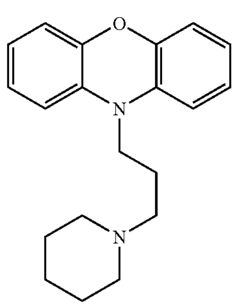 [SMILES: c1ccc2c(c1)Oc1ccccc1N2CCCN1CCCCC1] | 2 @ HCl | |
| 143 | 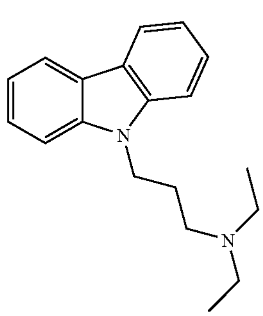 [SMILES: CCN(CC)CCCn1c2ccccc2c2ccccc21] | 2 @ HCl | |

TABLE 3-1-continued

Activity of compounds of structure I and III with potencies in the cardiomyocyte screening assay.

| # | STRUCTURE | Salt form | Activity |
|---|-----------|-----------|----------|
| 144 | 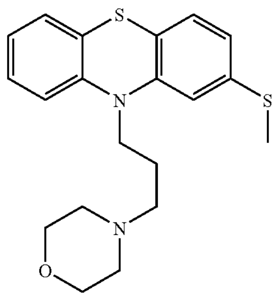 [SMILES: CSc1ccc2c(c1)N(CCCN1CCOCC1)c1ccccc1S2] | 2 @ HCl | |
| 145 | 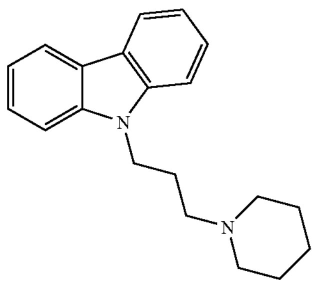 [SMILES: c1ccc2c(c1)c1ccccc1n2CCCN1CCCCC1] | 2 @ HCl | |
| 146 | 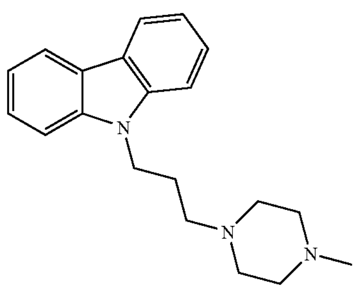 [SMILES: CN1CCN(CCCn2c3ccccc3c3ccccc32)CC1] | 3 @ HCl | |
| 147 | 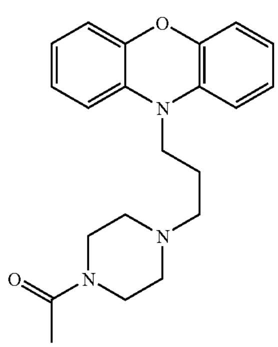 [SMILES: CC(=O)N1CCN(CCCN2c3ccccc3Oc3ccccc32)CC1] | 2 @ HCl | |
| 148 | 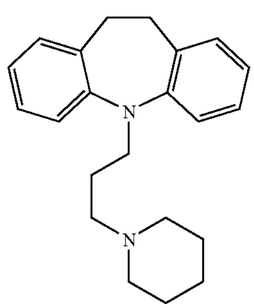 [SMILES: c1ccc2c(c1)CCc1ccccc1N2CCCN1CCCCC1] | 2 @ HCl | |

TABLE 3-1-continued

Activity of compounds of structure I and III with potencies in the cardiomyocyte screening assay.

| # | STRUCTURE | Salt form | Activity |
|---|---|---|---|
| 149 | 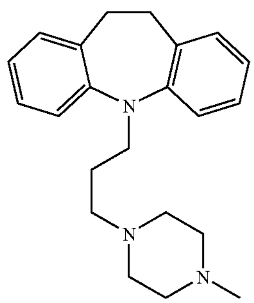 [SMILES: CN1CCN(CCCN2c3ccccc3CCc3ccccc32)CC1] | 3 @ HCl | |
| 150 | 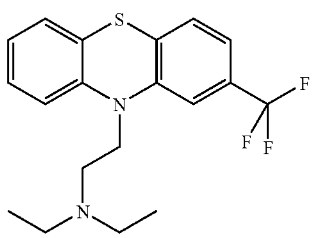 [SMILES: CCN(CC)CCN1c2ccccc2Sc2ccc(C(F)(F)F)cc21] | 2 @ HCl | |
| 151 | 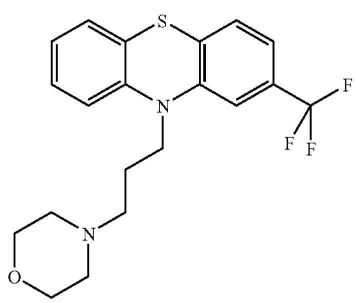 [SMILES: FC(F)(F)c1ccc2c(c1)N(CCCN1CCOCC1)c1ccccc1S2] | 2 @ HCl | |
| 152 | 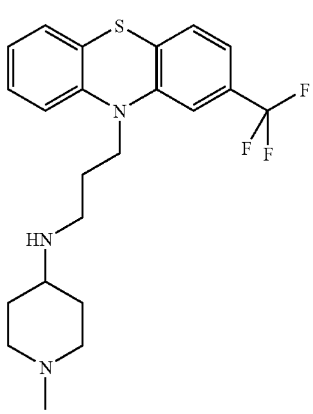 [SMILES: CN1CCC(NCCCN2c3ccccc3Sc3ccc(C(F)(F)F)cc32)CC1] | 3 @ HCl | |

TABLE 3-1-continued

Activity of compounds of structure I and III with potencies in the cardiomyocyte screening assay.

| # | STRUCTURE | Salt form | Activity |
|---|---|---|---|
| 153 | 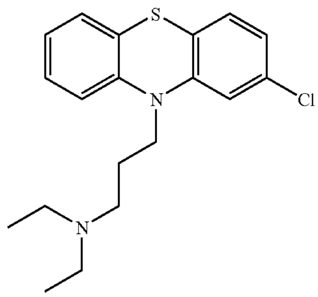 [SMILES: CCN(CC)CCCN1c2ccccc2Sc2ccc(Cl)cc21] | 2 @ HCl | |
| 154 | 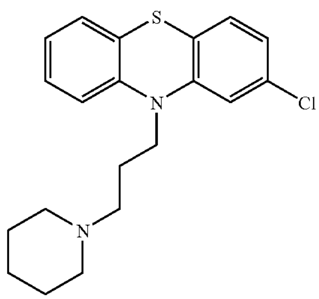 [SMILES: Clc1ccc2c(c1)N(CCCN1CCCCC1)c1ccccc1S2] | 2 @ HCl | |
| 155 | 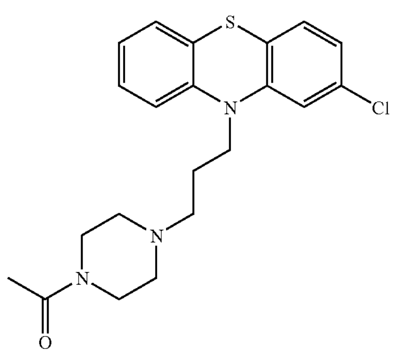 [SMILES: CC(=O)N1CCN(CCCN2c3ccccc3Sc3ccc(Cl)cc32)CC1] | 2 @ HCl | |
| 156 | 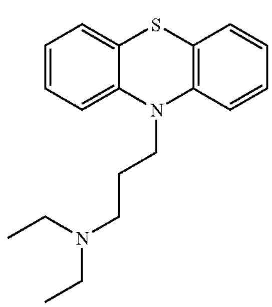 [SMILES: CCN(CC)CCCN1c2ccccc2Sc2ccccc21] | 2 @ HCl | |

TABLE 3-1-continued

Activity of compounds of structure I and III with potencies in the cardiomyocyte screening assay.

| # | STRUCTURE | Salt form | Activity |
|---|---|---|---|
| 157 | 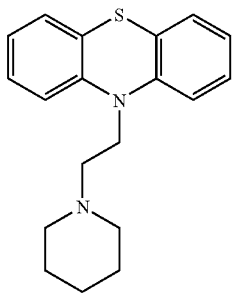 [SMILES: c1ccc2c(c1)Sc1ccccc1N2CCN1CCCCC1] | 2 @ HCl | |
| 158 | 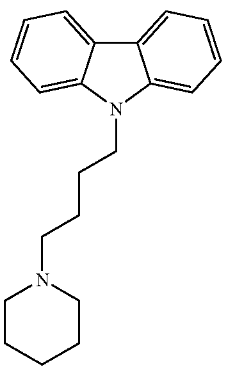 [SMILES: c1ccc2c(c1)c1ccccc1n2CCCCN1CCCCC1] | 2 @ HCl | |
| 159 | 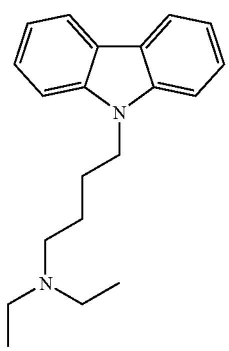 [SMILES: CCN(CC)CCCCn1c2ccccc2c2ccccc21] | 2 @ HCl | |
| 160 | 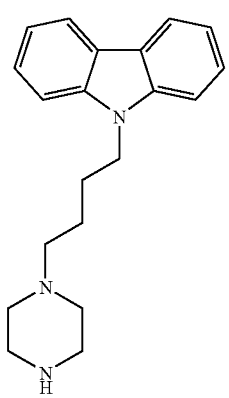 [SMILES: c1ccc2c(c1)c1ccccc1n2CCCCN1CCNCC1] | 3 @ HCl | |

TABLE 3-1-continued

Activity of compounds of structure I and III with potencies in the cardiomyocyte screening assay.

| # | STRUCTURE | Salt form | Activity |
|---|---|---|---|
| 161 | 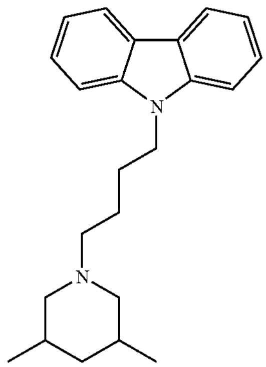 [SMILES: CC1CC(C)CN(CCCCn2c3ccccc3c3ccccc32)C1] | 2 @ HCl | |
| 162 | 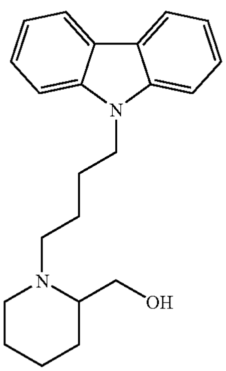 [SMILES: OCC1CCCCN1CCCCn1c2ccccc2c2ccccc21] | 2 @ HCl | |
| 163 | 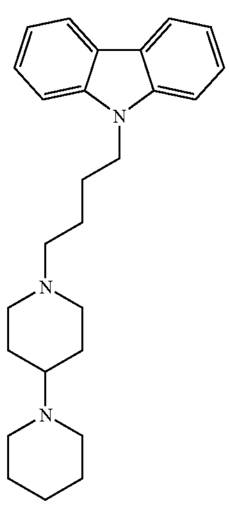 [SMILES: c1ccc2c(c1)c1ccccc1n2CCCCN1CCC(N2CCCCC2)CC1] | 3 @ HCl | |

TABLE 3-1-continued

Activity of compounds of structure I and III with potencies in the cardiomyocyte screening assay.

| # | STRUCTURE | Salt form | Activity |
|---|---|---|---|
| 164 | 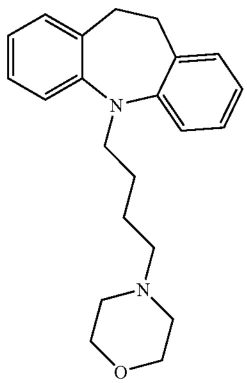 [SMILES: c1ccc2c(c1)CCc1ccccc1N2CCCCN1CCOCC1] | 2 @ HCl | |
| 165 | 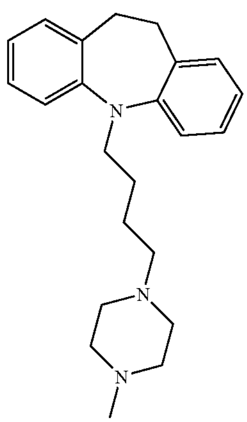 [SMILES: CN1CCN(CCCCN2c3ccccc3CCc3ccccc32)CC1] | 3 @ HCl | |
| 166 | 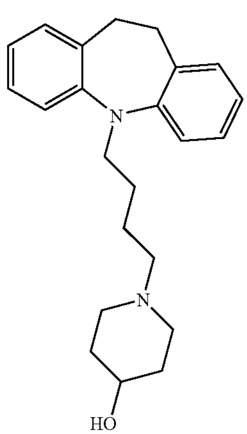 [SMILES: OC1CCN(CCCCN2c3ccccc3CCc3ccccc32)CC1] | 2 @ HCl | |

TABLE 3-1-continued
Activity of compounds of structure I and III with potencies in the cardiomyocyte screening assay.
| # | STRUCTURE | Salt form | Activity |
|---|---|---|---|
| 167 | 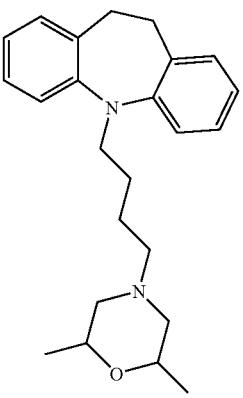 [SMILES: CC1CN(CCCCN2c3ccccc3CCc3ccccc32)CC(C)O1] | 2 @ HCl | |
| 168 | 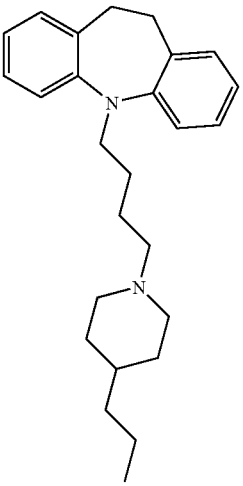 [SMILES: CCCC1CCN(CCCCN2c3ccccc3CCc3ccccc32)CC1] | 2 @ HCl | |
| 169 | 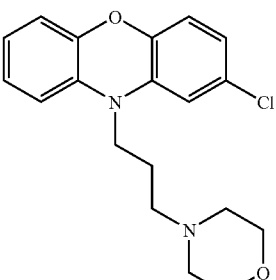 | 2 @ HCl | |
| 170 | 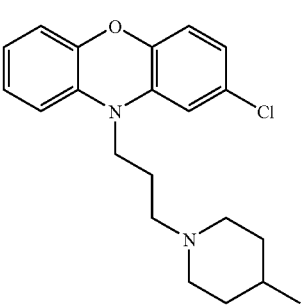 | 2 @ HCl | |

TABLE 3-1-continued
Activity of compounds of structure I and III with potencies in the cardiomyocyte screening assay.
| # | STRUCTURE | Salt form | Activity |
|---|---|---|---|
| 171 | 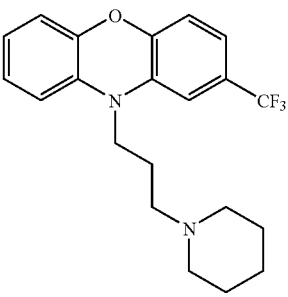 [SMILES: FC(F)(F)c1ccc2c(c1)N(CCCN1CCCCC1)c1ccccc1O2] | 2 @ HCl | |
| 172 | 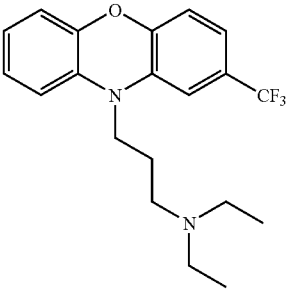 [SMILES: CCN(CC)CCCN1c2ccccc2Oc2ccc(C(F)(F)F)cc21] | 2 @ HCl | |
| 173 | 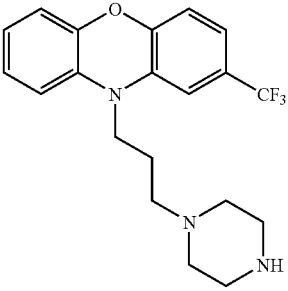 [SMILES: FC(F)(F)c1ccc2c(c1)N(CCCN1CCNCC1)c1ccccc1O2] | 3 @ HCl | |
| 174 | 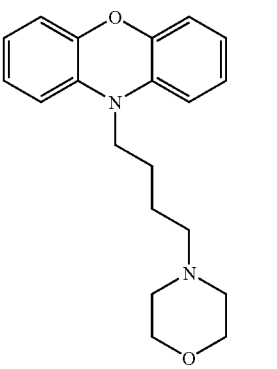 [SMILES: c1ccc2c(c1)Oc1ccccc1N2CCCCN1CCOCC1] | 2 @ HCl | |

TABLE 3-1-continued

Activity of compounds of structure I and III with potencies in the cardiomyocyte screening assay.

| # | STRUCTURE | Salt form | Activity |
|---|-----------|-----------|----------|
| 175 | 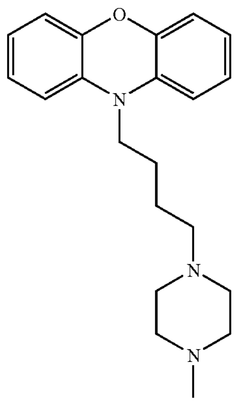 [SMILES: CN1CCN(CCCCN2c3ccccc3Oc3ccccc32)CC1] | 3 @ HCl | |
| 176 | 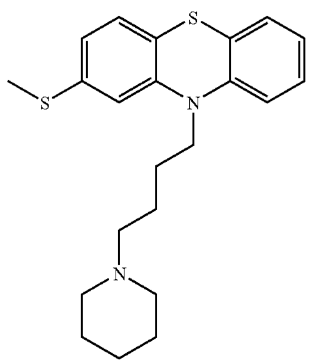 [SMILES: CSc1ccc2c(c1)N(CCCCN1CCCCC1)c1ccccc1S2] | 2 @ HCl | |
| 177 | 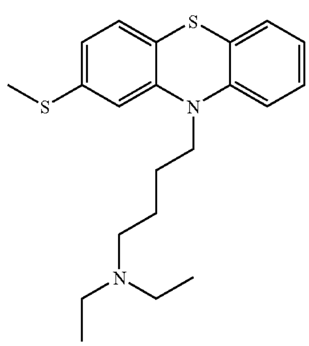 [SMILES: CCN(CC)CCCCN1c2ccccc2Sc2ccc(SC)cc21] | 2 @ HCl | |
| 178 | 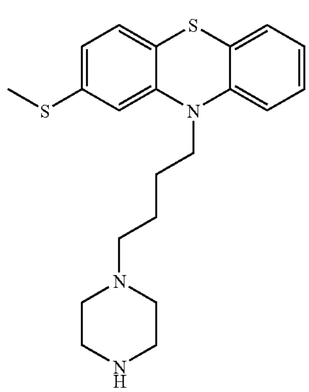 [SMILES: CSc1ccc2c(c1)N(CCCCN1CCNCC1)c1ccccc1S2] | 3 @ HCl | |

TABLE 3-1-continued

Activity of compounds of structure I and III with potencies in the cardiomyocyte screening assay.

| # | STRUCTURE | Salt form | Activity |
|---|-----------|-----------|----------|
| | | 1 | |
| 179 | phenoxazine-N-(CH2)4-N(Et)2 | 2 @ HCl | |
| 180 | phenoxazine-N-(CH2)4-(4-methylpiperazin-1-yl) | 3 @ HCl | |
| 181 | phenoxazine-N-(CH2)4-(piperazin-1-yl) | 3 @ HCl | |

TABLE 3-1-continued

Activity of compounds of structure I and III with potencies in the cardiomyocyte screening assay.

| # | STRUCTURE | Salt form | Activity |
|---|---|---|---|
| 182 | 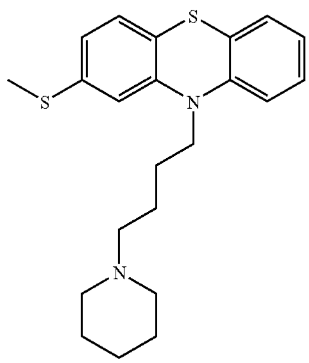 [SMILES: CSc1ccc2c(c1)N(CCCCN1CCCCC1)c1ccccc1S2] | 2 @ HCl | |
| 183 | 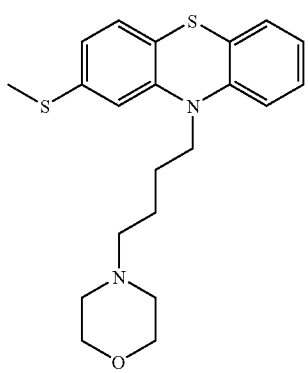 [SMILES: CSc1ccc2c(c1)N(CCCCN1CCOCC1)c1ccccc1S2] | 2 @ HCl | |
| 184 | 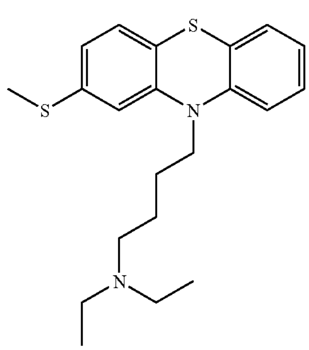 [SMILES: CCN(CC)CCCCN1c2ccccc2Sc2ccc(SC)cc21] | 2 @ HCl | |

TABLE 3-1-continued

Activity of compounds of structure I and III with potencies in the cardiomyocyte screening assay.

| # | STRUCTURE | Salt form | Activity |
|---|---|---|---|
| 185 | 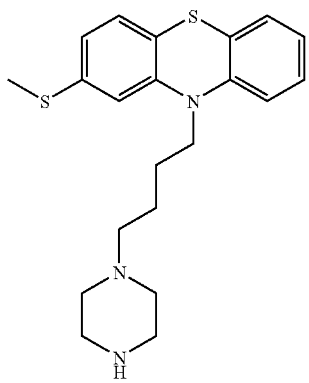 [SMILES: CSc1ccc2c(c1)N(CCCCN1CCNCC1)c1ccccc1S2] | HCl | |
| 186 | 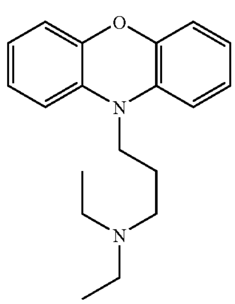 [SMILES: CCN(CC)CCCN1c2ccccc2Oc2ccccc21] | 2 @ HCl | |
| 187 | 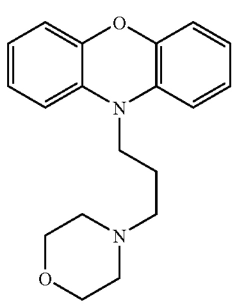 [SMILES: c1ccc2c(c1)Oc1ccccc1N2CCCN1CCOCC1] | 2 @ HCl | |
| 188 | 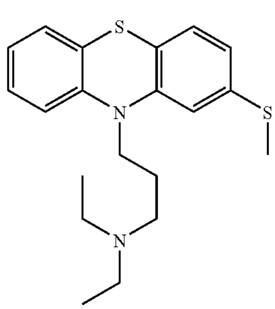 [SMILES: CCN(CC)CCCN1c2ccccc2Sc2ccc(SC)cc21] | 2 @ HCl | |

TABLE 3-1-continued
Activity of compounds of structure I and III with potencies in the cardiomyocyte screening assay.
| # | STRUCTURE | Salt form | Activity |
|---|-----------|-----------|----------|
| 189 | 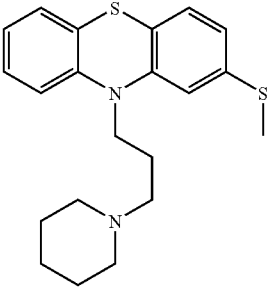 [SMILES: CSc1ccc2c(c1)N(CCCN1CCCCC1)c1ccccc1S2] | 2 @ HCl | |
| 190 | 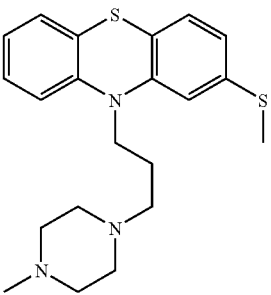 [SMILES: CSc1ccc2c(c1)N(CCCN1CCN(C)CC1)c1ccccc1S2] | 2 @ HCl | |
| 191 | 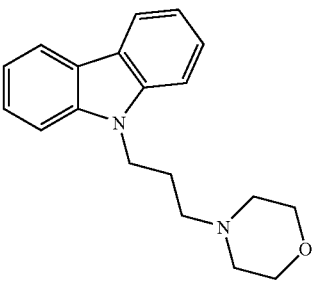 [SMILES: c1ccc2c(c1)c1ccccc1n2CCCN1CCOCC1] | 2 @ HCl | |
| 192 | 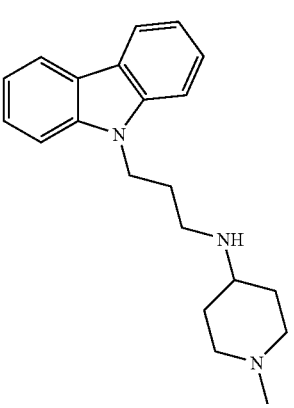 [SMILES: CN1CCC(NCCCn2c3ccccc3c3ccccc32)CC1] | 3 @ HCl | |

TABLE 3-1-continued

Activity of compounds of structure I and III with potencies in the cardiomyocyte screening assay.

| # | STRUCTURE | Salt form | Activity |
|---|---|---|---|
| 193 | 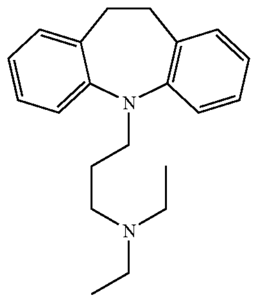 [SMILES: CCN(CC)CCCN1c2ccccc2CCc2ccccc21] | 2 @ HCl | |
| 194 | 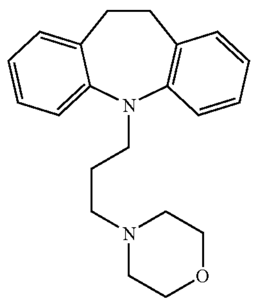 | 2 @ HCl | |
| 195 | 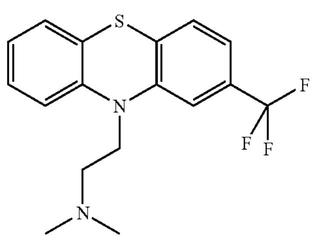 [SMILES: CN(C)CCN1c2ccccc2Sc2ccc(C(F)(F)F)cc21] | 2 @ HCl | |
| 196 | 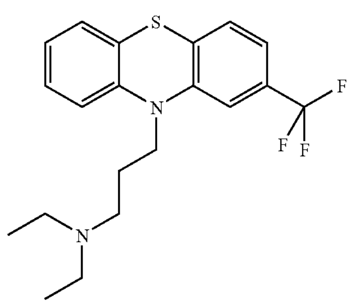 [SMILES: CCN(CC)CCCN1c2ccccc2Sc2ccc(C(F)(F)F)cc21] | 2 @ HCl | |
| 197 | 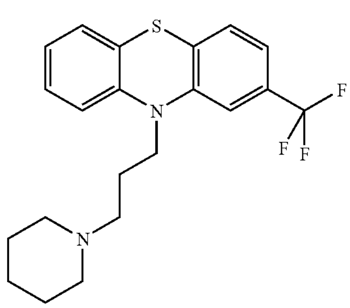 [SMILES: FC(F)(F)c1ccc2c(c1)N(CCCN1CCCCC1)c1ccccc1S2] | 2 @ HCl | |

TABLE 3-1-continued
Activity of compounds of structure I and III with potencies in the cardiomyocyte screening assay.
| # | STRUCTURE | Salt form | Activity |
|---|-----------|-----------|----------|
| 198 | 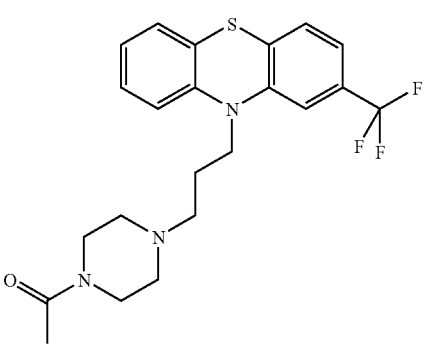 [SMILES: CC(=O)N1CCN(CCCN2c3ccccc3Sc3ccc(C(F)(F)F)cc32)CC1] | 2 @ HCl | |
| 199 | 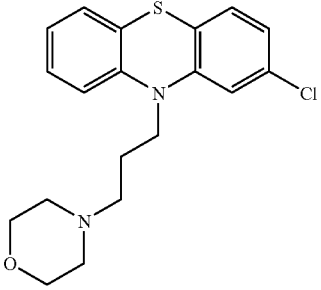 [SMILES: Clc1ccc2c(c1)N(CCCN1CCOCC1)c1ccccc1S2] | 2 @ HCl | |
| 200 | 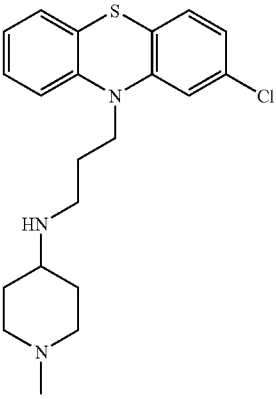 [SMILES: CN1CCC(NCCCN2c3ccccc3Sc3ccc(Cl)cc32)CC1] | 3 @ HCl | |
| 201 | 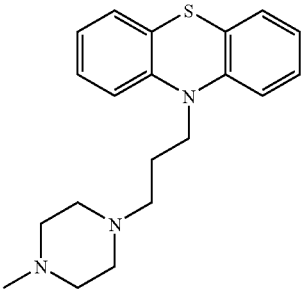 [SMILES: CN1CCN(CCCN2c3ccccc3Sc3ccccc32)CC1] | 3 @ HCl | |

TABLE 3-1-continued

Activity of compounds of structure I and III with potencies in the cardiomyocyte screening assay.

| # | STRUCTURE | Salt form | Activity |
|---|---|---|---|
| 202 | 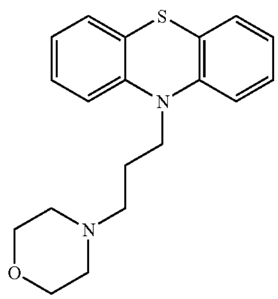 [SMILES: c1ccc2c(c1)Sc1ccccc1N2CCCN1CCOCC1] | 2 @ HCl | |
| 203 | 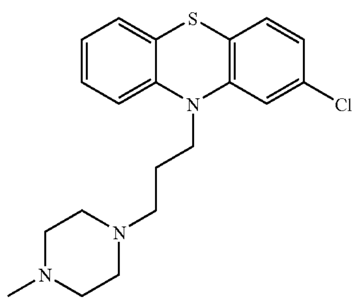 [SMILES: CN1CCN(CCCN2c3ccccc3Sc3ccc(Cl)cc32)CC1] | 3 @ HCl | |
| 204 | 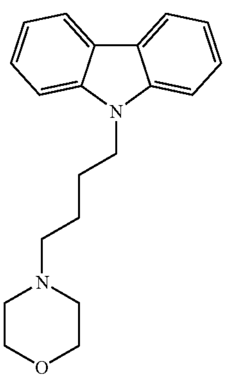 [SMILES: c1ccc2c(c1)c1ccccc1n2CCCCN1CCOCC1] | 2 @ HCl | |
| 205 | 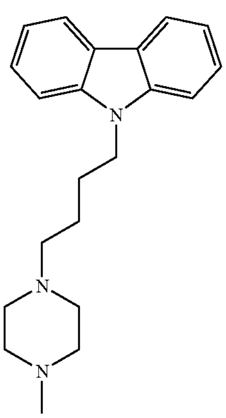 [SMILES: CN1CCN(CCCCn2c3ccccc3c3ccccc32)CC1] | 3 @ HCl | |

TABLE 3-1-continued
Activity of compounds of structure I and III with potencies in the cardiomyocyte screening assay.
| # | STRUCTURE | Salt form | Activity |
|---|---|---|---|
| 206 | 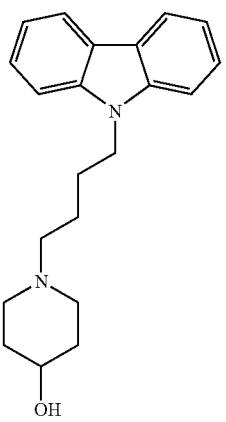 [SMILES: OC1CCN(CCCCn2c3ccccc3c3ccccc32)CC1] | 2 @ HCl | |
| 207 | 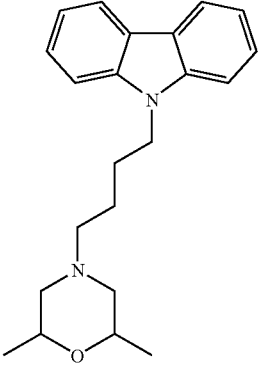 [SMILES: CC1CN(CCCCn2c3ccccc3c3ccccc32)CC(C)O1] | 2 @ HCl | |
| 208 | 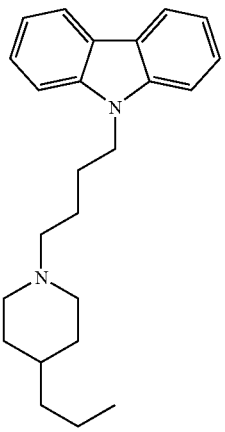 [SMILES: CCCC1CCN(CCCCn2c3ccccc3c3ccccc32)CC1] | 2 @ HCl | |

TABLE 3-1-continued
Activity of compounds of structure I and III with potencies in the cardiomyocyte screening assay.
| # | STRUCTURE | Salt form | Activity |
|---|-----------|-----------|----------|
| 209 | 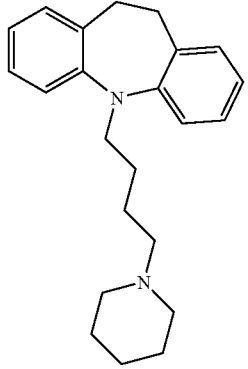 [SMILES: c1ccc2c(c1)CCc1ccccc1N2CCCCN1CCCCC1] | 2 @ HCl | |
| 210 | 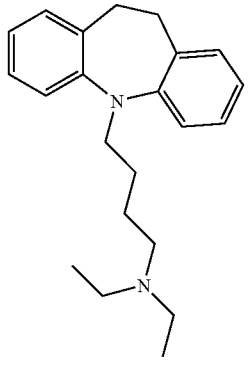 [SMILES: CCN(CC)CCCCN1c2ccccc2CCc2ccccc21] | 2 @ HCl | |
| 211 | 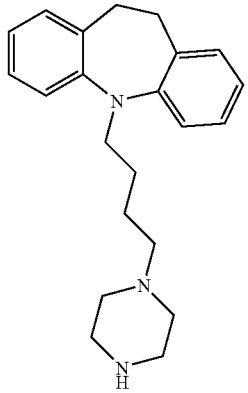 [SMILES: c1ccc2c(c1)CCc1ccccc1N2CCCCN1CCNCC1] | 3 @ HCl | |
| 212 | 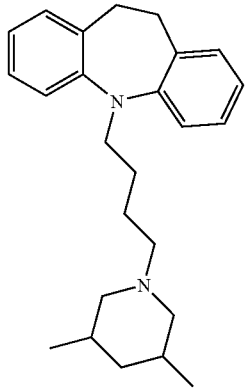 | 2 @ HCl | |

TABLE 3-1-continued

Activity of compounds of structure I and III with potencies in the cardiomyocyte screening assay.

| # | STRUCTURE | Salt form | Activity |
|---|---|---|---|
| 213 | 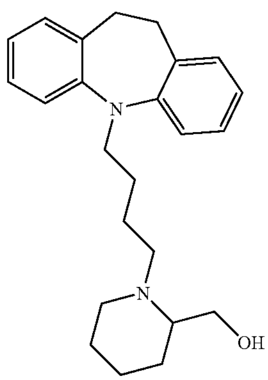 [SMILES: OCC1CCCCN1CCCCN1c2ccccc2CCc2ccccc21] | 2 @ HCl | |
| 214 | 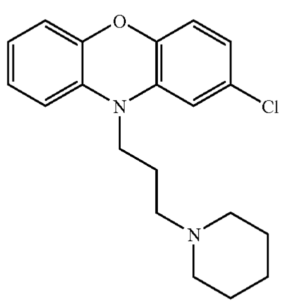 | 2 @ HCl | |
| 215 | 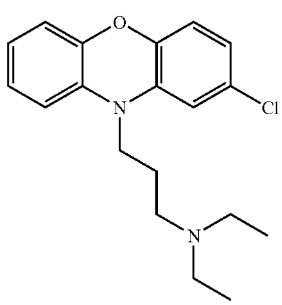 [SMILES: CCN(CC)CCCN1c2ccccc2Oc2ccc(Cl)cc21] | 2 @ HCl | |
| 216 | 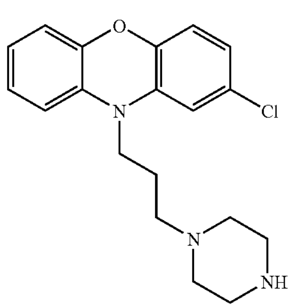 [SMILES: Clc1ccc2c(c1)N(CCCN1CCNCC1)c1ccccc1O2] | 2 @ HCl | |

TABLE 3-1-continued
Activity of compounds of structure I and III with potencies in the cardiomyocyte screening assay.
| # | STRUCTURE | Salt form | Activity |
|---|---|---|---|
| 217 | 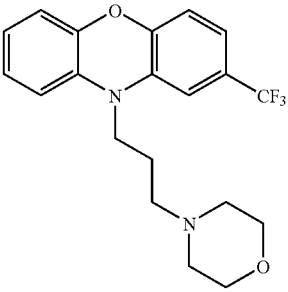 [SMILES: FC(F)(F)c1ccc2c(c1)N(CCCN1CCOCC1)c1ccccc1O2] | 2 @ HCl | |
| 218 | 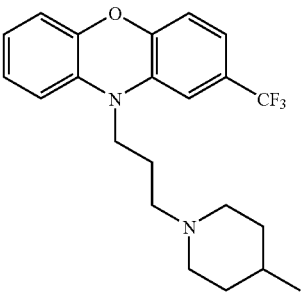 | 2 @ HCl | |
| 219 | 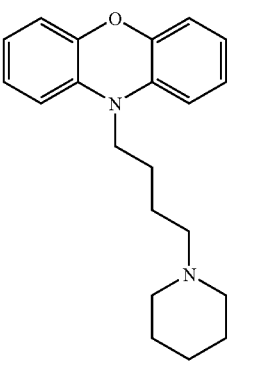 [SMILES: c1ccc2c(c1)Oc1ccccc1N2CCCCN1CCCCC1] | 2 @ HCl | |
| 220 | 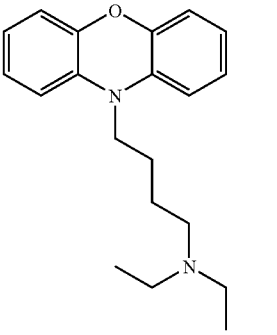 [SMILES: CCN(CC)CCCCN1c2ccccc2Oc2ccccc21] | 2 @ HCl | |

TABLE 3-1-continued
Activity of compounds of structure I and III with potencies in the cardiomyocyte screening assay.
| # | STRUCTURE | Salt form | Activity |
|---|---|---|---|
| 221 | 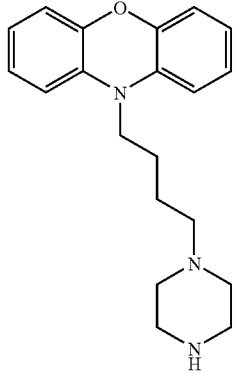 [SMILES: c1ccc2c(c1)Oc1ccccc1N2CCCCN1CCNCC1] | 3 @ HCl | |
| 222 | 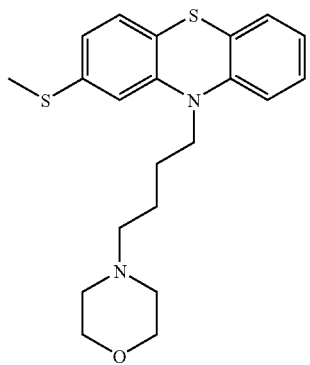 [SMILES: CSc1ccc2c(c1)N(CCCCN1CCOCC1)c1ccccc1S2] | 2 @ HCl | |
| 223 | 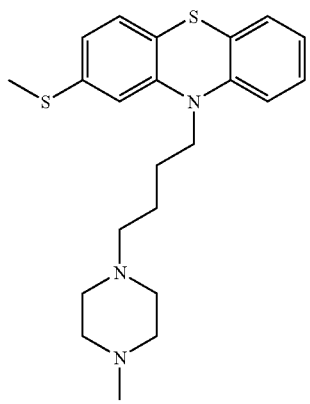 | 3 @ HCl | |

TABLE 3-1-continued

Activity of compounds of structure I and III with potencies in the cardiomyocyte screening assay.

| # | STRUCTURE | Salt form | Activity |
|---|---|---|---|
| 224 | 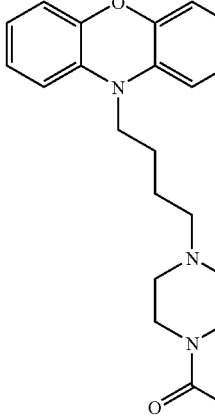 | 2 @ HCl | |
| 225 | 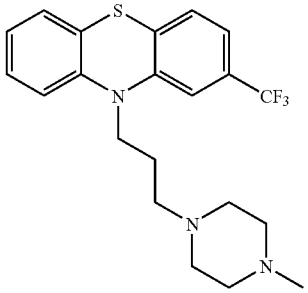 [SMILES: CN1CCN(CCCN2c3ccccc3Sc3ccc(C(F)(F)F)cc32)CC1] | 2 @ HCl | + |

The potencies (i.e., the $EC_{50}$ values) of the compounds of the above shown general structure II using the above-described testing methods is measured. The results are shown in Table 3-2.

TABLE 3-2

Activity of compounds of structure I and III with potencies in the cardiomyocyte screening assay.

| # | Structure | Salt form | Activity |
|---|---|---|---|
| 226 | 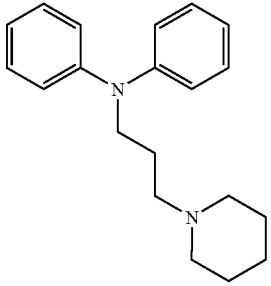 [SMILES: c1ccc(N(CCCN2CCCCC2)c2ccccc2)cc1] | 2@HCl | |
| 227 | 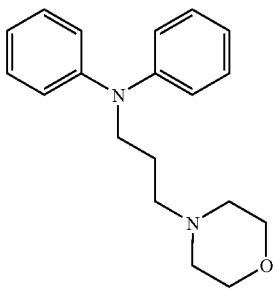 [SMILES: c1ccc(N(CCCN2CCOCC2)c2ccccc2)cc1] | 2@HCl | |
| 228 | 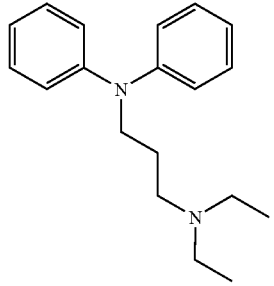 [SMILES: CCN(CC)CCCN(c1ccccc1)c1ccccc1] | 2@HCl | |

TABLE 3-2-continued

Activity of compounds of structure I and III with potencies in the cardiomyocyte screening assay.

| # | Structure | Salt form | Activity |
|---|-----------|-----------|----------|
| 229 | 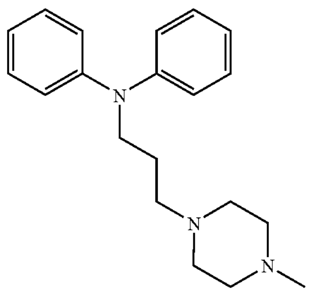 [SMILES: CN1CCN(CCCN(c2ccccc2)c2ccccc2)CC1] | 3@HCl | |
| 230 | 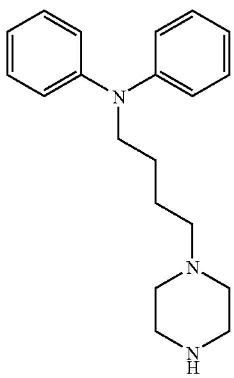 [SMILES: c1ccc(N(CCCCN2CCNCC2)c2ccccc2)cc1] | 3@HCl | |
| 231 | 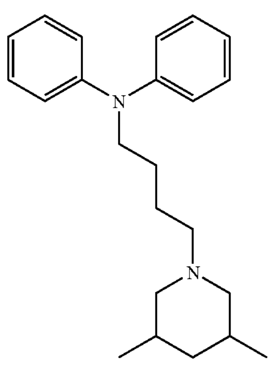 [SMILES: CC1CC(C)CN(CCCCN(c2ccccc2)c2ccccc2)C1] | 2@HCl | |
| 232 | 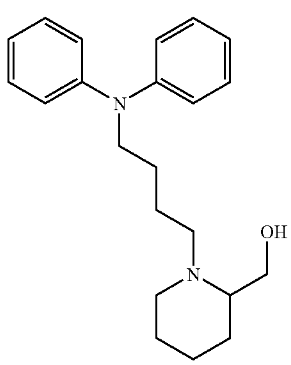 [SMILES: OCC1CCCCN1CCCCN(c1ccccc1)c1ccccc1] | 2@HCl | |
| 233 | | 2@HCl | |
| 234 | | 2@HCl | |
| 235 | | 2@HCl | |
| 236 | | 2@HCl | |

TABLE 3-2-continued

Activity of compounds of structure I and III with potencies in the cardiomyocyte screening assay.

| # | Structure | Salt form | Activity |
|---|-----------|-----------|----------|
| 237 | 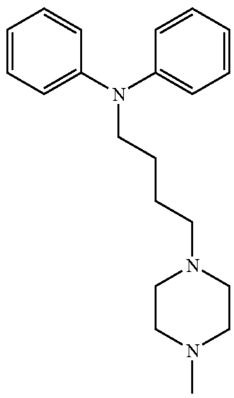 [SMILES: CN1CCN(CCCCN(c2ccccc2)c2ccccc2)CC1] | 3@HCl | |
| 238 | 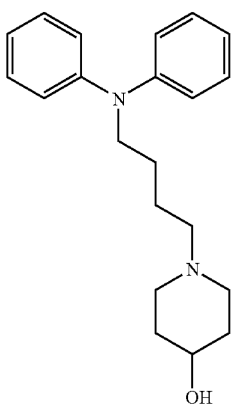 [SMILES: OC1CCN(CCCCN(c2ccccc2)c2ccccc2)CC1] | 2@HCl | |
| 239 | 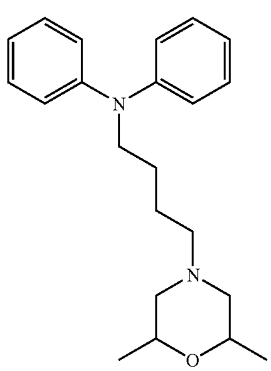 [SMILES: CC1CN(CCCCN(c2ccccc2)c2ccccc2)CC(C)O1] | 2@HCl | |
| 240 | 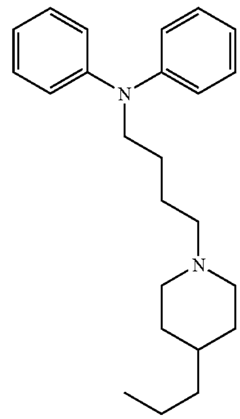 [SMILES: CCCC1CCN(CCCCN(c2ccccc2)c2ccccc2)CC1] | 2@HCl | |

TABLE 3-3

Characterization of compounds of structure I, II and III. Nuclear magnetic resonance data were recorded on a Varian Mercury 300 MHz Spectrometer using TMS as the internal standard and $CDCl_3$ as the solvent except where indicated. Electrospray mass spectral (MS) data was obtained using a Hitachi M-7000.

| STRUCTURE | MW | Mass Spec |
|-----------|------|-----------|
| 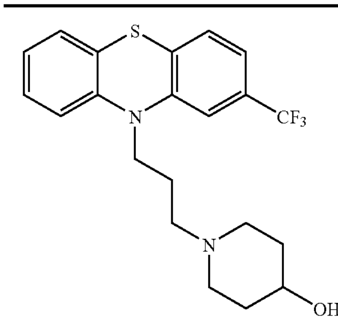 | 408.48 | [M + 1] ESI M/Z 409.73 |
| 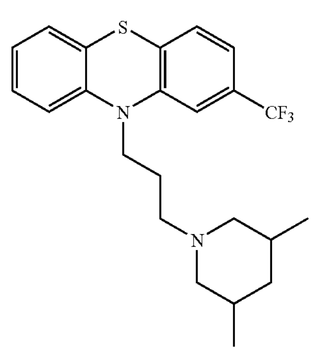 [SMILES: CC1CC(C)CN(CCCN2c3ccccc3Sc3ccc(C(F)(F)F)cc32)C1] | 420.53 | [M + 1] ESI M/Z 421.70 |

TABLE 3-3-continued

Characterization of compounds of structure I, II and III. Nuclear magnetic resonance data were recorded on a Varian Mercury 300 MHz Spectrometer using TMS as the internal standard and CDCl$_3$ as the solvent except where indicated. Electrospray mass spectral (MS) data was obtained using a Hitachi M-7000.

| STRUCTURE | MW | Mass Spec |
|---|---|---|
| (structure) | 422.51 | [M + 1] ESI M/Z 423.70 |
| (structure) | 406.51 | [M + 1] ESI M/Z 407.80 |
| (structure) | 322.44 | [M + 1] ESI M/Z 323.73 |
| (structure) | 324.42 | [M + 1] ESI M/Z 325.60 |
| (structure) | 399.62 | [M + 1] ESI M/Z 400.60 |
| (structure) | 365.47 | [M + 1] ESI M/Z 366.53 |
| (structure) | 323.43 | [M + 1] ESI M/Z 324.68 |
| (structure) | 308.42 | [M + 1] ESI M/Z 309.32 |

TABLE 3-3-continued

Characterization of compounds of structure I,
II and III. Nuclear magnetic
resonance data were recorded on a Varian
Mercury 300 MHz Spectrometer using TMS as the
internal standard and CDCl₃ as the solvent
except where indicated. Electrospray mass spectral
(MS) data was obtained using a Hitachi M-7000.

| STRUCTURE | MW | Mass Spec |
|---|---|---|
| 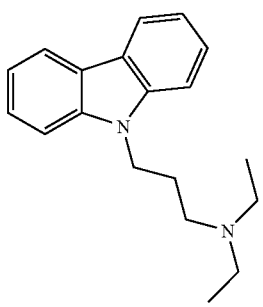 [SMILES: CCN(CC)CCCn1c2ccccc2c2ccccc21] | 380.41 | [M + 1] ESI M/Z 281.00 |
| 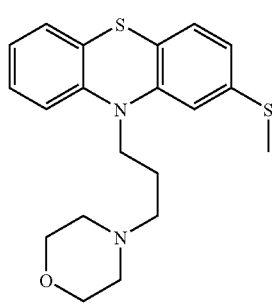 | 372.55 | [M + 1] ESI M/Z |
| 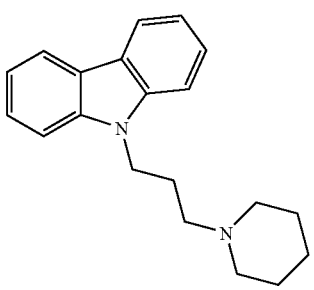 [SMILES: c1ccc2c(c1)c1ccccc1n2CCCN1CCCCC1] | 292.42 | [M + 1] ESI M/Z 293.07 |
| 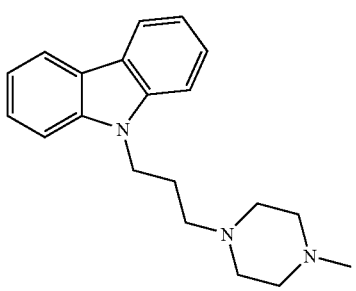 [SMILES: CN1CCN(CCCn2c3ccccc3c3ccccc32)CC1] | 307.43 | [M + 1] ESI M/Z 308.07 |
| 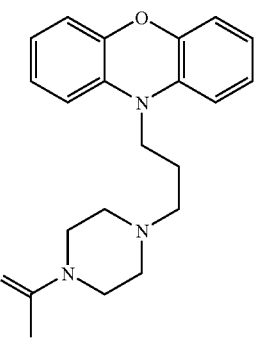 | 351.44 | [M + 1] ESI M/Z 352.35 |
| 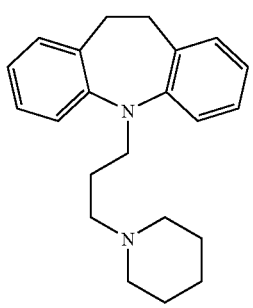 [SMILES: c1ccc2c(c1)CCc1ccccc1N2CCCN1CCCCC1] | 320.47 | [M + 1] ESI M/Z 321.73 |
| 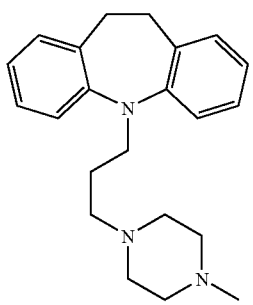 [SMILES: CN1CCN(CCCN2c3ccccc3CCc3ccccc32)CC1] | 335.49 | [M + 1] ESI M/Z 336.80 |
| 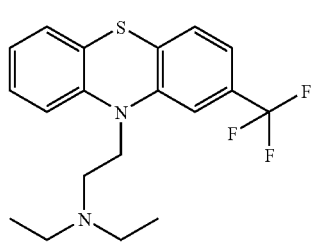 [SMILES: CCN(CC)CCN1c2ccccc2Sc2ccc(C(F)(F)F)cc21] | 366 | ¹H NMR (CDCl3, 300 MHz): 7.23-7.1 (m, 5H), 6.95-6.92 (m, 2 H), 3.98 (t, J = 6.9 Hz, 2H), 2.82 (t, J = 6.9 Hz, 2H), 2.60 (q, J = 6.9 Hz, 4H), 1.05 (t, =6.9 Hz, 6H) |

TABLE 3-3-continued

Characterization of compounds of structure I,
II and III. Nuclear magnetic
resonance data were recorded on a Varian
Mercury 300 MHz Spectrometer using TMS as the
internal standard and CDCl$_3$ as the solvent
except where indicated. Electrospray mass spectral
(MS) data was obtained using a Hitachi M-7000.

| STRUCTURE | MW | Mass Spec |
|---|---|---|
| | | $^1$H NMR (CDCl3, 300 MHz): 7.18-7.11 (m, 5H), 6.94-6.91 (m, 2 H), 3.98 (t, J = 6.9 Hz, 2H), 3.69-3.6 (m, 4H), 2.49-2.28 (m, 6H), 1.93 (t, J = 6.9 Hz, 6H) |
| 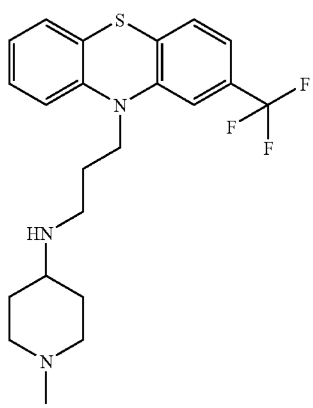 [SMILES: CN1CCC(NCCCN2c3ccccc3Sc3ccc(C(F)(F)F)cc32)CC1] | 421.53 | [M + 2] ESI M/Z 423.68 |
| 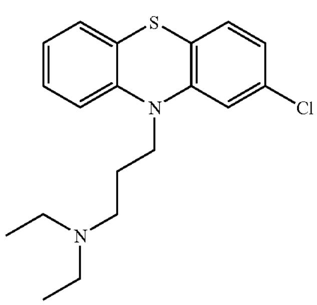 [SMILES: CCN(CC)CCCN1c2ccccc2Sc2ccc(Cl)cc21] | 346.9 | [M + 1] ESI M/Z 347.07 |
| 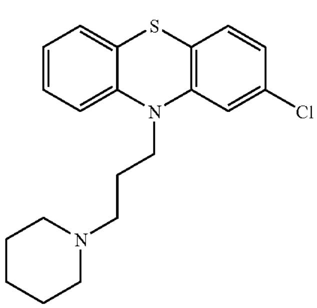 [SMILES: Clc1ccc2c(c1)N(CCCN1CCCCC1)c1ccccc1S2] | 358.9 | [M + 1] ESI M/Z 359.27 |
| | 306.44 | [M + 1] ESI M/Z 307.00 |
| | 294.43 | [M + 1] ESI M/Z 295.00 |
| | 307.43 | [M + 1] ESI M/Z 308.25 |

TABLE 3-3-continued

Characterization of compounds of structure I, II and III. Nuclear magnetic resonance data were recorded on a Varian Mercury 300 MHz Spectrometer using TMS as the internal standard and CDCl$_3$ as the solvent except where indicated. Electrospray mass spectral (MS) data was obtained using a Hitachi M-7000.

| STRUCTURE | MW | Mass Spec |
|---|---|---|
| 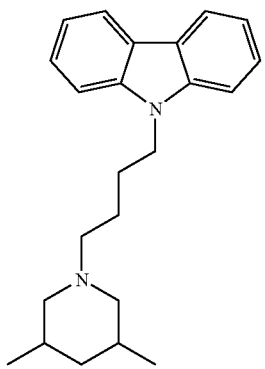 [SMILES: CC1CC(C)CN(CCCCn2c3ccccc3c3ccccc32)C1] | 334.50 | [M + 1] ESI M/Z 335.02 |
| 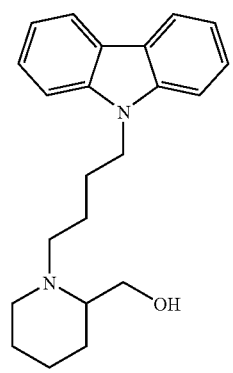 [SMILES: OCC1CCCCN1CCCCn1c2ccccc2c2ccccc21] | 336.47 | [M + 1] ESI M/Z 337.00 |
| 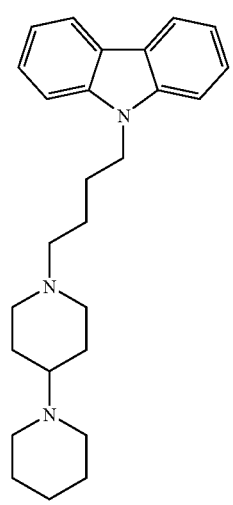 [SMILES: c1ccc2c(c1)c1ccccc1n2CCCCN1CCC(N2CCCCC2)CC1] | 389.58 | [M + 1] ESI M/Z 389.87 |

TABLE 3-3-continued

Characterization of compounds of structure I, II and III. Nuclear magnetic resonance data were recorded on a Varian Mercury 300 MHz Spectrometer using TMS as the internal standard and CDCl$_3$ as the solvent except where indicated. Electrospray mass spectral (MS) data was obtained using a Hitachi M-7000.

| STRUCTURE | MW | Mass Spec |
|---|---|---|
| 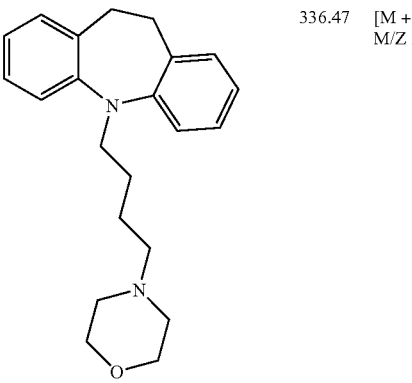 | 336.47 | [M + 1] ESI M/Z 337.27 |
| 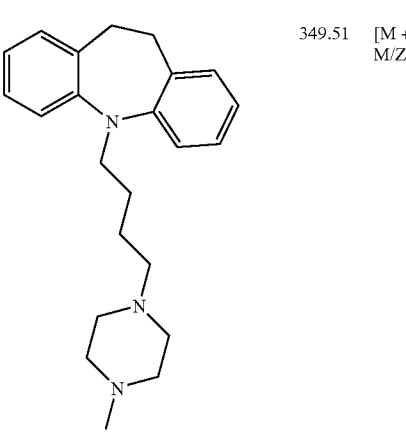 | 349.51 | [M + 1] ESI M/Z 350.53 |
| 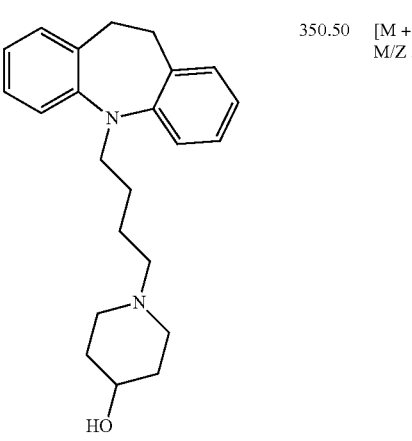 | 350.50 | [M + 1] ESI M/Z 351.47 |

TABLE 3-3-continued

Characterization of compounds of structure I, II and III. Nuclear magnetic resonance data were recorded on a Varian Mercury 300 MHz Spectrometer using TMS as the internal standard and CDCl₃ as the solvent except where indicated. Electrospray mass spectral (MS) data was obtained using a Hitachi M-7000.

| STRUCTURE | MW | Mass Spec |
|---|---|---|
| (10,11-dihydrodibenzazepine with N-butyl-2,6-dimethylmorpholine) | 364.52 | [M + 1] ESI M/Z 365.33 |
| (10,11-dihydrodibenzazepine with N-butyl-4-propylpiperidine) | 376.58 | [M + 1] ESI M/Z 377.53 |
| (2-chlorophenoxazine with N-propylmorpholine) | 344.84 | [M + 1] ESI M/Z 345.80 |
| (2-chlorophenoxazine with N-propyl-4-methylpiperidine) | 357.88 | [M + 1] ESI M/Z 358.93 |
| (2-CF₃-phenoxazine with N-propylpiperidine) | 376.42 | [M + 1] ESI M/Z 377.60 |
| (2-CF₃-phenoxazine with N-propyldiethylamine) | 364.40 | [M + 1] ESI M/Z 365.87 |
| (diphenylamine with N-propylpiperidine) | 294.43 | [M + 1] ESI M/Z 295.87 |

TABLE 3-3-continued

Characterization of compounds of structure I, II and III. Nuclear magnetic resonance data were recorded on a Varian Mercury 300 MHz Spectrometer using TMS as the internal standard and CDCl₃ as the solvent except where indicated. Electrospray mass spectral (MS) data was obtained using a Hitachi M-7000.

| STRUCTURE | MW | Mass Spec |
|---|---|---|
| 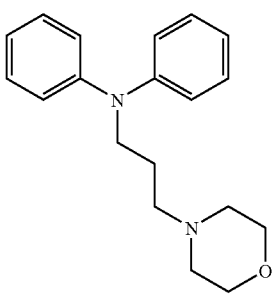 [SMILES: c1ccc(N(CCCN2CCOCC2)c2ccccc2)cc1] | 296.41 | [M + 1] ESI M/Z 297.80 |
| 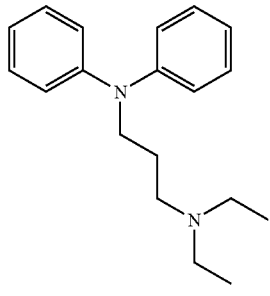 [SMILES: CCN(CC)CCCN(c1ccccc1)c1ccccc1] | 282.42 | [M + 1] ESI M/Z 283.87 |
| 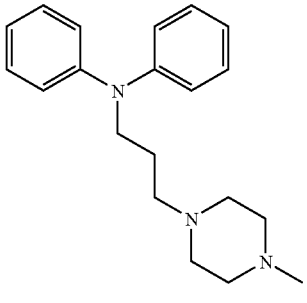 [SMILES: CN1CCN(CCCN(c2ccccc2)c2ccccc2)CC1] | 309.45 | [M + 1] ESI M/Z 310.87 |
| 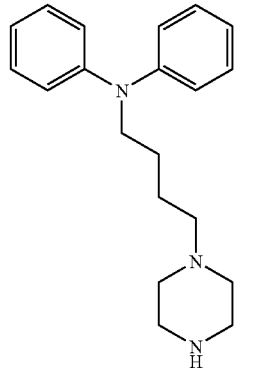 [SMILES: c1ccc(N(CCCCN2CCNCC2)c2ccccc2)cc1] | 309.46 | [M + 1] ESI M/Z 310.52 |
| 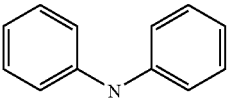 | 336.51 | [M + 1] ESI M/Z 337.80 |
| 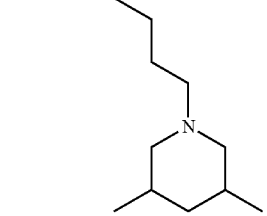 | 338.49 | [M + 1] ESI M/Z 339.80 |
| 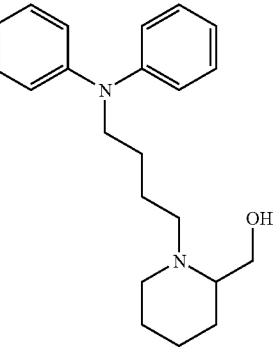 | 391.59 | [M + 1] ESI M/Z 392.87 |

TABLE 3-3-continued

Characterization of compounds of structure I, II and III. Nuclear magnetic resonance data were recorded on a Varian Mercury 300 MHz Spectrometer using TMS as the internal standard and CDCl₃ as the solvent except where indicated. Electrospray mass spectral (MS) data was obtained using a Hitachi M-7000.

| STRUCTURE | MW | Mass Spec |
|---|---|---|
| 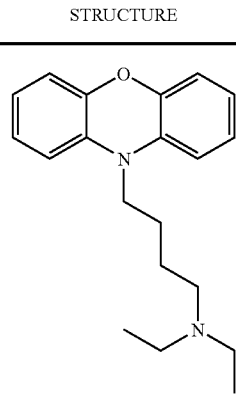 | 310.43 | [M + 1] ESI M/Z 311.87 |
| 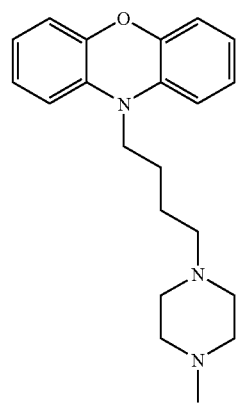 [SMILES: CN1CCN(CCCCN2c3ccccc3Oc3ccccc32)CC1] | 337.46 | [M + 1] ESI M/Z 338.60 |
| 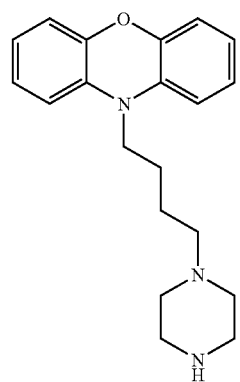 [SMILES: c1ccc2c(c1)Oc1ccccc1N2CCCCN1CCNCC1] | 323.43 | [M + 1] ESI M/Z 324.93 |

TABLE 3-3-continued

Characterization of compounds of structure I, II and III. Nuclear magnetic resonance data were recorded on a Varian Mercury 300 MHz Spectrometer using TMS as the internal standard and CDCl₃ as the solvent except where indicated. Electrospray mass spectral (MS) data was obtained using a Hitachi M-7000.

| STRUCTURE | MW | Mass Spec |
|---|---|---|
| 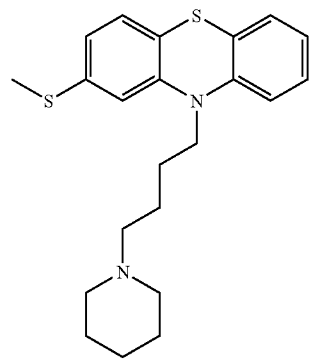 [SMILES: CSc1ccc2c(c1)N(CCCCN1CCCCC1)c1ccccc1S2] | 384.60 | [M + 1] ESI M/Z 385.47 |
| 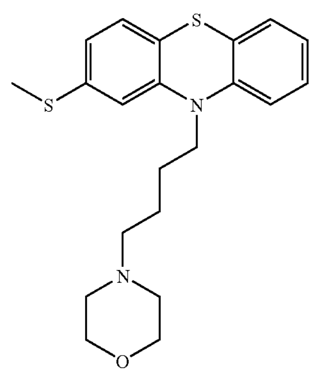 [SMILES: CSc1ccc2c(c1)N(CCCCN1CCOCC1)c1ccccc1S2] | 386.57 | [M + 1] ESI M/Z 387.40 |
| 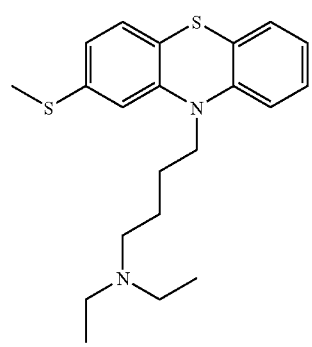 [SMILES: CCN(CC)CCCCN1c2ccccc2Sc2ccc(SC)cc21] | 372.59 | [M + 1] ESI M/Z 373.60 |
| 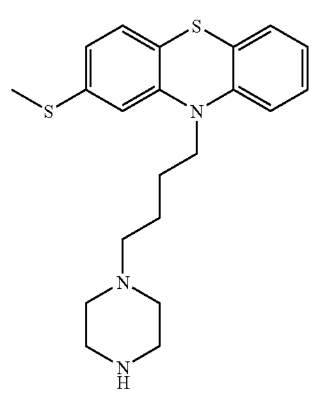 [SMILES: CSc1ccc2c(c1)N(CCCCN1CCNCC1)c1ccccc1S2] | 385.59 | [M + 1] ESI M/Z 386.67 |

TABLE 3-3-continued

Characterization of compounds of structure I, II and III. Nuclear magnetic resonance data were recorded on a Varian Mercury 300 MHz Spectrometer using TMS as the internal standard and CDCl₃ as the solvent except where indicated. Electrospray mass spectral (MS) data was obtained using a Hitachi M-7000.

| STRUCTURE | MW | Mass Spec |
|---|---|---|
| (phenoxazine N-propyl-N,N-diethylamine) | 296.41 | [M + 1] ESI M/Z 297.56 |
| (phenoxazine N-propyl-morpholine) | 310.39 | [M + 1] ESI M/Z 311.52 |
| (phenothiazine-SMe N-propyl-N,N-diethylamine) | 358.56 | [M + 1] ESI M/Z 359.73 |
| (phenothiazine-SMe N-propyl-piperidine) | 370.58 | [M + 1] ESI M/Z 371.80 |
| (phenothiazine-SMe N-propyl-N-methylpiperazine) | 385.59 | [M + 1] ESI M/Z 386.80 |
| (carbazole N-propyl-morpholine) | 294.39 | [M + 1] ESI M/Z 295.07 |
| (carbazole N-propyl-4-amino-N-methylpiperidine) | 321.46 | [M + 1] ESI M/Z 322.00 |
| (dibenzazepine N-propyl-N,N-diethylamine) | 308.46 | [M + 1] ESI M/Z 308.56 |

TABLE 3-3-continued

Characterization of compounds of structure I, II and III. Nuclear magnetic resonance data were recorded on a Varian Mercury 300 MHz Spectrometer using TMS as the internal standard and CDCl$_3$ as the solvent except where indicated. Electrospray mass spectral (MS) data was obtained using a Hitachi M-7000.

| STRUCTURE | MW | Mass Spec |
|---|---|---|
| 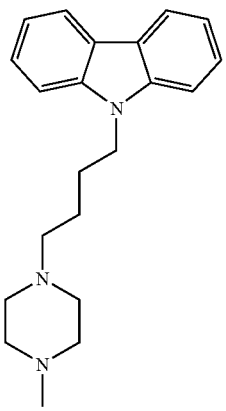 [SMILES: CN1CCN(CCCCn2c3ccccc3c3ccccc32)CC1] | 321.46 | [M + 1] ESI M/Z 322.07 |
| 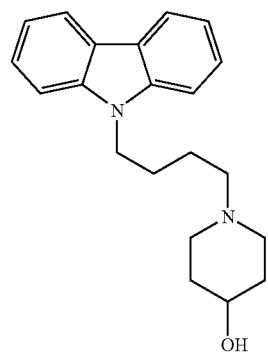 [SMILES: OC1CCN(CCCCn2c3ccccc3c3ccccc32)CC1] | 322.44 | [M + 1] ESI M/Z 323.00 |
| 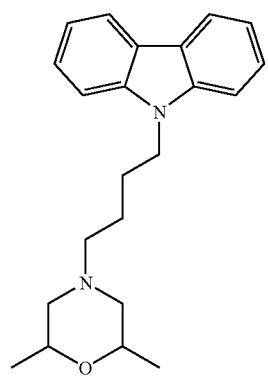 [SMILES: CC1CN(CCCCn2c3ccccc3c3ccccc32)CC(C)O1] | 336.47 | [M + 1] ESI M/Z 337.01 |
| 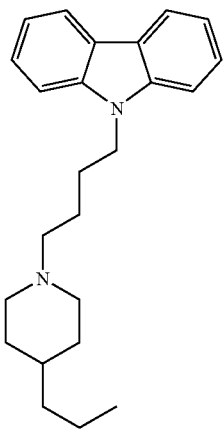 | 348.52 | [M + 1] ESI M/Z 349.07 |
| 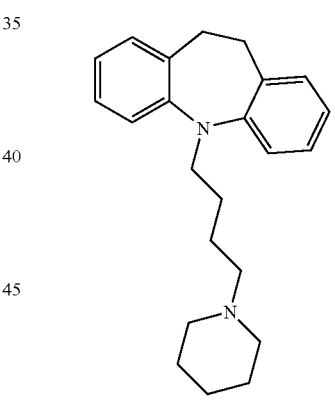 | 334.50 | [M + 1] ESI M/Z 335.53 |
| 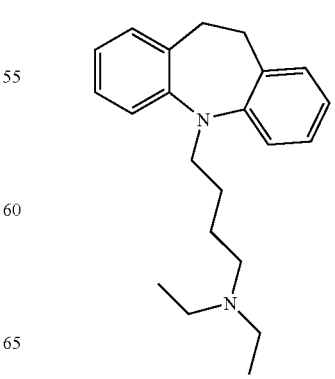 | 322.49 | [M + 1] ESI M/Z 323.47 |

TABLE 3-3-continued

Characterization of compounds of structure I, II and III. Nuclear magnetic resonance data were recorded on a Varian Mercury 300 MHz Spectrometer using TMS as the internal standard and CDCl₃ as the solvent except where indicated. Electrospray mass spectral (MS) data was obtained using a Hitachi M-7000.

| STRUCTURE | MW | Mass Spec |
|---|---|---|
| 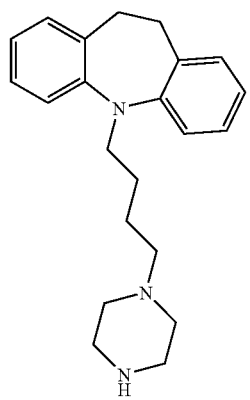 [SMILES: c1ccc2c(c1)CCc1ccccc1N2CCCCN1CCNCC1] | 335.49 | [M + 1] ESI M/Z3 36.25 |
| 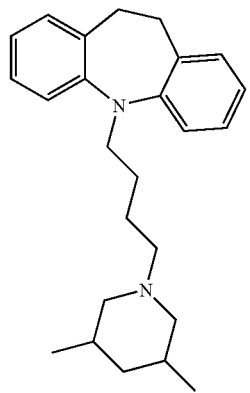 [SMILES: CC1CC(C)CN(CCCCN2c3ccccc3CCc3ccccc32)C1] | 362.55 | [M + 1] ESI M/Z 363.33 |
| 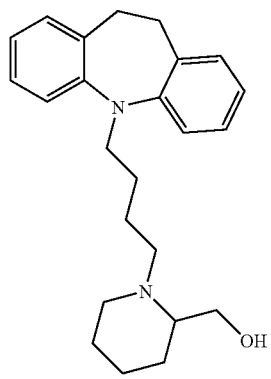 [SMILES: OCC1CCCCN1CCCCN1c2ccccc2CCc2ccccc21] | 364.52 | [M + 1] ESI M/Z 365.02 |

TABLE 3-3-continued

Characterization of compounds of structure I, II and III. Nuclear magnetic resonance data were recorded on a Varian Mercury 300 MHz Spectrometer using TMS as the internal standard and CDCl₃ as the solvent except where indicated. Electrospray mass spectral (MS) data was obtained using a Hitachi M-7000.

| STRUCTURE | MW | Mass Spec |
|---|---|---|
| 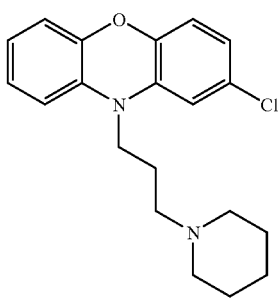 [SMILES: Clc1ccc2c(c1)N(CCCN1CCCCC1)c1ccccc1O2] | 342.86 | [M + 1] ESI M/Z 343.08 |
| 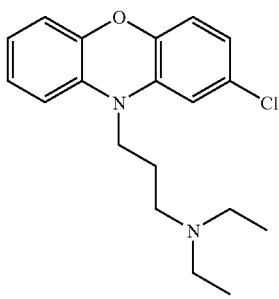 [SMILES: CCN(CC)CCCN1c2ccccc2Oc2ccc(Cl)cc21] | 330.85 | [M + 1] ESI M/Z 331.00 |
| 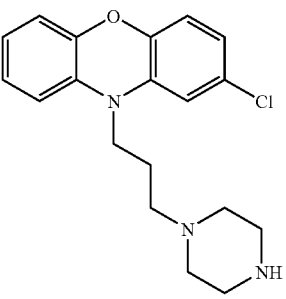 [SMILES: Clc1ccc2c(c1)N(CCCN1CCNCC1)c1ccccc1O2] | 343.85 | [M + 1] ESI M/Z 344.60 |
| 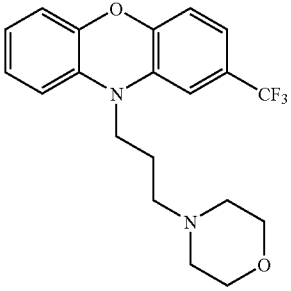 [SMILES: FC(F)(F)c1ccc2c(c1)N(CCCN1CCOCC1)c1ccccc1O2] | 378.39 | [M + 1] ESI M/Z 379.80 |

TABLE 3-3-continued

Characterization of compounds of structure I, II and III. Nuclear magnetic resonance data were recorded on a Varian Mercury 300 MHz Spectrometer using TMS as the internal standard and CDCl₃ as the solvent except where indicated. Electrospray mass spectral (MS) data was obtained using a Hitachi M-7000.

| STRUCTURE | MW | Mass Spec |
|---|---|---|
| 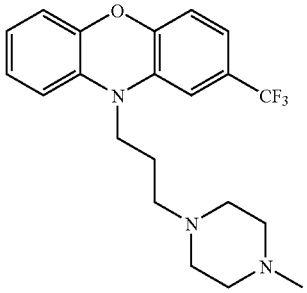 | 391.43 | [M + 1] ESI M/Z 392.12 |
| 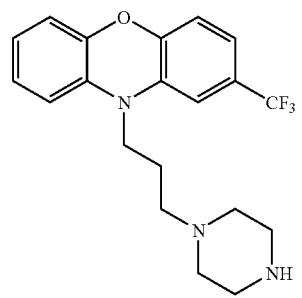 [SMILES: FC(F)(F)c1ccc2c(c1)N(CCCN1CCNCC1)c1ccccc1O2] | 377.40 | [M + 1] ESI M/Z 378.67 |
| 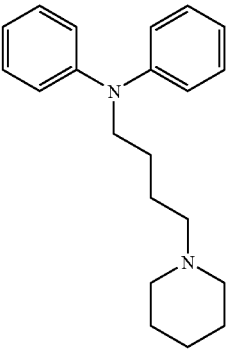 [SMILES: c1ccc(N(CCCCN2CCCCC2)c2ccccc2)cc1] | 308.46 | [M + 1] ESI M/Z 309.67 |
| 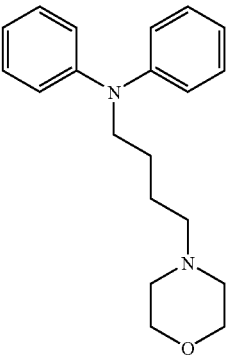 [SMILES: c1ccc(N(CCCCN2CCOCC2)c2ccccc2)cc1] | 310.43 | [M + 1] ESI M/Z 311.67 |
| 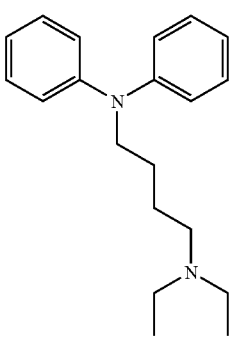 [SMILES: CCN(CC)CCCCN(c1ccccc1)c1ccccc1] | 296.45 | [M + 1] ESI M/Z 297.72 |
| 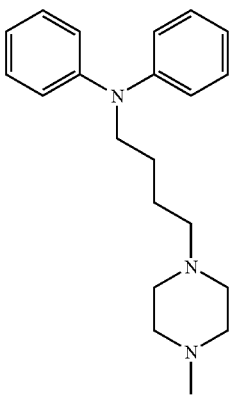 [SMILES: CN1CCN(CCCCN(c2ccccc2)c2ccccc2)CC1] | 323.48 | [M + 1] ESI M/Z 32473 |
| 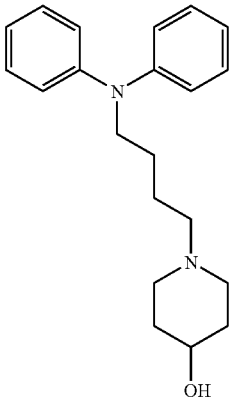 [SMILES: OC1CCN(CCCCN(c2ccccc2)c2ccccc2)CC1] | 324.46 | [M + 1] ESI M/Z 325.73 |

TABLE 3-3-continued

Characterization of compounds of structure I, II and III. Nuclear magnetic resonance data were recorded on a Varian Mercury 300 MHz Spectrometer using TMS as the internal standard and CDCl₃ as the solvent except where indicated. Electrospray mass spectral (MS) data was obtained using a Hitachi M-7000.

| STRUCTURE | MW | Mass Spec |
|---|---|---|
| 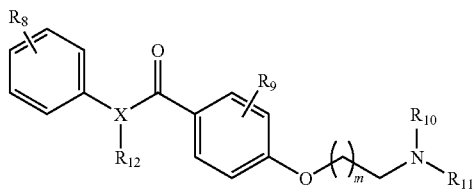 | 338.49 | [M + 1] ESI M/Z 339.67 |
| 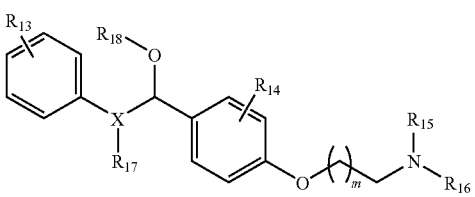 | 350.54 | [M + 1] ESI M/Z 351.80 |

Example 7

General Synthetic Procedure for Obtaining Compounds of Structure V, VI, and VII The tamoxifen-based compounds of structure V, VI and VII:

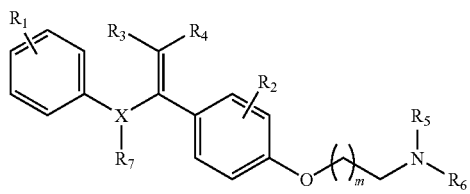

V

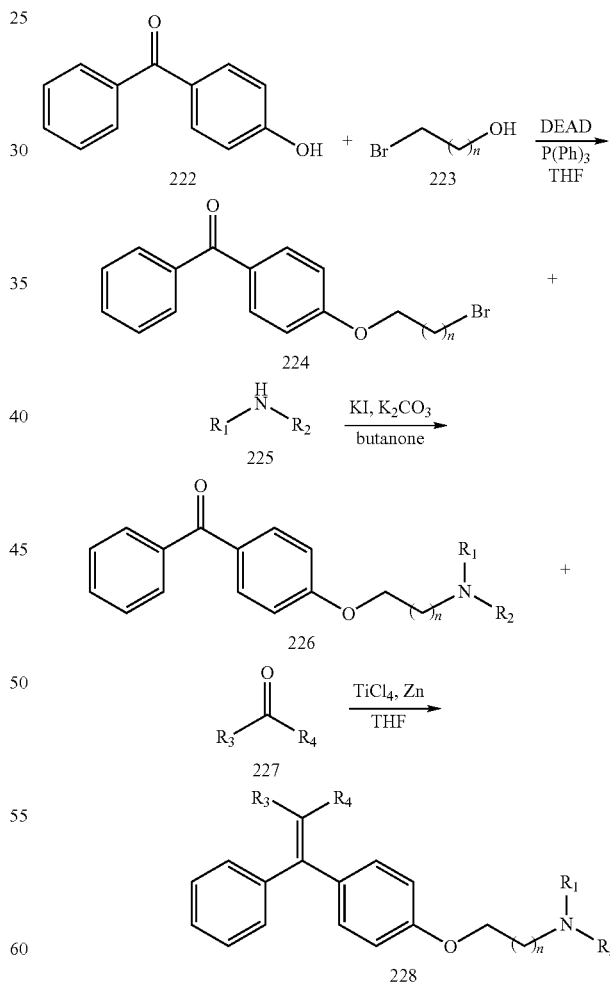

may be synthesized according to the following schemes.

The compounds of the above shown general structure VI and VII may be synthesized according to the following schemes.

Scheme 27: Synthesis of tamoxifen like analogs.

R1 = methyl, ethyl, cycloalkyl, phenyl
R2 = methyl, ethyl, cycloalkyl, phenyl
R1 and R2 can be connected via ring
R3 = methyl, ethyl, propyl, phenyl, benzyl
R4 = methyl, ethyl, propyl, phenyl, benzyl
n = 0-4 methylene units Scheme 28: Synthesis of alkyl tamoxifen-like analogs.

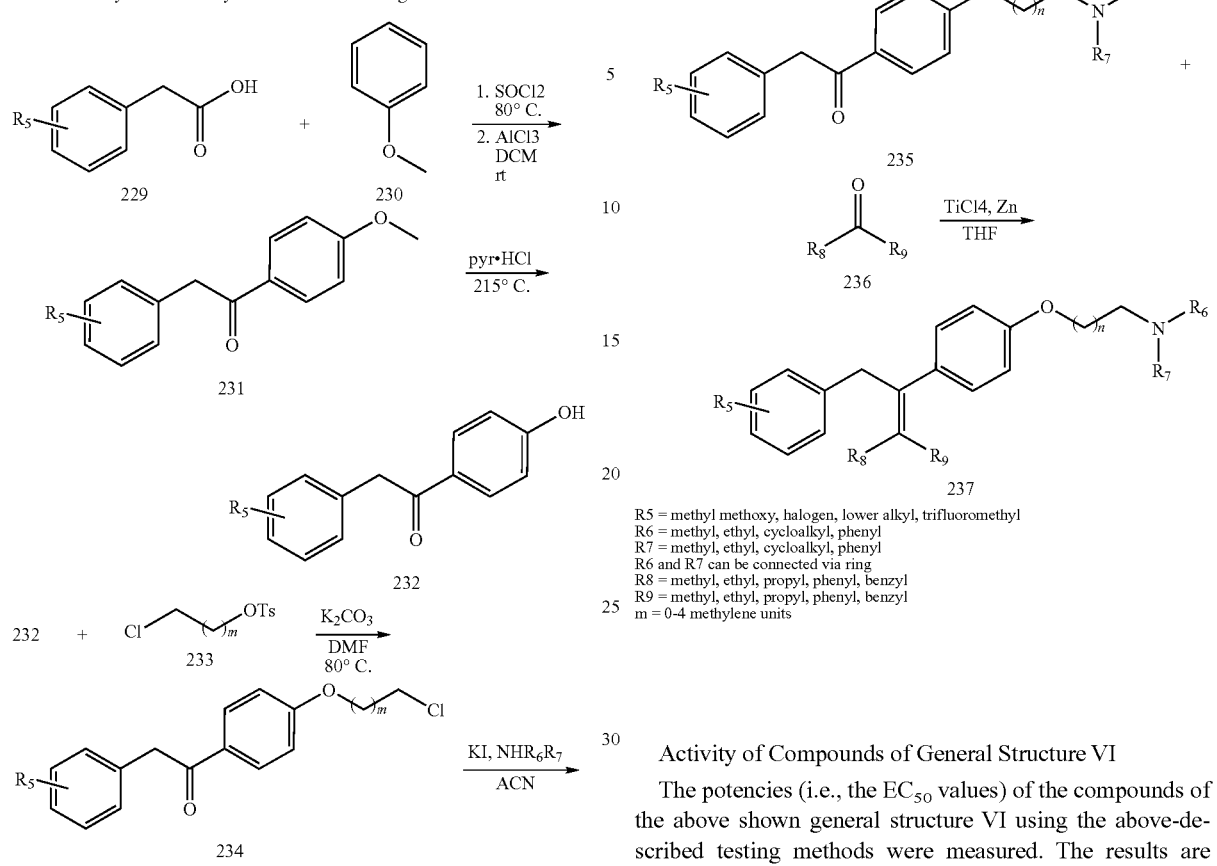

R5 = methyl methoxy, halogen, lower alkyl, trifluoromethyl
R6 = methyl, ethyl, cycloalkyl, phenyl
R7 = methyl, ethyl, cycloalkyl, phenyl
R6 and R7 can be connected via ring
R8 = methyl, ethyl, propyl, phenyl, benzyl
R9 = methyl, ethyl, propyl, phenyl, benzyl
m = 0-4 methylene units Activity of Compounds of General Structure VI The potencies (i.e., the $EC_{50}$ values) of the compounds of the above shown general structure VI using the above-described testing methods were measured. The results are shown in Table 4-1.

TABLE 4-1

Activity of compounds of structure VI with potencies in the cardiomyocyte screening assay.

| # | Structure | Salt form | Activity |
|---|-----------|-----------|----------|
| 240 | 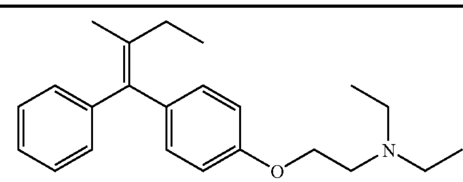 | HCl | |
| 241 | 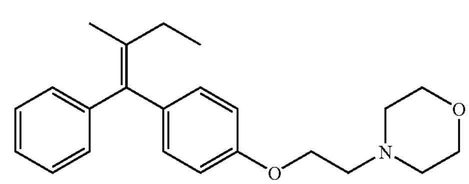 [SMILES: CC/C(C)=C(/c1ccccc1)c1ccc(OCCN2CCOCC2)cc1] | HCl | |
| 242 | 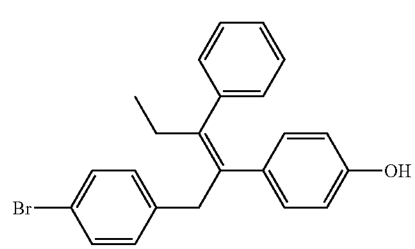 [SMILES: CC/C(=C(\Cc1ccc(Br)cc1)c1ccc(O)cc1)c1ccccc1] | NA | |

TABLE 4-1-continued

Activity of compounds of structure VI with potencies in the cardiomyocyte screening assay.

| # | Structure | Salt form | Activity |
|---|-----------|-----------|----------|
| 243 | 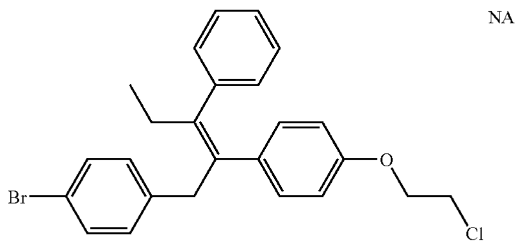 | NA | |
| 244 | 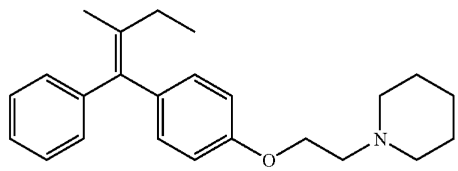 [SMILES: CC/C(C)=C(/c1ccccc1)c1ccc(OCCN2CCCCC2)cc1] | HCl | |
| 245 | 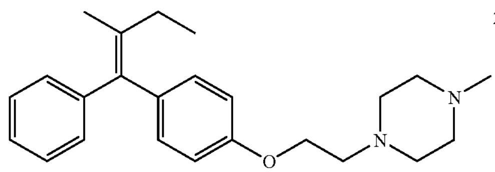 | 2@HCl | |
| 246 | 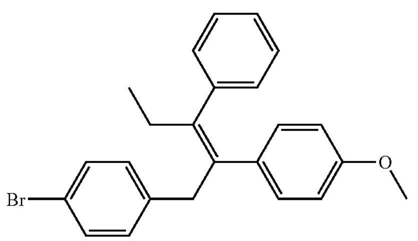 [SMILES: CC/C(=C(\Cc1ccc(Br)cc1)c1ccc(OC)cc1)c1ccccc1] | NA | |

Activity of Compounds of General Structure VII

The potencies (i.e., the $EC_{50}$ values) of the compounds of the above shown general structure VII using the above-described testing methods were measured. The results are shown in Table 4-2.

TABLE 4-2

Activity of compounds of structure VII with potencies in the cardiomyocyte screening assay.

| # | structure | Salt form | Activity |
|---|-----------|-----------|----------|
| 247 | 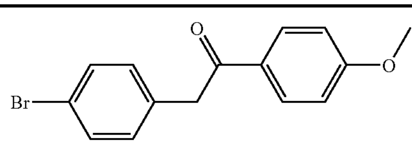 | NA | |
| 248 | 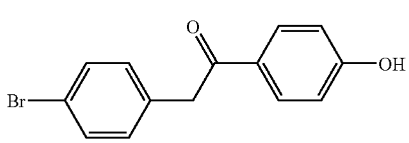 | NA | |

TABLE 4-2-continued

Activity of compounds of structure VII with potencies in the cardiomyocyte screening assay.

| # | structure | Salt form | Activity |
|---|---|---|---|
| 249 | 4-bromophenyl-CH(CH₃)-C(=O)-4-hydroxyphenyl | | NA |
| 250 | 4-bromophenyl-CH₂-C(=O)-phenyl-O-CH₂CH₂-N(CH₃)₂ | HCl | |
| 251 | phenyl-C(=O)-phenyl-O-CH₂CH₂CH₂-N(CH₂CH₃)₂ | HCl | |
| 252 | phenyl-C(=O)-phenyl-O-CH₂CH₂CH₂-piperidine | HCl | |
| 253 | phenyl-C(=O)-phenyl-O-CH₂CH₂CH₂-piperazine-N-Boc | | NA |
| 254 | phenyl-C(=O)-phenyl-O-CH₂CH₂-(4-methylpiperazine) | 2@HCl | |
| 255 | phenyl-C(=O)-phenyl-O-CH₂CH₂-morpholine | HCl | |

TABLE 4-2-continued
Activity of compounds of structure VII with potencies
in the cardiomyocyte screening assay.
| # | structure | Salt form | Activity |
|---|-----------|-----------|----------|
| 256 | 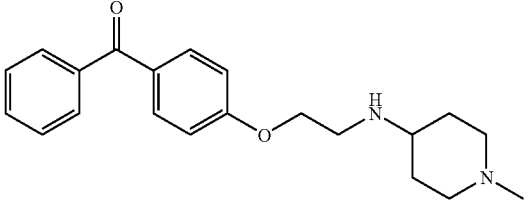 [SMILES: CN1CCC(NCCOc2ccc(C(=O)c3ccccc3)cc2)CC1] | 2@HCl | |
| 257 | 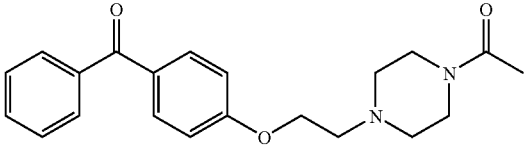 [SMILES: CC(=O)N1CCN(CCOc2ccc(C(=O)c3ccccc3)cc2)CC1] | HCl | |
| 258 | 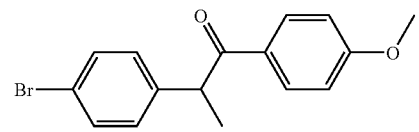 | NA | |
| 259 | 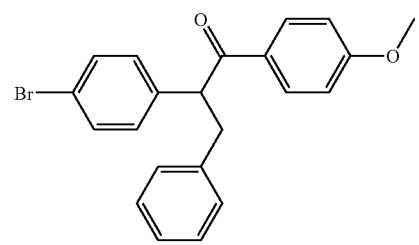 [SMILES: COc1ccc(C(=O)C(Cc2ccccc2)c2ccc(Br)cc2)cc1] | NA | |
| 260 | 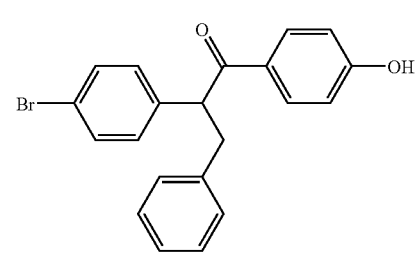 | NA | |
| 261 | 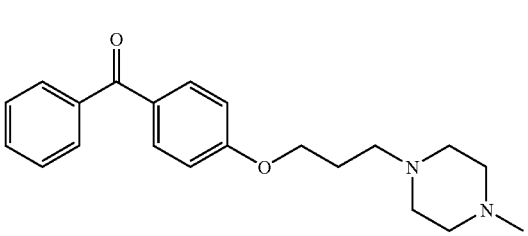 [SMILES: CN1CCN(CCCOc2ccc(C(=O)c3ccccc3)cc2)CC1] | 2@HCl | |
| 262 | 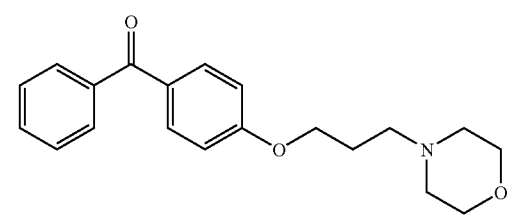 [SMILES: O=C(c1ccccc1)c1ccc(OCCCN2CCOCC2)cc1] | HCl | |

TABLE 4-2-continued
Activity of compounds of structure VII with potencies in the cardiomyocyte screening assay.
| # | structure | Salt form | Activity |
|---|-----------|-----------|----------|
| 263 | 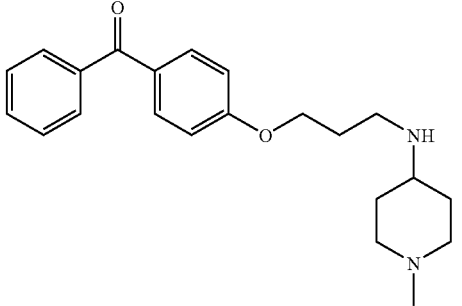 [SMILES: CN1CCC(NCCCOc2ccc(C(=O)c3ccccc3)cc2)CC1] | 2@HCl | |
| 264 | 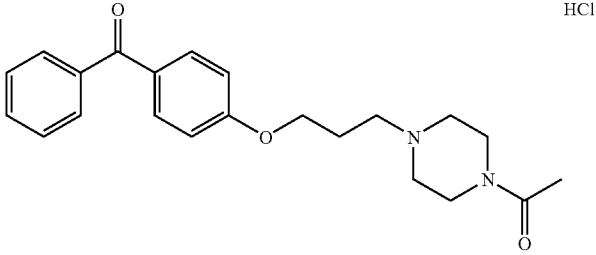 | HCl | |
| 265 | 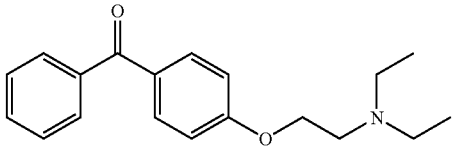 [SMILES: CCN(CC)CCOc1ccc(C(=O)c2ccccc2)cc1] | HCl | |
| 266 | 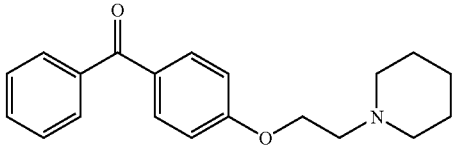 [SMILES: O=C(c1ccccc1)c1ccc(OCCN2CCCCC2)cc1] | HCl | |
| 267 | 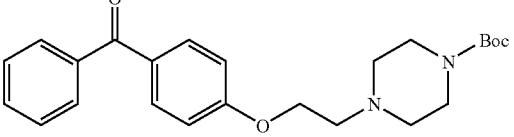 | NA | |
| 268 | 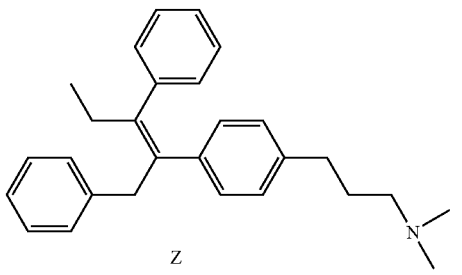 [SMILES: CC/C(=C(\Cc1ccccc1)c1ccc(CCCN(C)C)cc1)c1ccccc1] | HCl | + |

General Synthesis of Compound Formula VIII

The compounds of the structure. VIII may be synthesized according to the following synthetic schemes.

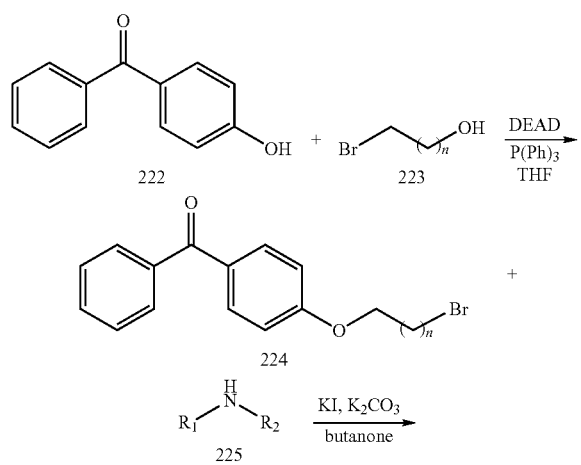

Scheme 29. Synthesis of reduced ketone analogs.

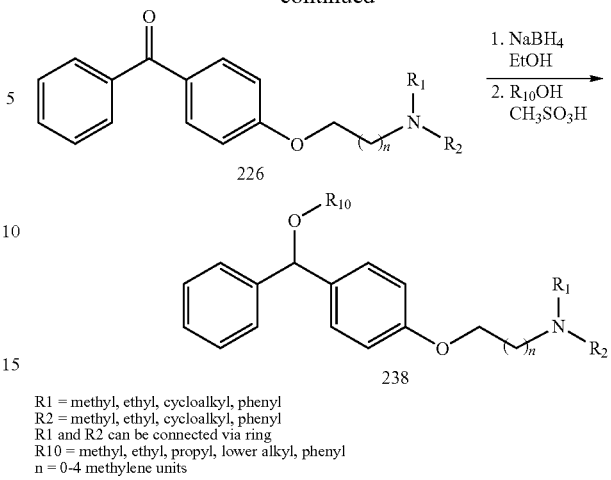

R1 = methyl, ethyl, cycloalkyl, phenyl
R2 = methyl, ethyl, cycloalkyl, phenyl
R1 and R2 can be connected via ring
R10 = methyl, ethyl, propyl, lower alkyl, phenyl
n = 0-4 methylene units Activity of Compounds of General Structure VIII The potencies (i.e., the $EC_{50}$ values) of the compounds of the above shown general structure VIII using the above-described testing methods were measured. The results are shown in Table 4-3.

TABLE 4-3

Activity of compounds of structure VIII with potencies in the cardiomyocyte screening assay.

| # | Structure | Salt form | Activity |
|---|---|---|---|
| 269 | 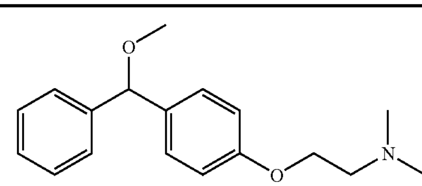 | HCl | |
| 270 | 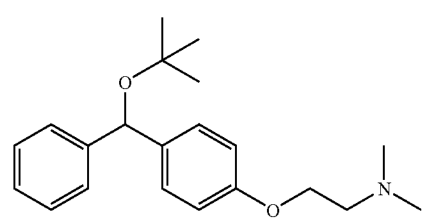 [SMILES: CN(C)CCOc1ccc(C(OC(C)(C)C)c2ccccc2)cc1] | HCl | |
| 271 | 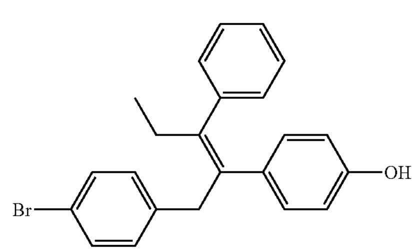 [SMILES: CC/C(=C(\Cc1ccc(Br)cc1)c1ccc(O)cc1)c1ccccc1] | NA | |

TABLE 4-3-continued

Activity of compounds of structure VIII with potencies in the cardiomyocyte screening assay.

| # | Structure | Salt form | Activity |
|---|-----------|-----------|----------|
| 272 | 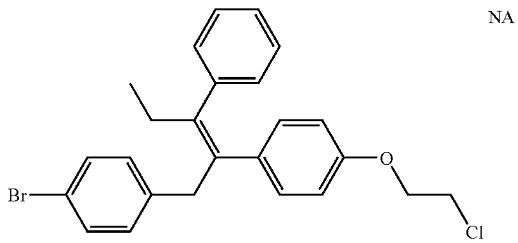 | NA | |
| 273 | 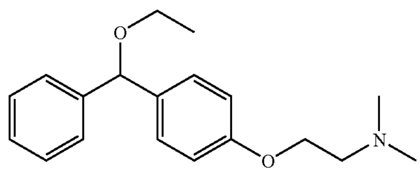 [SMILES: CCOC(c1ccccc1)c1ccc(OCCN(C)C)cc1] | HCl | |
| 274 | 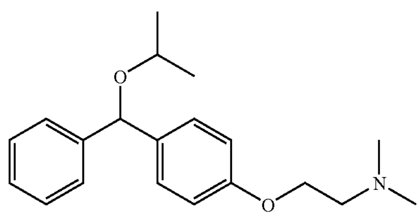 [SMILES: CC(C)OC(c1ccccc1)c1ccc(OCCN(C)C)cc1] | HCl | |
| 275 | 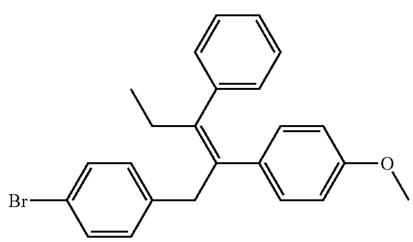 [SMILES: CC/C(=C(\Cc1ccc(Br)cc1)c1ccc(OC)cc1)c1ccccc1] | NA | |

TABLE 4-4

Characterization of compounds of structure V, VI, and VII. Nuclear magnetic resonance data were recorded on a Varian Mercury 300 MHz Spectrometer using TMS as the internal standard and CDCl$_3$ as the solvent except where indicated. Electrospray mass spectral (MS) data was obtained using a Hitachi M-7000.

| STRUCTURE | MW | Mass Spec |
|-----------|-----|-----------|
| 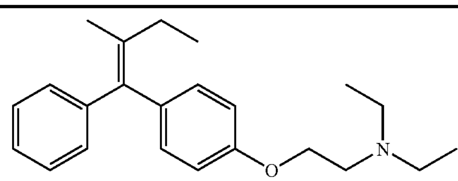 | 337.50 | [M + 1] ESI M/Z 338.00 |
| 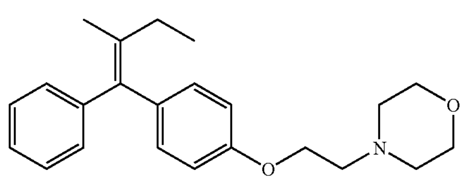 [SMILES: CC/C(C)=C(/c1ccccc1)c1ccc(OCCN2CCOCC2)cc1] | 351.48 | [M + 1] ESI M/Z 352.00 |

TABLE 4-4-continued
| Structure | Value | Notation |
|---|---|---|
| 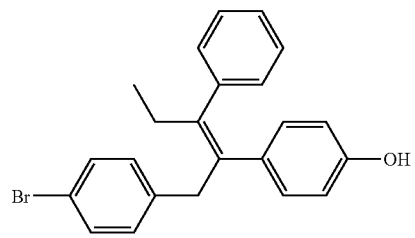 [SMILES: CC/C(=C(\Cc1ccc(Br)cc1)c1ccc(O)cc1)c1ccccc1] | | [M + 1] ESI M/Z |
| 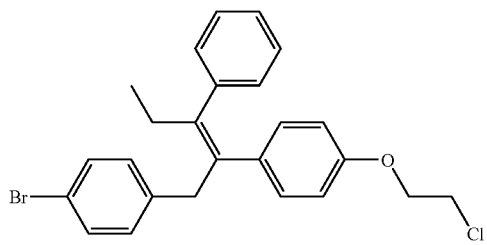 [SMILES: CC/C(=C(\Cc1ccc(Br)cc1)c1ccc(OCCCl)cc1)c1ccccc1] | | [M + 1] ESI M/Z |
| 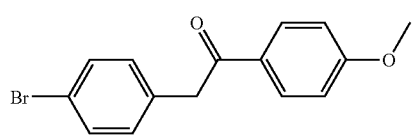 [SMILES: COc1ccc(C(=O)Cc2ccc(Br)cc2)cc1] | 304.87 | [M + 1] ESI M/Z |
| 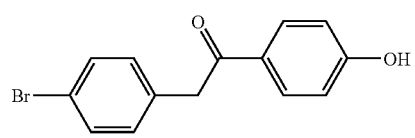 [SMILES: O=C(Cc1ccc(Br)cc1)c1ccc(O)cc1] | 289.13 | [M − 1] ESI M/Z |
| 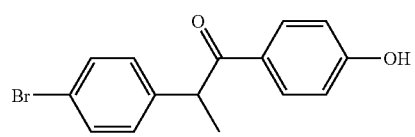 [SMILES: CC(C(=O)c1ccc(O)cc1)c1ccc(Br)cc1] | 303.13 | [M − 1] ESI M/Z |
| 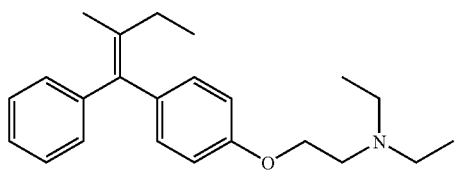 [SMILES: CC/C(C)=C(/c1ccccc1)c1ccc(OCCN(CC)CC)cc1] | 337.50 | [M + 1] ESI M/Z 338.00 |
| 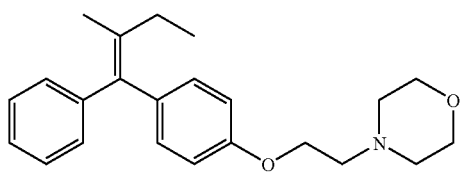 [SMILES: CC/C(C)=C(/c1ccccc1)c1ccc(OCCN2CCOCC2)cc1] | 351.48 | [M + 1] ESI M/Z 352.00 |
| 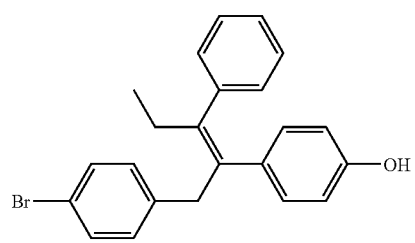 | 393.00 | [M − 1] ESI M/Z |

TABLE 4-4-continued
| | | |
|---|---|---|
| 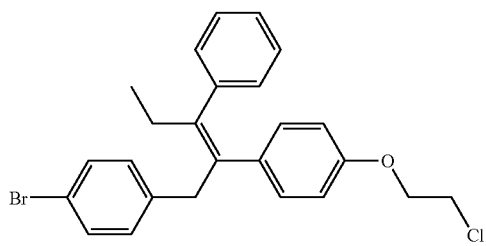 [SMILES: CC/C(=C(\Cc1ccc(Br)cc1)c1ccc(OCCCl)cc1)c1ccccc1] | 454.67 | [M + 1] ESI M/Z |
| 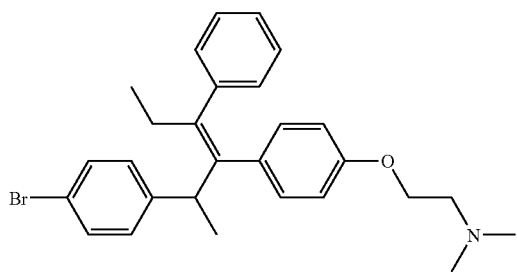 [SMILES: CC/C(=C(/c1ccc(OCCN(C)C)cc1)C(C)c1ccc(Br)cc1)c1ccccc1] | 478.33 | [M + 1] ESI M/Z |
| 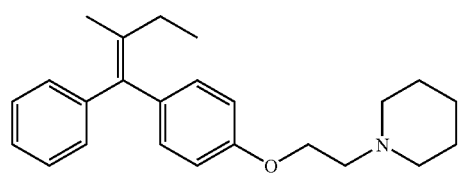 [SMILES: CC/C(C)=C(/c1ccccc1)c1ccc(OCCN2CCCCC2)cc1] | 349.51 | [M + 1] ESI M/Z 350.07 |
| 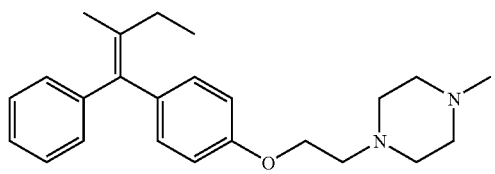 [SMILES: CC/C(C)=C(/c1ccccc1)c1ccc(OCCN2CCN(C)CC2)cc1] | 364.52 | [M + 1] ESI M/Z 364.93 |
| 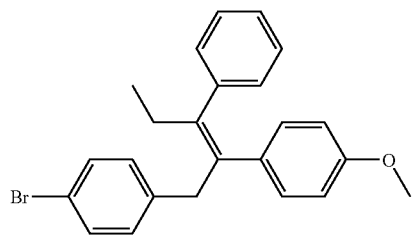 | | [M + 1] ESI M/Z |
| 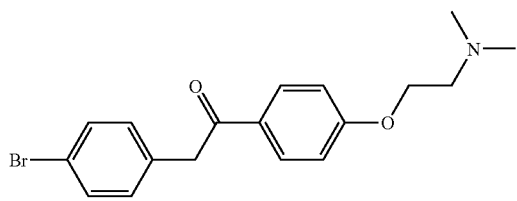 [SMILES: CN(C)CCOc1ccc(C(=O)Cc2ccc(Br)cc2)cc1] | 361.93 | [M + 1] ESI M/Z |
| 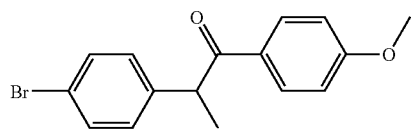 [SMILES: COc1ccc(C(=O)C(C)c2ccc(Br)cc2)cc1] | 318.73 | [M + 1] ESI M/Z |

TABLE 4-4-continued
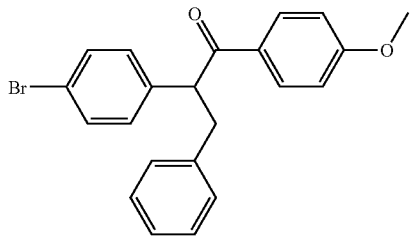 [SMILES: COc1ccc(C(=O)C(Cc2ccccc2)c2ccc(Br)cc2)cc1] 394.73 [M + 1] ESI M/Z
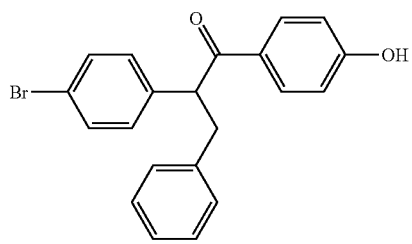 [SMILES: O=C(c1ccc(O)cc1)C(Cc1ccccc1)c1ccc(Br)cc1] 379.07 [M − 1] ESI M/Z
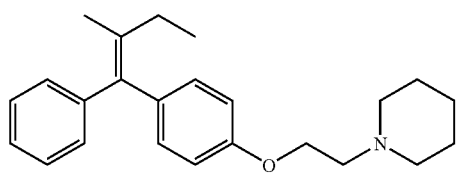 [SMILES: CC/C(C)=C(/c1ccccc1)c1ccc(OCCN2CCCCC2)cc1] 349.51 [M + 1] ESI M/Z 350.07
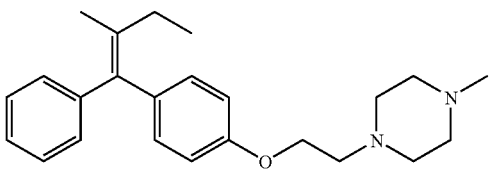 [SMILES: CC/C(C)=C(/c1ccccc1)c1ccc(OCCN2CCN(C)CC2)cc1] 364.52 [M + 1] ESI M/Z 364.93
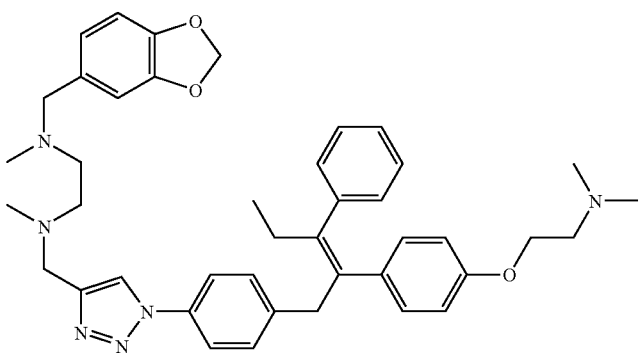 684.93 [M + 1] ESI M/Z
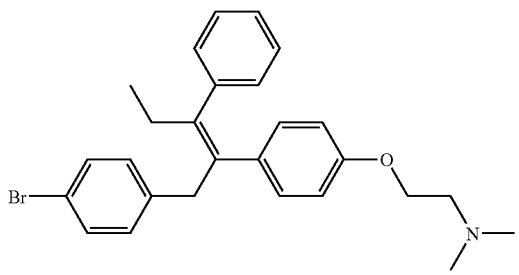 [SMILES: CC/C(=C(\Cc1ccc(Br)cc1)c1ccc(OCCN(C)C)cc1)c1ccccc1] 464.53 [M + 1] ESI M/Z TABLE 4-4-continued

| Structure | |
|---|---|
| (structure with Br-phenyl, phenyl, ethyl, benzyl, and 4-(2-dimethylaminoethoxy)phenyl groups on a central alkene) | 554.40 [M + 1] ESI M/Z |

| Structure | ¹H NMR (CDCl₃, 300 MHz) |
|---|---|
| (benzhydryl methyl ether with 4-(2-dimethylaminoethoxy)phenyl) | 7.33–7.23 (m, 7H), 6.87 (d, J = 8.8 Hz, 2H), 5.20 (s, 1H), 4.04 (t, J = 5.8 Hz, 2H), 3.36 (s, 3H), 2.72 (t, J = 5.8 Hz, 2H), 2.32 (s, 6H) |
| (benzhydryl isopropyl ether analog) | 7.37–7.19 (m, 7H), 6.86 (d, J = 8.8 Hz, 2H), 5.20 (s, 1H), 4.04 (t, J = 5.8 Hz, 2H), 3.65 (q, J = 6 Hz, 1H), 2.71 (t, J = 5.8 Hz, 2H), 2.32 (s, 6H), 1.21 (d, J = 6.05 Hz, 6H) |
| (benzhydryl ethyl ether analog) | 7.37–7.19 (m, 7H), 6.87 (d, J = 6.8 Hz, 2H), 5.44 (s, 1H), 4.04 (t, J = 5.8 Hz, 2H), 3.65 (p, J = 6.3 Hz, 2H), 2.71 (t, J = 5.8 Hz, 2H), 2.32 (s, 6H), 1.21 (t, J = 6 Hz, 3H) |
| (tetrasubstituted alkene with Br-phenyl, phenyl, ethyl, benzyl, and 4-methoxyphenyl) | 7.34 (d, J = 10.8 Hz, 2H), 7.10–6.99 (m, 7H), 6.79 (d, J = 11.6 Hz, 2H), 6.53 (d, J = 11.6 Hz, 2H), 3.86 (s, 2H), 3.66 (s, 3H), 2.62 (q, J = 7.5 Hz, 2H), 0.96 (t, J = 7.5 Hz, 3H) |
| (benzhydryl tert-butyl ether analog) | 7.37–7.19 (m, 7H), 6.87 (d, J = 6.8 Hz, 2H), 5.44 (s, 1H), 4.04 (t, J = 5.8 Hz, 2H), 3.65 (p, J = 6.3 Hz, 2H), 2.71 (t, J = 5.8 Hz, 2H), 2.32 (s, 6H), 1.21 (t, J = 6 Hz, 3H) |

Example 8

Study of Small Molecule Inducers of Stem Cell Cardiogenesis

A mouse embryonic stem cell (mESC)-based high throughput assay used to screen a commercially available and diverse small molecule library to identify small molecules that stimulate cardiomyocyte differentiation. The assay is developed to probe compounds that act between 2 and 6 days of differentiation in monolayer culture, corresponding to the time window when the ESCs become specified to follow the cardiomyocyte lineage. The assay readout is eGFP expression from the cardiomyocyte-specific alpha myosin heavy chain (aMHC) gene. eGFP fluorescence is imaged by high throughput microscopy (HTM) and quantified by calculating the integrated fluorescence intensity within intensity thresholded mask of areas of cardiomyocyte differentiation. About 30,000 data points were screened encompassing ~14,000 unique small molecules, each tested at 1 and 5 µg/mL doses. After data analysis and filtration of artifacts using statistics and visual confirmation in images, 14 compounds were reordered and verified with, a secondary confirmation screen. Of the potential hits, 3 compounds with strong cardiogenic potential are described below.

A biological time course experiment suggested the biological action of each molecule is maximized at overlapping but non-identical developmental windows between days 2 to 5 of mESC to cardiomyocyte differentiation. Early analysis of molecular markers induced in secondary assays suggest that these compounds act by regulating mesoderm and endodermal patterning, consistent with the time frame when they are active. An SAR effort is undertaken to investigate the structure-activity relationship (SAR) of all 3 "hit" molecules with the goal of identifying an optimized structure yielding maximum biological potency; and molecular space amenable to affinity ligand linkage without abrogating biological activity. The medicinal chemistry and SAR studies for 1) benzimidazole, 2) dihydropyridine and 3) phenothiazine classes are described.

The molecules would be expected to be used for stimulating differentiation of stem cell cells, in particular but not limited to embryonic stem cells (ESCs) and induced pluripotent stem cells (IPSCs) to endoderm (e.g. liver, lung and pancreas) and cardiac derivatives.

Tissue recombination assays were used leading to the identification of non-cardiac mesoderm and endoderm as sources of heart-inducing factors. The results are demonstrated by FIG. 1 (for mouse), demonstrating comparison of heart induction in mouse embryos and mESCs. ESCs induced to differentiate by aggregation into embryoid bodies (EBs) form all three germ layers (ectoderm, mesoderm and endoderm) then spontaneously develop a small number of cardiomyocytes, probably by preserving cellular interactions that occur in normal embryogenesis.

As can be seen from the information shown by FIG. 1, mESCs are derived from the inner cell mass of pre-implantation embryos (~E3.5, top). Heart induction in EBs probably recapitulates cell-cell interactions in early embryo, in which anterior visceral and definitive endoderm initiates cardiogenesis within the adjacent heart-forming mesoderm (dark red). Most of the endoderm (yellow) in this diagram is shown peeled away. The heart-inducing region (grey) consists of the extra-embryonic anterior visceral endoderm and anterior definitive endoderm.

Example 9

Study of Natural Protein Inducers

Figure 2:
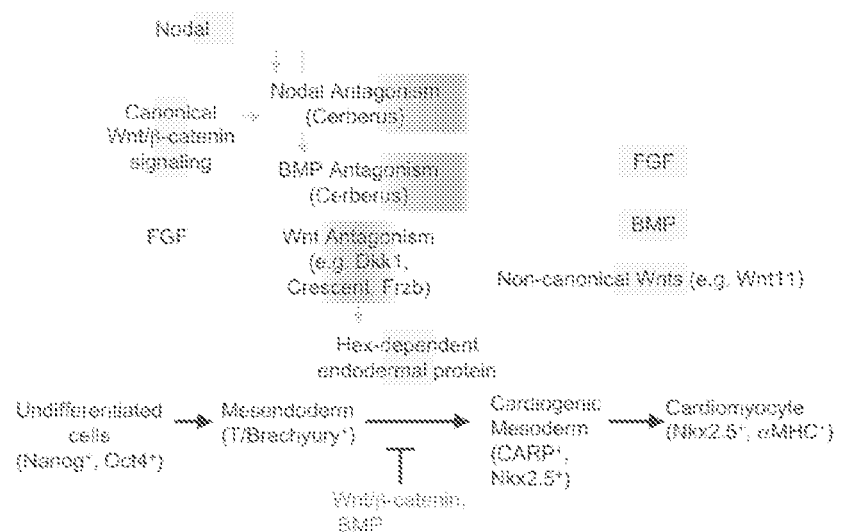
FIG. 2 provides a summary model for signaling pathways in cardiomyocyte formation.

Natural proteins that induce heart tissue in embryos operate in temporally complex patterns so that some factors act early, then are repressed and later re-activated, as shown by FIG. 2 which provides summary model for signaling pathways in cardiomyocyte formation and demonstrates the dynamics of secreted pathway activators functioning alternately with pathway antagonists during the developmental progression from stem cells to cardiomyocytes. In parentheses are the gene promoters to be used in the proposed research to mark the discrete stages of cardiomyogenesis.

It has been previously reported that fibroblast growth factor (FGF), Wnt and Nodal are essential for mesendoderm formation (mammalian streak tissue) along the anteroposterior body axis. Wnt antagonists, particularly Dickkopf 1 (Dkk) 1, are involved in patterning anterior mesendoderm and initiate cardiogenesis by activating the homeodomain protein Hex. Cardiogenesis is enhanced by activation of non-canonical (non-β-catenin) Wnt signaling pathways. Canonical Wnt signaling acts early in both ESCs and embryos, whereas its inhibition appears to occur later. TGF β-family member Nodal and its co-receptor Cripto also induce heart cells in embryos and mESCs. BMPs via Smad transcription factors promote cardiogenesis in embryos and synergize with FGF isoforms to extend the cardiogenic region posteriorly. Embryological studies in *Xenopus* suggest that BMPs function after Wnt antagonism or Nodal to sustain cardiogenesis from the Nkx2.5+ state onward. Findings that BMPs also stimulate cardiogenesis of ESCs and adult heart Sca1+ cells support the concept that factors operating during embryogenesis can stimulate ESC and potentially adult stem cell cardiomyogenesis.

There have been a few publwashed screens for small molecule inducers of ESC cardiogenesis. These include a very small screen of a few hundred compounds that identified ascorbic acid, a larger screen that identified a few compounds that were named cardiogenols, an earlier hit from the screen described in this application that resembled PPAR agonists but did not activate any PPAR, and a recent screen that identified a sulfonamide compound. The latter compound appears to act earlier than the disclosure compounds.

Example 10

Study of Activities of Disclosure Compounds

Figure 3:
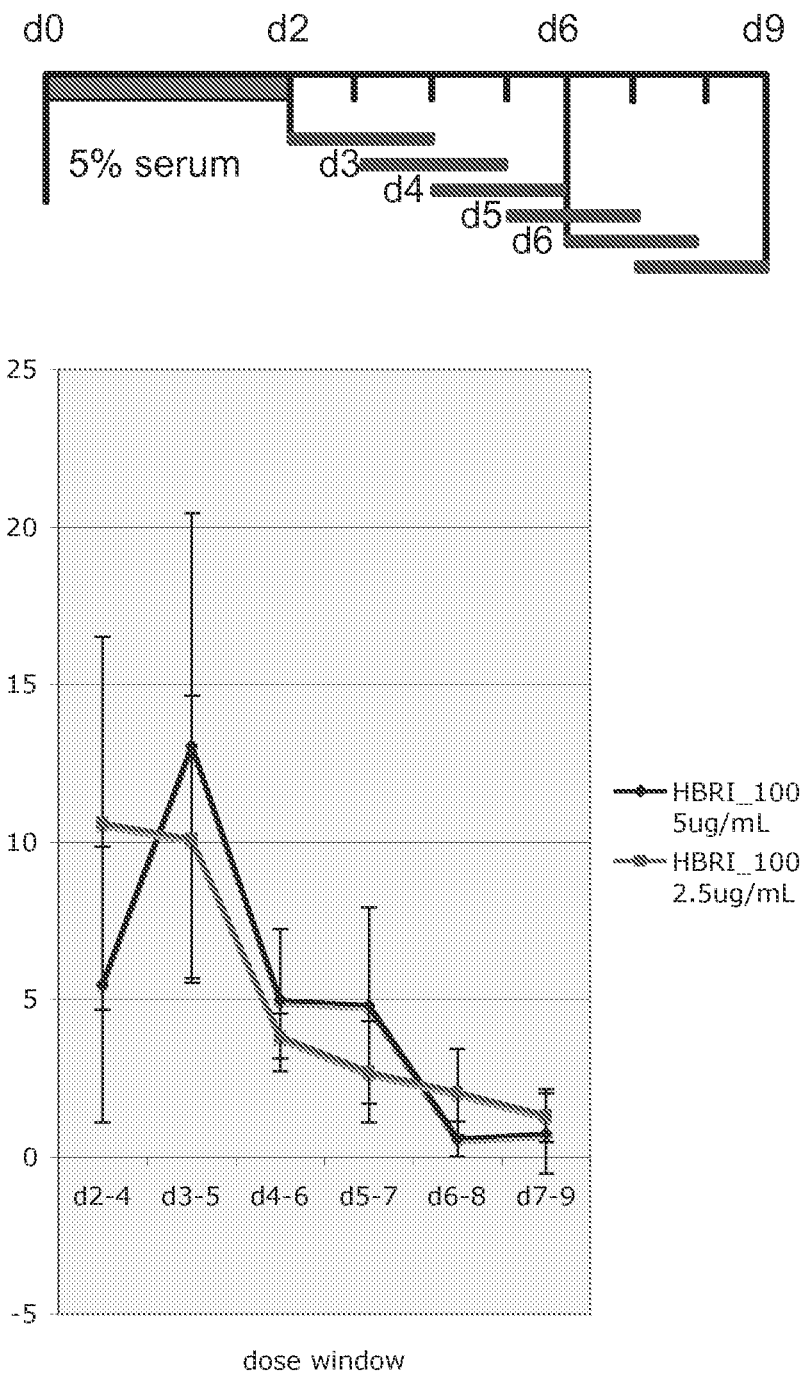
FIG. 3 provides data on windows of exposure and activity for some of the disclosed compounds.

Compounds were examined for activity potency in different 2 day windows, spanning 2-4, 3-5, 4-6, 5-7 and 6-8 days of differentiation. FIG. 3 shows that the compounds are active between days 2-4 and 3-5, but not thereafter.

The time frame of 2-5 days is consistent with action after the primary mesoderm is induced and when this tissue is specified to differentiate into the particular types of mesoderm and endoderm that form in the cultures. This process is termed mesoderm and endoderm patterning and is essential to produce the correct types of mesoderm and endoderm for further differentiation. The heart, as well as adjacent tissues of the head, pancreas, liver, lung, thymus, among other tissues, form from anterior mesoderm and endoderm specified at this time.

Figure 4:
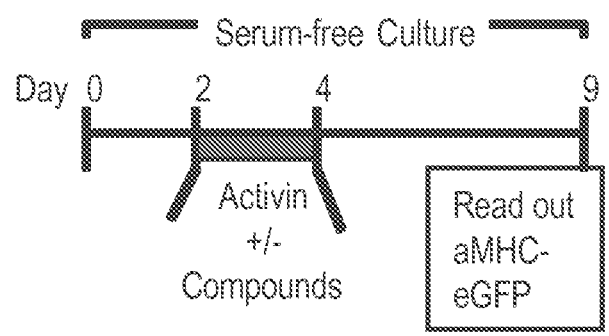
FIG. 4 provides a diagram of the serum-free assay used for the biological MOA studies.

To define the point of action in more detail, a more focused assay is designed to probe the activities of the compounds between days 2-4 of differentiation. Of note is that the original assay is performed in the presence of serum, which activates many pathways that obscure the targets of the small molecules. Since serum activates many pathways and many genes, its presence confounds analysis of downstream targets. Thus, a serum-free mESC cardiac differentiation assay is set up to more precisely validate the activity of the compounds and determine if they acted independently or synergized with a known inducer. The refined assay, diagrammed in FIG. 4, tested the ability of the small molecules to stimulate mesodermal differentiation from day 2 to day 4. Differentiation is initiated by aggregating mESC into embryoid bodies (EBs) in serum free conditions. Day 2 EBs were dispersed in the presence of growth factors or small molecules to allow maximal exposure. Cells were allowed to re-aggregate into EBs until day 4 when they were dispersed and plated in conducive conditions for cardiac differentiation to day 9, at which point eGFP is imaged and quantified by the algorithm described above. The conducive environment in some experiments is to plate the treated stem cells onto another cell line, END2, and in other experiments is to plate the treated stem cells onto fibronectin in the presence of other growth factors, including FGF2, because both provide a permissive environment for cardiogenic mesoderm to develop to cardiomyocytes but do not induce cardiomyocytes.

Figure 5:
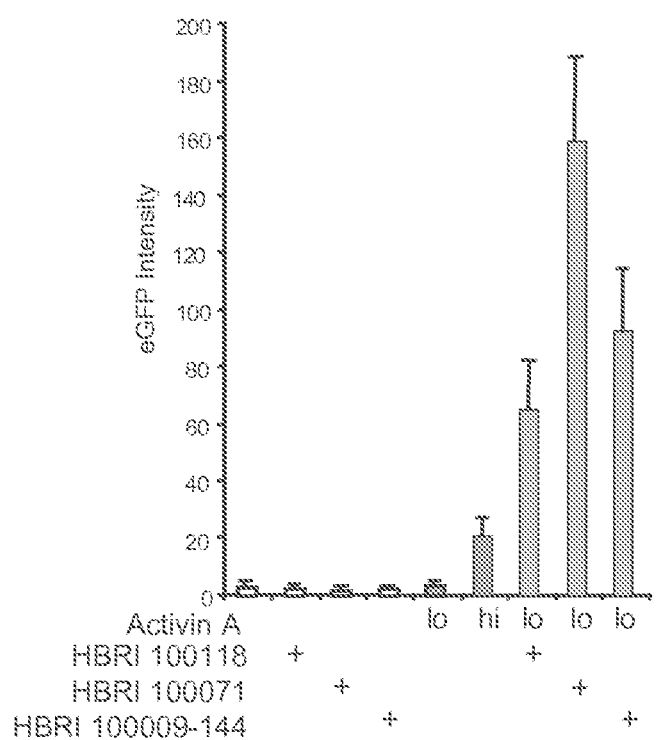
FIG. 5 demonstrates synergy of the small molecules with activin/Nodal signaling.

FIG. 5 summarizes experiments showing synergy with Activin/Nodal signaling. Exposure to high Activin A, an inducer of anterior mesoderm and endoderm, in the day 2 to day 4 window of this assay results in efficient cardiogenesis, whereas treatment with posteriorizing growth factors such as BMP4 does not. When the small molecules from the three classes alone are added in this time frame, no activity is observed, suggesting that they do not themselves mimic Activin/Nodal signaling but "synergize" with this pathway. Indeed, when the small molecules were added in presence of low doses of Activin A from day 2 to day 4, an increased amount of cardiomyocytes is observed, suggesting they potentiate the biological effect of Activin A.

Figure 6:
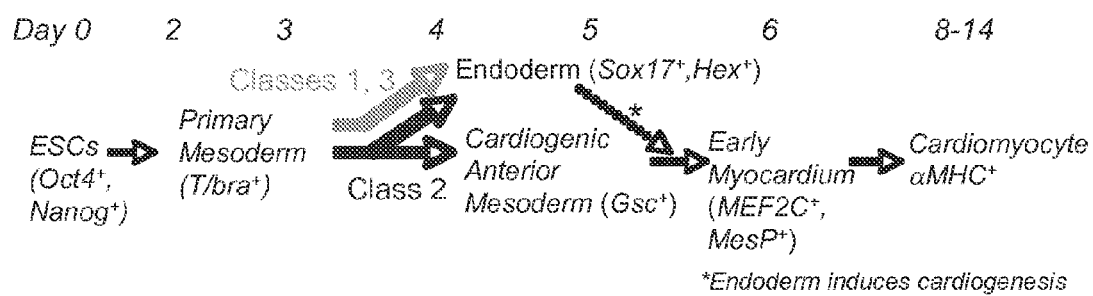
FIG. 6 provides a diagram of step in stem cell cardiogenesis when gene expression data indicate that the compounds act.

Using small molecule-treated day 4 EBs in small scale transcriptional profiling of typical mesoderm markers suggests that HBRI_100071 a dihydropyridine) enhances the induction of anterior mesoderm marked by Gsc (mesoderm part) and Sox17 (endoderm part), whereas HBRI_100118 a (benzimidazole) and HBRI_100009-144 a phenothiazine) only promote the formation of endoderm and do not appear to affect anterior mesoderm. None of the small molecules were found to induce pan-mesoderm markers such as Brachyury or Flk1, indicating they are involved in mesoderm patterning rather than mesoderm induction. Based on marker analysis, the series including HBRI_100071 dihydropyridines) would enhance cardiogenesis by enhancing anterior mesoderm formation, but might also stimulate cardiogenesis indirectly by promoting endoderm. In contrast, the marker analysis indicates that the series including HBRI_100118 (benzimidazoles) and HBRI_100009-144 (phenothiazines) act to induce endoderm only and thus would therefore stimulate cardiogenesis indirectly since the endoderm would provide the natural signals that direct primary mesoderm to become cardiac mesoderm. FIG. 6 summarizes the conclusions of the biological mechanism of action studies.

To begin to investigate signaling pathways targeted by the compounds, we asked if they mimic or synergize with Wnt signaling. Wnt signaling is known to synergize with Activin/Nodal signaling to induce and pattern mesoderm. To date, we have studied the HBRI_100118 (benzimidazoles) and HBRI_100071 (dihydropyridines) series.

Figure 7:
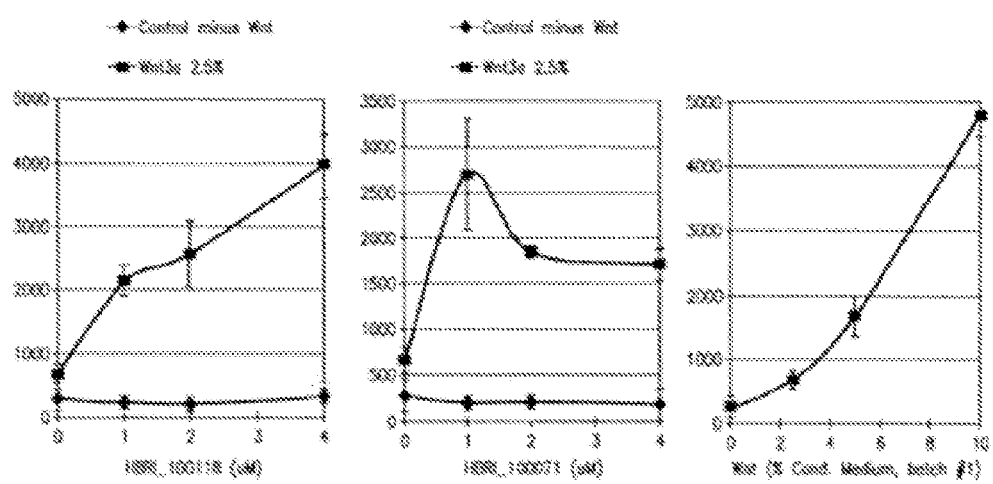
FIG. 7 is a graph showing the effects of Wnt in combination with some of the disclosed compounds.

Signaling is tested using a standard luciferase response system for canonical Wnt/b-catenin/TCF signaling. Briefly, we used a cell line (RKO) that had been stably transfected with a luciferase reporter gene under the control of the response element for T $CF_3$, a transcription factor that is activated by association with beta-catenin and is the target of canonical Wnt signaling. Using this assay, HBRI_100118 and HBRI_100071 did not activate luciferase; thus, they do not mimic Wnt/beta-catenin signaling. However, both increased activity of a submaximal dose of Wnt3a (FIG. 7), indicating that they activate signals that converge on the pathway to increase its activity. As shown in FIG. 7, HBRI_100118 and HBRI_100071 synergize with Wnt to activate the canonical Wnt/b-catenin signal transduction pathway. Compounds along do not activate 9red liens) but synergize with low level (2.5% conditioned medium, blue lines). Control activation by Wnt3a conditioned medium (right panel).

The signaling effects of the phenothiazine series is under investigation. Also, we are investigating the effect of the compounds on Activin/Nodal signaling using an analogous luciferase expression system.

To summarize, using an assay based on a mouse ESC reporter line with GFP under control of the cardiac specific alpha Myosin heavy chain (aMHC) gene, 3 distinct chemical classes of molecules were identified, dihydropyridines, benzimidazoles and phenothiazines, as discussed above. They were found to act in the early window of mesoderm differentiation at the point of dictating mesoderm and endodermal lineages. Due to the fact that the original assay is performed in the presence of serum, which activates many pathways that obscure the targets of the small molecules, analysis of downstream targets is more difficult. To facilitate the analysis of these compounds, a serum-free mESC cardiac differentiation assay is developed that allows the study of growth factors and/or small molecules in the early mesoderm differentiation time frame and their effect on cardiogenesis. Results with this assay revealed that the hits "synergize" with Activin/Nodal signaling, but do not themselves activate this pathway.

In summary, each series of compounds appeared to promote cardiomyogenesis at a different time point in the differentiation cascade. Based on the initial "hit," a dihydropyridine, approximately 100 analogs were synthesized that provided a drug-like "smart library" with various new chemical substituents. Some of the results are provided in some of the above Examples. The analogs were tested in the cardiomyocyte assay described above and the results showed a structure-activity relationship (SAR) for the "smart library". Several of the synthetic analogs showed increased activity (i.e., $IC_{50}$ values in the 0.06 and 2.1 um range) and possessed greater drug-like properties.

For the second "hit," a benzimidazole, over 600 analogs of that class were synthesized, tested in the cardiomyocyte assay and the data also described an SAR for this second drug-like "smart library."

For the third "hit", a Tamoxifen analog, over 100 analogs . . . to add in view of comment mlg28. For the fourth "hit" (i.e. phenothiazine), a "smart library" of a total of 45 analogs were synthesized.

Small scale transcriptional profiling of typical mesoderm markers suggested that benzimidazoles enhance the induction of anterior mesoderm marked by Gsc (mesoderm part) and Sox17 (endoderm part), whereas dihydropyridines only promote the formation of endoderm and does not appear to affect mesoderm. None of the small molecules were found to induce pan-mesoderm markers such as Brachyury or Flk1, indicating they are involved in mesoderm patterning rather than mesoderm induction. In conclusion, these classes of small molecules act by patterning uncommitted primary mesoderm into endoderm and cardiogenic mesoderm.

Although the disclosure has been described with reference to the above examples, it will be understood that modifications and variations are encompassed within the spirit and scope of the disclosure. Accordingly, the disclosure is limited only by the following claims.

What is claimed is:

1. A method for producing mammalian mesodermal or cardiomyocyte cells from mammalian stem cells, comprising contacting within the same suitable medium Activin A and the stem cells with a compound of structure II in the form of a free base or a pharmaceutically acceptable salt, hydrate, solvate or N-oxide thereof:

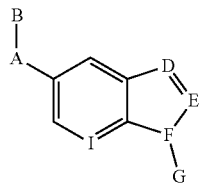

wherein:

A is NH; and

B is an aromatic ring, wherein the aromatic ring is optionally substituted phenyl, optionally substituted benzyl, or has the structure of

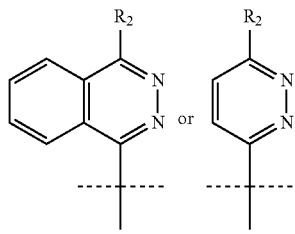

or is an unsaturated 5 or 6 member ring, optionally substituted, containing a heteroatom wherein the heteroatom is N or O, or A is absent and B is optionally substituted phenyl, D is N or CH, E is N, CH, C—R, or C—OH;

F is N or CH,

G is aryl, heteroaryl or cyclohexyl optionally substituted by 1 to 5 $R_1$;

I is N or C;

R is hydrogen or $(C_1-C_6)$alkyl;

$R_1$, when present, independently are $(C_1-C_6)$alkyl, $(C_1-C_6)$alkoxy, $(C_1-C_6)$thioalkoxy, hydroxy, halogen, $CF_3$, or $C_2F_5$; and $R_2$ independently are hydrogen, $(C_1-C_6)$alkyl, optionally substituted phenyl, optionally substituted benzyl, or $(C_1-C_6)$alkoxy.

2. The method of claim 1, wherein the compound of structure II has formula:

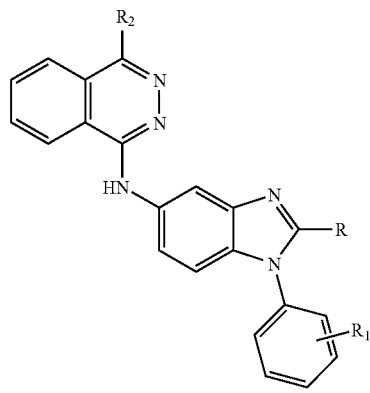

wherein

R is hydrogen, methyl, or amino;

$R_1$, if present, independently are hydrogen, hydroxyl, pyridyl, methyl, trifluoromethyl, methoxy or methylthio;

$R_2$ is hydrogen, phenyl, benzyl, methoxy, methyl or halogen.

3. The method of claim 1, wherein the compound of structure II has structure IIA, IIB, IIC, IID, IIE, IIF, IIG, or IIM in the form of a free base or a pharmaceutically acceptable salt, hydrate, solvate or N-oxide thereof:

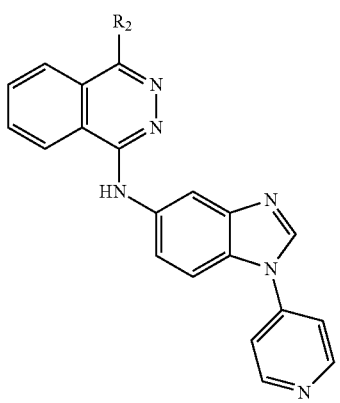

IIA

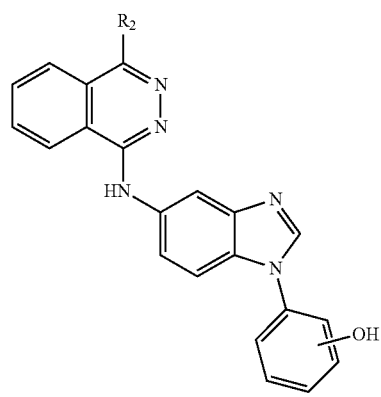

IIB

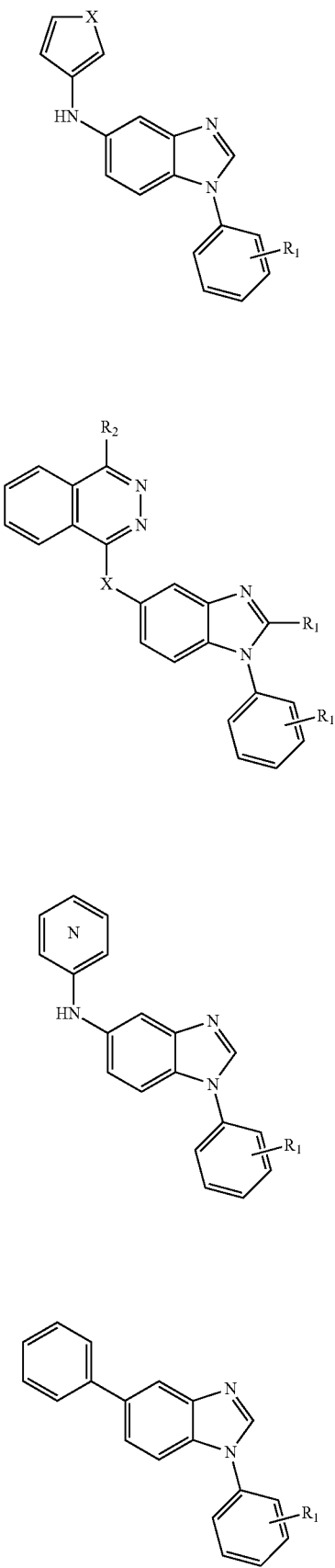

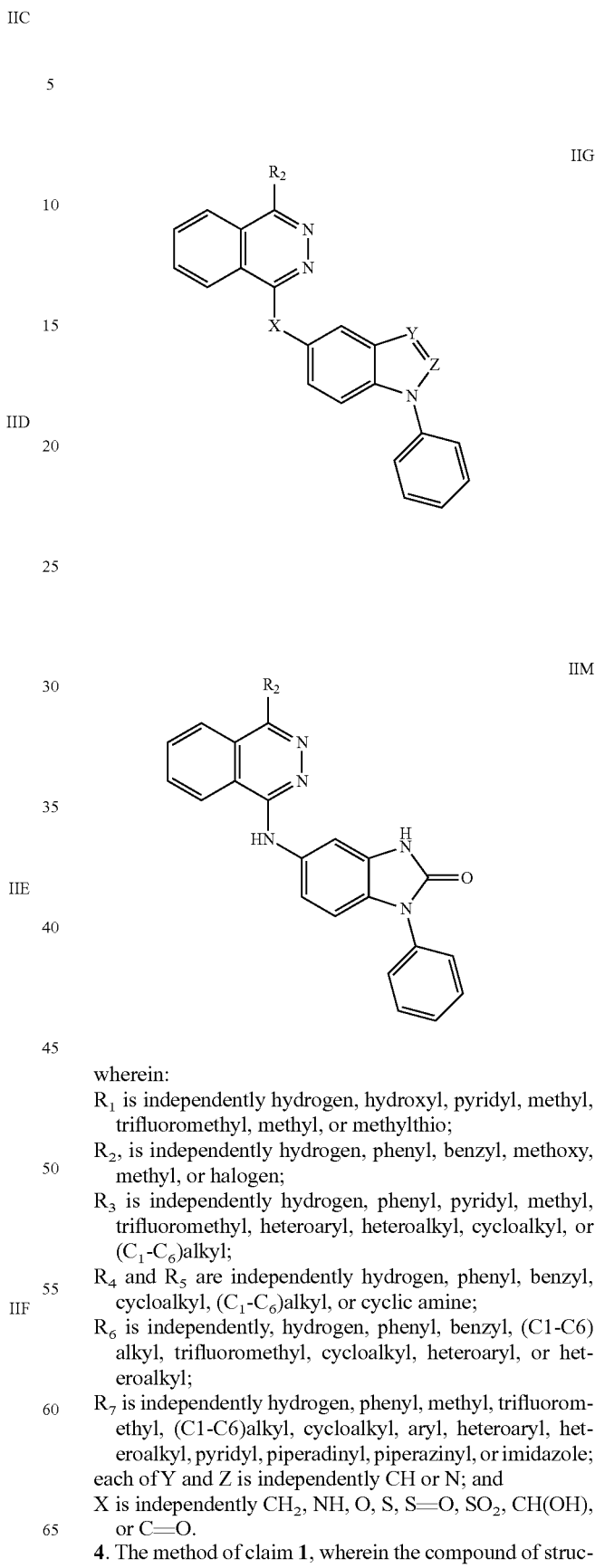

wherein:
R₁ is independently hydrogen, hydroxyl, pyridyl, methyl, trifluoromethyl, methyl, or methylthio;
R₂, is independently hydrogen, phenyl, benzyl, methoxy, methyl, or halogen;
R₃ is independently hydrogen, phenyl, pyridyl, methyl, trifluoromethyl, heteroaryl, heteroalkyl, cycloalkyl, or (C₁-C₆)alkyl;
R₄ and R₅ are independently hydrogen, phenyl, benzyl, cycloalkyl, (C₁-C₆)alkyl, or cyclic amine;
R₆ is independently, hydrogen, phenyl, benzyl, (C1-C6) alkyl, trifluoromethyl, cycloalkyl, heteroaryl, or heteroalkyl;
R₇ is independently hydrogen, phenyl, methyl, trifluoromethyl, (C1-C6)alkyl, cycloalkyl, aryl, heteroaryl, heteroalkyl, pyridyl, piperadinyl, piperazinyl, or imidazole;
each of Y and Z is independently CH or N; and
X is independently CH₂, NH, O, S, S=O, SO₂, CH(OH), or C=O.

4. The method of claim 1, wherein the compound of structure II has the formula:

297
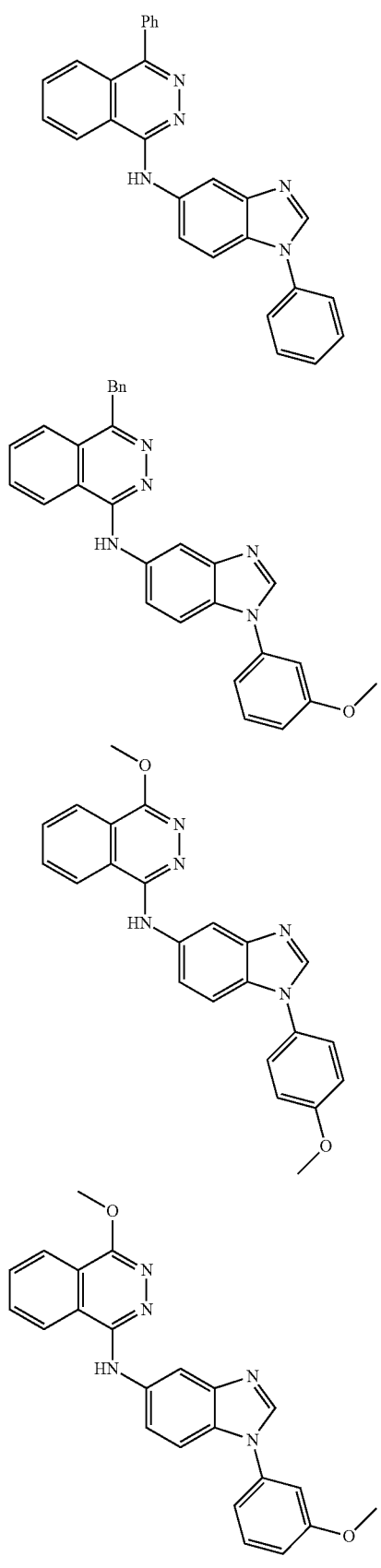
298
-continued
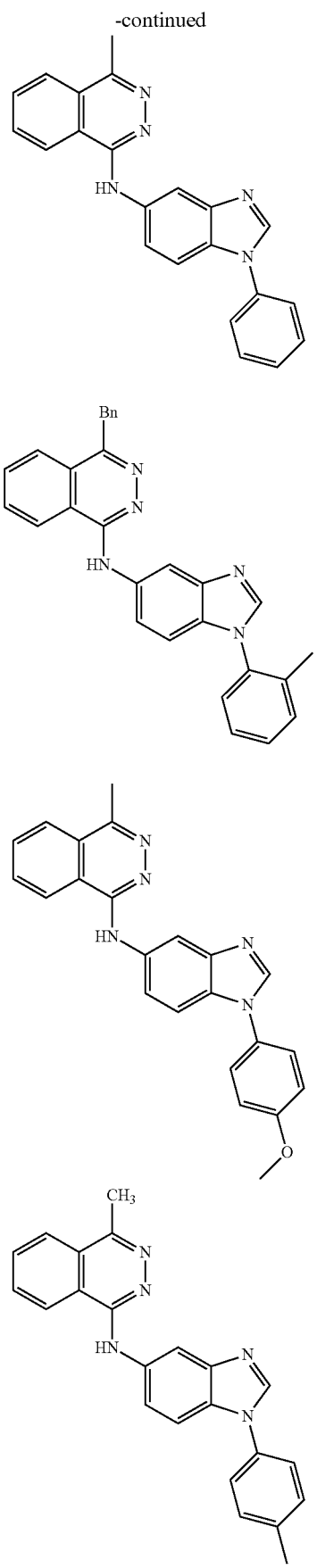

299
-continued
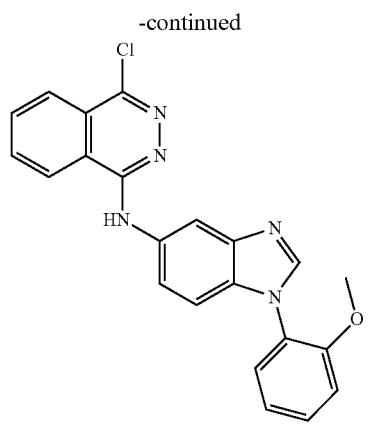
300
-continued
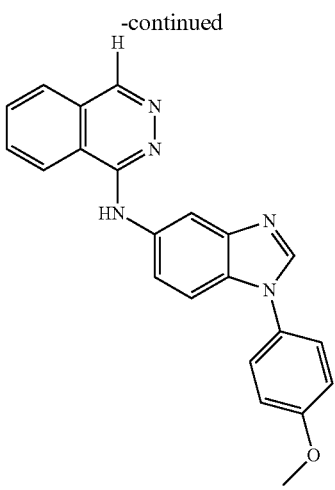
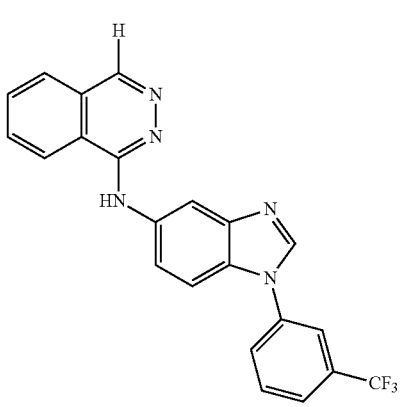
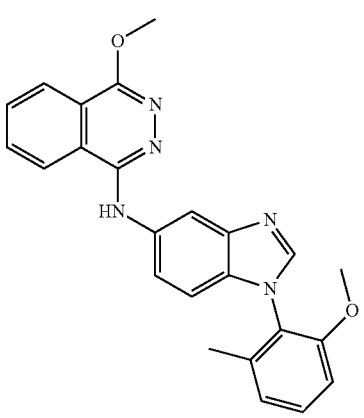
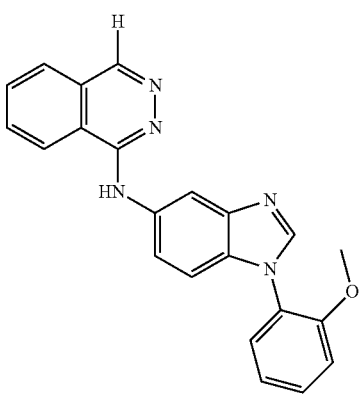

301
-continued
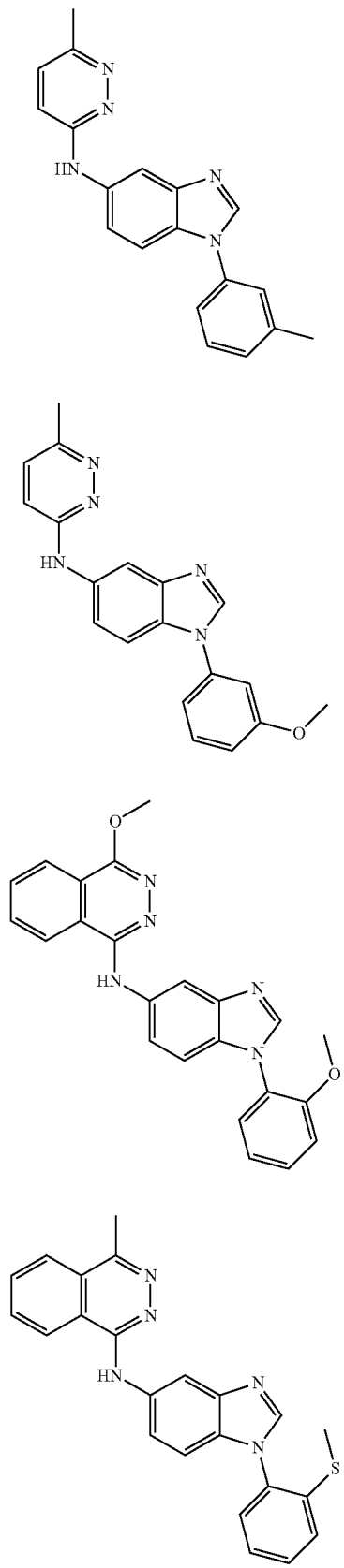
302
-continued
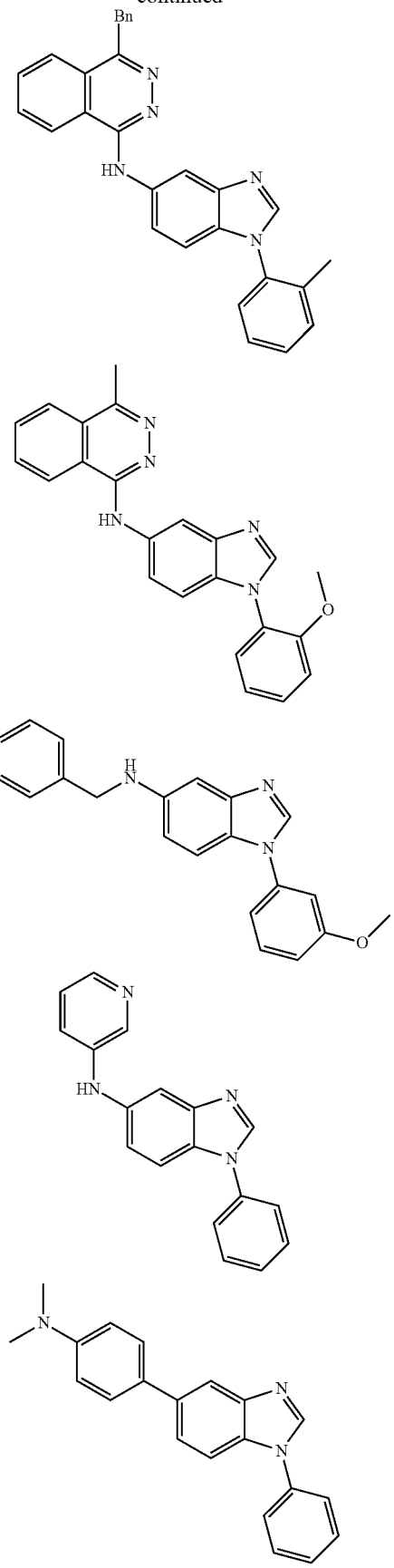

303
-continued

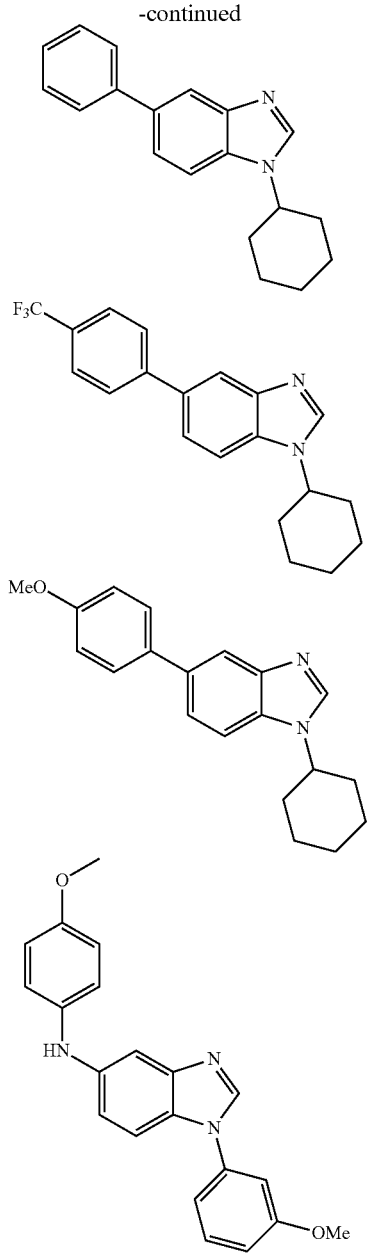

304
-continued

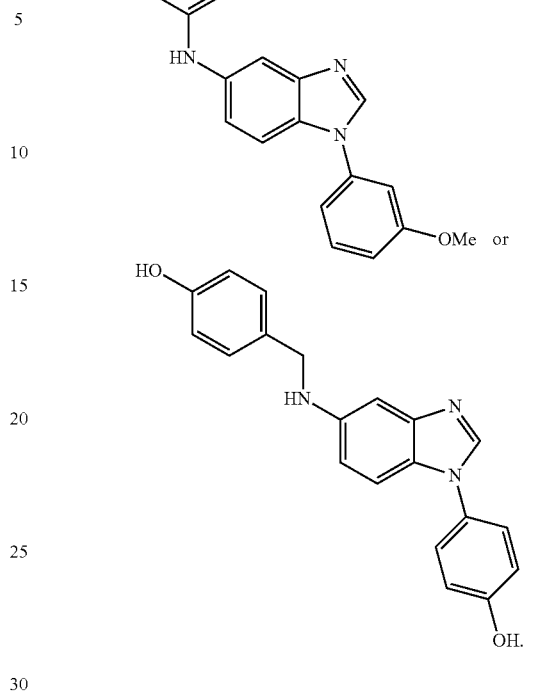

5. The method of claim 1, wherein the contacting is for a period of time between about 24 hours to 192 hours.

6. The method of claim 5, wherein the contacting is between about 48 hours to 144 hours.

7. The method of claim 1, wherein cells produced from mammalian stem cells are cardiomyocytes.

8. The method of claim 1, wherein the cells produced from mammalian stem cells are mesodermal cells.

9. The method of claim 1, further comprising contacting the cells with a Wnt protein.

10. The method of claim 9, wherein the Wnt protein is Wnt3a.

11. The method of claim 1, wherein the stem cells are embryonic stem cells, induced pluripotent stem cells or adult stem cells.

* * * * *

UNITED STATES PATENT AND TRADEMARK OFFICE
CERTIFICATE OF CORRECTION

| | |
|---|---|
| PATENT NO. | : 9,012,217 B2 |
| APPLICATION NO. | : 12/561235 |
| DATED | : April 21, 2015 |
| INVENTOR(S) | : Mark Mercola et al. |

It is certified that error appears in the above-identified patent and that said Letters Patent is hereby corrected as shown below:

In the Specification

In Column 1, Lines 16 through 19, please replace:
"This invention is made with government support under Comprehensive NIH Grant No. HL071913 awarded by the National Institutes of Health. The Government has certain rights in the invention."
With:
"This invention was made with government support under R21 HL071913 awarded by the National Institutes of Health. The government has certain rights in the invention."

Signed and Sealed this
Eighteenth Day of June, 2024

Katherine Kelly Vidal
*Director of the United States Patent and Trademark Office*